(12) United States Patent
Lofstrand et al.

(10) Patent No.: US 12,054,486 B2
(45) Date of Patent: Aug. 6, 2024

(54) PYRIDINE DERIVATIVES AND THEIR USE AS SODIUM CHANNEL ACTIVATORS

(71) Applicant: Xenon Pharmaceuticals Inc., Burnaby (CA)

(72) Inventors: Verner Alexander Lofstrand, Burnaby (CA); Jung Yun Kim, Burnaby (CA); Helen Clement, Burnaby (CA); Kristen Nicole Burford, Burnaby (CA); Paul Charifson, Burnaby (CA); Shawn Johnstone, Burnaby (CA); Juliette Sabbatani, Burnaby (CA); Jan Felix Scholtes, Burnaby (CA); Wei Zhang, Burnaby (CA); Shaoyi Sun, Coquitlam (CA)

(73) Assignee: Xenon Pharmaceuticals Inc., Burnaby (CA)

( * ) Notice: Subject to any disclaimer, the term of this patent is extended or adjusted under 35 U.S.C. 154(b) by 0 days.

(21) Appl. No.: 17/951,640

(22) Filed: Sep. 23, 2022

(65) Prior Publication Data
US 2023/0144095 A1 May 11, 2023

Related U.S. Application Data

(60) Provisional application No. 63/248,330, filed on Sep. 24, 2021.

(51) Int. Cl.
| | | |
|---|---|---|
| *C07D 471/04* | (2006.01) | |
| *C07D 401/04* | (2006.01) | |
| *C07D 401/14* | (2006.01) | |
| *C07D 413/14* | (2006.01) | |
| *C07D 487/04* | (2006.01) | |
| *C07D 491/052* | (2006.01) | |

(52) U.S. Cl.
CPC ......... *C07D 471/04* (2013.01); *C07D 401/04* (2013.01); *C07D 401/14* (2013.01); *C07D 413/14* (2013.01); *C07D 487/04* (2013.01); *C07D 491/052* (2013.01)

(58) Field of Classification Search
CPC ................ C07D 471/04; C07D 401/04; C07D 401/14; C07D 413/14; C07D 487/04; C07D 491/052
See application file for complete search history.

(56) References Cited

U.S. PATENT DOCUMENTS

| | | | |
|---|---|---|---|
| 3,845,770 A | 11/1974 | Theeuwes et al. | |
| 4,326,525 A | 4/1982 | Swanson et al. | |
| 2022/0347175 A1 | 11/2022 | Nishida et al. | |
| 2023/0150972 A1* | 5/2023 | Lofstrand | C07D 498/08 514/256 |
| 2023/0203007 A1* | 6/2023 | Lofstrand | C07D 487/04 514/63 |

FOREIGN PATENT DOCUMENTS

| | | | |
|---|---|---|---|
| EP | 3029083 A1 | 6/2016 | |
| WO | WO 9850016 A2 | 11/1998 | |
| WO | WO-2004018461 A2 | 3/2004 | |
| WO | WO-2007009661 A2 | 1/2007 | |
| WO | WO-2008009406 A1 * | 1/2008 | ............ A01N 43/58 |
| WO | WO-2012025237 A1 | 3/2012 | |
| WO | WO-2012176123 A1 | 12/2012 | |
| WO | WO-2013006596 A1 | 1/2013 | |
| WO | WO-2013064465 A1 | 5/2013 | |
| WO | WO-2014029723 A1 | 2/2014 | |
| WO | WO-2015069593 A1 | 5/2015 | |
| WO | WO-2020017587 A1 | 1/2020 | |
| WO | WO-2020092187 A1 | 5/2020 | |
| WO | WO-2020092667 A1 | 5/2020 | |
| WO | WO-2020123395 A1 | 6/2020 | |
| WO | WO-2020163102 A1 | 8/2020 | |
| WO | WO-2021039961 A1 | 3/2021 | |
| WO | WO-2021141041 A1 | 7/2021 | |
| WO | WO 2021141041 A1 | 7/2021 | |
| WO | WO-2021149767 A1 | 7/2021 | |

(Continued)

OTHER PUBLICATIONS

Lukyanov; Tetrahedron 2006, 62, 1849-1863. https://doi.org/10.1016/j.tet.2005.11.039 (Year: 2006).*
Said; Monatsh Chem 2009, 140, 573-579. https://doi.org/10.1007/s00706-008-0091-5 (Year: 2009).*
Stanovnik; Synthesis 1986, 807-810. DOI: 10.1055/s-1986-31787 (Year: 1986).*
Wood; J Neurobiol. 2004, 61, 55-71. https://doi.org/10.1002/neu.20094 (Year: 2004).*
Brown et al., "Muscarinic suppression of a novel voltage-sensitive K$^+$ current in a vertebrate neurone," Nature 283:673-676, Feb. 14, 1980.
Catterall, "Forty Years of Sodium Channels: Structure, Function, Pharmacology, and Epilepsy," *Neurochem. Res.* 42(9):2495-2504, Sep. 2017.
Catterall, "Sodium Channels, Inherited Epilepsy, and Antiepileptic Drugs," *Ann. Rev. Pharmacol. Toxicol.* 54:317-338, 2014.

(Continued)

*Primary Examiner* — Daniel R Carcanague
(74) *Attorney, Agent, or Firm* — Sterne, Kessler, Goldstein & Fox P.L.L.C.

(57) ABSTRACT

The present disclosure is directed to compounds of formula (I):

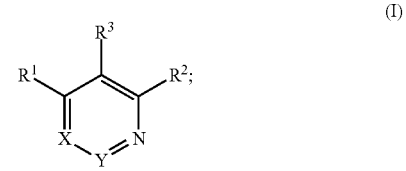

wherein X, Y, $R^1$, $R^2$ and $R^3$ are as described herein, as stereoisomers, enantiomers or tautomers thereof or mixtures thereof; or pharmaceutically acceptable salts, solvates or prodrugs thereof, and pharmaceutical compositions comprising the compounds of formula (I), as described herein, which are useful as voltage-gated sodium channel modulators and are therefore are useful in treating seizure disorders such as epilepsy.

35 Claims, No Drawings

(56) References Cited

FOREIGN PATENT DOCUMENTS

| | | |
|---|---|---|
| WO | WO-2023049364 A1 | 3/2023 |
| WO | WO-2023049367 A1 | 3/2023 |
| WO | WO-2023049369 A2 | 3/2023 |
| WO | WO-2023205465 A1 | 10/2023 |

OTHER PUBLICATIONS

Catterall, "Voltage-gated sodium channels at 60: structure, function and pathophysiology," J. Physiol. 590(11): 2577-2589, 2012.
Han et al., "Autistic behavior in Senla$^{+/-}$ mice and rescue by enhanced GABAergic transmission," Nature 489:385-390, 2012.
Hirtz et al., "How common are the "common" neurologic disorders?" Neurology 68(5):326-337, Jan. 30, 2007.
Hitiris et al., "Mortality in epilepsy," Epilepsy and Behavior 10:363-373, 2007.
Hu et al., "Distinct contributions of $Na_v1.6$ and $Na_v1.2$ in action potential initiation and backpropagation," Nat. Neurosci. 12(8):996-1002, Aug. 2009 (7 pages).
Kuzma et al., "Progress in the Development of Ultra-Long-Acting Local Anesthetics," Regional Anesthesia 22(6):543-551, 1997.
Mantegazza et al., "Identification of an $Na_v1.1$ sodium channel (SCN1A) loss-of-function mutation associated with familial simple febrile seizures," Proc Natl Acad Sci USA 102(50):18177-18182, Dec. 13, 2005.
Miyazaki et al., "Discovery of novel 4-phenyl-2-(pyrrolidinyl)nicotinamide derivatives as potent $Na_v1.1$ activators," Bioorg. Med. Chem. Lett. 29(6):815-820, 2019.
Ogiwara et al., "$Na_v1.1$ Localizes to Axons of Parvalbumin-Positive Inhibitory Interneurons: A Circuit Basis for Epileptic Seizures in Mice Carrying an Scn1a Gene Mutation," The Journal of Neuroscience 27(22):5903-5914, May 30, 2007.
Richards et al., "Selective $Na_v1.1$ activation rescues Dravet syndrome mice from seizures and premature death," PNAS 115(34):E8077-E8085, Aug. 3, 2018.
Verret et al., "Inhibitory Interneuron Deficit Links Altered Network Activity and Cognitive Dysfunction in Alzheimer Model," Cell 149:708-721, Apr. 27, 2012.
Vincent, "The Molecular Genetics of the Long QT Syndrome: Genes Causing Fainting and Sudden Death," Annu. Rev. Med. 49:263-274, 1998 (abstract only).
Ward, "Chiral Separations," Anal. Chem. 74(12):2863-2872, 2002.
Bundgaard, H., et al., "Design of prodrugs: Bioreversible derivatives for various functional groups and chemical entities," in Design of Prodrugs p. 1, Elsevier Science Publishers B.V., Netherlands (1985).
Silverman, R. B., et al., "Chapter 8: Prodrugs and Drug Delivery Systems," in The Organic Chemistry of Drug Design and Drug Action, pp. 352-400, Academic Press, Inc. United States (1992).
Wolff, M. et al., "vol. I: Principles and Practice," in Burger's Medicinal Chemistry and Drug Design, 5th Ed., pp. 975-977, Wiley, United States (1995).
Banker, G. S., et al., "Prodrugs," in Modern Pharmaceutics 3rd Ed., pp. 396 and 451, Marcel Dekker, Inc., United States (1996).
Large, C. H., et al., "The Efficacy of Sodium Channel Blockers to Prevent Phencyclidine-Induced Cognitive Dysfunction in the Rat: Potential for Novel Treatments for Schizophrenia," J Pharm Exp Ther 338(1):100-113, American Society for Pharmacology and Experimental Therapeutics (2011).
Eijkelkamp, N., et al., "Neurological perspectives on voltage-gated sodium channels," Brain: A Journal of Neurology 135: 2585-2612, Oxford University Press, United Kingdom (2012).
Hulikal, V., "Deuterium Labeled Compounds in Drug Discovery Process," Abstract, 2010.
Pimlott, S. L., et al., "Radiotracer development in psychiatry," PubMed Abstract of Nucl Med Commun 26(3):183-188, British Nuclear Medicine Society, United Kingdom (2005).
STN Registry RN 1002291-65-7 and RN 1002291-61-3 (2008).
Higuchi, T., and Stella, V., eds., Pro-drugs as Novel Delivery Systems, A.C.S. Symposium Series, vol. 14, American Chemical Society, Washington, D.C., United States (1975).
Elger, C.E., et al., "Modern management of epilepsy: A practical approach," Epilepsy Behav. 12:501-539, Elsevier, Netherlands (2008).
Oakley, J.C., et al., "Insights into pathophysiology and therapy from a mouse model of Dravet syndrome," Epilepsia 52(Suppl. 2):59-61, Wiley-Blackwell, United States (2011).
Jensen, H.S., et al., "Therapeutic potential of Na(V)1.1 activators," Trends Pharmacol Sci 35(3):113-118, Elsevier, Netherlands (2014).
Crestey, F., et al., "Identification and Electrophysiological Evaluation of 2-methylbenzamide Derivatives as Nav1.1 Modulators," ACS Chem Neurosci 6:1302-1308, American Chemical Society, United States (2015).
Frederiksen, K., et al., "A small molecule activator of Nav 1.1 channels increases fast-spiking interneuron excitability and GABAergic transmission in vitro and has anti-convulsive effects in vivo," Eur J Neurosci 46:1887-1896, Wiley-Blackwell, United States (2017).
Von Schoubyea, N.L., et al., "The sodium channel activator Lu AE98134 normalizes the altered firing properties of fast spiking interneurons in Dlx5/6+/− mice," Neurosci Lett 662:29-35, Elsevier, Netherlands (2018).
Gong, B., et al., "Type I and Type II Na(+) Channel a-Subunit Polypeptides Exhibit Distinct Spatial and Temporal Patterning, and Association with Auxiliary Subunits in Rat Brain," J Comp Neurol 412:342-352, Wiley, United States (1999).
Bundgard, H., ed., Design of Prodrugs, pp. 7-9, 21-24, Elsevier, Netherlands (1985).
International Search Report and Written Opinion for International Application No. PCT/US2022/044562, European Patent Office, Netherlands, mailed on Dec. 2, 2022, 7 pages.
International Search Report and Written Opinion for International Application No. PCT/US2022/044566, European Patent Office, Netherlands, mailed on Mar. 24, 2023, 13 pages.
International Search Report and Written Opinion for International Application No. PCT/US2022/044559, European Patent Office, Netherlands, mailed on Nov. 29, 2022, 8 pages.
Godard, A., et al., "Metallation in connection with cross-coupling reactions. Coupling of hindered aryls for the synthesis of 4-phenylpyridines as part of Streptonigrin and Lavendamycin analogues," Journal of Organometallic Chemistry 517(1):25-36, Elsevier, Netherlands ( 1996).
Marsais F et al., "Synthesis of 3-Amino-4-phenylpyridines: A Novel Strategy for the Preparation of CD Ring Models of Streptonigrin," J Chem Soc Perkin Trans21(51):18, Wiley, United States (1990).
Hobbs, H., et al., "Discovery of 3-Oxabicyclo[4.1.0]heptane, a Non-nitrogen Containing Morpholine Isostere, and Its Application in Novel Inhibitors of the PI3K-AKT-mTOR Pathway," J Med Chem 62(15):6972-6984, American Chemical Society, United States (2019).
Frolov, A.I., et al., "Selective α-Methylation of Ketones," J Org Chem 86(11):7333-7346, American Chemical Society, United States (2021).
Wang, L., et al., "Addition of a single methyl group to a small molecule sodium channel inhibitor introduces a new mode of gating modulation," British Journal of Pharmacology 172:4905-4918, Wiley-Blackwell, United Kingdom (2015).
Tikhonov, D.B., et al., "Sodium channel activators: Model of binding inside the pore and a possible mechanism of action," FEBS Letters 579(29809):4207-4212, Wiley, United States (2005).
Wang, L., et al., "PF-06526290 can both enhance and inhibit conduction through voltage-gated sodium channels," British Journal of Pharmacology 175(14):2926-2939, Wiley-Blackwell, United Kingdom (2018).
Mingorance, A., "Dravet syndrome pipeline and opportunities review," Dravet syndrome pipeline 2017, Dracaena Report, Spain (2017).
Lersch, R., et al., "Targeted Molecular Strategies for Genetic Neurodevelopmental Disorders: Emerging Lessons from Dravet Syndrome," The Neuroscientist 29(6):732-750, Sage Publishing, United States (2022).
Catterall, W.A., "Dravet Syndrome: A Sodium Channel Interneuropathy," Curr Opin Physiol 2:42-50, Elsevier, Netherlands (2018).

(56) References Cited

OTHER PUBLICATIONS

Catterall, W.A., et al., "Nav1.1 channels and epilepsy," J Physiol 588.11:1849-1859, Wiley-Blackwell, United Kingdom (2010).

Mohi El-Deen, E.M., et al., "Synthesis, Molecular Docking and Cytotoxicity Evaluation of Novel 1,2-Disubstituted Benzimidazole Derivatives Against Liver and Breast Cancer Cell Lines," Res J Pharm, Biol Chem Sci 7(5):1599-1615 RJPBCS, India (2016).

Girgis, A.S., et al., "Novel synthesis of nicotinamide derivatives of cytotoxic properties," Bioorganic & Medicinal Chemistry 14:4466-4476, Elsevier, Netherlands (2006).

Katritzky, A.R., et al., "QSAR modeling, synthesis and bioassay of diverse leukemia RPMI-8226 cell line active agents," Euro J Med Chem 45:5183-5199, Elsevier, Netherlands (2010).

Goodchild, S.J., et al., "A Selective NaV1.1 Potentiator Enhances Interneuron Excitability to Normalize Motor Performance in a Dravet Syndrome Mouse Model," Poster 2.247 presented at the American Epilepsy Society Annual Meeting in Orlando, FL on Dec. 1-5, 2023.

Goodchild, S.J., et al., "Selective Sodium Channel Inhibitors and Potentiators; Pharmacology in Cortical Slices from Wild Type and Dravet Mice," poster presented at the 73rd Annual Meeting of the American Epilepsy Society on Dec. 6-10, 2019.

Goodchild, S.J., et al., "Selective Potentiation of Inhibitory Networks Prevents Seizures in a Mouse Model of Dravet Syndrome," poster #861 presented at the American Epilepsy Society Annual Meeting on Dec. 4-8, 2023.

Goodchild, S.J., et al., "Selective Potentiation of Inhibitory Networks Prevents Seizures in aMouse Model of Dravet Syndrome," oral presentation at the American Epilepsy Society Annual Meeting on Dec. 7, 2023; abstract published Nov. 21, 2020.

Goodchild, S.J., et al., "NaV1.1 Selective Potentiators Normalize Inhibition/Excitation Imbalance and Prevent Seizures in a Mouse Model of Dravet Syndrome," poster V.006 presented at the American Epilepsy Society Annual Meeting on Dec. 3-7, 2021.

Goodchild, S.J., et al., "Molecularly Selective NaV1.1 Potentiators Increase PV+ Fast-Spiking Interneuron Excitability and Restore Motor Performance in a Mouse Model of Dravet Syndrome," poster 3.049 presented at the American Epilepsy Society Annual Meeting on Dec. 2-6, 2022.

Goodchild, S.J., et al., A Selective NaV1.1 PotentiatorEnhances Interneuron Excitability toNormalize Motor Performance in aDravet Syndrome Mouse Model, oral presentation at the American Epilepsy Society Annual Meeting on Dec. 3, 2023.

\* cited by examiner

PYRIDINE DERIVATIVES AND THEIR USE AS SODIUM CHANNEL ACTIVATORS

TECHNICAL FIELD

This disclosure is directed to pyridine derivatives, as stereoisomers, enantiomers or tautomers thereof or mixtures thereof; or pharmaceutically acceptable salts, solvates or prodrugs thereof, and pharmaceutical compositions comprising the pyridine derivatives, which are useful as voltage-gated sodium channel activators and are therefore are useful in treating seizure disorders such as epilepsy.

BACKGROUND

Epilepsy is a common seizure disorder, with a worldwide estimated prevalence of 0.7% of the population (50 million people) (see Hirtz, D. et al., *Neurology*. (2007), 68:326-337). It is characterized by abnormal electrical activities in the brain leading to seizures. For epidemiological purposes, the definition requires more than one unprovoked seizure of any type.

Patients with epilepsy have an increased mortality risk compared with the general population due primarily to the etiology of the disease. However, in patients with uncontrolled epilepsy, the greatest seizure-related risk of mortality is due to sudden unexpected death in epilepsy (SUDEP) (see, Hitiris, N. et al., *Epilepsy and Behavior* (2007), 10:363-376. Patients who participate in clinical trials of investigational antiepileptic drugs (AEDs) generally have had epilepsy for more than 10 years and have failed multiple AED therapies.

The pathophysiology of most forms of epilepsy remains poorly understood, but it is known that epileptic seizures arise from an excessively synchronous and sustained firing of a group of neurons. Persistent increase in neuronal excitability is common to all epileptic syndromes. The therapeutic strategy in treating epilepsy involves reducing neuronal excitability through various mechanistic pathways. Over the past two decades, several new AEDs were developed and marketed to expand the therapeutic spectrum by targeting different mechanisms of action and to improve the risk/benefit profile. Currently available AEDs are considered to act by inhibition of synaptic vesicle glycoprotein, potentiation of the inhibitory GABAergic neurotransmission, reduction of glutamate-mediated excitatory neurotransmission, or inhibition of voltage-gated sodium or calcium channels. Despite this, up to 30% of patients remain refractory to conventional treatment and continue to have uncontrolled seizures (see Brown, D. A. et al., *Nature* (1980), 283:673-676, and Elger, C. E. et al., *Epilepsy Behav*. (2008), 12:501-539. The quality of life in refractory patients is poor; they cannot drive a car, and they have difficulty working or living independently. Additionally, many patients have behavioral, neurological, and/or intellectual disturbances as sequelae of their seizure disorder. Current agents have minimal to no effects on neuronal sodium-gated channels, in spite of the fact that these channels have a major role in the control of neuronal excitability. Medicines with novel mechanisms of action, or medicines that improve on the already marketed AEDs are therefore needed to address the significant unmet clinical need for seizure control in patients with treatment-resistant epilepsy.

$Na_V1.1$ is a voltage-gated sodium channel ($Na_V$), comprising one pore-forming α-subunit encoded by SCN1A and two associated β-subunits encoded by SCN1B-SCN4B. $Na_V1.1$ as well as its subfamilies ($Na_V1.2$, $Na_V1.3$ and $Na_V1.6$), is predominantly expressed in the central nervous system (CNS) (Catterall, W. A., *J Physiol* (2012), Vol. 590, pp. 2577-2589, and Catterall, W. A., *Neurochem Res* (2017), Vol. 42, pp. 2495-2504). $Na_V1.1$ is largely expressed in parvalbuminpositive fast spiking interneurons (FSINs) and is involved in membrane depolarization and action potential (AP) firing (Ogiwara, I. et al., *J Neurosci* (2007), Vol. 27, pp. 5903-5914). Therefore, loss of function of the $Na_V1.1$ channels could lead to disinhibition of excitatory pyramidal neurons causing various diseases of the CNS (Han, S. et al., *Nature* (2012), Vol. 489, pp. 385-390, Oakley, J. C. et al. *Epilepsia* (2011), Vol. 52(Suppl. 2), pp. 59-61, and Verret, L. et al., *Cell* (2012), Vol. 149, pp. 708-721). Dravet syndrome is a rare genetic epileptic encephalopathy, where more than 70% of patients have de novo heterozygous mutations of the SCN1A gene (Catterall, W. A., *Ann Rev Pharmacol Toxicol* (2014), Vol. 54, pp. 317-338). In these mutations, a loss of function of the $Na_V1.1$ channels has been reported (Mantegazza, M. et al., *Proc Natl Acad Sci USA* (2005), Vol. 102, pp. 18177-18182). The genetic link between Dravet syndrome patients and $Na_V1.1$ channels suggest that a brain penetrant $Na_V1.1$ activator could possess significant therapeutic potential for treating Dravet syndrome (Jensen, H. S. et al., *Trends Pharmacol Sci* (2014), Vol. 35, pp. 113-118, and Richards, K. L. et al., *Proc Natl Acad Sci USA* (2018), Vol. 115, pp. E8077-E8085). However, potent and selective $Na_V1.1$ activators have not been reported to date. Recently, a few $Na_V1.1$ activators have been reported by Lundbeck: a 2-methylbenzamide derivative (Crestey, F. et al., *ACS Chem Neurosci* (2015), Vol. 6, pp. 1302-1308), AA43279 (Frederiksen, K. et al., *Eur J Neurosci* (2017), Vol. 46, pp. 1887-1896) and Lu AE98134 (von Schoubyea, N. L. et al., *Neurosci Lett* (2018), Vol. 662, pp. 29-35). The most recently developed activator, Lu AE98134, increases the total area under the curve for the duration of the depolarizing pulse from 1 μM in $Na_V1.1$-expressing HEK cells, while issues of low selectivity against $Na_V1.5$ and moderate selectivity against $Na_V1.2$ were observed. Biologically, $Na_V1.5$ is a major cardiac sodium channel (Vincent, G. M., *Annu Rev Med* (1998), Vol. 49, pp. 263-274) and $Na_V1.2$ is dominantly expressed in excitatory neurons (Gong, B. et al., *J Comp Neurol* (1999), Vol. 412, pp. 342-352, and Hu, W. et al., *Nat Neurosci* (2009), Vol. 12, pp. 996-1002). Therefore, high selectivity against $Na_V1.5$ and $Na_V1.2$ is preferable for drug candidates. On the other hand, the electrophysiology data regarding Lu AE98134 reveals promising potency as a $Na_V1.1$ activator for increasing the excitability of FSINs. The discovery of a 4-phenyl-2-(pyrrolidinyl)nicotinamide derivative as a highly potent $Na_V1.1$ activator with improved selectivity against $Na_V1.2$ and $Na_V1.5$ compared with previously reported $Na_V1.1$ activators was recently published (Miyazaki, T. et al., *Bioorg Med Chem Lett* (2019), Vo. 29, No. 6, pp. 815-820).

While significant advances have been made in this field, there remains a substantial need for compounds which are voltage-gated sodium channel activators, thereby being useful in treating seizure disorders, preferably epilepsy, in a mammal, preferably a human.

BRIEF SUMMARY

The present disclosure is directed to pyridine derivatives, as stereoisomers, enantiomers or tautomers thereof or mixtures thereof; or pharmaceutically acceptable salts, solvates or prodrugs thereof, and pharmaceutical compositions comprising the pyridine derivatives, which are useful as voltage-gated sodium channel activators, particularly $Na_V1.1$ activators, and are therefore are useful in treating seizure disorders such as epilepsy and Dravet syndrome.

Accordingly, in some embodiments, the present disclosure is directed to compounds of formula (I):

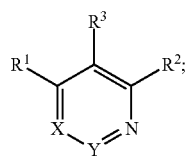

(I)

wherein:
X is =C(R⁹)— or =N—;
Y is =C(R⁹)— or —N=; provided that X is not =N— when Y is —N= and Y is not —N= when X is =N—;
R¹ is selected from:

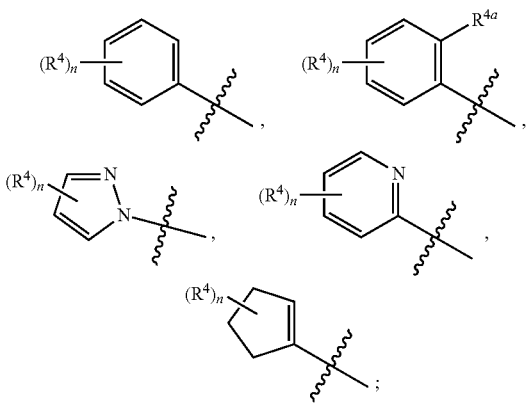

wherein:
each n is independently 1, 2 or 3;
each R⁴ is independently hydrogen, halo, alkyl, haloalkyl, or —R¹⁰—OR¹¹;
or two adjacent R⁴'s, together with the carbons to which they are attached, form an optionally substituted N-heteroaryl; and
R⁴ᵃ is hydrogen;
R² is —R¹⁰—OR¹¹ or —R¹⁰—N(R¹¹)₂;
or R² is selected:

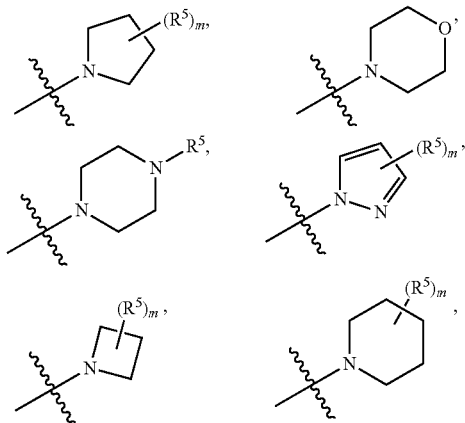

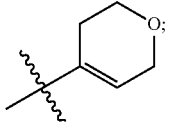

wherein:
each m is independently 1 or 2;
each R⁵ is independently hydrogen, halo, alkyl, haloalkyl or —R¹⁰—CN;
or two R⁵'s, together with the carbon to which they are both attached, form an optionally substituted O-heterocyclyl;
or two R⁵'s, together with the carbon to which they are both attached, form an optionally substituted cycloalkyl;
or two adjacent R⁵'s, together with the carbons to which they are attached, form an optionally substituted cycloalkyl;
R³ is selected from:

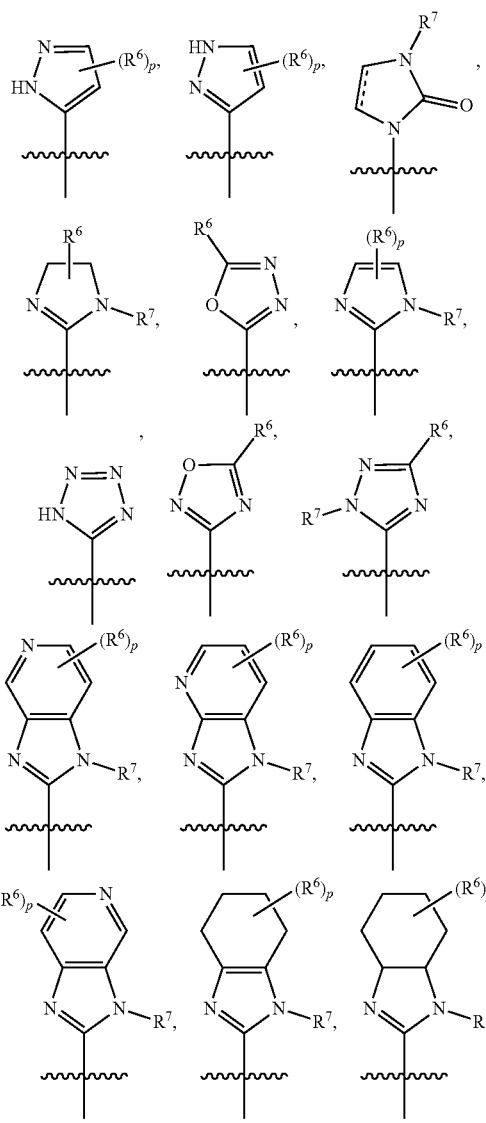

-continued

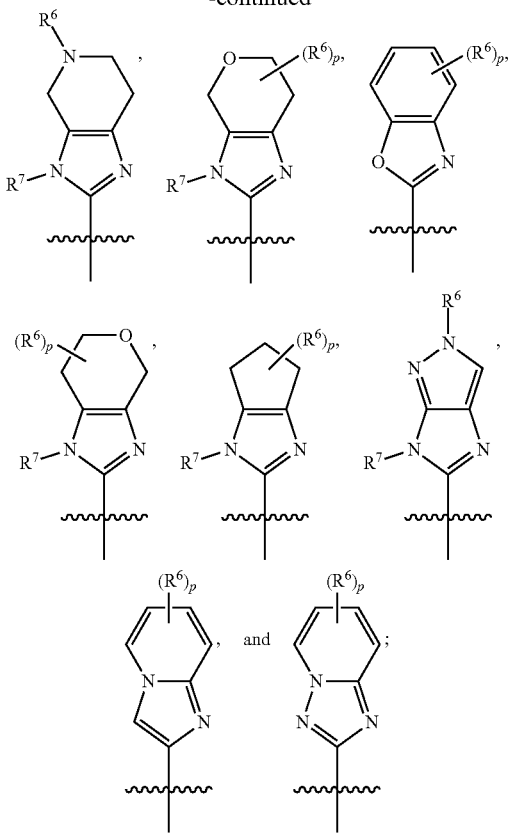

wherein:
==== is a double or single bond;
each p is independently 1, 2, 3, or 4;
each $R^6$ is independently hydrogen, halo, alkyl, haloalkyl, optionally substituted aryl, optionally substituted aralkyl, —$R^{10}$—$OR^{11}$, —$R^{10}$—$C(O)OR^{12}$, —$R^{10}$—$C(O)R^{12}$, —$R^{10}$—$N(R^{11})_2$, an optionally substituted O-heterocyclyl or

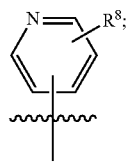

or two $R^6$'s, together with the carbon to which they are both attached, form an optionally substituted cycloalkyl;
each $R^7$ is independently hydrogen, alkyl, —$R^{10}$—$C(O)OR^{12}$ or

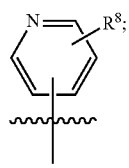

or $R^7$ together with $R^{4a}$ form a bond; and
each $R^8$ is independently hydrogen, alkyl or halo, each $R^9$ is independently hydrogen or alkyl;
each $R^{10}$ is independently a direct bond or an optionally substituted alkylene chain;
each $R^{11}$ is independently hydrogen, alkyl, haloalkyl, optionally substituted cycloakyl or optionally substituted cycloalkylalkyl; and
each $R^{12}$ is hydrogen, alkyl or optionally substituted aralkyl;
  as a stereoisomer, enantiomer or tautomer thereof or a mixture thereof; or a pharmaceutically acceptable salt, solvate or prodrug thereof.

In other embodiments, this disclosure is directed to pharmaceutical compositions comprising a pharmaceutically acceptable excipient and a compound of formula (I), as a stereoisomer, enantiomer or tautomer thereof or a mixture thereof; or a pharmaceutically acceptable salt, solvate or prodrug thereof, as described above.

In other embodiments, this disclosure is directed to methods of treating a disease or condition in a mammal modulated by a voltage-gated sodium channel, wherein the methods comprise administering to a mammal in need thereof a therapeutically effective amount of a compound of formula (I), as a stereoisomer, enantiomer or tautomer thereof or a mixture thereof; or a pharmaceutically acceptable salt, solvate or prodrug thereof, as described above.

In other embodiments, this disclosure is directed to methods for the treatment of epilepsy and/or epileptic seizure disorder in a mammal, preferably a human, wherein the methods comprise administering to the mammal in need thereof a therapeutically effective amount of a compound of formula (I), as set forth above, as a stereoisomer, enantiomer or tautomer thereof or mixtures thereof; or a pharmaceutically acceptable salt, solvate or prodrug thereof, or a pharmaceutical composition comprising a therapeutically effective amount of a compound of formula (I), as set forth above, as a stereoisomer, enantiomer or tautomer thereof or mixtures thereof, or a pharmaceutically acceptable salt, solvate or prodrug thereof, and a pharmaceutically acceptable excipient.

In other embodiments, this disclosure is directed to methods of preparing a compound of formula (I), as set forth above, as a stereoisomer, enantiomer or tautomer thereof or mixtures thereof; or a pharmaceutically acceptable salt, solvate or prodrug thereof, or a pharmaceutical composition comprising a therapeutically effective amount of a compound of formula (I), as set forth above, as a stereoisomer, enantiomer or tautomer thereof or mixtures thereof, or a pharmaceutically acceptable salt, solvate or prodrug thereof, and a pharmaceutically acceptable excipient.

In other embodiments, this disclosure is directed to pharmaceutical therapy in combination with one or more other compounds of formula (I) or one or more other accepted therapies or as any combination thereof to increase the potency of an existing or future drug therapy or to decrease the adverse events associated with the accepted therapy. In one embodiment, this disclosure is directed to a pharmaceutical composition combining a compound of formula (I) with established or future therapies for the indications listed herein.

DETAILED DESCRIPTION

Definitions

Certain chemical groups named herein may be preceded by a shorthand notation indicating the total number of carbon atoms that are to be found in the indicated chemical group. For example; $C_7$-$C_{12}$alkyl describes an alkyl group, as defined below, having a total of 7 to 12 carbon atoms, and $C_4$-$C_{12}$cycloalkylalkyl describes a cycloalkylalkyl group, as defined below, having a total of 4 to 12 carbon atoms. The total number of carbons in the shorthand notation does not include carbons that may exist in substituents of the group described.

In addition to the foregoing, as used in the specification and appended claims, unless specified to the contrary, the following terms have the meaning indicated:

"Compound of the disclosure" or "compounds of the disclosure" refer to compounds of formula (I), as described above in the Brief Summary, as stereoisomers, enantiomers or tautomers thereof or mixtures thereof; or pharmaceutically acceptable salts, solvates or prodrugs thereof.

"Present disclosure" or "disclosure" refers to this entire disclosure.

"Amino" refers to the —$NH_2$ radical.
"Cyano" refers to the —CN radical.
"Hydroxy" refers to the —OH radical.
"Imino" refers to the =NH substituent.
"Nitro" refers to the —$NO_2$ radical.
"Oxo" refers to the =O substituent.
"Thioxo" refers to the =S substituent.
"Trifluoromethyl" refers to the —$CF_3$ radical.

"Alkyl" refers to a straight or branched hydrocarbon chain radical consisting solely of carbon and hydrogen atoms, containing no unsaturation, having from one to twelve carbon atoms, preferably one to eight carbon atoms or one to six carbon atoms, and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, and the like. Unless stated otherwise specifically in the specification, an alkyl group may be optionally substituted by one of the following groups: alkyl, alkenyl, halo, haloalkenyl, cyano, nitro, aryl, cycloalkyl, heterocyclyl, heteroaryl, oxo, trimethylsilanyl, —$OR^{20}$, —OC(O)—$R^{20}$, —$N(R^{20})_2$, —C(O)$R^{20}$, —C(O)O$R^{20}$, —C(O)N($R^{20})_2$, —$N(R^{20})C(O)OR^{22}$, —$N(R^{20})C(O)R^{22}$, —$N(R^{20})S(O)_tR^{22}$ (where t is 1 to 2), —$S(O)_tOR^{22}$ (where t is 1 to 2), —$S(O)_pR^{22}$ (where p is 0 to 2), and —$S(O)_tN(R^{20})_2$ (where t is 1 to 2) where each $R^{20}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each $R^{22}$ is alkyl, haloalkyl, cycloalkyl, cycloalkylalkyl, aryl, aralkyl, heterocyclyl, heterocyclylalkyl, heteroaryl or heteroarylalkyl.

"Alkenyl" refers to a straight or branched hydrocarbon chain radical group consisting solely of carbon and hydrogen atoms, containing at least one double bond, having from two to twelve carbon atoms, preferably two to eight carbon atoms and which is attached to the rest of the molecule by a single bond, e.g., ethenyl, prop-1-enyl, but-1-enyl, pent-1-enyl, penta-1,4-dienyl, and the like. Unless stated otherwise specifically in the specification, an alkenyl group may be optionally substituted by one of the following groups: alkyl, alkenyl, halo, haloalkenyl, cyano, nitro, aryl, cycloalkyl, heterocyclyl, heteroaryl, oxo, trimethylsilanyl, —$OR^{20}$, —OC(O)—$R^{20}$, —$N(R^{20})_2$, —C(O)$R^{20}$, —C(O)O$R^{20}$, —C(O)N($R^{20})_2$, —$N(R^{20})C(O)OR^{22}$, —$N(R^{20})C(O)R^{22}$, —$N(R^{20})S(O)_tR^{22}$ (where t is 1 to 2), —$S(O)_tOR^{22}$ (where t is 1 to 2), —$S(O)_pR^{22}$ (where p is 0 to 2), and —$S(O)_tN(R^{20})_2$ (where t is 1 to 2) where each $R^{20}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each $R^{22}$ is alkyl, haloalkyl, cycloalkyl, cycloalkylalkyl, aryl, aralkyl, heterocyclyl, heterocyclylalkyl, heteroaryl or heteroarylalkyl.

"Alkynyl" refers to a straight or branched hydrocarbon chain radical group consisting solely of carbon and hydrogen atoms, containing at least one triple bond, having from two to twelve carbon atoms, preferably one to eight carbon atoms and which is attached to the rest of the molecule by a single bond, e.g., ethynyl, propynyl, butynyl, pentynyl, hexynyl, and the like. Unless stated otherwise specifically in the specification, an alkynyl group is optionally substituted by one or more of the following groups: alkyl, alkenyl, halo, haloalkenyl, cyano, nitro, aryl, cycloalkyl, heterocyclyl, heteroaryl, oxo, trimethylsilanyl, —$OR^{20}$, —OC(O)—$R^{20}$, —$N(R^{20})_2$, —C(O)$R^{20}$, —C(O)O$R^{20}$, —C(O)N($R^{20})_2$, —$N(R^{20})C(O)OR^{22}$, —$N(R^{20})C(O)R^{22}$, —$N(R^{20})S(O)_tR^{22}$ (where t is 1 to 2), —$S(O)_tOR^{22}$ (where t is 1 to 2), —$S(O)PR^{22}$ (where p is 0 to 2), or —$S(O)_tN(R^{20})_2$ (where t is 1 to 2), where each $R^{20}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each $R^{22}$ is alkyl, haloalkyl, cycloalkyl, cycloalkylalkyl, aryl, aralkyl, heterocyclyl, heterocyclylalkyl, heteroaryl or heteroarylalkyl.

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, e.g., methylene, ethylene, propylene, n-butylene, and the like. The alkylene chain is attached to the rest of the molecule through a single bond and to the radical group through a single bond. The points of attachment of the alkylene chain to the rest of the molecule and to the radical group can be through one carbon or any two carbons within the chain. Unless stated otherwise specifically in the specification, an alkylene chain may be optionally substituted by one of the following groups: alkyl, alkenyl, halo, haloalkenyl, cyano, nitro, aryl, cycloalkyl, heterocyclyl, heteroaryl, oxo, trimethylsilanyl, —$OR^{20}$, —OC(O)—$R^{20}$, —$N(R^{20})_2$, —C(O)$R^{20}$, —C(O)O$R^{20}$, —C(O)N($R^{20})_2$, —$N(R^{20})C(O)OR^{22}$, —$N(R^{20})C(O)R^{22}$, —$N(R^{20})S(O)_tR^{22}$ (where t is 1 to 2), —$S(O)_tOR^{22}$ (where t is 1 to 2), —$S(O)_pR^{22}$ (where p is 0 to 2), and —$S(O)_tN(R^{20})_2$ (where t is 1 to 2) where each $R^{20}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each $R^{22}$ is alkyl, haloalkyl, cycloalkyl, cycloalkylalkyl, aryl, aralkyl, heterocyclyl, heterocyclylalkyl, heteroaryl or heteroarylalkyl.

"Alkenylene" or "alkenylene chain" refers to a straight or branched divalent hydrocarbon chain linking the rest of the molecule to a radical group, consisting solely of carbon and hydrogen, containing at least one double bond and having from two to twelve carbon atoms, e.g., ethenylene, propenylene, n-butenylene, and the like. The alkenylene chain is attached to the rest of the molecule through a single bond and to the radical group through a double bond or a single bond. The points of attachment of the alkenylene chain to the rest of the molecule and to the radical group can be through one carbon or any two carbons within the chain. Unless stated otherwise specifically in the specification, an alkenylene chain may be optionally substituted by one of the following groups: alkyl, alkenyl, halo, haloalkenyl, cyano, nitro, aryl, cycloalkyl, heterocyclyl, heteroaryl, oxo, trimethylsilanyl, —$OR^{20}$, —OC(O)—$R^{20}$, —$N(R^{20})_2$, —C(O)$R^{20}$, —C(O)O$R^{20}$, —C(O)N($R^{20})_2$, —$N(R^{20})C(O)OR^{22}$, —$N(R^{20})S(O)_tR^{22}$ (where t is 1 to 2), —$S(O)_tOR^{22}$ (where t is 1 to 2), —$S(O)_pR^{22}$ (where p is 0 to 2), and —$S(O)_tN(R^{20})_2$ (where t is 1 to 2) where each $R^{20}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each $R^{22}$ is alkyl, haloalkyl, cycloalkyl, cycloalkylalkyl, aryl, aralkyl, heterocyclyl, heterocyclylalkyl, heteroaryl or heteroarylalkyl.

"Aryl" refers to a hydrocarbon ring system radical comprising hydrogen, 6 to 18 carbon atoms and at least one aromatic ring. For purposes of this disclosure, the aryl radical may be a monocyclic, bicyclic, tricyclic or tetracyclic ring system, which may included fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, an aryl group may be optionally substituted by one or more substituents independently selected from the group consisting of alkyl, alkenyl, halo, haloalkyl, haloalkenyl, cyano, nitro, aryl, aralkyl, cycloalkyl, cycloalkylalkyl, heterocyclyl, heterocyclylalkyl, heteroaryl, heteroarylalkyl, —$R^{21}$—$OR^{20}$, —$R^{21}$—OC(O)—$R^{20}$, —$R^{21}$—N($R^{20})_2$, —$R^{21}$—C(O)$R^{20}$, —$R^{21}$—C(O)$OR^{20}$, —$R^{21}$—C(O)N($R^{20})_2$, —$R^{21}$—N($R^{20}$)C(O)$R^{22}$, —$R^{21}$—N($R^{20}$)C(O)$OR^{22}$, —$R^{21}$—N($R^{20}$)S(O)$_t$$R^{22}$ (where t is 1 to 2), —$R^{21}$—N=C($OR^{20}$)$R^{20}$, —$R^{21}$—S(O)$_t$$OR^{22}$ (where t is 1 to 2), —$R^{21}$—S(O)P$R^{22}$ (where p is 0 to 2), and —$R^{21}$—S(O)$_t$N($R^{20})_2$ (where t is 1 to 2) where each $R^{20}$ is independently hydrogen, alkyl, haloalkyl, cycloalkyl, cycloalkylalkyl, aryl, aralkyl, heterocyclyl, heterocyclylalkyl, heteroaryl or heteroarylalkyl; each $R^{21}$ is independently a direct bond or a straight or branched alkylene or alkenylene chain; and each $R^{22}$ is alkyl, haloalkyl, cycloalkyl, cycloalkylalkyl, aryl, aralkyl, heterocyclyl, heterocyclylalkyl, heteroaryl or heteroarylalkyl.

"Aralkyl" refers to a radical of the formula —$R_b$—R, where $R_b$ is an alkylene chain as defined above and R, is one or more aryl radicals as defined above, for example, benzyl, diphenylmethyl and the like. The alkylene chain part of the aralkyl radical may be optionally substituted as described above for an alkylene chain. The aryl part of the aralkyl radical may be optionally substituted as described above for an aryl group.

"Aralkenyl" refers to a radical of the formula —$R_d$—$R_c$ where $R_d$ is an alkenylene chain as defined above and R, is one or more aryl radicals as defined above. The aryl part of the aralkenyl radical may be optionally substituted as described above for an aryl group. The alkenylene chain part of the aralkenyl radical may be optionally substituted as defined above for an alkenylene group.

"Cycloalkyl" refers to a stable non-aromatic monocyclic or polycyclic hydrocarbon radical consisting solely of carbon and hydrogen atoms, which may include fused or bridged ring systems, having from three to fifteen carbon atoms, preferably having from three to ten carbon atoms, and which is saturated or unsaturated and attached to the rest of the molecule by a single bond. Monocyclic radicals include, for example, cyclopropyl, cyclobutyl, cyclopentyl, cyclohexyl, cycloheptly, and cyclooctyl. Polycyclic radicals include, for example, adamantyl, norbornyl, decalinyl, 7,7-dimethyl-bicyclo[2.2.1]heptanyl, and the like. Unless otherwise stated specifically in the specification, a cycloalkyl group may be optionally substituted by one or more substituents independently selected from the group consisting of alkyl, alkenyl, halo, haloalkyl, haloalkenyl, cyano, nitro, oxo, aryl, aralkyl, cycloalkyl, cycloalkylalkyl, heterocyclyl, heterocyclylalkyl, heteroaryl, heteroarylalkyl, —$R^{21}$—$OR^{20}$, —$R^{21}$—OC(O)—$R^{20}$, —$R^{21}$—N($R^{20})_2$, —$R^{21}$—C(O)$R^{20}$, —$R^{21}$—C(O)$OR^{20}$, —$R^{21}$—C(O)N($R^{20})_2$, —$R^{21}$—N($R^{20}$)C(O)$R^{22}$, —$R^{21}$—N($R^{20}$)C(O)$OR^{22}$, —$R^{21}$—N($R^{20}$)S(O)$_t$$R^{22}$ (where t is 1 to 2), —$R^{21}$—N=C($OR^{20}$)$R^{20}$, —$R^{21}$—S(O)$_t$$OR^{22}$ (where t is 1 to 2), —$R^{21}$—S(O)$_p$$R^{22}$ (where p is 0 to 2), and —$R^{21}$—S(O)$_t$N($R^{20})_2$ (where t is 1 to 2) where each $R^{20}$ is independently hydrogen, alkyl, haloalkyl, cycloalkyl, cycloalkylalkyl, aryl, aralkyl, heterocyclyl, heterocyclylalkyl, heteroaryl or heteroarylalkyl; each $R^{21}$ is independently a direct bond or a straight or branched alkylene or alkenylene chain; and each $R^{22}$ is alkyl, haloalkyl, cycloalkyl, cycloalkylalkyl, aryl, aralkyl, heterocyclyl, heterocyclylalkyl, heteroaryl or heteroarylalkyl.

"Cycloalkylalkyl" refers to a radical of the formula —$R_b$$R_g$ where $R_b$ is an alkylene chain as defined above and $R_g$ is a cycloalkyl radical as defined above. The alkylene chain and the cycloalkyl radical may be optionally substituted as defined above.

"Fused" refers to any ring system described herein which is fused to an existing ring structure in the compounds of the disclosure. When the fused ring system is a heterocyclyl or a heteroaryl, any carbon in the existing ring structure which becomes part of the fused ring system may be replaced with a nitrogen.

"Halo" refers to bromo, chloro, fluoro or iodo.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1-fluoromethyl-2-fluoroethyl, 3-bromo-2-fluoropropyl, 1-bromomethyl-2-bromoethyl, and the like. The alkyl part of the haloalkyl radical may be optionally substituted as defined above for an alkyl group.

"Haloalkenyl" refers to an alkenyl radical, as defined above, that is substituted by one or more halo radicals, as defined above. The alkenyl part of the haloalkyl radical may be optionally substituted as defined above for an alkenyl group.

"Heterocyclyl" refers to a stable 3- to 18-membered non-aromatic ring radical which consists of two to twelve carbon atoms and from one to six heteroatoms selected from the group consisting of nitrogen, oxygen and sulfur. Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, dioxolanyl, dioxinyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trioxanyl, trithianyl, triazinanyl, tetrahydropyranyl, thiomorpholinyl, thiamorpholinyl, 1-oxo-thiomorpholinyl, and 1,1-dioxo-thiomorpholinyl. Unless stated otherwise specifically in the specification, a heterocyclyl group may be optionally substituted by one or more substituents selected from the group consisting of alkyl, alkenyl, halo, haloalkyl, haloalkenyl, cyano, oxo, thioxo, nitro, aryl, aralkyl, cycloalkyl, cycloalkylalkyl, heterocyclyl, heterocyclylalkyl, heteroaryl, heteroarylalkyl, —$R^{21}$—$OR^{20}$, —$R^{21}$—OC(O)—$R^{20}$, —$R^{21}$—N($R^{20})_2$, —$R^{21}$—C(O)$R^{20}$, —$R^{21}$—C(O)$OR^{20}$, —$R^{21}$—C(O)N($R^{20})_2$, —$R^{21}$—N($R^{20}$)C(O)$R^{22}$, —$R^{21}$—N($R^{20}$)C(O)$R^{22}$, —$R^{21}$—N($R^{20}$)S $(O)_tR^{22}$ (where t is 1 to 2), —$R^{21}$—N=C(OR$^{20}$)R$^{20}$, —$R^{21}$—S(O)$_t$OR$^{22}$ (where t is 1 to 2), —$R^{21}$—S(O)$_p$R$^{22}$ (where p is 0 to 2), and —$R^{21}$—S(O)$_t$N(R$^{20}$)$_2$ (where t is 1 to 2) where each R$^{20}$ is independently hydrogen, alkyl, alkenyl, haloalkyl, cycloalkyl, cycloalkylalkyl, aryl, aralkyl, heterocyclyl, heterocyclylalkyl, heteroaryl or heteroarylalkyl; each R$^{21}$ is independently a direct bond or a straight or branched alkylene or alkenylene chain; and each R$^{22}$ is alkyl, alkenyl, haloalkyl, cycloalkyl, cycloalkylalkyl, aryl, aralkyl, heterocyclyl, heterocyclylalkyl, heteroaryl or heteroarylalkyl.

"O-heterocyclyl" refers to a heterocycyl radical as defined above containing at least one oxygen atom and no nitrogen atom. An O-heterocyclyl radical may be optionally substituted as described above for heterocyclyl radicals.

"Heterocyclylalkyl" refers to a radical of the formula —R$_b$R$_h$ where R$_b$ is an alkylene chain as defined above and R$_h$ is a heterocyclyl radical as defined above, and if the heterocyclyl is a nitrogen-containing heterocyclyl, the heterocyclyl may be attached to the alkyl radical at the nitrogen atom. The alkylene chain of the heterocyclylalkyl radical may be optionally substituted as defined above for an alkyene chain. The heterocyclyl part of the heterocyclylalkyl radical may be optionally substituted as defined above for a heterocyclyl group.

"Heteroaryl" refers to a 5- to 14-membered ring system radical comprising hydrogen atoms, one to thirteen carbon atoms, one to six heteroatoms selected from the group consisting of nitrogen, oxygen and sulfur, and at least one aromatic ring. For purposes of this disclosure, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzthiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, benzoxazolinonyl, benzimidazolthionyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, pteridinonyl, purinyl, pyrrolyl, pyrazolyl, pyridinyl, pyridinonyl, pyrazinyl, pyrimidinyl, pryrimidinonyl, pyridazinyl, pyrrolyl, pyrido[2,3-d]pyrimidinonyl, quinazolinyl, quinazolinonyl, quinoxalinyl, quinoxalinonyl, quinolinyl, isoquinolinyl, tetrahydroquinolinyl, thiazolyl, thiadiazolyl, thieno[3,2-d]pyrimidin-4-onyl, thieno[2,3-d]pyrimidin-4-onyl, triazolyl, tetrazolyl, triazinyl, and thiophenyl (i.e. thienyl). Unless stated otherwise specifically in the specification, a heteroaryl group may be optionally substituted by one or more substituents selected from the group consisting of alkyl, alkenyl, halo, haloalkyl, haloalkenyl, cyano, oxo, thioxo, nitro, thioxo, aryl, aralkyl, cycloalkyl, cycloalkylalkyl, heterocyclyl, heterocyclylalkyl, heteroaryl, heteroarylalkyl, —R$^{21}$—OR$^{20}$, —R$^{21}$—OC(O)—R$^{20}$, —R$^{21}$—N(R$^{20}$)$_2$, —R$^{21}$—C(O)R$^{20}$, —R$^{21}$—C(O)OR$^{20}$, —R$^{21}$—C(O)N(R$^{20}$)$_2$, —R$^{21}$—N(R$^{20}$)C(O)OR$^{22}$, —R$^{21}$—N(R$^{20}$)C(O)R$^{22}$, —R$^{21}$—N(R$^{20}$)S(O)$_t$R$^{22}$ (where t is 1 to 2), —R$^{21}$—N=C(OR$^{20}$)R$^{20}$, —R$^{21}$—S(O)$_t$OR$^{22}$ (where t is 1 to 2), —R$^{21}$—S(O)$_p$R$^{22}$ (where p is 0 to 2), and —R$^{21}$—S(O)$_t$N(R$^{20}$)$_2$ (where t is 1 to 2) where each R$^{20}$ is independently hydrogen, alkyl, alkenyl, haloalkyl, cycloalkyl, cycloalkylalkyl, aryl, aralkyl, heterocyclyl, heterocyclylalkyl, heteroaryl or heteroarylalkyl; each R$^{21}$ is independently a direct bond or a straight or branched alkylene or alkenylene chain; and each R$^{22}$ is alkyl, alkenyl, haloalkyl, cycloalkyl, cycloalkylalkyl, aryl, aralkyl, heterocyclyl, heterocyclylalkyl, heteroaryl or heteroarylalkyl.

"N-heteroaryl" refers to a heteroaryl radical as defined above containing at least one nitrogen. An N-heteroaryl radical may be optionally substituted as described above for heteroaryl radicals.

"Heteroarylalkyl" refers to a radical of the formula —R$_b$R$_i$ where R$_b$ is an alkylene chain as defined above and R$_i$ is a heteroaryl radical as defined above. The heteroaryl part of the heteroarylalkyl radical may be optionally substituted as defined above for a heteroaryl group. The alkylene chain part of the heteroarylalkyl radical may be optionally substituted as defined above for an alkylene chain.

"Prodrugs" is meant to indicate a compound that may be converted under physiological conditions or by solvolysis to a biologically active compound of the disclosure. Thus, the term "prodrug" refers to a metabolic precursor of a compound of the disclosure that is pharmaceutically acceptable. A prodrug may be inactive when administered to a subject in need thereof, but is converted in vivo to an active compound of the disclosure. Prodrugs are typically rapidly transformed in vivo to yield the parent compound of the disclosure, for example, by hydrolysis in blood. The prodrug compound often offers advantages of solubility, tissue compatibility or delayed release in a mammalian organism (see, Bundgard, H., *Design of Prodrugs* (1985), pp. 7-9, 21-24 (Elsevier, Amsterdam)). A discussion of prodrugs is provided in Higuchi, T., et al., "Pro-drugs as Novel Delivery Systems," A.C.S. Symposium Series, Vol. 14, and in Bioreversible Carriers in Drug Design, Ed. Edward B. Roche, American Pharmaceutical Association and Pergamon Press, 1987, both of which are incorporated in full by reference herein.

The term "prodrug" is also meant to include any covalently bonded carriers, which release the active compound of the disclosure in vivo when such prodrug is administered to a mammalian subject. Prodrugs of a compound of the disclosure may be prepared by modifying functional groups present in the compound of the disclosure in such a way that the modifications are cleaved, either in routine manipulation or in vivo, to the parent compound of the disclosure. Prodrugs include compounds of the disclosure wherein a hydroxy, amino or mercapto group is bonded to any group that, when the prodrug of the compound of the disclosure is administered to a mammalian subject, cleaves to form a free hydroxy, free amino or free mercapto group, respectively. Examples of prodrugs include, but are not limited to, acetate, formate and benzoate derivatives of alcohol or amide derivatives of amine functional groups in the compounds of the disclosure and the like.

"Stable compound" and "stable structure" are meant to indicate a compound that is sufficiently robust to survive isolation to a useful degree of purity from a reaction mixture, and formulation into an efficacious therapeutic agent.

"Mammal" includes humans and both domestic animals such as laboratory animals and household pets, (e.g., cats, dogs, swine, cattle, sheep, goats, horses, rabbits), and non-domestic animals such as wildlife and the like.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution ("unsubstituted"). When a functional group is described as "optionally substituted," and in turn, substituents on the functional group are also "optionally substituted" and so on, for the purposes of this disclosure, such iterations are limited to five, preferably such iterations are limited to two.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Often crystallizations produce a solvate of the compound of the disclosure. As used herein, the term "solvate" refers to an aggregate or solid form that comprises one or more molecules of a compound of the disclosure with one or more molecules of solvent. The solvent may be water, in which case the solvate may be a hydrate. Alternatively, the solvent may be an organic solvent. Thus, the compounds of the present disclosure may exist as a hydrate, including a monohydrate, dihydrate, hemihydrate, sesquihydrate, trihydrate, tetrahydrate and the like, as well as the corresponding solvated forms. The compound of the disclosure may be true solvates, while in other cases; the compound of the disclosure may merely retain adventitious water or be a mixture of water plus some adventitious solvent.

A "pharmaceutical composition" refers to a formulation of a compound of the disclosure and a medium generally accepted in the art for the delivery of the biologically active compound to mammals, e.g., humans. Such a medium includes all pharmaceutically acceptable carriers, diluents or excipients therefor.

"Seizure disorders" refers to seizures and disorders associated with seizures such as partial onset (focal) seizures, photosensitive epilepsy, self-induced syncope, intractable epilepsy, Angelman syndrome, benign rolandic epilepsy, CDKL5 disorder, childhood and juvenile absence epilepsy, Dravet syndrome, frontal lobe epilepsy, Glut1 deficiency syndrome, hypothalamic hamartoma, infantile spasms/West's syndrome, juvenile myoclonic epilepsy, Landau-Kleffner syndrome, Lennox-Gastaut syndrome (LGS), epilepsy with myoclonic-absences, Ohtahara syndrome, Panayiotopoulos syndrome, PCDH19 epilepsy, progressive myoclonic epilepsies, Rasmussen's syndrome, ring chromosome 20 syndrome, reflex epilepsies, temporal lobe epilepsy, Lafora progressive myoclonus epilepsy, neurocutaneous syndromes, tuberous sclerosis complex, early infantile epileptic encephalopathy, early onset epileptic encephalopathy, generalized epilepsy with febrile seizures+, Rett syndrome, multiple sclerosis, Alzheimer's disease, autism, ataxia, hypotonia and paroxysmal dyskinesia. Preferably, the term "seizure disorder" refers to partial onset (focal) epilepsy.

"Therapeutically effective amount" refers to a range of amounts of a compound of the disclosure, which, upon administration to a human, treats, ameliorates or prevents a seizure disorder, preferably epilepsy, in the human, or exhibits a detectable therapeutic or preventative effect in the human having a seizure disorder. The effect is detected by, for example, a reduction in seizures (frequency) or by the severity of seizures (quality). The precise therapeutically effective amount for a given human will depend upon the human's size and health, the nature and extent of the seizure disorder, the presence of any concomitant medications, and other variables known to those of skill in the art. The therapeutically effective amount for a given situation is determined by routine experimentation and is within the judgment of the clinician.

"Treatment" refers to therapeutic applications to slow or stop progression of a seizure disorder, prophylactic application to prevent development of a seizure disorder, and/or reversal of a seizure disorder. Reversal of a seizure disorder differs from a therapeutic application which slows or stops a seizure disorder in that with a method of reversing, not only is progression of a seizure disorder completely stopped, cellular behavior is moved to some degree toward a normal state that would be observed in the absence of the seizure disorder.

"Treating" or "treatment" as used herein covers the treatment of the disease or condition of interest in a mammal, preferably a human, having the disease or condition of interest, and includes:

(a) preventing the disease or condition from occurring in a mammal, in particular, when such mammal is predisposed to the condition but has not yet been diagnosed as having it;

(b) inhibiting the disease or condition, i.e., arresting its development;

(c) relieving (or ameliorating) the disease or condition, i.e., causing regression of the disease or condition; or (d) relieving (or ameliorating) the symptoms resulting from the disease or condition, i.e., relieving a seizure disorder without addressing the underlying disease or condition.

As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The compounds of this disclosure may contain at least one asymmetric carbon atom and thus may exist as racemates, enantiomers and/or diastereoisomers. For the present disclosure, the words diastereomer and diastereoisomer and related terms are equivalent and interchangeable. Unless otherwise indicated, this disclosure includes all enantiomeric and diastereoisomeric forms of the compounds of formula (I). Pure stereoisomers, mixtures of enantiomers and/or diastereoisomers, and mixtures of different compounds of the disclosure are included within this disclosure. Thus, compounds of formula (I) may occur as racemates, racemic or diastereoisomeric mixtures and as individual diastereoisomers, or enantiomers, unless a specific stereoisomer enantiomer or diastereoisomer is identified, with all isomeric forms being included in the present disclosure. For this disclosure, a racemate or racemic mixture implies a 50:50 mixture of stereoisomers only. Other enantiomerically or diastereomerically enriched mixtures of varying ratios of stereoisomers are also contemplated.

"Enantiomers" refer to asymmetric molecules that can exist in two different isomeric forms which have different configurations in space. Other terms used to designate or refer to enantiomers include "stereoisomers" (because of the different arrangement or stereochemistry around the chiral center; although all enantiomers are stereoisomers, not all stereoisomers are enantiomers) or "optical isomers" (because of the optical activity of pure enantiomers, which is the ability of different pure enantiomers to rotate plane-polarized light in different directions). Because they do not have a plane of symmetry, enantiomers are not identical with their mirror images; molecules which exist in two enantiomeric forms are chiral, which means that they can be regarded as occurring in "left" and "right" handed forms. The most common cause of chirality in organic molecules is the presence of a tetrahedral carbon bonded to four different substituents or groups. Such a carbon is referred to as a chiral center, or stereogenic center.

Enantiomers have the same empirical chemical formula, and are generally chemically identical in their reactions, their physical properties, and their spectroscopic properties. However, enantiomers show different chemical reactivity toward other asymmetric compounds, and respond differently toward asymmetric physical disturbances. The most common asymmetric disturbance is polarized light.

An enantiomer can rotate plane-polarized light; thus, an enantiomer is optically active. Two different enantiomers of the same compound will rotate plane-polarized light in the opposite direction; thus, the light can be rotated to the left or counterclockwise for a hypothetical observer (this is levarotatory or "l", or minus or "−") or it can be rotated to the right or clockwise (this is dextrorotatory or "d" or plus or "+"). The sign of optical rotation (+) or (−), is not related to the R,S designation. A mixture of equal amounts of two chiral enantiomers is called a racemic mixture, or racemate, and is denoted either by the symbol (+/−) or by the prefix "d,l" to indicate a mixture of dextrorotatory and levorotatory forms. Racemates or racemic mixtures show zero optical rotation because equal amounts of the (+) and (−) forms are present. In general, the presence of a single enantiomer rotates polarized light in only one direction; thus, a single enantiomer is referred to as optically pure.

The designations "R" and "S" are used to denote the three-dimensional arrangement of atoms (or the configuration) of the stereogenic center. The designations may appear as a prefix or as a suffix; they may or may not be separated from the enantiomer name by a hyphen; they may or may not be hyphenated; and they may or may not be surrounded by parentheses. A method for determining the designation is to refer to the arrangement of the priority of the groups at the stereogenic center when the lowest priority group is oriented away from a hypothetical observer: If the arrangement of the remaining three groups from the higher to the lower priority is clockwise, the stereogenic center has an "R" configuration; if the arrangement is counterclockwise, the stereogenic center has an "S" configuration.

"Resolution" or "resolving" when used in reference to a racemic compound or mixture refers to the separation of a racemate into its two enantiomeric forms (i.e., (+) and (−); (R) and (S) forms).

"Enantiomeric excess" or "ee" refers to a product wherein one enantiomer is present in excess of the other, and is defined as the absolute difference in the mole fraction of each enantiomer. Enantiomeric excess is typically expressed as a percentage of an enantiomer present in a mixture relative to the other enantiomer. For purposes of this disclosure, the (S)-enantiomer of a compound prepared by the methods disclosed herein is considered to be "substantially free" of the corresponding (R)-enantiomer when the (S)-enantiomer is present in enantiomeric excess of greater than 80%, preferably greater than 90%, more preferably greater than 95% and most preferably greater than 99%.

A "tautomer" refers to a proton shift from one atom of a molecule to another atom of the same molecule. The present disclosure includes tautomers of any compound of formula (I) as described herein.

The use of parentheses and brackets in substituent groups may be used herein to conserve space. Accordingly, the use of parenthesis in a substituent group indicates that the group enclosed within the parentheses is attached directly to the atom preceding the parenthesis. The use of brackets in a substituent group indicates that the group enclosed within the brackets is also attached directly to the atom preceding the parenthesis.

For example, a compound of formula (I) wherein

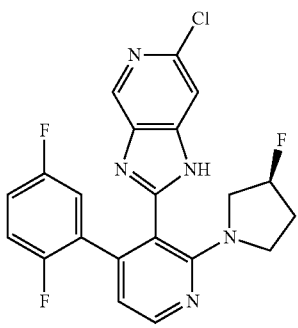 [SMILES: Fc1ccc(F)c(-c2ccnc(N3CC[C@H](F)C3)c2-c2nc3cnc(Cl)cc3[nH]2)c1]

is named herein as (S)-6-chloro-2-(4-(2,5-difluorophenyl)-2-(3-fluoropyrrolidin-1-yl)pyridin-3-yl)-1H-imidazo[4,5-c]pyridine.

Embodiments

One embodiment of the disclosure are compounds of formula (I), as set forth above in the Brief Summary, as individual stereoisomers, enantiomers or tautomers thereof or as mixtures thereof; or pharmaceutically acceptable salts, solvates or prodrugs thereof.

Accordingly, in some embodiments:
X is $=C(R^5)—$;
Y is $=C(R^9)—$;
$R^1$ is selected from:

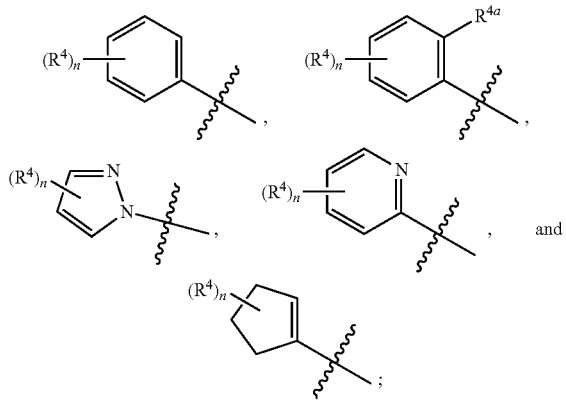

wherein:
each n is independently 1, 2 or 3;
each $R^4$ is independently hydrogen, halo, alkyl, haloalkyl, or $—R^{10}—OR^{11}$;
or two adjacent $R^4$'s, together with the carbons to which they are attached, form an optionally substituted N-heteroaryl; and
$R^{4a}$ is hydrogen;
$R^2$ is $—R^{10}—OR^{11}$ or $—R^{10}—N(R^{11})_2$;
or $R^2$ is selected from:

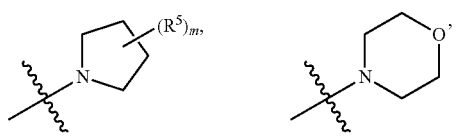

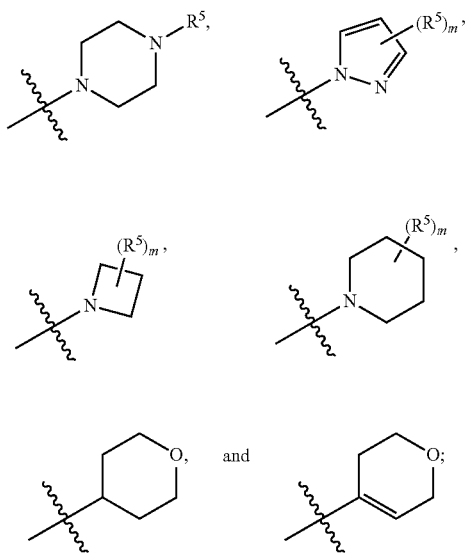

wherein:
each m is independently 1 or 2;
each $R^5$ is independently hydrogen, halo, alkyl, haloalkyl or $—R^{10}—CN$;
or two $R^5$'s, together with the carbon to which they are both attached, form an optionally substituted O-heterocyclyl;
or two $R^5$'s, together with the carbon to which they are both attached, form an optionally substituted cycloalkyl;
or two adjacent $R^5$'s, together with the carbons to which they are attached, form an optionally substituted cycloalkyl;
$R^3$ is selected from:

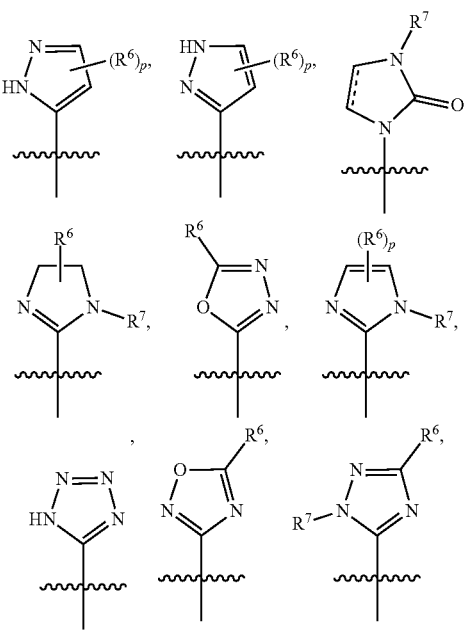

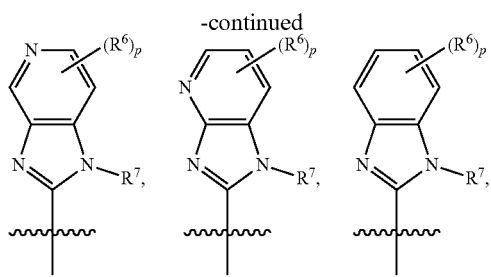

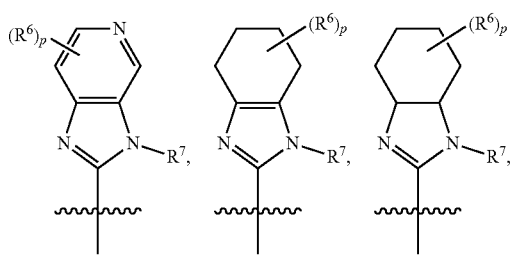

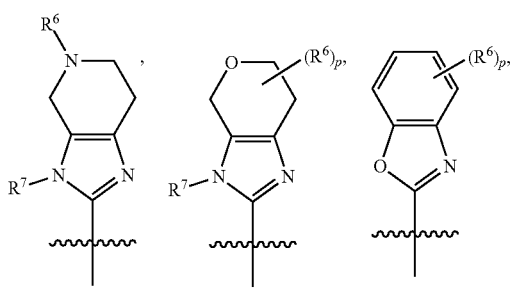

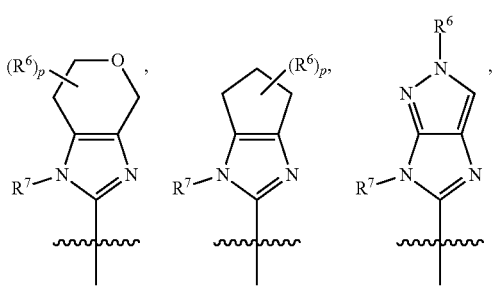

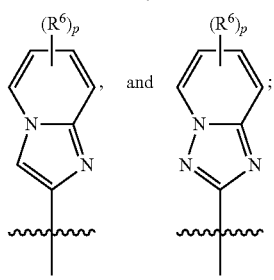

wherein:
 is a double or single bond;
each p is independently 1, 2, 3, or 4;
each $R^6$ is independently hydrogen, halo, alkyl, haloalkyl, optionally substituted aryl, optionally substituted aralkyl, —$R^{10}$—$OR^{11}$, —$R^{10}$—$C(O)OR^{12}$, —$R^{10}$—$C(O)R^{12}$, —$R^{10}$—$N(R^{11})_2$, an optionally substituted O-heterocyclyl or

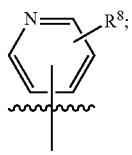

or two $R^6$'s, together with the carbon to which they are both attached, form an optionally substituted cycloalkyl;

each $R^7$ is independently hydrogen, alkyl, —$R^{10}$—$C(O)OR^{12}$ or

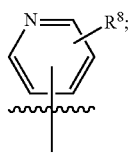

or $R^7$ together with $R^{4a}$ form a bond; and
each $R^a$ is independently hydrogen, alkyl or halo,
each $R^9$ is independently hydrogen or alkyl;
each $R^{10}$ is independently a direct bond or an optionally substituted alkylene chain;
each $R^{11}$ is independently hydrogen, alkyl, haloalkyl, optionally substituted cycloakyl or optionally substituted cycloalkylalkyl; and
each $R^{12}$ is hydrogen, alkyl or optionally substituted aralkyl;
as a stereoisomer, enantiomer or tautomer thereof or a mixture thereof; or a pharmaceutically acceptable salt, solvate or prodrug thereof.

In certain embodiments:
X is =$C(R^9)$—;
Y is =$C(R^9)$—;
$R^1$ is

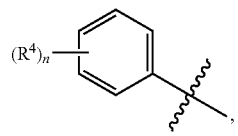

wherein:
n is 1, 2 or 3; and
each $R^4$ is independently hydrogen, halo, alkyl, haloalkyl, or —$R^{10}$—$OR^{11}$;
or two adjacent $R^4$'s, together with the carbons to which they are attached, form an optionally substituted N-heteroaryl;
$R^2$ is —$R^{10}$—$OR^{11}$ or —$R^{10}$—$N(R^{11})_2$;
or $R^2$ is selected from:

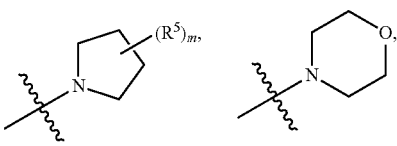

-continued

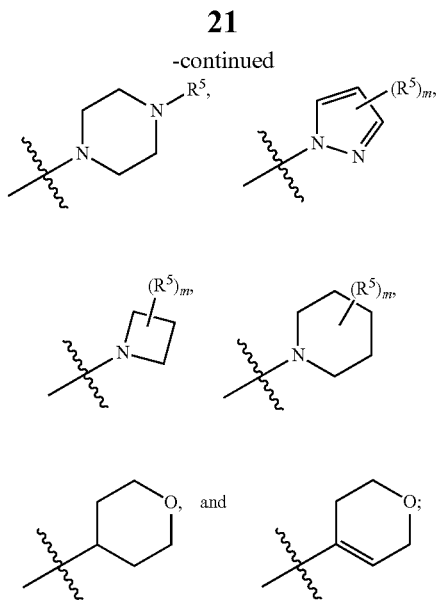

wherein:

each m is independently 1 or 2;

each $R^5$ is independently hydrogen, halo, alkyl, haloalkyl or —$R^{10}$—CN;

or two $R^5$'s, together with the carbon to which they are both attached, form an optionally substituted O-heterocyclyl;

or two $R^5$'s, together with the carbon to which they are both attached, form an optionally substituted cycloalkyl;

or two adjacent $R^5$'s, together with the carbons to which they are attached, form an optionally substituted cycloalkyl;

$R^3$ is selected from:

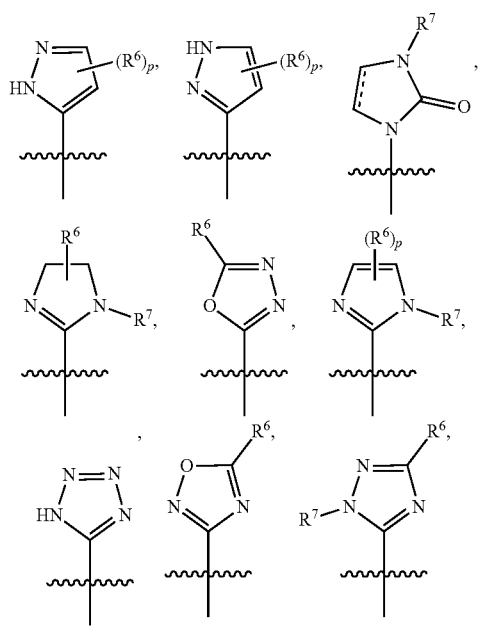

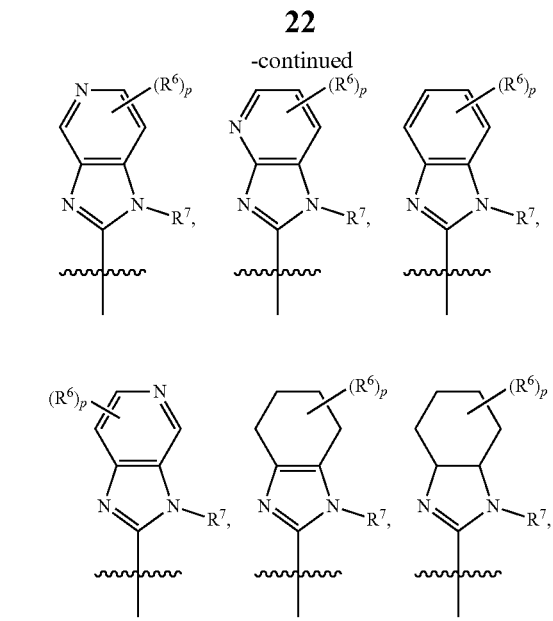

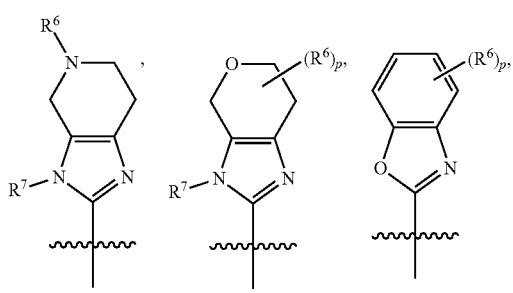

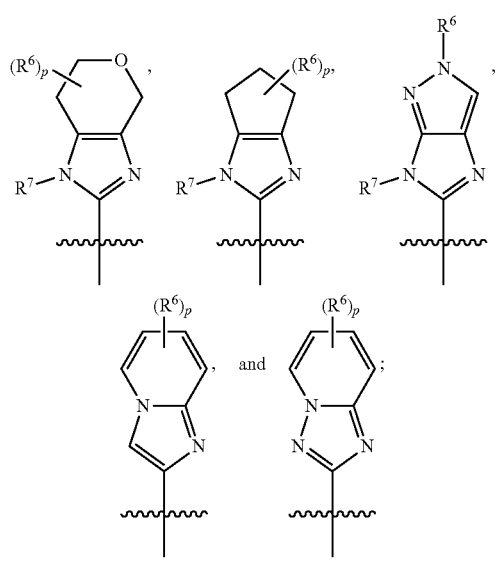

wherein:

==== is a double or single bond;

each p is independently 1, 2, 3, or 4;

each $R^6$ is independently hydrogen, halo, alkyl, haloalkyl, optionally substituted aryl, optionally substituted aralkyl, —$R^{10}$—$OR^{11}$, —$R^{10}$—C(O)$OR^{12}$, —$R^{10}$—C(O)$R^{12}$, —$R^{10}$—N($R^{11}$)$_2$, an optionally substituted O-heterocyclyl or

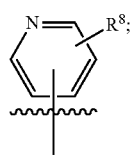

or two R$^6$'s, together with the carbon to which they are both attached, form an optionally substituted cycloalkyl;

each R$^7$ is independently hydrogen, alkyl, —R$^{10}$—C(O)OR$^{12}$ or

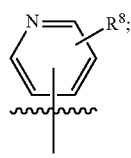

and each R$^8$ is independently hydrogen, alkyl or halo,
each R$^9$ is independently hydrogen or alkyl;
each R$^{10}$ is independently a direct bond or an optionally substituted alkylene chain;
each R$^{11}$ is independently hydrogen, alkyl, haloalkyl, optionally substituted cycloakyl or optionally substituted cycloalkylalkyl; and
each R$^{12}$ is hydrogen, alkyl or optionally substituted aralkyl;
as a stereoisomer, enantiomer or tautomer thereof or a mixture thereof; or a pharmaceutically acceptable salt, solvate or prodrug thereof.

In more specific embodiments:
X is =C(R$^9$)—;
Y is =C(R$^9$)—;
R$^1$ is

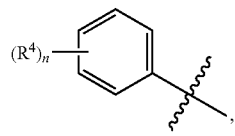

wherein:
n is 1, 2 or 3; and
each R$^4$ is independently hydrogen, halo, alkyl, haloalkyl, or —R$^{10}$—OR$^{11}$;
or two adjacent R$^4$'s, together with the carbons to which they are attached, form an optionally substituted N-heteroaryl;
R$^2$ is

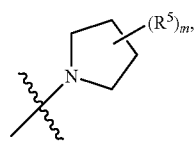

wherein:
m is 1 or 2;
each R$^5$ is independently hydrogen, halo, alkyl, haloalkyl or —R$^{10}$—CN;

or two R$^5$'s, together with the carbon to which they are both attached, form an optionally substituted O-heterocyclyl;
or two R$^5$'s, together with the carbon to which they are both attached, form an optionally substituted cycloalkyl;
or two adjacent R$^5$'s, together with the carbons to which they are attached, form an optionally substituted cycloalkyl;

R$^3$ is selected from:

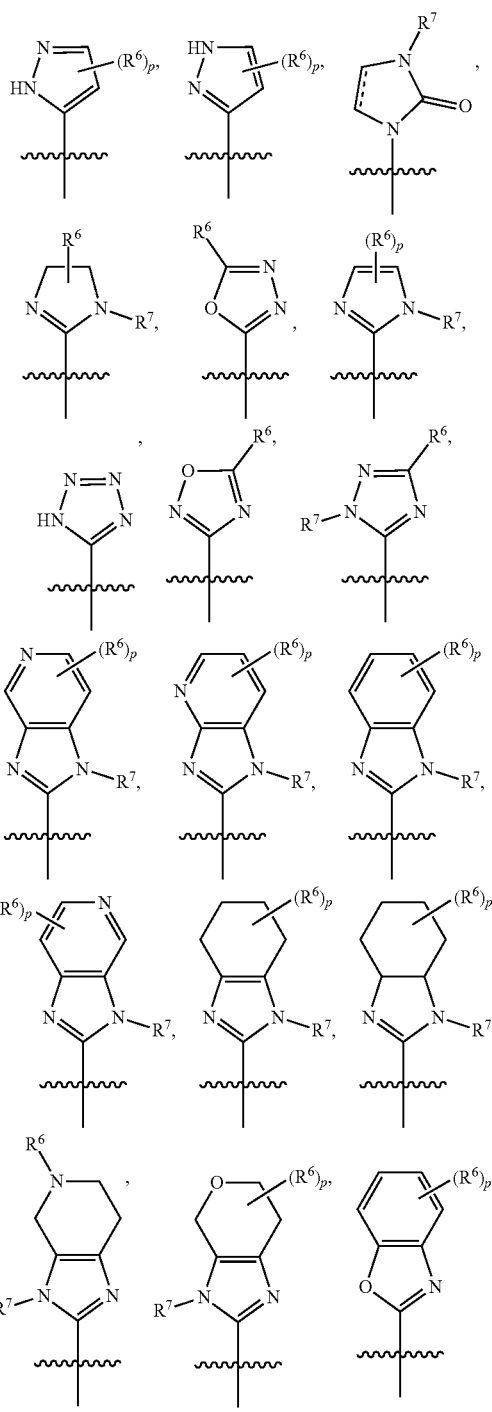

-continued

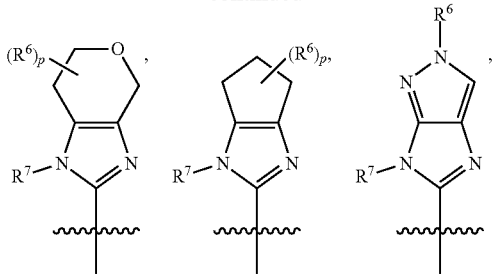

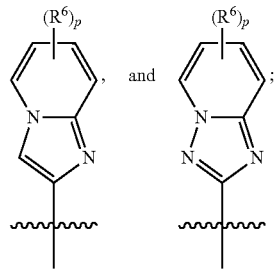

wherein:
---- is a double or single bond;
each p is independently 1, 2, 3, or 4;
each $R^6$ is independently hydrogen, halo, alkyl, haloalkyl, optionally substituted aryl, optionally substituted aralkyl, $-R^{10}-OR^{11}$, $-R^{10}-C(O)OR^{12}$, $-R^{10}-C(O)R^{12}$, $-R^{10}-N(R^{11})_2$, an optionally substituted O-heterocyclyl or

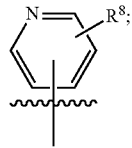

or two $R^6$'s, together with the carbon to which they are both attached, form an optionally substituted cycloalkyl;
each $R^7$ is independently hydrogen, alkyl, $-R^{10}-C(O)OR^{12}$ or

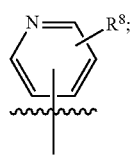

and
each $R^8$ is independently hydrogen, alkyl or halo,
each $R^9$ is independently hydrogen or alkyl;
each $R^{10}$ is independently a direct bond or an optionally substituted alkylene chain;
each $R^{11}$ is independently hydrogen, alkyl, haloalkyl, optionally substituted cycloakyl or optionally substituted cycloalkylalkyl; and
each $R^{12}$ is hydrogen, alkyl or optionally substituted aralkyl;
as a stereoisomer, enantiomer or tautomer thereof or a mixture thereof; or a pharmaceutically acceptable salt, solvate or prodrug thereof.

In certain specific embodiments:
X is $=C(R^9)-$;
Y is $=C(R^9)-$;
$R^1$ is

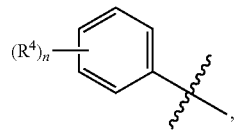

wherein:
n is 1, 2 or 3; and
each $R^4$ is independently hydrogen, halo, alkyl, haloalkyl, or $-R^{10}-OR^{11}$;
$R^2$ is

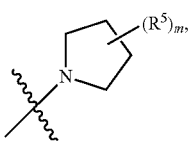

wherein:
m is 1 or 2;
each $R^5$ is independently hydrogen, halo, alkyl, haloalkyl or $-R^{10}-CN$;
$R^3$ is selected from:

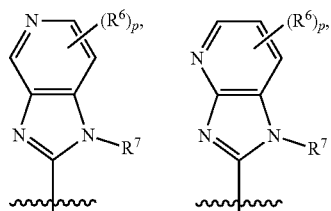

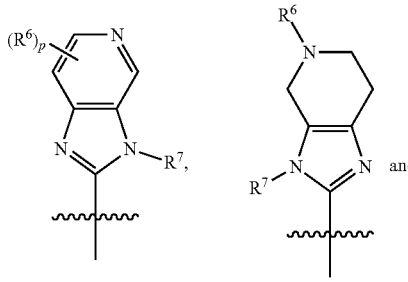

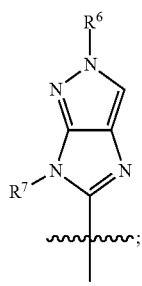

wherein:
each p is independently 1, 2, 3, or 4;

each $R^6$ is independently hydrogen, halo, alkyl, haloalkyl, optionally substituted aryl, optionally substituted aralkyl, $-R^{10}-OR^{11}$, $-R^{10}-C(O)OR^{12}$, $-R^{10}-C(O)R^{12}$, $-R^{10}-N(R^{11})_2$, or an optionally substituted O-heterocyclyl;

or two $R^6$'s, together with the carbon to which they are both attached, form an optionally substituted cycloalkyl; and each $R^7$ is independently hydrogen, alkyl, or $-R^{10}-C(O)OR^{12}$;

each $R^9$ is independently hydrogen or alkyl;

each $R^{10}$ is independently a direct bond or an optionally substituted alkylene chain;

each $R^{11}$ is independently hydrogen, alkyl, haloalkyl, optionally substituted cycloakyl or optionally substituted cycloalkylalkyl; and each $R^{12}$ is hydrogen, alkyl or optionally substituted aralkyl;

as a stereoisomer, enantiomer or tautomer thereof or a mixture thereof; or a pharmaceutically acceptable salt, solvate or prodrug thereof.

In some more specific embodiments, the compound is selected from:

(S)-6-chloro-2-(4-(2,5-difluorophenyl)-2-(3-fluoropyrrolidin-1-yl)pyridin-3-yl)-3H-imidazo[4,5-c]pyridine;
2-(4-(2-fluorophenyl)-2-(pyrrolidin-1-yl)pyridin-3-yl)-3H-imidazo[4,5-b]pyridine;
2-(4-(2-fluorophenyl)-2-(pyrrolidin-1-yl)pyridin-3-yl)-3H-imidazo[4,5-c]pyridine formic acid salt;
tert-butyl (S)-2-(2-(3-fluoropyrrolidin-1-yl)-4-phenylpyridin-3-yl)-3,4,6,7-tetrahydro-5H-imidazo[4,5-c]pyridine-5-carboxylate;
(S)-2-(2-(3-fluoropyrrolidin-1-yl)-4-phenylpyridin-3-yl)-4,5,6,7-tetrahydro-3H-imidazo[4,5-c]pyridine;
(S)-2-(2-(3-fluoropyrrolidin-1-yl)-4-phenylpyridin-3-yl)-5-methyl-4,5,6,7-tetrahydro-3H-imidazo[4,5-c]pyridine;
(S)-1-(2-(2-(3-fluoropyrrolidin-1-yl)-4-phenylpyridin-3-yl)-3,4,6,7-tetrahydro-5H-imidazo[4,5-c]pyridin-5-yl)ethan-1-one;
(S)-2-(2-(3-fluoropyrrolidin-1-yl)-4-phenylpyridin-3-yl)-5-isopropyl-4,5,6,7-tetrahydro-3H-imidazo[4,5-c]pyridine;
(S)-2-(2-(3-fluoropyrrolidin-1-yl)-4-phenylpyridin-3-yl)-5-(oxetan-3-yl)-4,5,6,7-tetrahydro-3H-imidazo[4,5-c]pyridine;
diethyl (S)-2-(2-(3-fluoropyrrolidin-1-yl)-4-phenylpyridin-3-yl)-6,7-dihydro-3H-imidazo[4,5-c]pyridine-3,5(4H)-dicarboxylate;
(S)-1-(2-(2-(3-fluoropyrrolidin-1-yl)-4-phenylpyridin-3-yl)-3,4,6,7-tetrahydro-5H-imidazo[4,5-c]pyridin-5-yl)-2-methylpropan-1-one;
(S)-5-benzyl-2-(2-(3-fluoropyrrolidin-1-yl)-4-phenylpyridin-3-yl)-4,5,6,7-tetrahydro-3H-imidazo[4,5-c]pyridine;
tert-butyl 2-(2-(3,3-difluoropyrrolidin-1-yl)-4-phenylpyridin-3-yl)-3,4,6,7-tetrahydro-5H-imidazo[4,5-c]pyridine-5-carboxylate;
2-(2-(3,3-difluoropyrrolidin-1-yl)-4-(2-fluorophenyl)pyridin-3-yl)-3H-imidazo[4,5-c]pyridine;
2-(2-(3,3-difluoropyrrolidin-1-yl)-4-(2-fluorophenyl)pyridin-3-yl)-6-methyl-3H-imidazo[4,5-c]pyridine; and
5-(2-(3,3-difluoropyrrolidin-1-yl)-4-(2-fluorophenyl)pyridin-3-yl)-2-methyl-2,4-dihydroimidazo[4,5-c]pyrazole;

as a stereoisomer, enantiomer or tautomer thereof or a mixture thereof; or a pharmaceutically acceptable salt, solvate or prodrug thereof.

In other embodiments:
X is $=C(R^9)-$;
Y is $=C(R^9)-$;

$R^1$ is

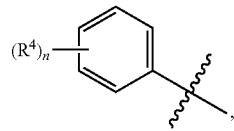

wherein:
n is 1, 2 or 3; and
each $R^4$ is independently hydrogen, halo, alkyl, haloalkyl, or $-R^{10}-OR^{11}$;

$R^2$ is

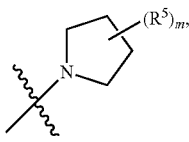

wherein:
m is 1 or 2;
each $R^5$ is independently hydrogen, halo, alkyl, haloalkyl or $-R^{10}-CN$;

$R^3$ is selected from:

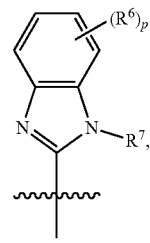

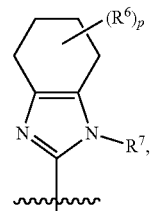

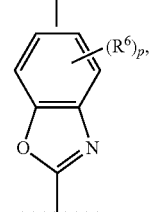

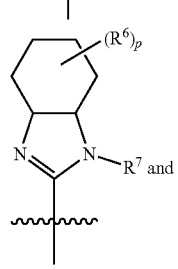

and

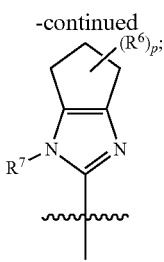

wherein:
each p is independently 1, 2, 3, or 4;
each $R^6$ is independently hydrogen, halo, alkyl, haloalkyl, optionally substituted aryl, optionally substituted aralkyl, $-R^{10}-OR^{11}$, $-R^{10}-C(O)OR^{12}$, $-R^{10}-C(O)R^{12}$, $-R^{10}-N(R^{11})_2$, or an optionally substituted O-heterocyclyl; and
each $R^7$ is independently hydrogen, alkyl or $-R^{10}-C(O)OR^{12}$;
each $R^9$ is independently hydrogen or alkyl;
each $R^{10}$ is independently a direct bond or an optionally substituted alkylene chain;
each $R^{11}$ is independently hydrogen, alkyl, haloalkyl, optionally substituted cycloakyl or optionally substituted cycloalkylalkyl; and
each $R^{12}$ is hydrogen, alkyl or optionally substituted aralkyl;
as a stereoisomer, enantiomer or tautomer thereof or a mixture thereof; or a pharmaceutically acceptable salt, solvate or prodrug thereof.

In more specific embodiments, the compound is selected from:
2-(4-(2-fluorophenyl)-2-(pyrrolidin-1-yl)pyridin-3-yl)-1H-benzo[d]imidazole;
2-(4-(2-chlorophenyl)-2-(pyrrolidin-1-yl)pyridin-3-yl)-1H-benzo[d]imidazole;
2-(2-(pyrrolidin-1-yl)-4-(o-tolyl)pyridin-3-yl)-1H-benzo[d]imidazole;
2-(2-(pyrrolidin-1-yl)-4-(4-(trifluoromethyl)phenyl)pyridin-3-yl)-1H-benzo[d]imidazole;
2-(4-phenyl-2-(pyrrolidin-1-yl)pyridin-3-yl)-1H-benzo[d]imidazole;
(S)-2-(2-(3-fluoropyrrolidin-1-yl)-4-phenylpyridin-3-yl)-1H-benzo[d]imidazole;
(S)-2-(4-(2-fluorophenyl)-2-(3-fluoropyrrolidin-1-yl)pyridin-3-yl)-1H-benzo[d]imidazole;
2-(4-(3,5-difluorophenyl)-2-(pyrrolidin-1-yl)pyridin-3-yl)-1H-benzo[d]imidazole;
(3aR,7aR)-2-(2-((S)-3-fluoropyrrolidin-1-yl)-4-phenylpyridin-3-yl)-3a,4,5,6,7,7a-hexahydro-1H-benzo[d]imidazole;
(S)-2-(2-(3-fluoropyrrolidin-1-yl)-4-phenylpyridin-3-yl)-4,5,6,7-tetrahydro-1H-benzo[d]imidazole;
6-(tert-butyl)-2-(4-phenyl-6-(pyrrolidin-1-yl)pyrimidin-5-yl)-1H-benzo[d]imidazole;
2-(2-(3,3-difluoropyrrolidin-1-yl)-4-phenylpyridin-3-yl)-1,4,5,6-tetrahydrocyclopenta[d]imidazol-5-ol;
2-(2-(3,3-difluoropyrrolidin-1-yl)-4-phenylpyridin-3-yl)-6-methoxy-4,5,6,7-tetrahydro-1H-benzo[d]imidazole;
(S)-2-(2-((S)-3-fluoropyrrolidin-1-yl)-4-phenylpyridin-3-yl)-6-methoxy-4,5,6,7-tetrahydro-1H-benzo[d]imidazole; and
(R)-2-(2-((S)-3-fluoropyrrolidin-1-yl)-4-phenylpyridin-3-yl)-6-methoxy-4,5,6,7-tetrahydro-1H-benzo[d]imidazole;
2-(2-((S)-3-fluoropyrrolidin-1-yl)-4-phenylpyridin-3-yl)-6-methoxy-4,5,6,7-tetrahydro-1H-benzo[d]imidazole;
(S)-2-(2-(3-fluoropyrrolidin-1-yl)-4-phenylpyridin-3-yl)benzo[d]oxazole;
2-(2-(3,3-difluoropyrrolidin-1-yl)-4-phenylpyridin-3-yl)-4,5,6,7-tetrahydro-1H-benzo[d]imidazole;
as a stereoisomer, enantiomer or tautomer thereof or a mixture thereof; or a pharmaceutically acceptable salt, solvate or prodrug thereof.

In still other embodiments:
X is $=C(R^9)-$;
Y is $=C(R^9)-$;
$R^1$ is

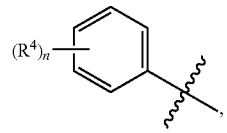

wherein:
n is 1, 2 or 3; and
each $R^4$ is independently hydrogen, halo, alkyl, haloalkyl, or $-R^{10}-OR^{11}$;
or two adjacent $R^4$'s, together with the carbons to which they are attached, form an optionally substituted N-heteroaryl;
$R^2$ is

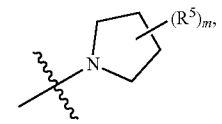

wherein:
m is 1 or 2;
each $R^5$ is independently hydrogen, halo, alkyl, haloalkyl or $-R^{10}-CN$;
or two adjacent $R^5$'s, together with the carbons to which they are attached, form an optionally substituted cycloalkyl;
$R^3$ is selected from:

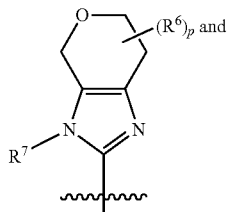

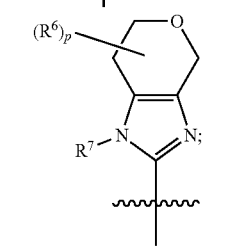

wherein:
each p is independently 1, 2, 3, or 4;

each $R^6$ is independently hydrogen, halo, alkyl, haloalkyl, optionally substituted aryl, optionally substituted aralkyl, $-R^{10}-OR^{11}$, $-R^{10}-C(O)OR^{12}$, $-R^{10}-C(O)R^{12}$, $-R^{10}-N(R^{11})_2$, or an optionally substituted O-heterocyclyl;

or two $R^6$'s, together with the carbon to which they are both attached, form an optionally substituted cycloalkyl; and each $R^7$ is independently hydrogen, alkyl or $-R^{10}-C(O)OR^{12}$;

each $R^9$ is independently hydrogen or alkyl;

each $R^{10}$ is independently a direct bond or an optionally substituted alkylene chain;

each $R^{11}$ is independently hydrogen, alkyl, haloalkyl, optionally substituted cycloakyl or optionally substituted cycloalkylalkyl; and each $R^{12}$ is hydrogen, alkyl or optionally substituted aralkyl;

as a stereoisomer, enantiomer or tautomer thereof or a mixture thereof; or a pharmaceutically acceptable salt, solvate or prodrug thereof.

In some specific embodiments, the compound is selected from:

2-(2-(3,3-difluoropyrrolidin-1-yl)-4-phenylpyridin-3-yl)-3,4,6,7-tetrahydropyrano[3,4-d]imidazole;

2-(2-(3,3-difluoropyrrolidin-1-yl)-4-phenylpyridin-3-yl)-6,6-dimethyl-3,4,6,7-tetrahydropyrano[3,4-d]imidazole;

(S)-2-(4-(2,5-difluorophenyl)-2-(3-fluoropyrrolidin-1-yl)pyridin-3-yl)-3,4,6,7-tetrahydropyrano[3,4-d]imidazole;

2-(2-(3,3-difluoropyrrolidin-1-yl)-4-(2-fluorophenyl)pyridin-3-yl)-1,4,6,7-tetrahydropyrano[3,4-d]imidazole;

2-(4-(2,5-difluorophenyl)-2-(3,3-difluoropyrrolidin-1-yl)pyridin-3-yl)-1,4,6,7-tetrahydropyrano[3,4-d]imidazole;

2-(2-(3,3-difluoropyrrolidin-1-yl)-4-(1H-indazol-5-yl)pyridin-3-yl)-1,4,6,7-tetrahydropyrano[3,4-d]imidazole;

2-(2-(3,3-difluoropyrrolidin-1-yl)-4-(3-fluorophenyl)pyridin-3-yl)-1,4,6,7-tetrahydropyrano[3,4-d]imidazole;

2-(4-phenyl-2-(pyrrolidin-1-yl)pyridin-3-yl)-3,4,6,7-tetrahydropyrano[3,4-d]imidazole;

2-(2-(6,6-difluoro-3-azabicyclo[3.1.0]hexan-3-yl)-4-phenylpyridin-3-yl)-3,4,6,7-tetrahydropyrano[3,4-d]imidazole;

2-(4-(2,5-difluorophenyl)-2-(3,3-difluoropyrrolidin-1-yl)pyridin-3-yl)-6,6-dimethyl-3,4,6,7-tetrahydropyrano[3,4-d]imidazole;

2-(2-((3S,4R)-3,4-difluoropyrrolidin-1-yl)-4-phenylpyridin-3-yl)-3,4,6,7-tetrahydropyrano[3,4-d]imidazole;

2-(4-(2,3-difluorophenyl)-2-(3,3-difluoropyrrolidin-1-yl)pyridin-3-yl)-3,4,6,7-tetrahydropyrano[3,4-d]imidazole;

1-(4-phenyl-3-(3,4,6,7-tetrahydropyrano[3,4-d]imidazol-2-yl)pyridin-2-yl)pyrrolidine-3-carbonitrile;

2'-(2-(3,3-difluoropyrrolidin-1-yl)-4-phenylpyridin-3-yl)-4',7'-dihydro-3'H-spiro[cyclobutane-1,6'-pyrano[3,4-d]imidazole];

2-(4-phenyl-2-(3-(trifluoromethyl)pyrrolidin-1-yl)pyridin-3-yl)-3,4,6,7-tetrahydropyrano[3,4-d]imidazole; and 2-(2-(3,3-difluoropyrrolidin-1-yl)-4-phenylpyridin-3-yl)-4,4-dimethyl-3,4,6,7-tetrahydropyrano[3,4-d]imidazole;

as a stereoisomer, enantiomer or tautomer thereof or a mixture thereof; or a pharmaceutically acceptable salt, solvate or prodrug thereof.

In certain embodiments:

X is $=C(R^9)-$;

Y is $=C(R^9)-$;

$R^1$ is

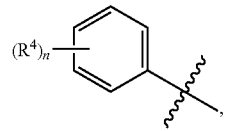

wherein:

n is 1, 2 or 3; and each $R^4$ is independently hydrogen, halo, alkyl, haloalkyl, or $-R^{10}-OR^{11}$;

$R^2$ is

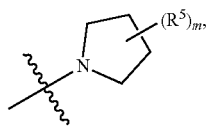

wherein;

m is 1 or 2;

each $R^5$ is independently hydrogen, halo, alkyl, haloalkyl or $-R^{10}-CN$;

$R^3$ is selected from:

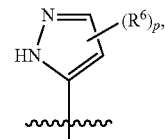

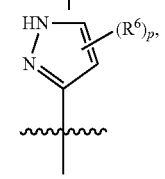

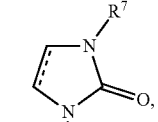

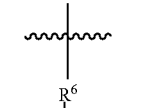

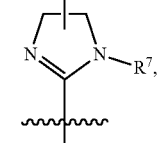

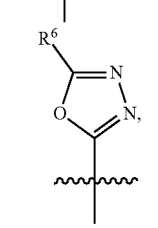

-continued

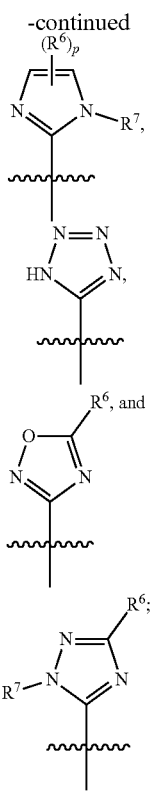

wherein:
each p is independently 1, 2, 3, or 4;
each $R^6$ is independently hydrogen, halo, alkyl, haloalkyl, optionally substituted aryl, optionally substituted aralkyl, $-R^{10}-OR^{11}$, $-R^{10}-C(O)OR^{12}$, $-R^{10}-C(O)R^{12}$, $-R^{10}-N(R^{11})_2$, an optionally substituted O-heterocyclyl or

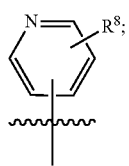

each $R^7$ is independently hydrogen, alkyl, $-R^{10}-C(O)OR^{12}$ or

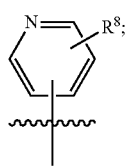

and
each $R^8$ is independently hydrogen, alkyl or halo,
each $R^9$ is independently hydrogen or alkyl;
each $R^{10}$ is independently a direct bond or an optionally substituted alkylene chain;
each $R^{11}$ is independently hydrogen, alkyl, haloalkyl, optionally substituted cycloakyl or optionally substituted cycloalkylalkyl; and each $R^{12}$ is hydrogen, alkyl or optionally substituted aralkyl;
as a stereoisomer, enantiomer or tautomer thereof or a mixture thereof; or a pharmaceutically acceptable salt, solvate or prodrug thereof.

In certain embodiments, the compound selected from:
5-(4-(2-fluorophenyl)-2-(pyrrolidin-1-yl)pyridin-3-yl)-1,3,4-oxadiazol-2-amine;
4-(2-fluorophenyl)-3-(5-isobutyl-4,5-dihydro-1H-imidazol-2-yl)-2-(pyrrolidin-1-yl)pyridine;
(S)-2-(4-(2-fluorophenyl)-2-(3-fluoropyrrolidin-1-yl)pyridin-3-yl)-1,3,4-oxadiazole;
(S)—N-butyl-5-(4-(2-fluorophenyl)-2-(3-fluoropyrrolidin-1-yl)pyridin-3-yl)-1,3,4-oxadiazol-2-amine;
(S)-2-(2-(3-fluoropyrrolidin-1-yl)-3-(5-isopentyl-1,3,4-oxadiazol-2-yl)pyridin-4-yl)phenol;
(S)-2-(4-(2-fluorophenyl)-2-(3-fluoropyrrolidin-1-yl)pyridin-3-yl)-5-isopentyl-1,3,4-oxadiazole;
(S)-2-(3-fluoropyrrolidin-1-yl)-4-phenyl-3-(3-(pyridin-3-yl)-1H-pyrazol-5-yl)pyridine;
(S)-2-(3-fluoropyrrolidin-1-yl)-3-(3-(4-isopropylphenyl)-1H-pyrazol-5-yl)-4-phenylpyridine;
(S)-1-(6-chloropyridin-3-yl)-3-(4-(2-fluorophenyl)-2-(3-fluoropyrrolidin-1-yl)pyridin-3-yl)imidazolidin-2-one;
(S)-1-(6-chloropyridin-3-yl)-3-(4-(2-fluorophenyl)-2-(3-fluoropyrrolidin-1-yl)pyridin-3-yl)-1,3-dihydro-2H-imidazol-2-one;
2-((S)-3-fluoropyrrolidin-1-yl)-3-(5-methyl-4,5-dihydro-1H-imidazol-2-yl)-4-phenylpyridine;
(S)-3-(4-bromo-5-methyl-1H-imidazol-2-yl)-2-(3-fluoropyrrolidin-1-yl)-4-phenylpyridine;
(S)-2-(2-(3-fluoropyrrolidin-1-yl)-4-phenylpyridin-3-yl)-5-(4-isopropylphenyl)-1,3,4-oxadiazole;
tert-butyl (S)-2-(2-(3-fluoropyrrolidin-1-yl)-4-phenylpyridin-3-yl)-3,4,6,7-tetrahydro-5H-imidazo[4,5-c]pyridine-5-carboxylate;
(S)-2-(3-fluoropyrrolidin-1-yl)-3-(4-methyl-5-(trifluoromethyl)-1H-imidazol-2-yl)-4-phenylpyridine;
2-(3,3-difluoropyrrolidin-1-yl)-3-(5-methyl-4-phenyl-1H-imidazol-2-yl)-4-phenylpyridine;
5-(tert-butyl)-3-(2-(3,3-difluoropyrrolidin-1-yl)-4-phenylpyridin-3-yl)-1,2,4-oxadiazole; and
(S)-2-(3-fluoropyrrolidin-1-yl)-4-phenyl-3-(3-phenyl-1H-1,2,4-triazol-5-yl)pyridine;
as a stereoisomer, enantiomer or tautomer thereof or a mixture thereof; or a pharmaceutically acceptable salt, solvate or prodrug thereof.

In certain specific embodiments:
X is $=C(R^9)-$;
Y is $=C(R^9)-$;
$R^1$ is

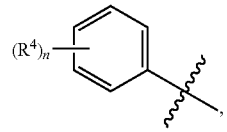

wherein:
n is 1, 2 or 3; and
each $R^4$ is independently hydrogen, halo, alkyl, haloalkyl, or $-R^{10}-OR^{11}$;
$R^2$ is $-R^{10}-OR^{11}$ or $-R^{10}-N(R^{11})_2$;

or R² is selected from:

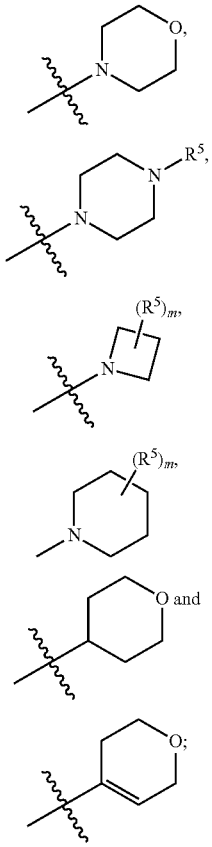

wherein:

each m is independently 1 or 2;

each R⁵ is independently hydrogen, halo, alkyl, haloalkyl or —R¹⁰—CN;

or two R⁵'s, together with the carbon to which they are both attached, form an optionally substituted O-heterocyclyl;

or two R⁵'s, together with the carbon to which they are both attached, form an optionally substituted cycloalkyl;

R³ is selected from:

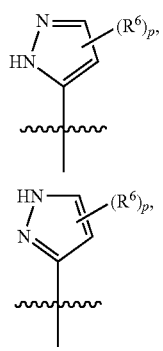

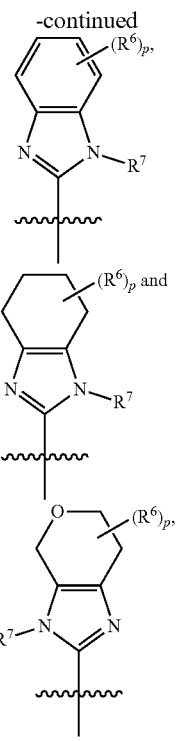

wherein:

each p is independently 1, 2, 3, or 4;

each R⁶ is independently hydrogen, halo, alkyl, haloalkyl, optionally substituted aryl, optionally substituted aralkyl, —R¹⁰—OR¹¹, —R¹⁰—C(O)OR¹², o-R¹⁰—C(O)R¹², —R¹⁰—N(R¹¹)₂, or an optionally substituted O-heterocyclyl;

or two R⁶'s, together with the carbon to which they are both attached, form an optionally substituted cycloalkyl; and each R⁷ is independently hydrogen, alkyl, or —R¹⁰—C(O)OR¹²;

each R⁹ is independently hydrogen or alkyl;

each R¹⁰ is independently a direct bond or an optionally substituted alkylene chain;

each R¹¹ is independently hydrogen, alkyl, haloalkyl, optionally substituted cycloakyl or optionally substituted cycloalkylalkyl; and each R¹² is hydrogen, alkyl or optionally substituted aralkyl;

as a stereoisomer, enantiomer or tautomer thereof or a mixture thereof; or a pharmaceutically acceptable salt, solvate or prodrug thereof.

In some embodiments, the compound is selected from:

4-(3-(1H-benzo[d]imidazol-2-yl)-4-(o-tolyl)pyridin-2-yl)morpholine;

2-(2-(4-methylpiperazin-1-yl)-4-(o-tolyl)pyridin-3-yl)-1H-benzo[d]imidazole;

4-(3-(3-(4-isopropylphenyl)-1H-pyrazol-5-yl)-4-phenylpyridin-2-yl)morpholine;

4-(3-((3aR,7aR)-3a,4,5,6,7,7a-hexahydro-1H-benzo[d]imidazol-2-yl)-4-phenylpyridin-2-yl)morpholine;

4-(4-phenyl-3-(4,5,6,7-tetrahydro-1H-benzo[d]imidazol-2-yl)pyridin-2-yl)morpholine;

2-(2-morpholino-4-phenylpyridin-3-yl)-3,4,6,7-tetrahydropyrano[3,4-d]imidazole;

2-(2-(3,3-difluoroazetidin-1-yl)-4-phenylpyridin-3-yl)-3,4,6,7-tetrahydropyrano[3,4-d]imidazole;

2-(4-phenyl-2-(2-oxa-6-azaspiro[3.3]heptan-6-yl)pyridin-3-yl)-3,4,6,7-tetrahydropyrano[3,4-d]imidazole;

2-(2-cyclobutoxy-4-phenylpyridin-3-yl)-3,4,6,7-tetrahydropyrano[3,4-d]imidazole;

2-(2-(3,3-difluoropiperidin-1-yl)-4-phenylpyridin-3-yl)-3,4,6,7-tetrahydropyrano[3,4-d]imidazole;

2-(2-(6,6-difluoro-2-azaspiro[3.3]heptan-2-yl)-4-phenylpyridin-3-yl)-3,4,6,7-tetrahydropyrano[3,4-d]imidazole;

4-phenyl-3-(3,4,6,7-tetrahydropyrano[3,4-d]imidazol-2-yl)-N-((1-(trifluoromethyl)cyclobutyl)methyl)pyridin-2-amine;

2-(4-phenyl-2-(tetrahydro-2H-pyran-4-yl)pyridin-3-yl)-3,4,6,7-tetrahydropyrano[3,4-d]imidazole; and 2-(2-(3,6-dihydro-2H-pyran-4-yl)-4-phenylpyridin-3-yl)-3,4,6,7-tetrahydropyrano[3,4-d]imidazole;

as a stereoisomer, enantiomer or tautomer thereof or a mixture thereof; or a pharmaceutically acceptable salt, solvate or prodrug thereof.

In more specific embodiments:

X is =C(R$^9$)—;

Y is =C(R$^9$)—;

R$^1$ is

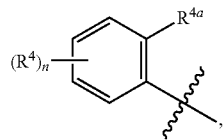

wherein:

each n is independently 1, 2 or 3;

each R$^4$ is independently hydrogen, halo, alkyl, haloalkyl, or —R$^{10}$—OR$^{11}$; and R$^{4a}$ is hydrogen;

R$^2$ is selected from:

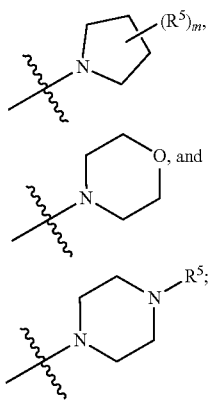

wherein:

each m is independently 1 or 2;

each R$^5$ is independently hydrogen, halo, alkyl, haloalkyl or —R$^{10}$—CN;

R$^3$ is

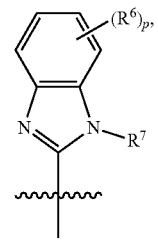

wherein:

p is 1 or 2;

each R$^6$ is independently hydrogen, halo, alkyl, haloalkyl, optionally substituted aryl, optionally substituted aralkyl, —R$^{10}$—OR$^{11}$, —R$^{10}$—C(O)OR$^{12}$, —R$^{10}$—C(O)R$^{12}$ or —R$^{10}$—N(R$^{11}$)$_2$; and R$^7$ together with R$^{4a}$ form a bond;

each R$^9$ is independently hydrogen or alkyl;

each R$^{10}$ is independently a direct bond or an optionally substituted alkylene chain;

each R$^{11}$ is independently hydrogen, alkyl, haloalkyl, optionally substituted cycloakyl or optionally substituted cycloalkylalkyl; and each R$^{12}$ is hydrogen, alkyl or optionally substituted aralkyl;

as a stereoisomer, enantiomer or tautomer thereof or a mixture thereof; or a pharmaceutically acceptable salt, solvate or prodrug thereof.

In some embodiments, the compound is selected from:

4-(benzo[c]benzo[4,5]imidazo[2,1-a][2,7]naphthyridin-1-yl)morpholine;

1-(4-methylpiperazin-1-yl)benzo[c]benzo[4,5]imidazo[2,1-a][2,7]naphthyridine; and 1-(pyrrolidin-1-yl)benzo[c]benzo[4,5]imidazo[2,1-a][2,7]naphthyridine;

as a stereoisomer, enantiomer or tautomer thereof or a mixture thereof; or a pharmaceutically acceptable salt, solvate or prodrug thereof.

In certain embodiments, wherein:

X is =C(R$^9$)—;

Y is =C(R$^9$)—;

R$^1$ is selected from:

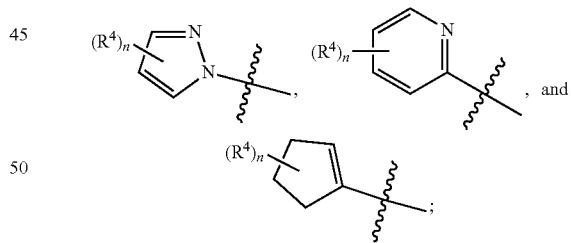

wherein:

each n is independently 1, 2 or 3; and each R$^4$ is independently hydrogen, halo, alkyl, haloalkyl, or —R$^{10}$—OR$^{11}$;

R$^2$ is selected from:

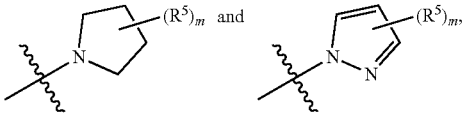

wherein:
each m is independently 1 or 2; and
each $R^5$ is independently hydrogen, halo, alkyl or haloalkyl;
$R^3$ is selected from:

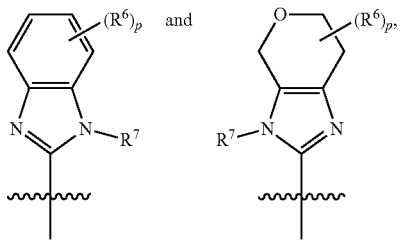

wherein:
each p is independently 1, 2, 3, or 4;
each $R^6$ is independently hydrogen, halo, alkyl, haloalkyl, optionally substituted aryl, optionally substituted aralkyl, $-R^{10}-OR^{11}$, $-R^{10}-C(O)OR^{12}$, or $-R^{10}-C(O)R^{12}$, $-R^{10}-N(R^{11})_2$; and
each $R^7$ is independently hydrogen, alkyl or $-R^{10}-C(O)OR^{12}$;
each $R^9$ is independently hydrogen or alkyl;
each $R^{10}$ is independently a direct bond or an optionally substituted alkylene chain;
each $R^{11}$ is independently hydrogen, alkyl, haloalkyl, optionally substituted cycloakyl or optionally substituted cycloalkylalkyl; and
each $R^{12}$ is hydrogen, alkyl or optionally substituted aralkyl;
as a stereoisomer, enantiomer or tautomer thereof or a mixture thereof; or a pharmaceutically acceptable salt, solvate or prodrug thereof.

In certain more specific embodiments, the compound is selected from:
2-(2,4-di(1H-pyrazol-1-yl)pyridin-3-yl)-1H-benzo[d]imidazole;
2-(2'-(pyrrolidin-1-yl)-[2,4'-bipyridin]-3'-yl)-1H-benzo[d]imidazole;
2-(4-(1H-pyrazol-1-yl)-2-(pyrrolidin-1-yl)pyridin-3-yl)-1H-benzo[d]imidazole;
(S)-2-(4-(cyclopent-1-en-1-yl)-2-(3-fluoropyrrolidin-1-yl)pyridin-3-yl)-1H-benzo[d]imidazole;
2-(2'-(pyrrolidin-1-yl)-[2,4'-bipyridin]-3'-yl)-1H-benzo[d]imidazole; and
2-(2'-(3,3-difluoropyrrolidin-1-yl)-[2,4'-bipyridin]-3'-yl)-3,4,6,7-tetrahydropyrano[3,4-d]imidazole;
as a stereoisomer, enantiomer or tautomer thereof or a mixture thereof; or a pharmaceutically acceptable salt, solvate or prodrug thereof.

In certain embodiments:
X is =N— and Y is =C($R^9$) or
X is =C($R^9$) and Y is =N—;
$R^1$ is

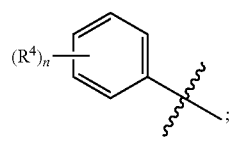

wherein:
n is independently 1, 2 or 3;
each $R^4$ is independently hydrogen, halo, alkyl, haloalkyl, or $-R^{10}-OR^{11}$;
$R^2$ is selected from:

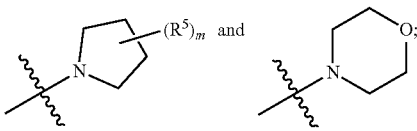

wherein:
m is 1 or 2;
$R^5$ is hydrogen, halo, alkyl, haloalkyl or $-R^{10}-CN$;
$R^3$ is selected from:

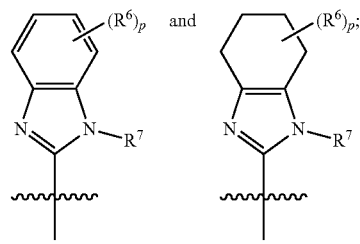

wherein:
each p is independently 1, 2, 3, or 4;
each $R^6$ is independently hydrogen, halo, alkyl, haloalkyl, optionally substituted aryl, optionally substituted aralkyl, $-R^{10}-OR^{11}$, $-R^{10}-C(O)OR^{12}$, $-R^{10}-C(O)R^{12}$, $-R^{10}-N(R^{11})_2$, or an optionally substituted O-heterocyclyl; and
each $R^7$ is independently hydrogen, alkyl or $-R^{10}-C(O)OR^{12}$;
each $R^9$ is independently hydrogen or alkyl;
each $R^{10}$ is independently a direct bond or an optionally substituted alkylene chain;
each $R^{11}$ is independently hydrogen, alkyl, haloalkyl, optionally substituted cycloakyl or optionally substituted cycloalkylalkyl; and
each $R^{12}$ is hydrogen, alkyl or optionally substituted aralkyl;
as a stereoisomer, enantiomer or tautomer thereof or a mixture thereof; or a pharmaceutically acceptable salt, solvate or prodrug thereof.

In more specific embodiments, the compound is selected from:
2-(5-phenyl-3-(pyrrolidin-1-yl)pyridazin-4-yl)-1H-benzo[d]imidazole; and
4-(5-phenyl-4-(4,5,6,7-tetrahydro-1H-benzo[d]imidazol-2-yl)pyridazin-3-yl)morpholine;
as a stereoisomer, enantiomer or tautomer thereof or a mixture thereof; or a pharmaceutically acceptable salt, solvate or prodrug thereof.

In certain specific embodiments:
X is =C($R^9$) and Y is =C($R^9$);
$R^1$ is

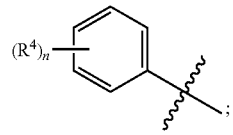

wherein:
n is independently 1, 2 or 3;
each $R^4$ is independently hydrogen, halo, alkyl, haloalkyl, or —$R^{10}$—$OR^{11}$;
$R^2$ is

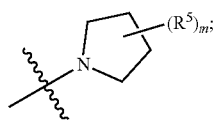

wherein:
m is 1 or 2;
$R^5$ is hydrogen, halo, alkyl, haloalkyl or —$R^{10}$—CN;
$R^3$ is selected from:

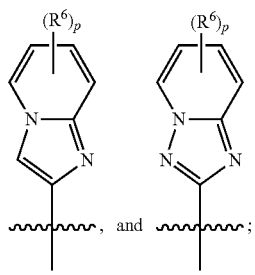

wherein:
each p is independently 1, 2, 3, or 4; and
each $R^6$ is independently hydrogen, halo, alkyl, haloalkyl, optionally substituted aryl, optionally substituted aralkyl, —$R^{10}$—$OR^{11}$, —$R^{10}$—C(O)$OR^{12}$, —$R^{10}$—C(O)$R^{12}$, —$R^{10}$—N($R^{11}$)$_2$, or an optionally substituted O-heterocyclyl;
each $R^9$ is independently hydrogen or alkyl;
each $R^{10}$ is independently a direct bond or an optionally substituted alkylene chain;
each $R^{11}$ is independently hydrogen, alkyl, haloalkyl, optionally substituted cycloakyl or optionally substituted cycloalkylalkyl; and
each $R^{12}$ is hydrogen, alkyl or optionally substituted aralkyl; as a stereoisomer, enantiomer or tautomer thereof or a mixture thereof; or a pharmaceutically acceptable salt, solvate or prodrug thereof.

In more specific embodiments, the compound is selected from:
(S)-2-(2-(3-fluoropyrrolidin-1-yl)-4-phenylpyridin-3-yl)imidazo[1,2-a]pyridine; and
(S)-2-(2-(3-fluoropyrrolidin-1-yl)-4-phenylpyridin-3-yl)-[1,2,4]triazolo[1,5-a]pyridine;
as a stereoisomer, enantiomer or tautomer thereof or a mixture thereof; or a pharmaceutically acceptable salt, solvate or prodrug thereof.

Another embodiment of the disclosure is a pharmaceutical composition comprising one or more pharmaceutically acceptable excipient(s) and a therapeutically effective amount of a compound of formula (I), as described above in the Brief Summary, as a stereoisomer, enantiomer or tautomer thereof or mixtures thereof; or a pharmaceutically acceptable salt, solvate or prodrug thereof.

Another embodiment of the disclosure is a method of treating a disease or condition in a mammal modulated by a voltage-gated sodium channel, wherein the method comprises administering to a mammal in need thereof a therapeutically effective amount of a compound of formula (I), as described above in the Summary of the disclosure, as a stereoisomer, enantiomer or tautomer thereof or mixtures thereof; or a pharmaceutically acceptable salt, solvate or prodrug thereof.

Another embodiment of the disclosure is a method of using the compounds of formula (I) as standards or controls in in vitro or in vivo assays in determining the efficacy of test compounds in modulating voltage-dependent sodium channels.

Specific embodiments of the compounds of the disclosure are described in more detail below in the Preparation of the Compounds.

Utility and Testing of the Compounds

In an embodiment, the present disclosure is directed to compounds of formula (I), as individual stereoisomers, enantiomers or tautomers thereof or mixtures thereof; or pharmaceutically acceptable salts, solvates or prodrugs thereof, which are useful in treating seizure disorders, for example, epilepsy and/or epileptic seizure disorders, in a mammal, preferably a human.

In another embodiment, compounds of formula (I), as individual stereoisomers, enantiomers or tautomers thereof or mixtures thereof; or pharmaceutically acceptable salts, solvates or prodrugs thereof, disclosed herein are useful in treating epilepsy, seizure disorders, partial seizures (such as simple, complex, secondary generalized, and focal onset), generalized seizures (such as absence, myoclonic, atonic, tonic and tonic clonic), and disorders including photosensitive epilepsy, self-induced syncope, intractable epilepsy, Angelman syndrome, benign rolandic epilepsy, CDKL5 disorder, childhood and juvenile absence epilepsy, Dravet syndrome, frontal lobe epilepsy, Glut1 deficiency syndrome, hypothalamic hamartoma, infantile spasms/West's syndrome, juvenile myoclonic epilepsy, Landau-Kleffner syndrome, Lennox-Gastaut syndrome (LGS), epilepsy with myoclonic-absences, Ohtahara syndrome, Panayiotopoulos syndrome, PCDH19 epilepsy, progressive myoclonic epilepsies, Rasmussen's syndrome, ring chromosome 20 syndrome, reflex epilepsies, temporal lobe epilepsy, Lafora progressive myoclonus epilepsy, neurocutaneous syndromes, tuberous sclerosis complex, early infantile epileptic encephalopathy, early onset epileptic encephalopathy, generalized epilepsy with febrile seizures plus (GEFS+), Rett syndrome, multiple sclerosis, Schizophrenia, autism, ataxia, hypotonia and paroxysmal dyskinesia, Alzheimer's disease, and Tauopathies, including but not limited to Alzheimer's disease, Pick's disease, progressive supranuclear palsy, corticobasal syndrome, frontotemporal dementias, Argyrophilic grain disease, frontotemporal lobar degeneration, globular glial tauopathies, MAPT mutation, primary age-related tauopathy, neurofibrillary tangle dementia, chronic traumatic encephalopathy (CTE), aging-related tau astrogliopathy, Richardson syndrome, Down Syndrome, parkinsonism, pure akinesia with gait freezing, motor neuron symptoms or cerebellar ataxia, posttraumatic stress disorders (PTSD) or any combination of the these.

The present disclosure readily affords many different means for identification of sodium channel modulating agents that are useful as therapeutic agents. Identification of modulators of sodium channels can be assessed using a variety of in vitro and in vivo assays, e.g., measuring current, measuring membrane potential, measuring ion flux, (e.g., sodium), measuring sodium concentration, measuring second messengers and transcription levels, measuring neurotransmitter levels and using voltage-sensitive dyes, radioactive tracers, multi-electrode arrays, and patch-clamp electrophysiology.

One such protocol involves the screening of chemical agents for ability to modulate the activity of a sodium channel thereby identifying it as a modulating agent.

A typical assay described in Crestey, F. et al., *ACS Chem Neurosci* (2015), Vol. 6, pp. 1302-1308, AA43279 (Frederiksen, K. et al., *Eur J Neurosci* (2017), Vol. 46, pp. 1887-1896) and Lu AE98134 (von Schoubyea, N. L. et al., *Neurosci Lett* (2018), Vol. 662, pp. 29-35) employs the use of automated planar patch clamp techniques to study the effects of the chemical agent on the gating of sodium channels. The sodium channel isoforms of interest are stably expressed in Human Embryonic Kidney Cells and the currents that flow through those channels in response to a depolarizing voltage clamp step from −120 mV to 0 mV are measured in the presence of increasing concentrations of the chemical agents. The area under the sodium current trace which correlates to the magnitude of sodium flux through the cell membrane is used to quantify the effects on gating of the channels. Other parameters that are measured in the assay include the peak current, time constant of open state inactivation and the voltage dependence of steady state inactivation properties. The concentration responses are used to determine potency of each chemical agents effects on modulating the sodium channel isoform gating. Such techniques are known to those skilled in the art, and may be developed, using current technologies, into low or medium throughput assays for evaluating compounds for their ability to modulate sodium channel behaviour.

The results of these assays provide the basis for analysis of the structure-activity relationship (SAR) between compounds of the disclosure and the sodium channel. Certain substituents on the core structure of a compound of the disclosure tend to provide more potent inhibitory or potentiating compounds. SAR analysis is one of the tools those skilled in the art may now employ to identify preferred embodiments of the compounds of the disclosure for use as therapeutic agents.

In an alternative use of the disclosure, the compounds of the disclosure can be used in in vitro or in vivo studies as exemplary agents for comparative purposes to find other compounds also useful in treatment of, or protection from, the various diseases disclosed herein.

In another embodiment, the compounds of formula (I), as individual stereoisomers, enantiomers or tautomers thereof or mixtures thereof; or pharmaceutically acceptable salts, solvates or prodrugs thereof, as set forth above in the Brief Summary, as stereoisomers, enantiomers, tautomers thereof or mixtures thereof, or pharmaceutically acceptable salts, solvates or prodrugs thereof, and/or the pharmaceutical compositions described herein which comprise a pharmaceutically acceptable excipient and one or more compounds of the disclosure, as set forth above in the Brief Summary, as a stereoisomer, enantiomer or tautomer thereof or mixtures thereof, or a pharmaceutically acceptable salt, solvate or prodrug thereof, can be used in the preparation of a medicament for the treatment of a sodium channel-mediated disease or condition in a mammal.

Pharmaceutical Compositions Administration

This disclosure is also directed to pharmaceutical compositions containing the compounds of formula (I), as described above in the Brief Summary, as stereoisomers, enantiomers or tautomers thereof or mixtures thereof; or pharmaceutically acceptable salts, solvates or prodrugs thereof. In one embodiment, the present disclosure relates to a pharmaceutical composition comprising compounds of formula (I), as described above in the Brief Summary, as stereoisomers, enantiomers or tautomers thereof or mixtures thereof; or pharmaceutically acceptable salts, solvates or prodrugs thereof, in a pharmaceutically acceptable carrier, excipient or diluent and in an amount effective to modulate, preferably inhibit, voltage-gated sodium channels to treat certain diseases or conditions, such as epilepsy, when administered to an animal, preferably a mammal, most preferably a human patient.

Administration of the compounds of formula (I), as described above in the Brief Summary, as stereoisomers, enantiomers or tautomers thereof or mixtures thereof; or pharmaceutically acceptable salts, solvates or prodrugs thereof, in pure form or in an appropriate pharmaceutical composition, can be carried out via any of the accepted modes of administration of agents for serving similar utilities. The pharmaceutical compositions of the disclosure can be prepared by combining a compound of the disclosure with an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. Typical routes of administering such pharmaceutical compositions include, without limitation, oral, topical, transdermal, inhalation, parenteral, sublingual, rectal, vaginal, and intranasal. The term "parenteral" as used herein includes subcutaneous injections, intravenous, intramuscular, intrathecal, intrasternal injection or infusion techniques. Pharmaceutical compositions of the disclosure are formulated so as to allow the active ingredients contained therein to be bioavailable upon administration of the composition to a patient. Compositions that will be administered to a subject or patient take the form of one or more dosage units, where for example, a tablet may be a single dosage unit, and a container of a compound of the disclosure in aerosol form may hold a plurality of dosage units. Actual methods of preparing such dosage forms are known, or will be apparent, to those skilled in this art; for example, see *The Science and Practice of Pharmacy*, 20th Edition (Philadelphia College of Pharmacy and Science, 2000). The composition to be administered will, in any event, contain a therapeutically effective amount of a compound of the disclosure, or a pharmaceutically acceptable salt thereof, for treatment of a disease or condition of interest in accordance with the teachings of this disclosure.

The pharmaceutical compositions useful herein also contain a pharmaceutically acceptable carrier, including any suitable diluent or excipient, which includes any pharmaceutical agent that does not itself induce the production of antibodies harmful to the individual receiving the composition, and which may be administered without undue toxicity. Pharmaceutically acceptable carriers include, but are not limited to, liquids, such as water, saline, glycerol and ethanol, and the like. A thorough discussion of pharmaceutically acceptable carriers, diluents, and other excipients is presented in REMINGTON'S PHARMACEUTICAL SCIENCES (Mack Pub. Co., N.J. current edition).

A pharmaceutical composition of the disclosure may be in the form of a solid or liquid. In one aspect, the carrier(s) are particulate, so that the compositions are, for example, in tablet or powder form. The carrier(s) may be liquid, with the compositions being, for example, an oral syrup, injectable liquid or an aerosol, which is useful in, for example, inhalatory administration.

When intended for oral administration, the pharmaceutical composition is preferably in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like form. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When the pharmaceutical composition is in the form of a capsule, for example, a gelatin capsule, it may contain, in addition to materials of the above type, a liquid carrier such as polyethylene glycol or oil.

The pharmaceutical composition may be in the form of a liquid, for example, an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions of the disclosure, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition of the disclosure intended for either parenteral or oral administration should contain an amount of a compound of the disclosure such that a suitable dosage will be obtained. Typically, this amount is at least 0.01% of a compound of the disclosure in the composition. When intended for oral administration, this amount may be varied to be between 0.1 and about 70% of the weight of the composition. Preferred oral pharmaceutical compositions contain between about 4% and about 50% of the compound of the disclosure. Preferred pharmaceutical compositions and preparations according to the present disclosure are prepared so that a parenteral dosage unit contains between 0.01 to 10% by weight of the compound prior to dilution of the disclosure.

The pharmaceutical composition of the disclosure may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the compound of the disclosure from about 0.1 to about 10% w/v (weight per unit volume).

The pharmaceutical composition of the disclosure may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter and polyethylene glycol.

The pharmaceutical composition of the disclosure may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

The pharmaceutical composition of the disclosure in solid or liquid form may include an agent that binds to the compound of the disclosure and thereby assists in the delivery of the compound. Suitable agents that may act in this capacity include a monoclonal or polyclonal antibody, a protein or a liposome.

The pharmaceutical composition of the disclosure may consist of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds of the disclosure may be delivered in single phase, bi-phasic, or tri-phasic systems in order to deliver the active ingredient(s). Delivery of the aerosol includes the necessary container, activators, valves, subcontainers, and the like, which together may form a kit. One skilled in the art, without undue experimentation may determine preferred aerosols.

The pharmaceutical compositions of the disclosure may be prepared by methodology well known in the pharmaceutical art. For example, a pharmaceutical composition intended to be administered by injection can be prepared by combining a compound of the disclosure with sterile, distilled water so as to form a solution. A surfactant may be added to facilitate the formation of a homogeneous solution or suspension. Surfactants are compounds that non-covalently interact with the compound of the disclosure so as to facilitate dissolution or homogeneous suspension of the compound in the aqueous delivery system.

The compounds of the disclosure, or their pharmaceutically acceptable salts, are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy. Generally, a therapeutically effective daily dose is (for a 70 kg mammal) from about 0.001 mg/kg (i.e., 0.07 mg) to about 100 mg/kg (i.e., 7.0 g); preferably a therapeutically effective dose is (for a 70 kg mammal) from about 0.01 mg/kg (i.e., 0.7 mg) to about 50 mg/kg (i.e., 3.5 g); more preferably a therapeutically effective dose is (for a 70 kg mammal) from about 1 mg/kg (i.e., 70 mg) to about 25 mg/kg (i.e., 1.75 g).

The ranges of effective doses provided herein are not intended to be limiting and represent preferred dose ranges. However, the most preferred dosage will be tailored to the individual subject, as is understood and determinable by one skilled in the relevant arts. (see, e.g., Berkow et al., eds., *The Merck Manual*, 16$^{th}$ edition, Merck and Co., Rahway, N.J., 1992; Goodmanetna., eds., *Goodman and Cilman's The Pharmacological Basis of Therapeutics*, 10$^{th}$ edition, Pergamon Press, Inc., Elmsford, N.Y., (2001); *Avery's Drug Treatment: Principles and Practice of Clinical Pharmacology and Therapeutics*, 3rd edition, ADIS Press, LTD., Williams and Wilkins, Baltimore, MD (1987), Ebadi, Pharmacology, Little, Brown and Co., Boston, (1985); Osolci al., eds., *Remington's Pharmaceutical Sciences*, 18$^{th}$ edition, Mack Publishing Co., Easton, PA (1990); Katzung, *Basic and Clinical Pharmacology*, Appleton and Lange, Norwalk, CT (1992)).

The total dose required for each treatment can be administered by multiple doses or in a single dose over the course of the day, if desired. Generally, treatment is initiated with smaller dosages, which are less than the optimum dose of the compound. Thereafter, the dosage is increased by small increments until the optimum effect under the circumstances is reached. The diagnostic pharmaceutical compound or composition can be administered alone or in conjunction with other diagnostics and/or pharmaceuticals directed to the pathology, or directed to other symptoms of the pathology. The recipients of administration of compounds and/or compositions of the disclosure can be any vertebrate animal, such as mammals. Among mammals, the preferred recipients are mammals of the Orders Primate (including humans, apes and monkeys), Arteriodactyla (including horses, goats, cows, sheep, pigs), Rodenta (including mice, rats, rabbits, and hamsters), and Carnivora (including cats, and dogs). Among birds, the preferred recipients are turkeys, chickens and other members of the same order. The most preferred recipients are humans.

For topical applications, it is preferred to administer an effective amount of a pharmaceutical composition according to the disclosure to target area, e.g., skin surfaces, mucous membranes, and the like, which are adjacent to peripheral neurons which are to be treated. This amount will generally range from about 0.0001 mg to about 1 g of a compound of the disclosure per application, depending upon the area to be treated, whether the use is diagnostic, prophylactic or therapeutic, the severity of the symptoms, and the nature of the topical vehicle employed. A preferred topical preparation is an ointment, wherein about 0.001 to about 50 mg of active ingredient is used per cc of ointment base. The pharmaceutical composition can be formulated as transdermal compositions or transdermal delivery devices ("patches"). Such compositions include, for example, a backing, active compound reservoir, a control membrane, liner and contact adhesive. Such transdermal patches may be used to provide continuous pulsatile, or on demand delivery of the compounds of the present disclosure as desired.

The compositions of the disclosure can be formulated so as to provide quick, sustained or delayed release of the active ingredient after administration to the patient by employing procedures known in the art. Controlled release drug delivery systems include osmotic pump systems and dissolutional systems containing polymer-coated reservoirs or drug-polymer matrix formulations. Examples of controlled release systems are given in U.S. Pat. Nos. 3,845,770 and 4,326,525 and in P. J. Kuzma et al., *Regional Anesthesia* 22 (6): 543-551 (1997), all of which are incorporated herein by reference.

The compositions of the disclosure can also be delivered through intra-nasal drug delivery systems for local, systemic, and nose-to-brain medical therapies. Controlled Particle Dispersion (CPD)™ technology, traditional nasal spray bottles, inhalers or nebulizers are known by those skilled in the art to provide effective local and systemic delivery of drugs by targeting the olfactory region and paranasal sinuses.

The disclosure also relates to an intravaginal shell or core drug delivery device suitable for administration to the human or animal female. The device may be comprised of the active pharmaceutical ingredient in a polymer matrix, surrounded by a sheath, and capable of releasing the compound in a substantially zero order pattern on a daily basis similar to devises used to apply testosterone as described in PCT Published Patent Application No. WO 98/50016.

Current methods for ocular delivery include topical administration (eye drops), subconjunctival injections, periocular injections, intravitreal injections, surgical implants and iontophoresis (uses a small electrical current to transport ionized drugs into and through body tissues). Those skilled in the art would combine the best suited excipients with the compound for safe and effective intra-occular administration.

The most suitable route will depend on the nature and severity of the condition being treated. Those skilled in the art are also familiar with determining administration methods (e.g., oral, intravenous, inhalation, sub-cutaneous, rectal etc.), dosage forms, suitable pharmaceutical excipients and other matters relevant to the delivery of the compounds to a subject in need thereof.

Combination Therapy

The compounds of the disclosure may be usefully combined with one or more other compounds of the disclosure or one or more other therapeutic agent or as any combination thereof, in the treatment of sodium channel-mediated diseases and conditions. For example, a compound of this disclosure may be administered simultaneously, sequentially or separately in combination with other therapeutic agents, including, but not limited to: Acetazolamide (Diamox), Brivaracetam (Briviact), Cannabidiol (Epidiolex), Carbamazepine (Tegretol), Cenobamate (Xcopri), Clobazam (Frisium), Clonazepam (Klonopin), Eslicarbazepine acetate (Aptiom, Zebinix), Ethosuximide (Zarontin), Felbamate (Felbatol), Fenfluramine (Fintepla), Gabapentin (Neurontin), Lacosamide (Vimpat), Lamotrigine (Lamictal), Levetiracetam (Keppra), Oxcarbazepine (Trileptal), Perampanel (Fycompa), Phenobarbital (Luminal), Phenytoin (Dilantin), Pregabalin (Lyrica), Primidone, Retigabine (Ezogabine), Rufinamide (Banzel), Stiripentol (Diacomit), Sulthiame, Tiagabine (Gabitril), Topiramate (Topamax), Valproate (Depakote), Vigabatrin (Sabril), Zonisamide (Zonegran).

As used herein "combination" refers to any mixture or permutation of one or more compounds of the disclosure and one or more other compounds of the disclosure or one or more additional therapeutic agent. Unless the context makes clear otherwise, "combination" may include simultaneous or sequentially delivery of a compound of the disclosure with one or more therapeutic agents. Unless the context makes clear otherwise, "combination" may include dosage forms of a compound of the disclosure with another therapeutic agent. Unless the context makes clear otherwise, "combination" may include routes of administration of a compound of the disclosure with another therapeutic agent. Unless the context makes clear otherwise, "combination" may include formulations of a compound of the disclosure with another therapeutic agent. Dosage forms, routes of administration and pharmaceutical compositions include, but are not limited to, those described herein.

Kits-of-Parts

The present disclosure also provides kits that contain a pharmaceutical composition which includes one or more compounds of the disclosure. The kit also includes instructions for the use of the pharmaceutical composition for modulating the activity of sodium channels, for the treatment of a seizure disorder, such as epilepsy, as well as other utilities as disclosed herein. Preferably, a commercial package will contain one or more unit doses of the pharmaceutical composition. For example, such a unit dose may be an amount sufficient for the preparation of an intravenous injection. It will be evident to those of ordinary skill in the art that compounds which are light and/or air sensitive may require special packaging and/or formulation. For example, packaging may be used which is opaque to light, and/or sealed from contact with ambient air, and/or formulated with suitable coatings or excipients.

Preparation of the Compounds

The following Reaction Schemes illustrate methods to make compounds of the disclosure, i.e., compounds of formula (I), as described above in the Brief Summary, as stereoisomers, enantiomers or tautomers thereof or mixtures thereof; or pharmaceutically acceptable salts, solvates or prodrugs thereof.

It is also understood that one skilled in the art would be able to make the compounds of the disclosure by similar methods or by methods known to one skilled in the art. It is also understood that one skilled in the art would be able to make in a similar manner as described below other compounds of the disclosure not specifically illustrated below by using the appropriate starting components and modifying the parameters of the synthesis as needed. In general, starting components may be obtained from sources such as Sigma Aldrich, Alfa Aesar, Combi-Blocks, Oakwood Chemicals, Matrix Scientific, and TCI, etc. or synthesized according to sources known to those skilled in the art (see, e.g., M. B. Smith and J. March, *Advanced Organic Chemistry: Reactions, Mechanisms, and Structure,* 6th edition (Wiley, 2007)) or prepared as described herein.

It is also understood that in the following description, combinations of substituents and/or variables of the depicted formulae are permissible only if such contributions result in stable compounds.

It will also be appreciated by those skilled in the art that in the process described below the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (e.g., t-butyldimethylsilyl, t-butyldiphenylsilyl or trimethylsilyl), tetrahydropyranyl, benzyl, and the like. Suitable protecting groups for amino, include t-butoxycarbonyl, benzyloxycarbonyl, p-methoxybenzyl, trityl and the like.

Protecting groups may be added or removed in accordance with standard techniques, which are known to one skilled in the art and as described herein.

The use of protecting groups is described in detail in Greene, T. W. and P. G. M. Wuts, *Greene's Protective Groups in Organic Synthesis* (2006), 4$^{th}$ Ed., Wiley. The protecting group may also be a polymer resin such as a Wang resin or a 2-chlorotrityl-chloride resin.

It will also be appreciated by those skilled in the art, although such protected derivatives of compounds of this disclosure may not possess pharmacological activity as such, they may be administered to a mammal and thereafter metabolized in the body to form compounds of the disclosure which are pharmacologically active. Such derivatives may therefore be described as "prodrugs". All prodrugs of compounds of this disclosure are included within the scope of the disclosure.

The compounds of formula (I) may contain at least one asymmetric carbon atom and thus can exist as racemates, enantiomers and/or diastereoisomers. Specific enantiomers or diastereoisomers may be prepared by utilizing the appropriate chiral starting material or through the use of suitable asymmetric synthetic methods. Alternatively, diastereoisomeric mixtures or racemic mixtures of compounds of formula (I) may be resolved into their respective enantiomers or diastereoisomers. Methods for resolution of diastereoisomeric mixtures or racemic mixtures of the compounds of formula (I), as described herein, or intermediates prepared herein, are well known in the art (e.g., E. L. Eliel and S. H. Wilen, in *Stereochemistry of Organic Compounds*; John Wiley & Sons: New York, 1994; Chapter 7, and references cited therein). Suitable processes such as crystallization (e.g., preferential crystallization, preferential crystallization in the presence of additives), asymmetric transformation of racemates, chemical separation (e.g., formation and separation of diastereomers such as diastereomeric salt mixtures or the use of other resolving agents; separation via complexes and inclusion compounds), kinetic resolution (e.g., with titanium tartrate catalyst), enzymatic resolution (e.g., lipase mediated) and chromatographic separation (e.g., HPLC with chiral stationary phase and/or with simulated moving bed technology, or supercritical fluid chromatography and related techniques) are some of the examples that may be applied (see e.g., T. J. Ward, Analytical Chemistry, 2002, 2863-2872).

In general, compounds of formula (I) (e.g., as described above in the Brief Summary) are synthesized according to the following Reaction Schemes 1-22. Some substituents (e.g., $R^1$, $R^2$, etc.) in Reaction Schemes 1-22 are as defined in various embodiments throughout the disclosure. Other substituents (e.g., $Z^1$, $Z^2$, etc.) are as defined and described in the experimental examples disclosed herein.

Namely, in some embodiments, $Z^1$ is halo (e.g., iodo, chloro). In certain embodiments, $Z^2$ is halo (e.g., iodo, fluoro, or chloro). In some embodiments, $Z^2$ is iodo or chloro and $Z^{35}$ are, for example, but not limited to B(OH)$_2$, 4,4,5,5-tetramethyl-1,3,2λ2-dioxaborolane, or zinc bromide solution. In some embodiments, $Z^3$ is an appropriate coupling partner to $Z^1$ (e.g., a boronic acid or ester). In certain embodiments, $Z^4$ is is an appropriate coupling partner to $Z^2$ (e.g., a proton from the protonated version of $R^2$—for example, an optionally substituted pyrrolidine hydrochloride). In some embodiments, $Z^5$ is a suitable coupling partner, such as a boronic acid or ester. In some embodiments, PG is a suitable protecting group (e.g., Boc, a trimethylsilylether). In some embodiments, $x^1$, $x^2$, $x^3$, and $x^4$ are each independently carbon or nitrogen, depending on the desired product.
REACTION SCHEME 1
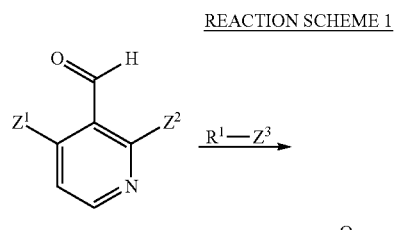
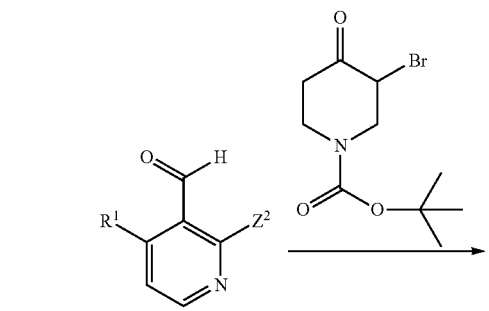
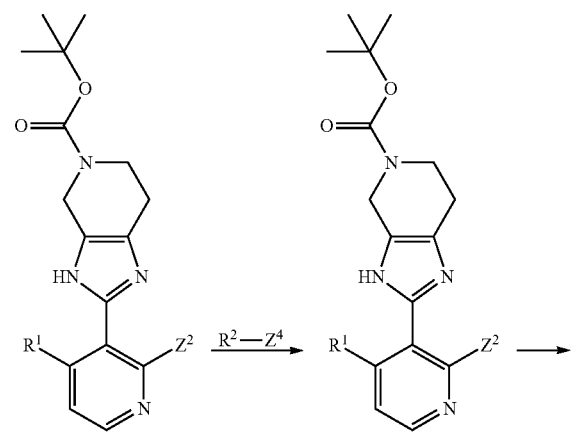
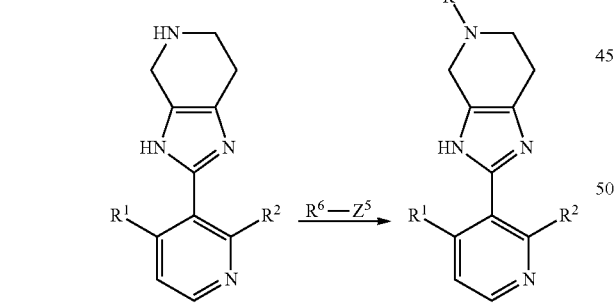
REACTION SCHEME 2
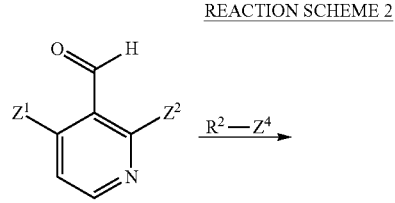
-continued
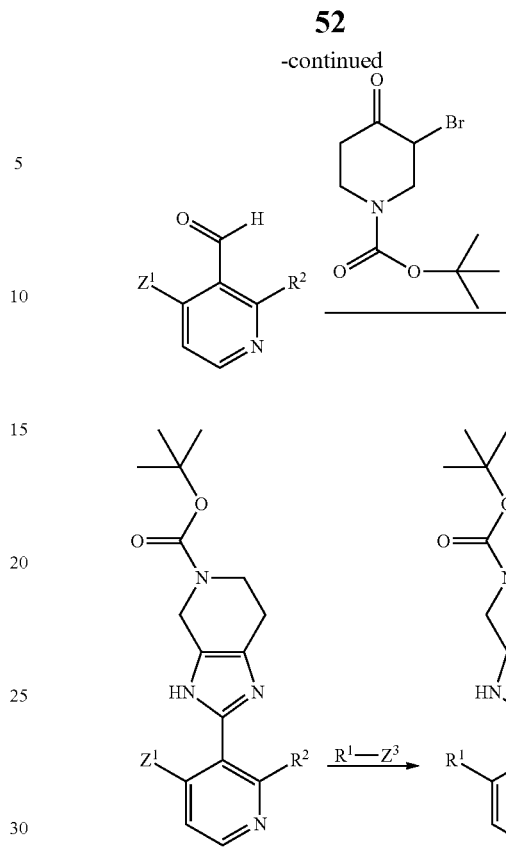
REACTION SCHEME 3
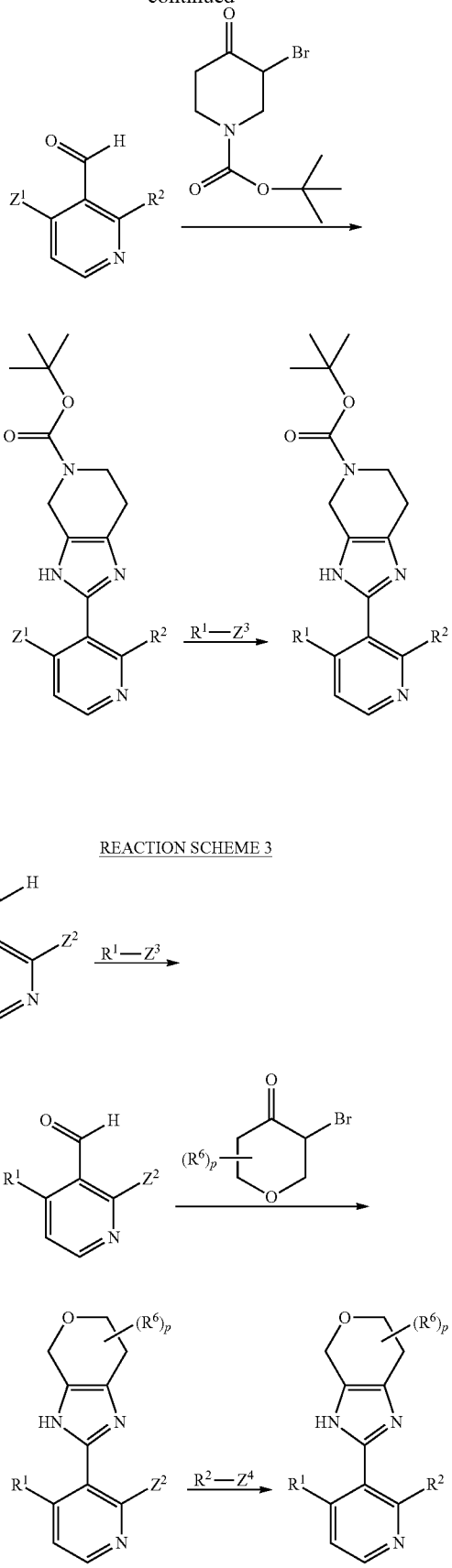

REACTION SCHEME 4
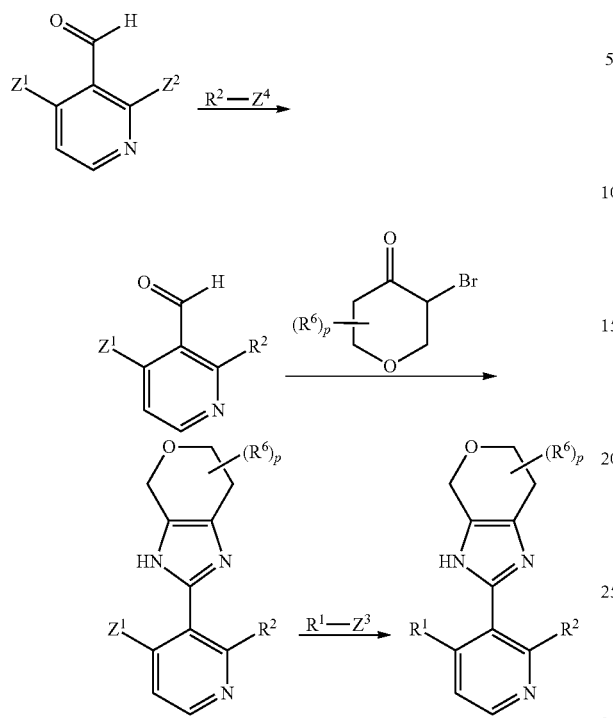
REACTION SCHEME 5
REACTION SCHEME 6
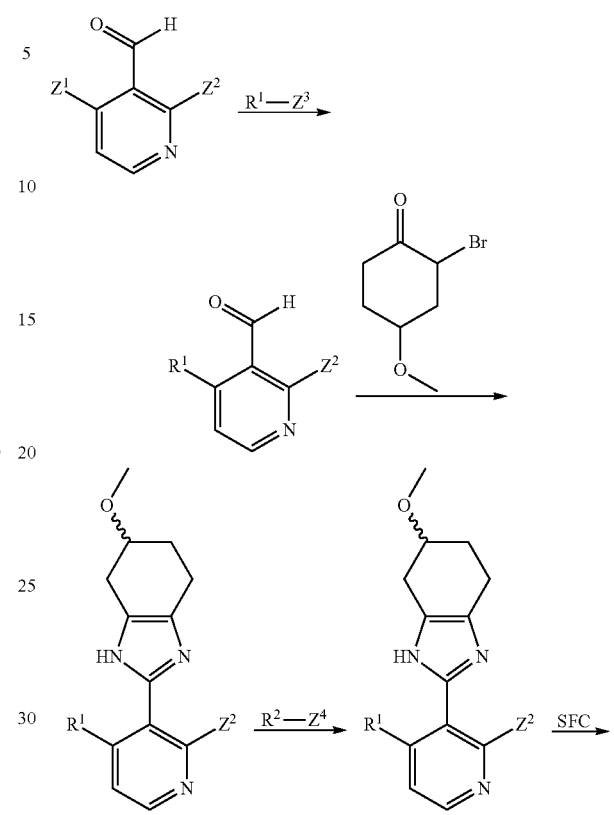
REACTION SCHEME 7
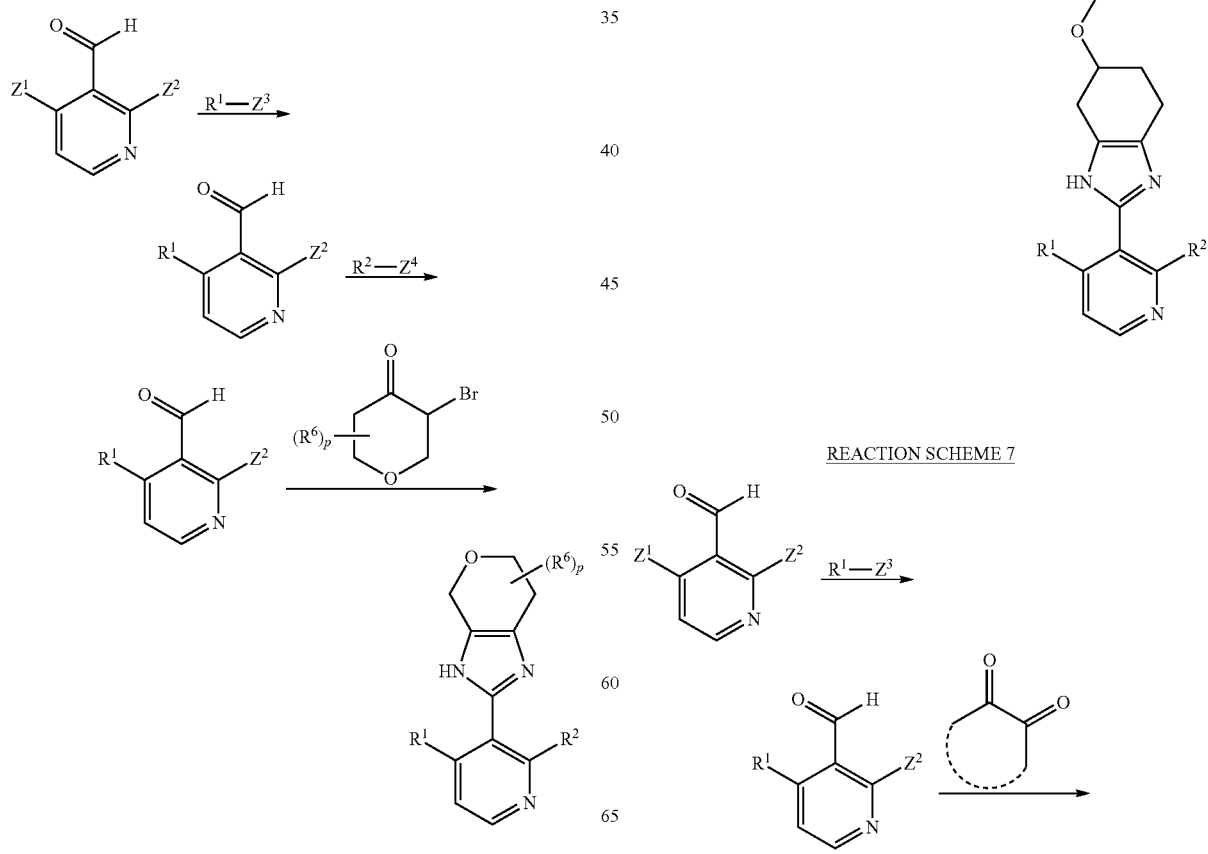

55
-continued
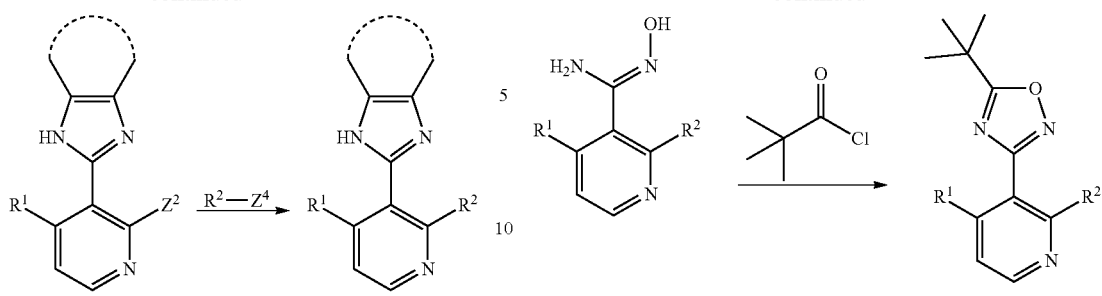
56
-continued
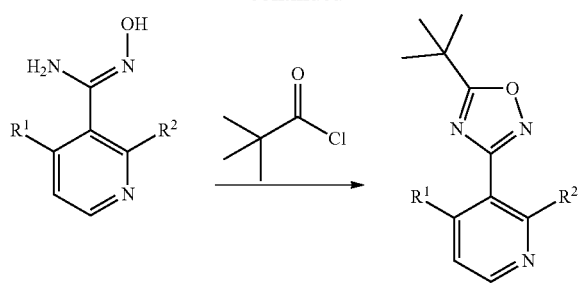
REACTION SCHEME 8
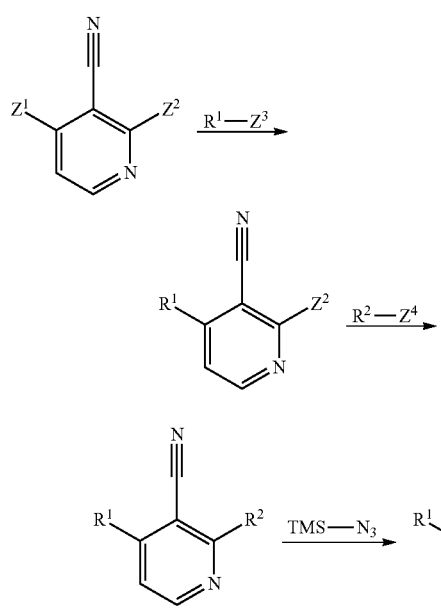
REACTION SCHEME 10
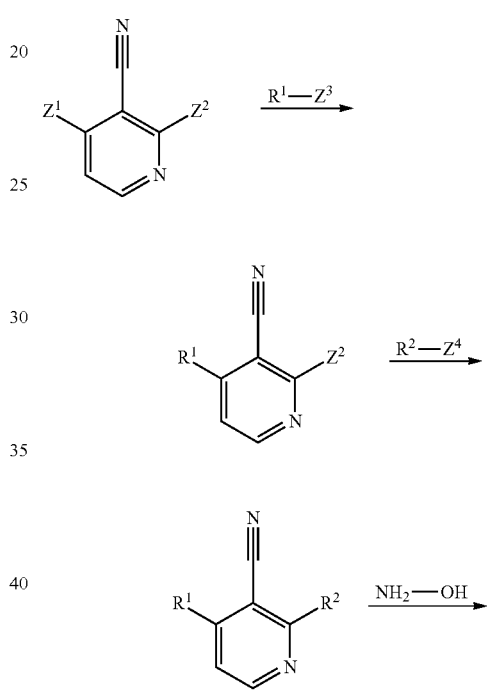
REACTION SCHEME 9
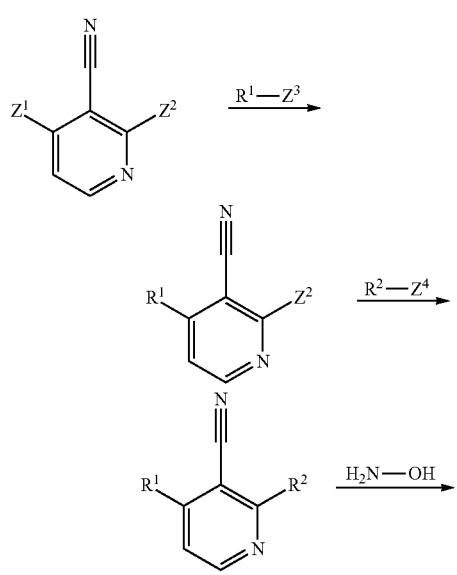
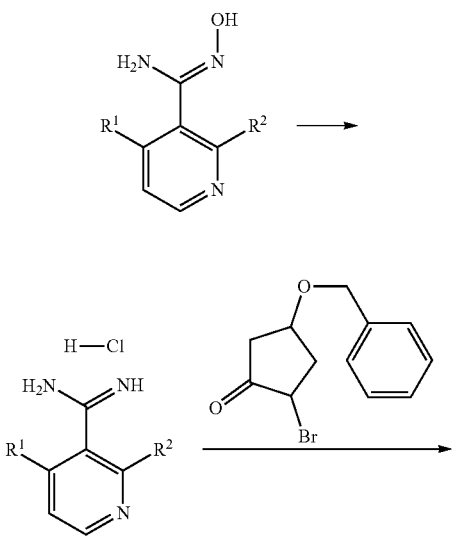

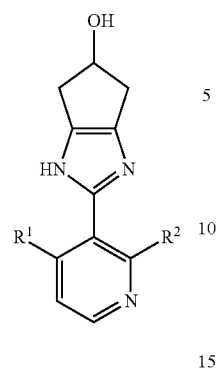
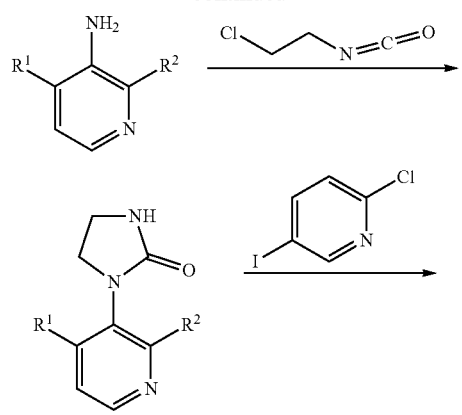
REACTION SCHEME 11
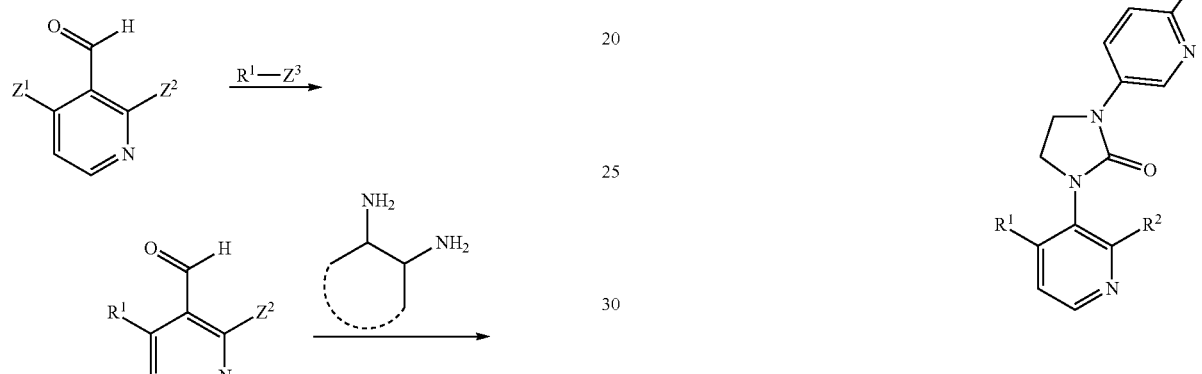
REACTION SCHEME 12
REACTION SCHEME 13
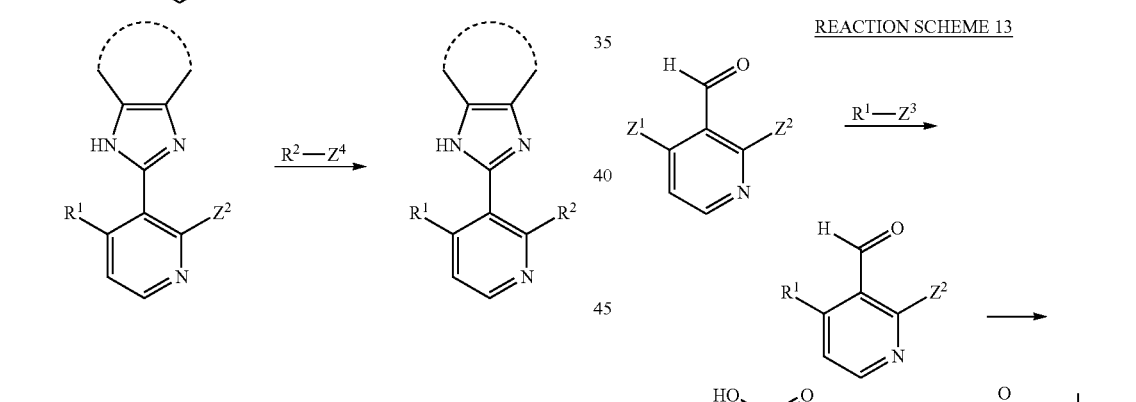
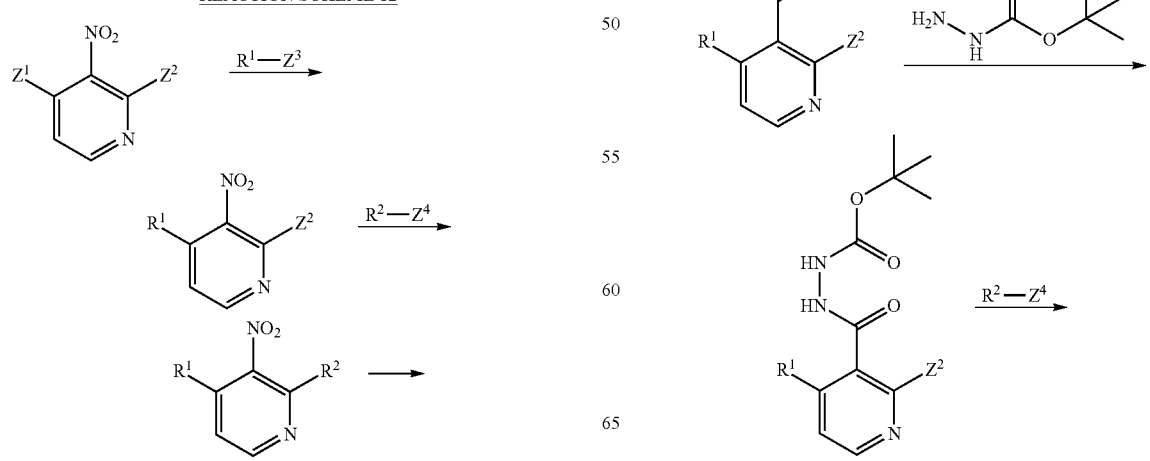

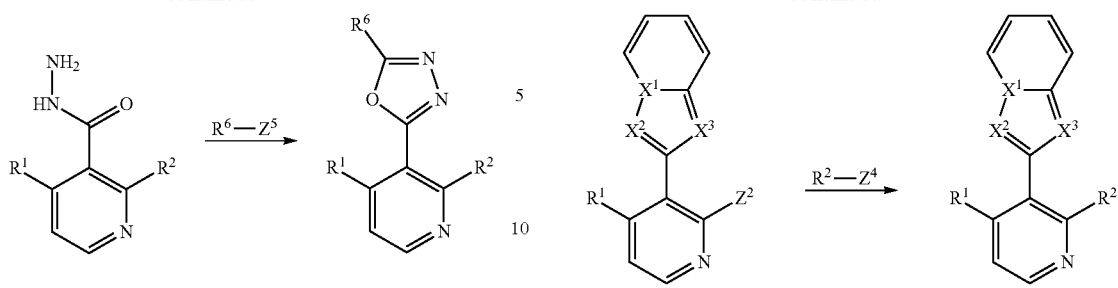
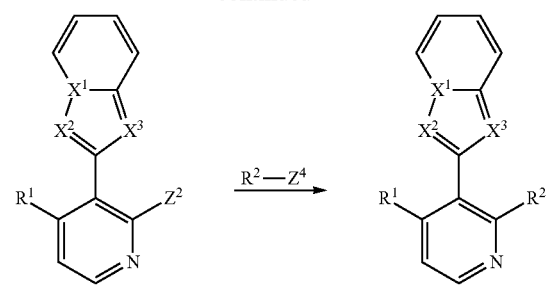
REACTION SCHEME 14
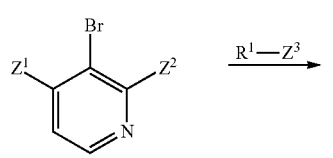
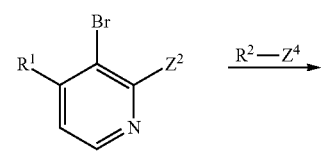
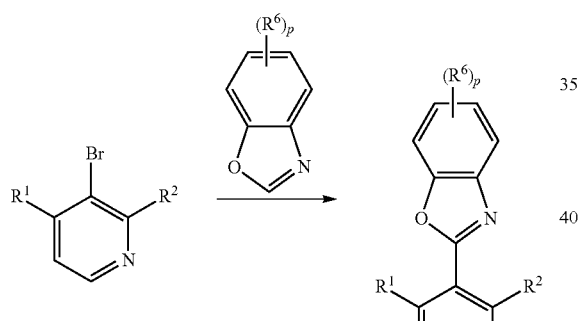
REACTION SCHEME 15
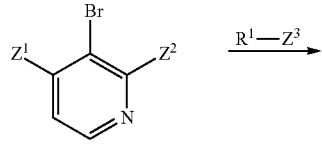
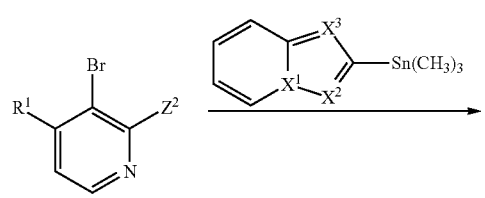
REACTION SCHEME 16
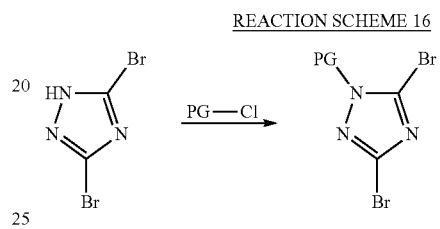
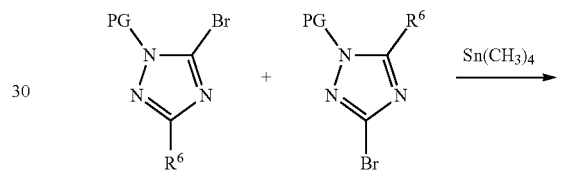
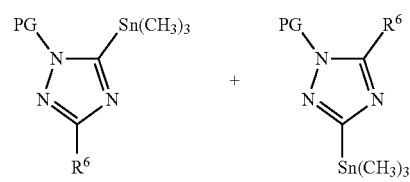
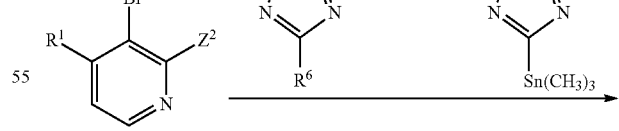
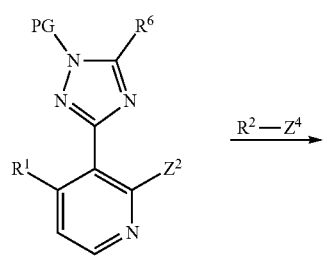

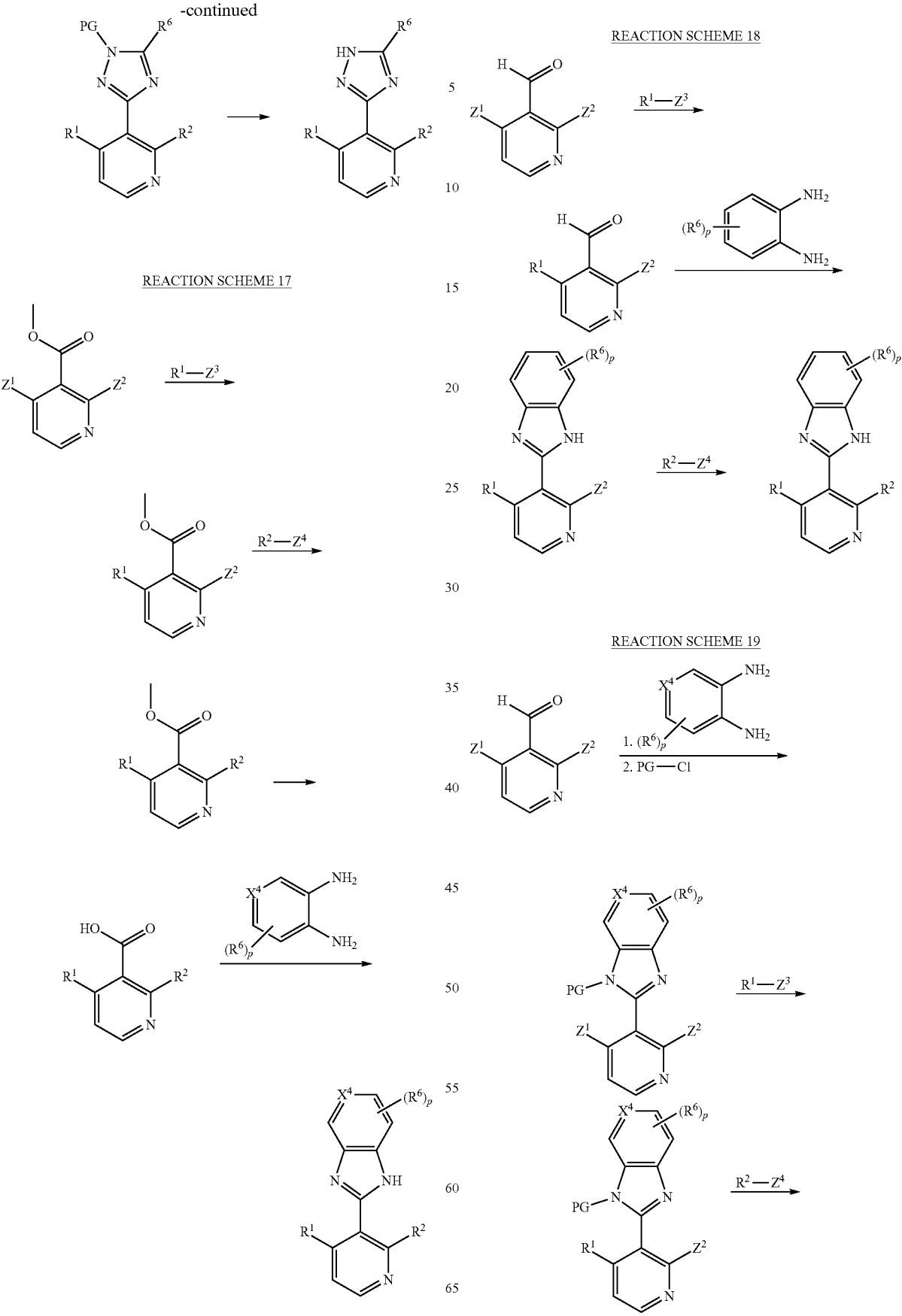

63
-continued
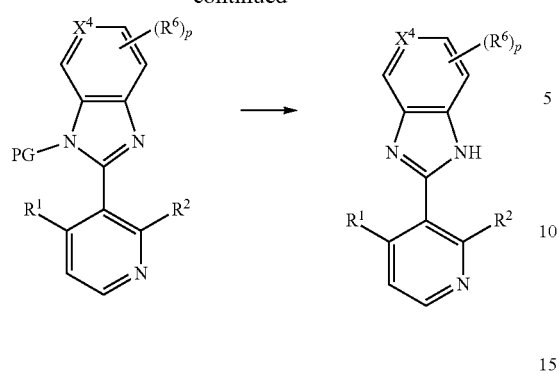
REACTION SCHEME 20
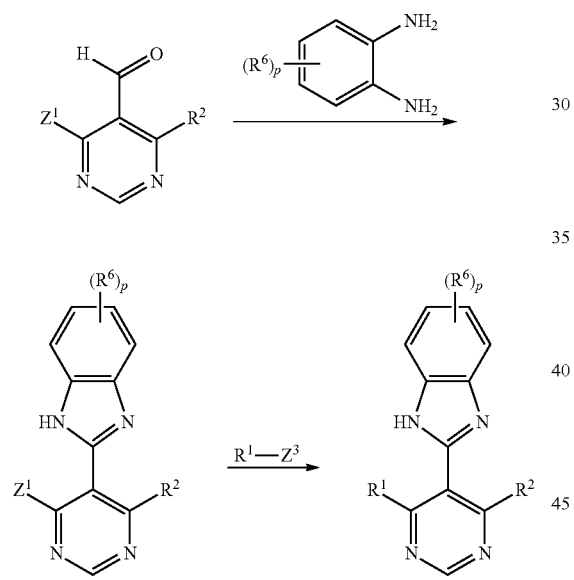
REACTION SCHEME 21
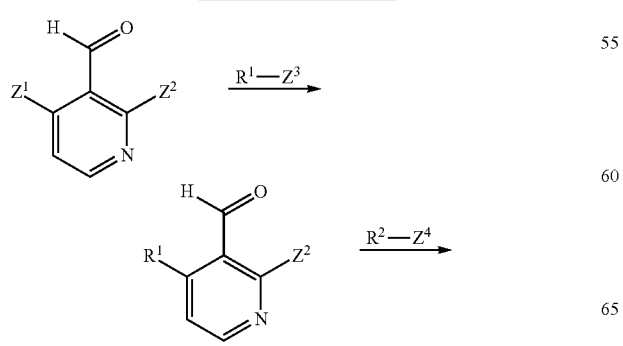
64
-continued
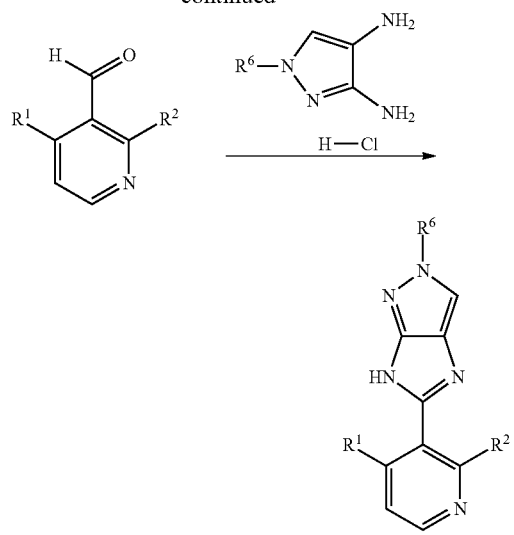
REACTION SCHEME 22
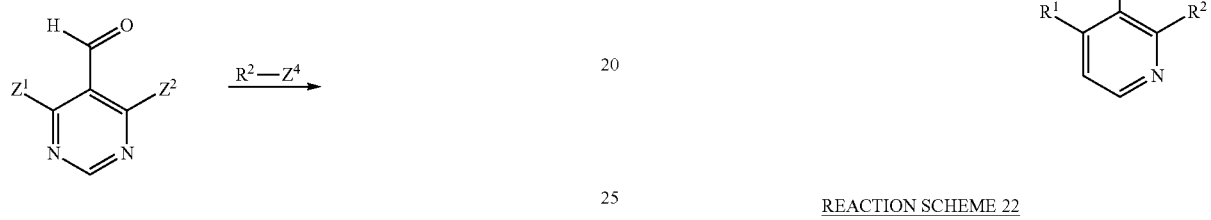
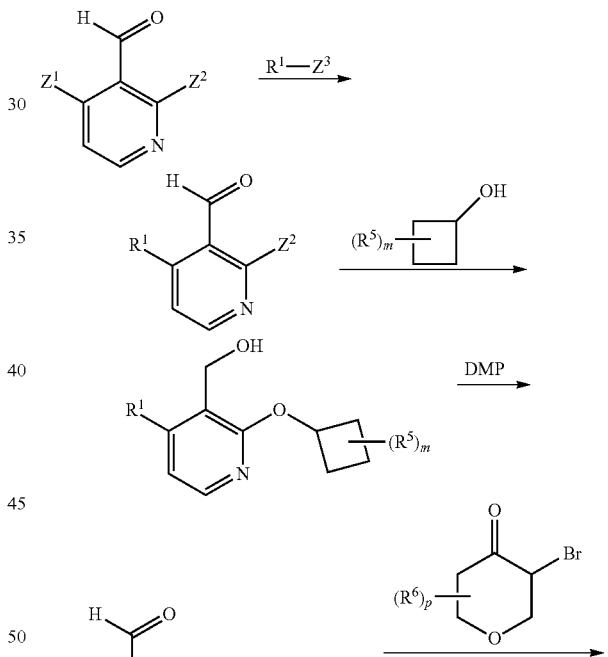
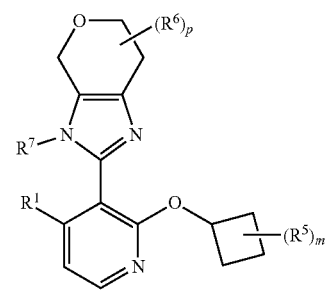

All of the compounds described below as being prepared which may exist in free base or acid form may be converted to their pharmaceutically acceptable salts by treatment with the appropriate inorganic or organic base or acid. Salts of the compounds prepared below may be converted to their free base or acid form by standard techniques. Furthermore, all compounds of the disclosure which contain an acid or an ester group can be converted to the corresponding ester or acid, respectively, by methods known to one skilled in the art or by methods described herein.

The present disclosure also relates to novel intermediate compounds as defined above, all salts, solvates and complexes thereof and all solvates and complexes of salts thereof as defined hereinbefore for compounds of formula (I). The disclosure includes all polymorphs of the aforementioned species and crystal habits thereof.

Embodiments disclosed herein are also meant to encompass all compounds being isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively.

Isotopically-labeled compounds can generally be prepared by conventional techniques known to those skilled in the art or by processes analogous to those described below and in the following Examples using an appropriate isotopically-labeled reagent in place of the non-labeled reagent previously employed.

The following Examples, which are directed to the synthesis of the compounds of the disclosure; and the following Biological Examples are provided as a guide to assist in the practice of the disclosure, and are not intended as a limitation on the scope of the disclosure.

In the Preparations and Examples below, unless otherwise indicated all temperatures are set forth in degrees Celsius. Commercially available reagents were purchased from suppliers such as Sigma Aldrich, Alfa Aesar, Combi-Blocks, Oakwood Chemicals, Matrix Scientific, and TCI, etc. and were used without further purification unless otherwise indicated. The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried. Yields were not optimized. Melting points were determined on a BQchi hot-stage apparatus and are uncorrected. $^{1}H$ NMR, $^{19}F$ and $^{13}C$ NMR data were obtained in deuterated $CDCl_3$, DMSO-$d_6$, $CD_3OD$, $CD_3CN$, or acetone-$d_6$ solvent solutions with chemical shifts (b) reported in parts-per-million (ppm) relative to trimethylsilane (TMS) or the residual non-deuterated solvent peaks as the reference standard. Data are reported as follows, if applicable: chemical shift, multiplicity, coupling constant in Hz, and number of protons, fluorine or carbon atoms. When peak multiplicities are reported, the following abbreviates are used: s (singlet), d (doublet), t (triplet), q (quartet), m (multiplet, br (broadened), dd (doublet of doublets), dt (doublet of triplets). Coupling constants, when given, are reported in Hz (Hertz).

Example 1

Synthesis of (S)-6-chloro-2-(4-(2,5-difluorophenyl)-2-(3-fluoropyrrolidin-1-yl)pyridin-3-yl)-1H-imidazo[4,5-c]pyridine

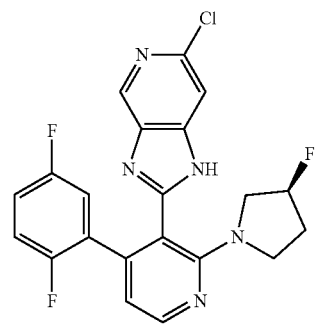 [SMILES: Fc1ccc(F)c(-c2ccnc(N3CC[C@H](F)C3)c2-c2nc3cnc(Cl)cc3[nH]2)c1]

Step 1. Preparation of (S)-6-chloro-2-(4-(2,5-difluorophenyl)-2-(3-fluoropyrrolidin-1-yl)pyridin-3-yl)-1H-imidazo[4,5-c]pyridine

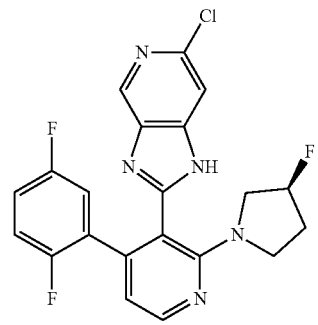 [SMILES: Fc1ccc(F)c(-c2ccnc(N3CC[C@H](F)C3)c2-c2nc3cnc(Cl)cc3[nH]2)c1]

A vial containing (S)-4-(2,5-difluorophenyl)-2-(3-fluoropyrrolidin-1-yl)nicotinic acid (0.117 g, 0.363 mmol) and phosphoryl trichloride (0.111 g, 0.727 mmol) was sealed and heated at 85° C. for 1 h. After cooling to ambient temperature and 6-chloropyridine-3,4-diamine (0.057 g, 0.40 mmol) in tetrahydrofuran (1 mL) was added. The vial was sealed and heated at 60° C. for 1 h. After cooling to ambient temperature, the reaction mixture was diluted with ethyl acetate (150 mL) and washed with saturated potassium carbonate (2×50 mL). The organic phase was dried over anhydrous sodium sulfate and filtered. The filtrate was concentrated in vacuo. The residue was dissolved in phosphoryl trichloride (6.6 g, 43 mmol) and heated at 85° C. for 6 h. After cooling to ambient temperature and concentrated in vacuo. The residue was diluted with ethyl acetate (150 mL) and washed with saturated potassium carbonate (2×50 mL). The organic phase was dried over anhydrous sodium sulfate, and filtered. The filtrate was concentrated in vacuo and the residue purified by column chromatography, eluting with a gradient of 15-100% of ethyl acetate in heptane, to afford the title compound as a colorless solid (0.031 g, 20% yield): $^{1}H$-NMR (300 MHz; DMSO-$d_6$) δ 8.65 (dd, J=3.0, 0.6 Hz, 1H), 8.37 (s, 1H), 7.60 (s, 1H), 7.16-7.07 (m, 2H), 6.99-6.88 (m, 1H), 6.79-6.78 (m, 1H), 5.29-5.10 (m, 1H), 3.34-3.28 (m, 1H), 3.24-3.15 (m, 3H), 2.08-2.01 (m, 1H), 1.94-1.75 (m, 1H); MS (ESI+) 430.0 m/z (M+1), 432.0 m/z (M+1).

Example 2

Synthesis of 2-(4-(2-fluorophenyl)-2-(pyrrolidin-1-yl)pyridine-3-yl)-1H-imidazo[4,5-b]pyridine

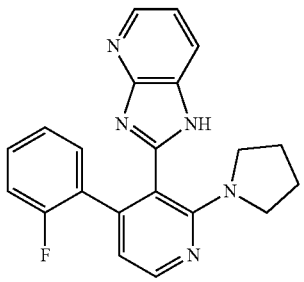

Step 1. Preparation of 2-(4-(2-fluorophenyl)-2-(pyrrolidin-1-yl)pyridine-3-yl)-1H-imidazo[4,5-b]pyridine

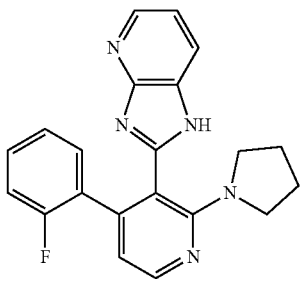 [SMILES: Fc1ccccc1-c1ccnc(N2CCCC2)c1-c1nc2ncccc2[nH]1]

A mixture of 4-(2-fluorophenyl)-2-(pyrrolidin-1-yl)nicotinic acid (0.26 g, 0.90 mmol), pyridine-1,2-diamine (0.20 g, 1.8 mmol), and 2-chloro-1-methylpyridin-1-ium iodide (0.343 g, 1.34 mmol) was dissolved in anhydrous tetrahydrofuran (20 mL). A reflux condenser was attached and the reaction mixture was heated to reflux for 1 h. To the hot reaction mixture was added N-ethyl-N-isopropylpropan-2-amine (0.447 g, 3.60 mmol) and the reaction mixture was heated to reflux for 1 h. After cooling to ambient temperature, the reaction was diluted with ethyl acetate (250 mL). The organic layer was washed with saturated sodium bicarbonate solution (2×100 mL), and brine (100 mL). The organic layer was dried over anhydrous magnesium sulfate, filtered, and concentrated in vacuo. The residue was dissolved in phosphoryl trichloride (5 mL) and heated to reflux for 18 h. After cooling to ambient temperature, the reaction mixture was concentrated in vacuo. The residue was dissolved in ethyl acetate (200 mL) and the organic layer was washed with 1M sodium hydroxide solution (2×50 mL), saturated ammonium chloride (2×100 mL), and brine (100 mL). The organic layer was dried over anhydrous magnesium sulfate, filtered, and concentrated in vacuo. Purification of the residue by column chromatography, eluting with a gradient of 20-100% of ethyl acetate in heptane, afforded the title compound as a colorless solid (0.034 g, 11% yield):

$^1$H-NMR (300 MHz; DMSO-$d_6$) δ 8.30-8.27 (m, 1H), 8.27-8.22 (m, 1H), 7.88-7.86 (m, 1H), 7.24-7.13 (m, 2H), 7.11-7.02 (m, 2H), 6.94 (td, J=7.4, 1.2 Hz, 1H), 6.68-6.66 (m, 1H), 3.08-2.98 (m, 4H), 1.73-1.64 (m, 4H), missing one NH-peak; MS (ESI+) 360.2 m/z (M+1).

Example 3

Synthesis of 2-(4-(2-fluorophenyl)-2-(pyrrolidin-1-yl)pyridin-3-yl)-1H-benzo[d]imidazole

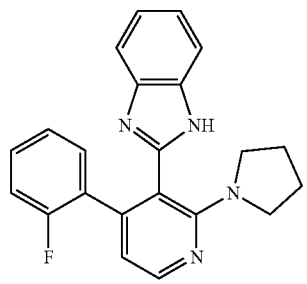 [SMILES: Fc1ccccc1-c1ccnc(N2CCCC2)c1-c1nc2ccccc2[nH]1]

Step 1. Preparation of Methyl 2-chloro-4-(2-fluorophenyl)nicotinate

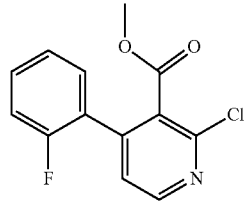 [SMILES: COC(=O)c1c(-c2ccccc2F)ccnc1Cl]

A mixture of methyl 2-chloro-4-iodo-pyridine-3-carboxylate (8.00 g, 26.9 mmol), (2-fluorophenyl)boronic acid (4.14 g, 29.6 mmol), potassium carbonate (9.29 g, 67.2 mmol), and [1,1'-bis(diphenylphosphino)ferrocene]dichloropalladium(II) complex with dichloromethane (1.97 g, 2.69 mmol) was dissolved in 1,4-dioxane (100 mL) and water (20 mL). The mixture was sparged with nitrogen for 10 min and heated at 80° C. for 12 h under nitrogen. After cooling to ambient temperature, the reaction mixture was filtered and concentrated in vacuo. Purification of the residue by column chromatography, eluting with a gradient of 0-10% of ethyl acetate in petroleum ether, afforded the title compound as a colorless solid (7.0 g, 98% yield): $^1$H-NMR (400 MHz; CDCl$_3$) δ 8.51 (d, J=5.2 Hz, 1H), 7.47-7.45 (m, 1H), 7.34-7.31 (m, 2H), 7.25-7.20 (m, 2H), 3.74 (s, 3H); MS (ES+) m/z 266 (M+1).

Step 2. Preparation of Methyl 4-(2-fluorophenyl)-2-(pyrrolidin-1-yl)nicotinate

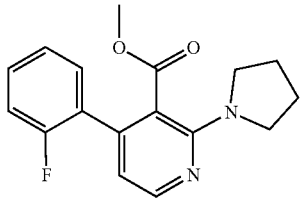 [SMILES: COC(=O)c1c(-c2ccccc2F)ccnc1N1CCCC1]

A mixture of methyl 2-chloro-4-(2-fluorophenyl)nicotinate (7.0 g, 26 mmol), pyrrolidine (3.75 g, 52.7 mmol), and potassium carbonate (10.9 g, 79.0 mmol) in N,N-dimethylformamide (70 mL) was heated at 100° C. for 12 h. After cooling to ambient temperature, water (200 mL) was added, and the mixture was extracted with ethyl acetate (3×200 mL). The combined organic fractions were washed with brine (3×200 mL). The organic phase was dried over anhydrous sodium sulfate and filtered. The filtrate was concentrated in vacuo and the residue purified by column chromatography, eluting with a gradient of 0-15% of ethyl acetate in petroleum ether, to afford the title compound as a colorless solid (5.5 g, 70% yield): $^1$H-NMR (400 MHz; CDCl$_3$) δ 8.24 (d, J=5.2 Hz, 1H), 7.40-7.32 (m, 1H), 7.24-7.10 (m, 3H), 6.53 (d, J=4.8 Hz, 1H), 3.51 (s, 3H), 3.49-3.46 (m, 4H), 2.02-1.90 (m, 4H); MS (ES+) m/z 301 (M+1).

Step 3. Preparation of 4-(2-fluorophenyl)-2-(pyrrolidin-1-yl)nicotinic Acid

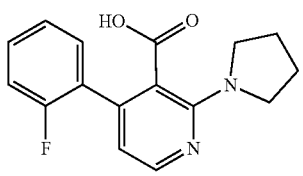 [SMILES: O=C(O)c1c(-c2ccccc2F)ccnc1N1CCCC1]

To a mixture of methyl 4-(2-fluorophenyl)-2-pyrrolidin-1-yl-pyridine-3-carboxylate (3.00 g, 9.99 mmol), water (20 mL), tetrahydrofuran (10 mL), and methanol (10 mL) was added sodium hydroxide (6.60 g, 165 mmol). A reflux condenser was added and the reaction mixture was stirred at 100° C. for 72 h. After cooling to ambient temperature, the aqueous phase was extracted with ethyl acetate (3×50 mL). The combined organic layers were concentrated in vacuo. The residue was triturated with ethyl acetate (50 mL) and filtered to afford the title compound as a colorless solid (2.5 g, 86% yield): $^1$H-NMR (300 MHz; DMSO-d$_6$) δ 7.82 (d, J=5.0 Hz, 1H), 7.47 (dt, J=1.8, 7.6 Hz, 1H), 7.34-7.25 (m, 1H), 7.19-7.04 (m, 2H), 6.26 (dd, J=1.8, 5.0 Hz, 1H), 3.61-3.52 (m, 4H), 1.86-1.76 (m, 4H); MS (ES+) m/z 287 (M+1).

Step 4. Preparation of 2-(4-(2-fluorophenyl)-2-(pyrrolidin-1-yl)pyridin-3-yl)-1H-benzo[d]imidazole

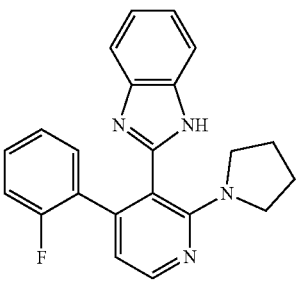

A mixture of 4-(2-fluorophenyl)-2-(pyrrolidin-1-yl)nicotinic acid (0.540 g, 1.89 mmol), benzene-1,2-diamine (0.247 g, 2.27 mmol), and 2-chloro-1-methylpyridin-1-ium iodide (0.724 g, 2.83 mmol) was dissolved in anhydrous tetrahydrofuran (40 mL). A reflux condenser was attached and the reaction mixture was heated to reflux for 1 h. To the hot reaction mixture was added N-ethyl-N-isopropylpropan-2-amine (0.704 g, 5.67 mmol) and the reaction mixture was heated to reflux for 1 h. After cooling to ambient temperature, the reaction mixture was diluted with ethyl acetate (250 mL). The organic phase was washed with saturated ammonium chloride (2×100 mL) and brine (100 mL). The organic phase was dried over anhydrous magnesium sulfate and filtered. The filtrate was concentrated in vacuo and the residue was dissolved in phosphoryl trichloride (10 mL) and heated to reflux for 18 h. After cooling to ambient temperature, the reaction mixture was concentrated in vacuo and dissolved with ethyl acetate (200 mL). The organic layer was washed with 1M sodium hydroxide solution (2×50 mL), saturated ammonium chloride (2×100 mL), and brine (100 mL). The organic layer was dried over anhydrous magnesium sulfate, filtered, and concentrated in vacuo. Purification of the residue by column chromatography, eluting with a gradient of 20-100% of ethyl acetate in heptane, afforded the title compound as a colorless solid (0.083 g, 12% yield): $^1$H-NMR (300 MHz; DMSO-d$_6$) δ 12.53-12.41 (m, 1H), 8.26 (d, J=5.0 Hz, 1H), 7.51-7.33 (m, 2H), 7.23-7.15 (m, 1H), 7.12-7.01 (m, 4H), 6.95-6.89 (m, 1H), 6.65-6.63 (m, 1H), 3.05-2.94 (m, 4H), 1.71-1.61 (m, 4H); MS (ESI+) m/z 359.2 (M+1).

Example 4

Synthesis of 5-(4-(2-fluorophenyl)-2-(pyrrolidin-1-yl)pyridin-3-yl)-1,3,4-oxadiazol-2-amine

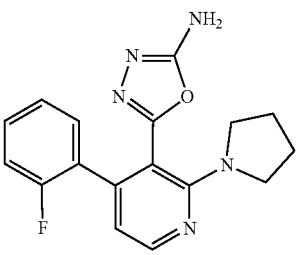 [SMILES: Nc1nnc(-c2c(-c3ccccc3F)ccnc2N2CCCC2)o1]

Step 1. Preparation of 2-chloro-4-(2-fluorophenyl)nicotinaldehyde

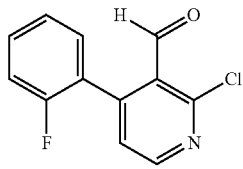 [SMILES: O=Cc1c(-c2ccccc2F)ccnc1Cl]

A mixture of 2-chloro-4-iodonicotinaldehyde (6.95 g, 26.0 mmol), 1,4-dioxane (86 mL), and water (10 mL) was sparged with nitrogen for 10 min. The flask was charged with 2-fluorophenylboronic acid (4.0 g, 29 mmol), potassium carbonate (9.0 g, 65 mmol), and [1,1'-bis(diphenylphosphino)ferrocene]dichloropalladium(II), complex with dichloromethane (2.22 g, 2.60 mmol), and sparged for 2 min. The reaction mixture was stirred at 80° C. for 2 h. After cooling to ambient temperature, the reaction mixture was diluted with ethyl acetate (300 mL). The organic layer was washed with saturated ammonium chloride (2×100 mL) and brine (150 mL). The organic solution was dried over anhydrous magnesium sulfate, filtered, and concentrated in vacuo. Purification of the residue by column chromatography, eluting with 0-30% ethyl acetate in heptane, afforded the title compound as a colorless oil that solidified upon standing (5.82 g, 95% yield): MS (ESI+) m/z 235.0 (M+1), 237.0 (M+1).

Step 2. Preparation of 2-chloro-4-(2-fluorophenyl)nicotinic Acid

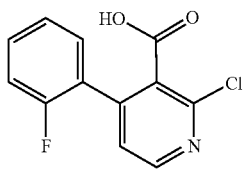 [SMILES: O=C(O)c1c(-c2ccccc2F)ccnc1Cl]

A mixture of 2-chloro-4-(2-fluorophenyl)nicotinaldehyde (5.0 g, 21 mmol), 1,4-dioxane (185 mL), and water (36 mL) was cooled in an ice/water bath. To this solution was added potassium permanganate (5.02 g, 31.8 mmol). The solution was warmed to ambient temperature and stirred for 4 h. The pH of the solution was adjusted to >12 with 5M sodium hydroxide solution (5 mL), and filtered. The pH of the filtrate was adjusted to <5 using concentrated hydrochloric acid (8 mL). The aqueous mixture was diluted with ethyl acetate (300 mL) and separated. The organic layer was washed with brine (2×100 mL). The organic solution was dried over magnesium sulfate, filtered, and concentrated in vacuo. The colorless oil was used without further purification (4.8 g, 90% yield): MS (ESI+) m/z 252.0 (M+1), 254.0 (M+1).

Step 3. Preparation of Tert-Butyl 2-(2-chloro-4-(2-fluorophenyl)nicotinoyl)hydrazine-1-carboxylate

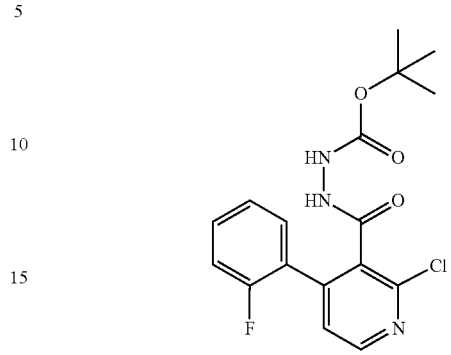

To a mixture of 2-chloro-4-(2-fluorophenyl)nicotinic acid (6.0 g, 24 mmol), and dichloromethane (240 mL) was added oxalyl chloride (3.7 g, 29 mmol), and 5 drops of N,N-dimethylformamide. The solution was stirred at ambient temperature for 2 h. The reaction mixture was cooled in an ice/water bath and a mixture of dichloromethane (50 mL), tert-butyl hydrazinecarboxylate (6.3 g, 48 mmol), and N-ethyl-N-isopropylpropan-2-amine (9.3 g, 72 mmol), was added dropwise over 30 min. The reaction mixture was warmed to ambient temperature and stirred for 1 h. The reaction mixture was diluted with ethyl acetate (300 mL). The organic layer was washed with saturated ammonium chloride (2×100 mL) and brine (100 mL). The organic layer was dried over magnesium sulfate, filtered, and concentrated in vacuo. Purification of the residue by column chromatography, eluting with 5-100% ethyl acetate in heptane, afforded the title compound as a colorless oil (8.0 g, 91% yield): MS (ESI+) m/z 366.0 (M+1), 368.0 (M+1).

Step 4. Preparation of 2-chloro-4-(2-fluorophenyl)nicotinohydrazide

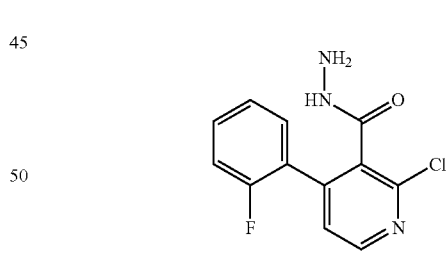

Trifluoroacetic acid (40 mL) was added to a flask charged with solid tert-butyl 2-(2-chloro-4-(2-fluorophenyl)nicotinoyl)hydrazine-1-carboxylate (8.0 g, 22 mmol). The solution was stirred for 8 h. The reaction mixture was concentrated in vacuo, and the residue was dissolved in ethyl acetate (500 mL). The organic solution was washed with saturated potassium carbonate solution (3×50 mL) and dried over magnesium sulfate. The suspension was filtered, and the filtrate was concentrated in vacuo. The title compound was obtained as a colorless oil and used as is (4.9 g, 84% yield): MS (ESI+) m/z 266.0 (M+1), 268.0 (M+1).

Step 5. Preparation of 5-(2-chloro-4-(2-fluorophenyl)pyridin-3-yl)-1,3,4-oxadiazol-2-amine

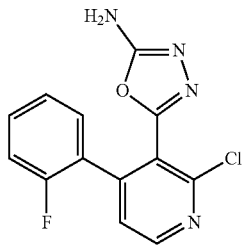 [SMILES: Nc1nnc(-c2c(-c3ccccc3F)ccnc2Cl)o1]

To a 1,4-dioxane solution (17 mL) of 2-chloro-4-(2-fluorophenyl)nicotinohydrazide (3.0 g, 8.0 mmol) was added sodium bicarbonate (1.47 g, 17.6 mmol) dissolved in water (13 mL) at ambient temperature. The reaction mixture was stirred at ambient temperature for 5 minutes before cyanic bromide (0.84 g, 8.0 mmol) was added. The solution was stirred at 65° C. for 2 h. After cooling to ambient temperature, the reaction mixture was diluted with ethyl acetate (200 mL). The organic layer was separated and washed with saturated sodium bicarbonate solution (100 mL) and brine (100 mL). The organic layer was dried over anhydrous magnesium sulfate, filtered, and concentrated in vacuo. The crude solid was suspended in dichloromethane (20 mL) and filtered, to afford the title compound as a beige solid. The filtrate was concentrated in vacuo, and purified by column chromatography eluting with a gradient of 0 to 100% ethyl acetate in heptane, to afford the title compound as a beige solid (1.0 g, 43% yield): MS (ESI+) m/z 291.0 (M+1), 293.0 (M+1).

Step 6. Preparation of 5-(4-(2-fluorophenyl)-2-(pyrrolidin-1-yl)pyridin-3-yl)-1,3,4-oxadiazol-2-amine

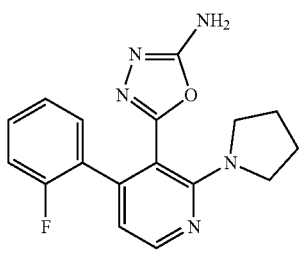 [SMILES: Nc1nnc(-c2c(-c3ccccc3F)ccnc2N2CCCC2)o1]

To a mixture of 5-(2-chloro-4-(2-fluorophenyl)pyridin-3-yl)-1,3,4-oxadiazol-2-amine (0.93 g, 3.2 mmol) in anhydrous dimethyl sulfoxide (16 mL) was added pyrrolidine (0.46 g, 6.4 mmol) and potassium carbonate (1.3 g, 9.6 mmol). The reaction mixture was stirred at 100° C. for 1 h. The resulting mixture was cooled to ambient temperature and diluted with ethyl acetate (200 mL). The organic layer was washed with saturated ammonium chloride (100 mL), water (100 mL), and brine (100 mL). The organic layer was dried over anhydrous magnesium sulfate, filtered, and concentrated in vacuo to afford the title compound as a beige solid (0.34 g, 33% yield): $^1$H-NMR (300 MHz; DMSO-$d_6$) δ 8.28 (d, J=5.0 Hz, 1H), 7.43-7.35 (m, 1H), 7.24-7.09 (m, 3H), 6.95 (s, 2H), 6.64 (dd, J=5.0, 0.7 Hz, 1H), 3.20-3.14 (m, 4H), 1.84-1.79 (m, 4H); MS (ESI+) m/z 326.2 (M+1).

Example 5

Synthesis of 4-(2-fluorophenyl)-3-(5-isobutyl-4,5-dihydro-1H-imidazol-2-yl)-2-(pyrrolidin-1-yl)pyridine

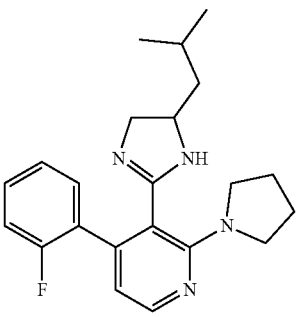 [SMILES: CC(C)CC1CN=C(c2c(-c3ccccc3F)ccnc2N2CCCC2)N1]

Step 1. Preparation of 4-(2-fluorophenyl)-3-(5-isobutyl-4,5-dihydro-1H-imidazol-2-yl)-2-(pyrrolidin-1-yl)pyridine

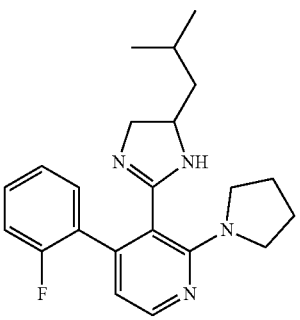 [SMILES: CC(C)CC1CN=C(c2c(-c3ccccc3F)ccnc2N2CCCC2)N1]

A mixture of 4-(2-fluorophenyl)-2-(pyrrolidin-1-yl)nicotinic acid (0.352 g, 1.23 mmol), 4-methylpentane-1,2-diamine (0.214 g, 1.85 mmol), and 2-chloro-1-methylpyridin-1-ium iodide (0.473 g, 1.85 mmol) was dissolved in anhydrous tetrahydrofuran (25 mL). A reflux condenser was added and the reaction mixture was heated to reflux for 1 h. To the hot reaction mixture was added N-ethyl-N-isopropylpropan-2-amine (0.459 g, 3.69 mmol) and the reaction mixture was heated to reflux for 1 h. After cooling to ambient temperature, the reaction mixture was diluted with ethyl acetate (250 mL). The organic layer was washed with saturated sodium bicarbonate solution (2×100 mL) and brine (brine (100 mL). The organic layer was dried over anhydrous magnesium sulfate, filtered, and concentrated in vacuo. The residue was dissolved in phosphoryl trichloride (5 mL) and heated to reflux for 18 h. After cooling to ambient temperature, the reaction mixture was concentrated in vacuo. The residue was diluted with ethyl acetate (200 mL) and the organic layer was washed with 1M sodium hydroxide solution (2×50 mL) and brine (brine (100 mL). The organic layer was dried over anhydrous magnesium sulfate, filtered, and concentrated in vacuo. Purification of the residue by preparative reverse phase HPLC, using acetonitrile in water containing 0.5% of formic acid as eluent, afforded the title compound as a colorless solid (0.034 g, 11% yield): $^1$H-NMR (300 MHz; DMSO-$d_6$) δ 8.29 (s, 1H), 8.23 (d, J=5.0 Hz, 1H), 7.51-7.43 (m, 1H), 7.34-7.20 (m, 3H), 6.59-6.57 (m, 1H), 3.97-3.85 (m, 1H), 3.77-3.70 (m, 1H), 3.55-3.44 (m, 4H), 3.09-3.02 (m, 1H), 1.93-1.82 (m, 4H), 1.42-1.33 (m, 1H), 0.89-0.82 (m, 2H), 0.74 (t, J=9.5 Hz, 6H); MS (ESI+) m/z 367.1 (M+1).

Example 6

Synthesis of 2-(4-(2-chlorophenyl)-2-(pyrrolidin-1-yl)pyridin-3-yl)-1H-benzo[d]imidazole

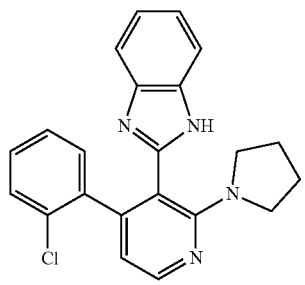 [SMILES: Clc1ccccc1-c1ccnc(N2CCCC2)c1-c1nc2ccccc2[nH]1]

Step 1. Preparation of 2-chloro-4-(2-chlorophenyl)nicotinaldehyde

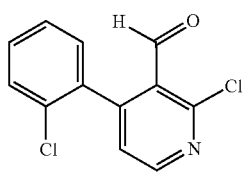

A mixture of 2-chloro-4-iodonicotinaldehyde (5.00 g, 18.7 mmol), 1,4-dioxane (62 mL), and water (7 mL) was sparged with nitrogen for 10 min. To the mixture was added 2-chlorophenylboronic acid (3.22 g, 20.6 mmol), potassium carbonate (6.45 g, 46.7 mmol), and [1,1'-bis(diphenylphosphino)ferrocene]dichloropalladium(II)] complex with dichloromethane (1.60 g, 1.87 mmol) The reaction mixture was heated to reflux for 2 h. After cooling to ambient temperature, the reaction mixture was diluted with ethyl acetate (250 mL). The organic layer was washed with saturated ammonium chloride (2×100 mL) and brine (100 mL). The organic layer was dried over anhydrous magnesium sulfate, filtered, and concentrated in vacuo. Purification of the residue by column chromatography, eluting with a gradient of 5-50% of ethyl acetate in heptane, afforded the title compound as a yellow solid (3.05 g, 65% yield): MS (ESI+) m/z 252 (M+1), 254 (M+1).

Step 2. Preparation of 2-(2-chloro-4-(2-chlorophenyl)pyridin-3-yl)-1H-benzo[d]imidazole

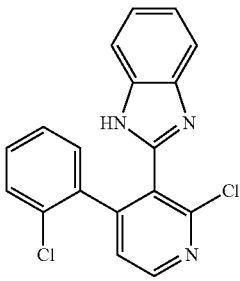

A mixture of 2-chloro-4-(2-chlorophenyl)nicotinaldehyde (3.05 g, 12.6 mmol), methanol (126 mL), and benzene-1,2-diamine (1.50 g, 13.9 mmol) was heated to reflux for 18 h. After cooling to ambient temperature, the reaction mixture was concentrated in vacuo. The residue was triturated with methanol (2×50 mL) and filtered to afford the title compound as an off white solid (1.53 g, 36% yield): $^1$H-NMR (300 MHz; CDCl$_3$) δ 8.76 (d, J=5.0 Hz, 1H), 7.67 (dd, J=6.0, 3.2 Hz, 2H), 7.61 (d, J=5.0 Hz, 1H), 7.47 (ddd, J=7.6, 6.1, 1.5 Hz, 2H), 7.39-7.29 (m, 4H); MS (ESI+) m/z 340 (M+1), 342 (M+1), 344 (M+1).

Step 3. Preparation of 2-(4-(2-chlorophenyl)-2-(pyrrolidin-1-yl)pyridin-3-yl)-1H-benzo[d]imidazole

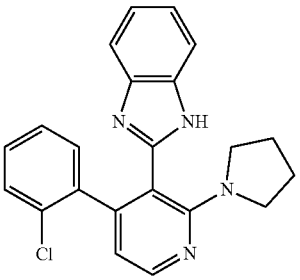

A mixture of 2-(2-chloro-4-(2-chlorophenyl)pyridin-3-yl)-1H-benzo[d]imidazole (0.200 g, 0.590 mmol), potassium carbonate (0.245 g, 1.77 mmol), pyrrolidine (0.050 g, 0.71 mmol), and dimethylsulfoxide (3 mL) was sparged with nitrogen for 2 min. The reaction vessel was sealed and heated at 90° C. for 18 h. After cooling to ambient temperature, the reaction mixture was diluted with ethyl acetate (250 mL). The organic layer was washed with saturated ammonium chloride (2×100 mL) and brine (100 mL). The organic layer was dried over anhydrous magnesium sulfate, filtered, and concentrated in vacuo. Purification of the residue by preparative reverse phase HPLC, using acetonitrile in water containing 0.1% of trifluoroacetic acid as eluent, afforded the title compound as a colorless solid (0.011 g, 5% yield): $^1$H-NMR (300 MHz; DMSO-$d_6$) δ 8.44-8.40 (m, 1H), 7.65-7.57 (m, 2H), 7.42-7.32 (m, 3H), 7.29-7.20 (m, 3H), 6.75-6.70 (m, 1H), 3.11-3.00 (m, 4H), 1.78-1.69 (m, 4H); MS (ESI+) m/z 375.1 (M+1), 377.1 (M+1).

Example 7

Synthesis of 2-(2-(pyrrolidin-1-yl)-4-(o-tolyl)pyridin-3-yl)-1H-benzo[d]imidazole

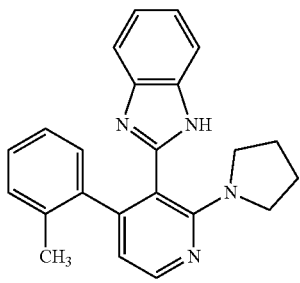 [SMILES: Cc1ccccc1-c1ccnc(N2CCCC2)c1-c1nc2ccccc2[nH]1]

Step 1. Preparation of 2-chloro-4-(o-tolyl)nicotinaldehyde

A mixture of 2-chloro-4-iodonicotinaldehyde (2.0 g, 7.5 mmol), 1,4-dioxane (25 mL), and water (2.8 mL) was sparged with nitrogen for 10 min. To the mixture was added 2-methylphenylboronic acid (1.12 g, 8.23 mmol), potassium carbonate (2.58 g, 18.7 mmol), and [1,1'-bis(diphenylphosphino)ferrocene]dichloropalladium(II), complex with dichloromethane (0.64 g, 0.75 mmol). The reaction mixture was heated at 90° C. for 3 h. After cooling to ambient temperature, the reaction mixture was diluted with ethyl acetate (250 mL). The organic layer was washed with saturated ammonium chloride (2×100 mL) and brine (100 mL). The organic layer was dried over anhydrous magnesium sulfate, filtered, and concentrated in vacuo. Purification of the residue by column chromatography, eluting with a gradient of 5-50% of ethyl acetate in heptane, afforded the title compound as a yellow solid (1.49 g, 86% yield): MS (ESI+) m/z 232 (M+1), 234 (M+1).

Step 2. Preparation of 2-(2-chloro-4-(o-(tolyl)pyridine-3-yl)-1H-benzo[d]imidazole

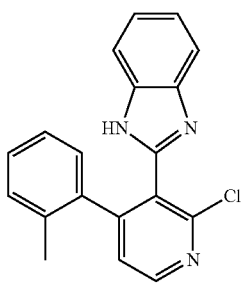 [SMILES: Cc1ccccc1-c1ccnc(Cl)c1-c1nc2ccccc2[nH]1]

A mixture of 2-chloro-4-(o-tolyl)nicotinaldehyde (1.49 g, 6.43 mmol), methanol (64 mL), and benzene-1,2-diamine (0.764 g, 7.07 mmol) was heated to reflux for 18 h. After cooling to ambient temperature, the reaction mixture was concentrated in vacuo. Purification of the residue by column chromatography, eluting with a gradient of 10-100% of ethyl acetate in heptane afforded the title compound as a yellow solid (2.00 g, 97% yield): $^1$H-NMR (300 MHz; DMSO-$d_6$) δ 12.60 (br s, 1H), 8.65-8.59 (d, J=4.8 Hz, 1H), 7.51 (d, J=5.1 Hz, 1H), 7.49 (br s, 2H), 7.21-6.98 (m, 6H), 2.13-2.11 (s, 3H); MS (ESI+) m/z 320 (M+1), 322 (M+1).

Step 3. Preparation of 2-(2-(pyrrolidin-1-yl)-4-(o-tolyl)pyridin-3-yl)-1H-benzo[d]imidazole

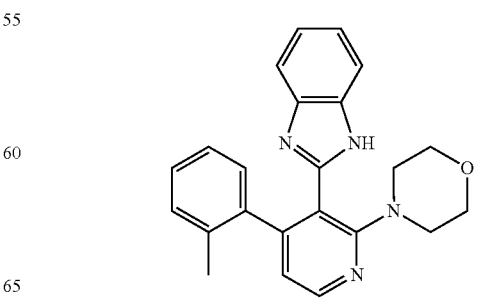

A mixture of 2-(2-chloro-4-(o-(tolyl)pyridine-3-yl)-1H-benzo[d]imidazole (0.100 g, 0.312 mmol), potassium carbonate (0.108 g, 0.780 mmol), pyrrolidine (0.170 g, 2.40 mmol), and dimethylsulfoxide (2 mL) was sparged with nitrogen for 2 min. The reaction vessel was sealed and heated at 90° C. for 12 h. After cooling to ambient temperature, the reaction mixture was diluted with ethyl acetate (150 mL). The organic layer was washed with saturated ammonium chloride (2×100 mL), dried over anhydrous magnesium sulfate, filtered, and concentrated in vacuo. Purification of the residue by column chromatography, eluting with a gradient of 5-80% of ethyl acetate (containing 10% 2-propanol and 10% triethylamine) in heptane, afforded the title compound as a colorless solid (0.011 g, 10% yield): $^1$H-NMR (300 MHz; DMSO-$d_6$) δ 12.27-12.24 (m, 1H), 8.23 (dd, J=5.9, 3.6 Hz, 1H), 7.49-7.45 (m, 1H), 7.32-7.26 (m, 1H), 7.11-6.89 (m, 6H), 6.49-6.48 (m, 1H), 3.05-2.94 (m, 4H), 2.14-2.08 (m, 3H), 1.68-1.61 (m, 4H); MS (ESI+) m/z 355.25 (M+1).

Example 8

Synthesis of 4-(3-(1H-benzo[d]imidazol-2-yl)-4-(o-tolyl)pyridin-2-yl)morpholine

Step 1. Preparation of 4-(3-(1H-benzo[d]imidazol-2-yl)-4-(o-tolyl)pyridin-2-yl)morpholine

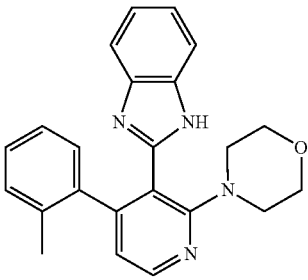 [SMILES: Cc1ccccc1-c1ccnc(N2CCOCC2)c1-c1nc2ccccc2[nH]1]

A mixture of 2-(2-chloro-4-(o-(tolyl)pyridine-3-yl)-1H-benzo[d]imidazole (0.100 g, 0.312 mmol), potassium carbonate (0.108 g, 0.780 mmol), morpholine (0.202 g, 2.32 mmol), and dimethylsulfoxide (2 mL) was sparged with nitrogen for 2 min. The reaction vessel was sealed and heated at 90° C. for 12 h. After cooling to ambient temperature, the reaction mixture was diluted with ethyl acetate (150 mL). The organic layer was washed with saturated ammonium chloride (2×100 mL), dried over anhydrous magnesium sulfate, filtered, and concentrated in vacuo. Purification of the residue by column chromatography, eluting with a gradient of 5-100% of ethyl acetate in heptane followed by 0-20% methanol in dichloromethane, afforded the title compound as a colorless solid (0.026 g, 23% yield): $^1$H-NMR (300 MHz; DMSO-$d_6$) δ 8.38 (d, J=5.0 Hz, 1H), 7.46-7.42 (m, 2H), 7.13-7.08 (m, 2H), 7.08-6.95 (m, 3H), 6.93-6.91 (m, 1H), 6.87 (d, J=5.0 Hz, 1H), 3.41 (q, J=5.1 Hz, 4H), 3.00 (t, J=4.5 Hz, 4H), 2.07-2.04 (m, 3H); MS (ESI+) m/z 371.2 (M+1).

Example 9

Synthesis of (S)-2-(4-(2-fluorophenyl)-2-(3-fluoropyrrolidin-1-yl)pyridin-3-yl)-1,3,4-oxadiazole

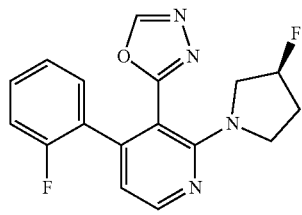 [SMILES: Fc1ccccc1-c1ccnc(N2CC[C@H](F)C2)c1-c1nnco1]

Step 1. Preparation of 2-(2-chloro-4-(2-fluorophenyl)pyridin-3-yl)-1,3,4-oxadiazole

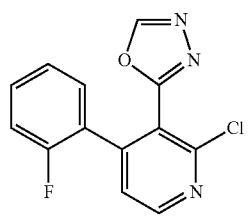 [SMILES: Fc1ccccc1-c1ccnc(Cl)c1-c1nnco1]

A mixture of hydrazide (0.20 g, 0.79 mmol), triethoxymethane (1.3 mL, 7.9 mmol), and concentrated hydrochloric acid (1 drop) was heated to 80° C. for 24 hours. The mixture was concentrated in vacuo. Purification of the residue by column chromatography, eluting with a gradient of 5-80% of ethyl acetate in heptane, afforded the title compound as a colorless solid (0.065 g, 30% yield): MS (ESI+) m/z 276.2, 278.2 (M+1).

Step 2. Synthesis of (S)-2-(4-(2-fluorophenyl)-2-(3-fluoropyrrolidin-1-yl)pyridin-3-yl)-1,3,4-oxadiazole

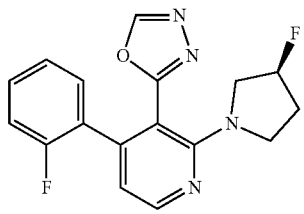 [SMILES: Fc1ccccc1-c1ccnc(N2CC[C@H](F)C2)c1-c1nnco1]

A mixture of 2-(2-chloro-4-(2-fluorophenyl)pyridin-3-yl)-1,3,4-oxadiazole (0.065 g, 0.24 mmol), (S)-fluoropyrrolidine hydrochloride (0.044 g, 0.35 mmol), potassium carbonate (0.10 g, 0.72 mmol), and dimethylsulfoxide (1.2 mL) was stirred at 110° C. for 2 hours. After cooling to ambient temperature, the mixture was diluted with ethyl acetate (10 mL) and saturated ammonium chloride (10 mL). The layers were separated and the aqueous phase was extracted with ethyl acetate (3×10 mL). The combined organic layers were washed with ammonium chloride (10 mL) and brine (10 mL), then dried with magnesium sulfate and filtered. The mixture was concentrated in vacuo. Purification of the residue by column chromatography, eluting with a gradient of 5-80% of ethyl acetate in heptane, afforded the title compound as a colorless solid (0.018 g, 22% yield): $^1$H-NMR (300 MHz; DMSO-$d_6$) δ 9.23 (s, 1H), 8.40 (d, J=5.0 Hz, 1H), 7.43-7.35 (m, 1H), 7.23-7.09 (m, 3H), 6.78 (dd, J=4.9, 0.5 Hz, 1H), 5.40-5.20 (m, 1H), 3.51-3.23 (m, 2H), 3.19-3.14 (m, 2H), 2.15-1.98 (m, 2H); MS (ESI+) m/z 329.1 (M+1).

Example 10

Synthesis of 2-(2'-(pyrrolidin-1-yl)-[2,4'-bipyridin]-3'-yl)-1H-benzo[d]imidazole

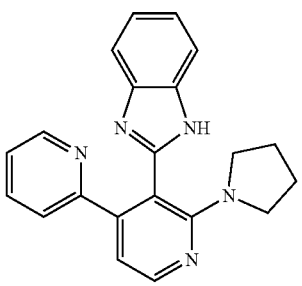 [SMILES: c1ccc(-c2ccnc(N3CCCC3)c2-c2nc3ccccc3[nH]2)nc1]

Step 1. Preparation of 2-(2-chloro-4-iodopyridin-3-yl)-1-((2-(trimethylsilyl)ethoxy)methyl)-1H-benzo[d]imidazole

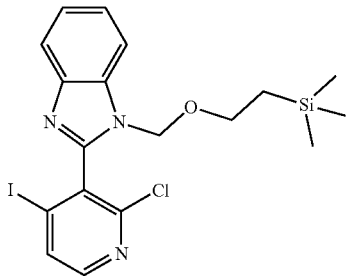 [SMILES: C[Si](C)(C)CCOCn1c(-c2c(I)ccnc2Cl)nc2ccccc21]

A mixture of 2-chloro-4-iodonicotinaldehyde (10.0 g, 37.4 mmol), methanol (374 mL), and benzene-1,2-diamine (4.25 g, 39.3 mmol) was heated to reflux for 18 h. After cooling to ambient temperature, the reaction mixture was concentrated in vacuo. The residue was triturated with methanol, filtered, and the filtrate was concentrated in vacuo. Purification of the residue by column chromatography, eluting with a gradient of 1-10% methanol in DCM, afforded an orange oil. The oil was immediately dissolved in N,N-dimethylformamide (77 mL), and cooled in an ice/water bath. Sodium hydride 60% in mineral oil (0.889 g, 23.1 mmol) was added to the solution and it was stirred for 1 h in the ice/water bath. To the solution was added (2-(chloromethoxy)ethyl)trimethylsilane (3.18 g, 18.6 mmol) and the mixture was allowed to warm to ambient temperature. The reaction mixture was stirred for 30 min. The reaction mixture was diluted with ethyl acetate (400 mL) and the organic layer was washed with saturated ammonium chloride (3×100 mL) and brine (100 mL). The organic layer was dried over anhydrous magnesium sulfate, filtered, and concentrated in vacuo. Purification of the residue by column chromatography, eluting with a gradient of 5-80% of ethyl acetate in heptane, afforded the title compound as a yellow solid (5.92 g, 33% yield); MS (ESI+) m/z 486 (M+1), 488 (M+1).

Step 2. Preparation of 2-(2'-chloro-[2,4'-bipyridin]-3'-yl)-1-((2-(trimethylsilyl)ethoxy)methyl)-1H-benzo[d]imidazole

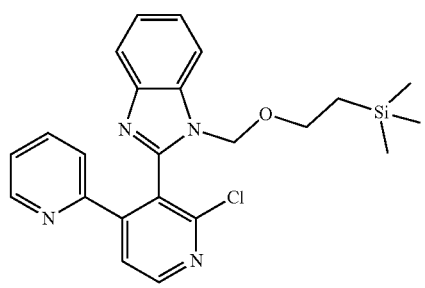 [SMILES: C[Si](C)(C)CCOCn1c(-c2c(-c3ccccn3)ccnc2Cl)nc2ccccc21]

A mixture of 2-(2-chloro-4-iodopyridin-3-yl)-1-((2-(trimethylsilyl)ethoxy)methyl)-1H-benzo[d]imidazole (0.972 g, 2.00 mmol) and tetrahydrofuran (4 mL) was sparged with nitrogen for 5 min. To the reaction mixture was added tetrakis(triphenylphosphine)palladium(0) (0.230 g, 0.200 mmol) and a 0.5 M solution of pyridin-2-ylzinc(II) bromide in tetrahydrofuran (8.0 mL, 4 mmol) The reaction mixture was heated to reflux for 2 h. After cooling to ambient temperature, the reaction mixture was diluted with ethyl acetate (200 mL). The organic layer was washed with saturated ammonium chloride (2×100 mL), and brine (100 mL). The organic phase was dried over anhydrous magnesium sulfate, filtered, and concentrated in vacuo. Purification of the residue by column chromatography, eluting with a gradient of 10-100% of ethyl acetate in heptane, afforded the title compound as a colorless solid (0.52 g, 59% yield): $^1$H-NMR (300 MHz; CDCl$_3$) δ 8.70 (d, J=5.1 Hz, 1H), 8.44 (dd, J=4.6, 0.3 Hz, 1H), 7.86-7.82 (m, 1H), 7.78 (d, J=5.2 Hz, 1H), 7.59-7.52 (m, 2H), 7.44-7.36 (m, 3H), 7.17 (ddd, J=7.5, 4.8, 1.2 Hz, 1H), 5.24 (d, J=8.7 Hz, 2H), 3.42 (dd, J=9.6, 7.1 Hz, 2H), 0.79 (ddd, J=9.7, 6.9, 4.1 Hz, 2H), −0.08-0.10 (m, 9H); MS (ESI+) m/z 437 (M+1), m/z 439 (M+1).

Step 3. Preparation of 2-(2'-(pyrrolidin-1-yl)-[2,4'-bipyridin]-3'-yl)-1-((2-(trimethylsilyl)ethoxy)methyl)-1H-benzo[d]imidazole

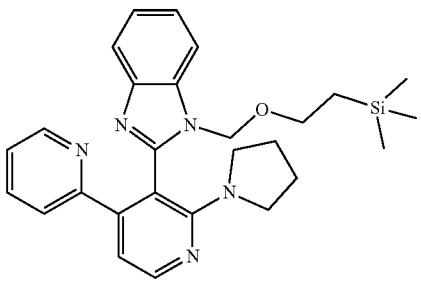 [SMILES: C[Si](C)(C)CCOCn1c(-c2c(-c3ccccn3)ccnc2N2CCCC2)nc2ccccc21]

A mixture of 2-(2'-chloro-[2,4'-bipyridin]-3'-yl)-1-((2-(trimethylsilyl)ethoxy)methyl)-1H-benzo[d]imidazole (0.52 g, 1.2 mmol), pyrrolidine (0.17 g, 2.4 mmol), potassium carbonate (0.656 g, 4.76 mmol), and dimethylsulfoxide (4 mL) was sparged with nitrogen for 2 min. The reaction vessel was sealed and heated at 95° C. for 8 h. After cooling to ambient temperature, the reaction mixture was diluted with ethyl acetate (250 mL). The organic layer was washed with saturated ammonium chloride (3×100 mL). The organic phase was dried over anhydrous magnesium sulfate, filtered, and concentrated in vacuo. Purification of the residue by column chromatography, eluting with a gradient of 10-100% of ethyl acetate in heptane, afforded the title compound as a colorless solid (0.31 g, 66% yield): $^1$H-NMR (300 MHz; CDCl$_3$) δ 8.44 (d, J=5.3 Hz, 1H), 8.37-8.36 (m, 1H), 7.77-7.74 (m, 1H), 7.47-7.41 (m, 2H), 7.35-7.30 (m, 2H), 7.22-7.18 (m, 1H), 7.07 (ddd, J=7.6, 4.9, 1.2 Hz, 1H), 6.90 (d, J=5.2 Hz, 1H), 5.23 (d, J=10.5 Hz, 1H), 5.02 (d, J=10.5 Hz, 1H), 3.51-3.43 (m, 2H), 3.41-3.32 (m, 2H), 3.15-3.08 (m, 2H), 1.77 (td, J=6.4, 3.0 Hz, 4H), 0.84-0.79 (m, 2H), −0.05 (s, 9H); MS (ESI+) m/z 437 (M+1), 439 (M+1).

Step 3. Preparation of 2-(2'-(pyrrolidin-1-yl)-[2,4'-bipyridin]-3'-yl)-1H-benzo[d]imidazole

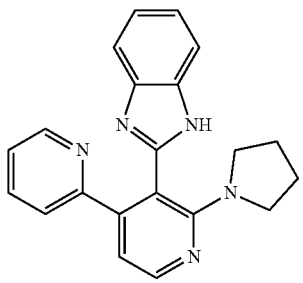 [SMILES: c1ccc(-c2ccnc(N3CCCC3)c2-c2nc3ccccc3[nH]2)nc1]

A mixture of 2-(2'-(pyrrolidin-1-yl)-[2,4'-bipyridin]-3'-yl)-1-((2-(trimethylsilyl)ethoxy)methyl)-1H-benzo[d]imidazole (0.31 g, 0.66 mmol), trifluoroacetic acid (5 mL), dichloromethane (5 mL), and concentrated hydrochloric acid (0.050 mL) was heated at 50° C. for 8 h. After cooling to ambient temperature, the reaction mixture was concentrated in vacuo. The residue was dissolved in ethyl acetate (250 mL) and washed with saturated potassium carbonate solution (3×100 mL). The organic phase was dried over anhydrous magnesium sulfate, filtered, and concentrated in vacuo. Purification of the residue by preparative reverse phase HPLC, using acetonitrile in water containing 0.1% of trifluoroacetic acid as eluent, afforded the title compound as a colorless solid (0.125 g, 55% yield): $^1$H-NMR (300 MHz; DMSO-$d_6$) δ 8.38 (t, J=4.2 Hz, 1H), 8.32-8.29 (m, 1H), 7.64-7.59 (m, 1H), 7.59-7.51 (m, 2H), 7.30-7.24 (m, 2H), 7.22-7.18 (m, 2H), 6.92 (d, J=5.1 Hz, 1H), 3.02 (q, J=6.6 Hz, 4H), 1.71-1.65 (m, 4H), missing one N—H signal; MS (ESI+) m/z 342.13 (M+1).

Example 11

Synthesis of 2-(4-(2-fluorophenyl)-2-(pyrrolidin-1-yl)pyridin-3-yl)-3H-imidazo[4,5-c]pyridine Formic Acid Salt

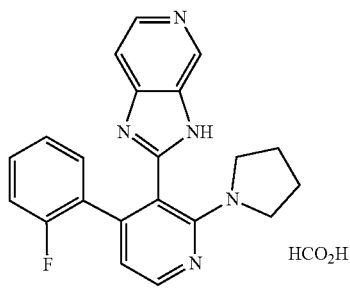 [SMILES: Fc1ccccc1-c1ccnc(N2CCCC2)c1-c1nc2ccncc2[nH]1 ; "HCO2H"]

Step 1. Preparation of 6-chloro-2-(4-(2-fluorophenyl)-2-(pyrrolidin-1-yl)pyridin-3-yl)-3H-imidazo[4,5-c]pyridine

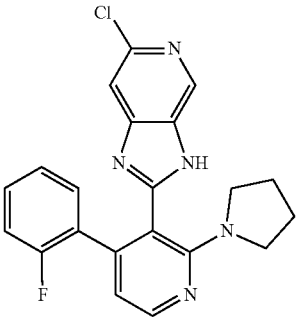 [SMILES: Fc1ccccc1-c1ccnc(N2CCCC2)c1-c1nc2cc(Cl)ncc2[nH]1]

A mixture of 4-(2-fluorophenyl)-2-(pyrrolidin-1-yl)nicotinic acid (1.20 g, 4.19 mmol), 6-chloropyridine-3,4-diamine (0.783 g, 5.45 mmol), and 2-chloro-1-methylpyridin-1-ium iodide (1.72 g, 6.72 mmol) was dissolved in tetrahydrofuran (84 mL). The reaction mixture was heated to reflux for 1 h. To the hot reaction mixture was added N-ethyl-N-isopropylpropan-2-amine (2.08 g, 16.0 mmol) and the reaction mixture was heated to reflux for 1 h. After cooling to ambient temperature, the reaction mixture was diluted with ethyl acetate (250 mL). The organic layer was washed with saturated ammonium chloride (2×100 mL) and brine (100 mL). The organic phase was dried over anhydrous magnesium sulfate, filtered, and concentrated in vacuo. The residue was dissolved in acetonitrile (2 mL), and phosphoryl trichloride (10 mL) was added. The reaction mixture was heated to reflux for 18 h. After cooling to ambient temperature, the reaction mixture was concentrated in vacuo. The residue was dissolved in ethyl acetate (200 mL) and washed with saturated ammonium chloride (2×100 mL) and brine (100 mL). The organic phase was dried over anhydrous magnesium sulfate, filtered, and concentrated in vacuo. Purification of the residue by column chromatography, eluting with a gradient of 20-100% of ethyl acetate in heptane, afforded the title compound as a yellow oil (0.200 g, 12% yield): MS (ESI+) m/z 394 (M+1), 396 (M+1).

Step 2. Preparation of 2-(4-(2-fluorophenyl)-2-(pyrrolidin-1-yl)pyridin-3-yl)-3H-imidazo[4,5-c]pyridine Formic Acid Salt

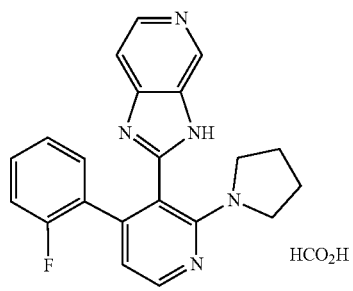 [SMILES: Fc1ccccc1-c1ccnc(N2CCCC2)c1-c1nc2ccncc2[nH]1 ; "HCO2H"]

To a mixture of 6-chloro-2-(4-(2-fluorophenyl)-2-(pyrrolidin-1-yl)pyridin-3-yl)-3H-imidazo[4,5-c]pyridine (0.20 g, 0.51 mmol), and palladium on carbon (0.20 g, 100% by mass) under nitrogen was added methanol (8.5 mL), ethanol (17 mL), and ammonium formate (0.32 g, 5.0 mmol). The reaction mixture was heated to reflux under nitrogen for 18 h. After cooling to ambient temperature, the reaction mixture was filtered through diatomaceous earth (i.e. Celite®) and concentrated in vacuo. Purification of the residue by preparative reverse phase HPLC, using acetonitrile in water containing 0.5% of formic acid as eluent, afforded the title compound as a colorless solid (0.023 g, 13% yield): $^1$H-NMR (300 MHz; DMSO-$d_6$) δ 9.22 (s, 1H), 8.46-8.44 (m, 1H), 8.35 (d, J=5.0 Hz, 1H), 8.14 (s, 1H), 7.88 (dd, J=6.3, 0.7 Hz, 1H), 7.24 (dddd, J=8.3, 7.1, 5.3, 2.0 Hz, 1H), 7.10-6.96 (m, 3H), 6.73-6.71 (m, 1H), 3.03 (q, J=6.6 Hz, 4H), 1.74-1.66 (m, 4H); MS (ESI+) m/z 360.11 (M+1).

Example 12

Synthesis of (S)—N-butyl-5-(4-(2-fluorophenyl)-2-(3-fluoropyrrolidin-1-yl)pyridin-3-yl)-1,3,4-oxadiazol-2-amine

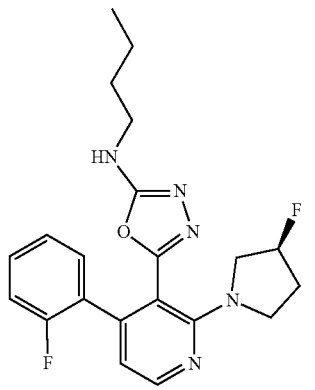 [SMILES: CCCCNc1nnc(-c2c(-c3ccccc3F)ccnc2N2CC[C@H](F)C2)o1]

Step 1. Preparation of N-butyl-5-(2-chloro-4-(2-fluorophenyl)pyridin-3-yl)-1,3,4-oxadiazol-2-amine

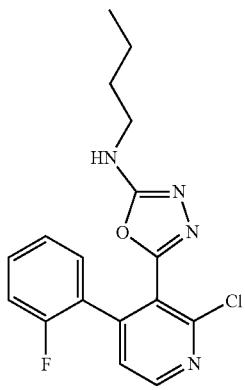 [SMILES: CCCCNc1nnc(-c2c(-c3ccccc3F)ccnc2Cl)o1]

A mixture of hydrazide (0.308 g, 1.07 mmol) and n-butyl isocyante (0.12 mL, 1.1 mmol) in acetonitrile (2 mL) was stirred at ambient temperature for 1 h. To the solution was added p-toluenesulfonylchloride (0.308 g, 1.07 mmol) and triethylamine (0.45 mL, 3.2 mmol). The mixture was stirred for 24 hours and then heated to 70° C. for 10 h. The mixture was diluted with ethyl acetate (20 mL) and water (20 mL). The layers were separated and the organic phase was washed with brine (10 mL), dried with magnesium sulfate, and filtered. The solution was concentrated in vacuo. The crude product was stirred with methanol (2 mL) and sodium hydroxide (1N, 1 mL) at ambient temperature for 24 h. The mixture was diluted with ethyl acetate (20 mL) and water (20 mL). The layers were separated and the organic phase was washed with brine (10 mL), dried with magnesium sulfate, and filtered. The solution was concentrated in vacuo. Purification of the residue by column chromatography, eluting with a gradient of 5-80% of ethyl acetate in heptane, afforded the title compound as a yellow oil (0.056 g, 16% yield): MS (ESI+) m/z 347.2 (M+1), 349.4 (M+1).

Step 2. Preparation of (S)—N-butyl-5-(4-(2-fluorophenyl)-2-(3-fluoropyrrolidin-1-yl)pyridin-3-yl)-1,3,4-oxadiazol-2-amine

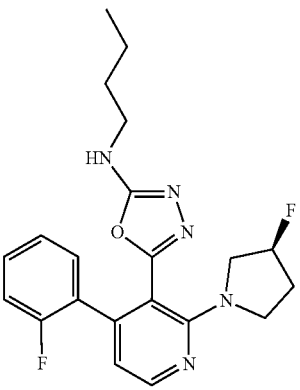 [SMILES: CCCCNc1nnc(-c2c(-c3ccccc3F)ccnc2N2CC[C@H](F)C2)o1]

A mixture of N-butyl-5-(2-chloro-4-(2-fluorophenyl)pyridin-3-yl)-1,3,4-oxadiazol-2-amine (0.056 g, 0.16 mmol), (S)-fluoropyrrolidine hydrochloride (0.030 g, 0.24 mmol), potassium carbonate (0.066 g, 0.48 mmol), and dimethylsulfoxide (0.8 mL) was heated at 90° C. for 20 h. After cooling to ambient temperature, the reaction mixture was diluted with ethyl acetate (15 mL) and aqueous ammonium chloride (15 mL). The layers were separated and the aqueous phase extracted with ethyl acetate (3×15 mL). The combined organic layers were washed with brine (20 mL). The organic phase was dried over anhydrous magnesium sulfate, filtered, and concentrated in vacuo. Purification of the residue by column chromatography, eluting with a gradient of 5-100% of ethyl acetate in heptane, afforded the title compound as a colorless solid (0.0138 g, 22% yield): $^1$H-NMR (300 MHz; DMSO-$d_6$): δ 8.33 (d, J=5.0 Hz, 1H), 7.49 (t, J=5.8 Hz, 1H), 7.44-7.36 (m, 1H), 7.24-7.12 (m, 3H), 6.73 (dd, J=5.0, 0.7 Hz, 1H), 5.43-5.24 (m, 1H), 3.60-3.27 (m, 4H), 3.05 (q, J=6.4 Hz, 2H), 2.18-1.97 (m, 2H), 1.44-1.34 (m, 2H), 1.29-1.16 (m, 2H), 0.85 (t, J=7.3 Hz, 3H); MS (ESI+) m/z 400.2 (M+1).

Example 13

Synthesis of (S)-2-(2-(3-fluoropyrrolidin-1-yl)-3-(5-isopentyl-1,3,4-oxadiazol-2-yl)pyridin-4-yl)phenol

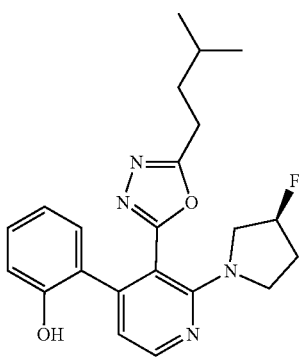 [SMILES: CC(C)CCc1nnc(-c2c(-c3ccccc3O)ccnc2N2CC[C@H](F)C2)o1]

Step 1. Preparation of 2-(2-chloro-4-(2-fluorophenyl)pyridin-3-yl)-5-isopentyl-1,3,4-oxadiazole

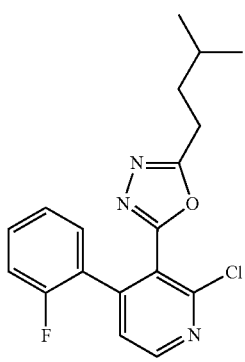 [SMILES: CC(C)CCc1nnc(-c2c(-c3ccccc3F)ccnc2Cl)o1]

To a mixture of 2-chloro-4-(2-fluorophenyl)nicotinohydrazide (0.500 g, 1.88 mmol) and 4-methylpentanoic acid (0.36 mL, 2.82 mmol) in anhydrous toluene (7.5 mL) was added phosphoryl trichloride (1.5 mL, 16 mmol). The reaction mixture was heated to 100° C. for 16 h. After cooling to ambient temperature, the reaction mixture was poured into ice water (40 mL) slowly, and extracted with ethyl acetate (3×20 mL). The combined organic phases were dried over anhydrous sodium sulfate, and filtered. The filtrate was concentrated in vacuo to give a residue, which was purified by column chromatography, eluting with a gradient of 5% to 35% of ethyl acetate in heptane, to provide the title compound as a light yellow solid (0.044 g, 13% yield): $^1$H-NMR (300 MHz; DMSO-$d_6$) δ 8.86 (d, J=5.1 Hz, 1H), 7.83 (dd, J=5.1, 0.7 Hz, 1H), 7.54 (dddd, J=8.3, 7.3, 5.5, 1.9 Hz, 1H), 7.42 (td, J=7.6, 1.8 Hz, 1H), 7.34-7.26 (m, 2H), 2.19 (dd, J=8.2, 7.2 Hz, 2H), 1.59-1.46 (m, 1H), 1.43-1.35 (m, 2H), 0.85 (d, J=6.5 Hz, 6H); MS (ES+) m/z 346.4 (M+1), 348.2 (M+1).

Step 2. Preparation of (S)-2-(2-(3-fluoropyrrolidin-1-yl)-3-(5-isopentyl-1,3,4-oxadiazol-2-yl)pyridin-4-yl)phenol

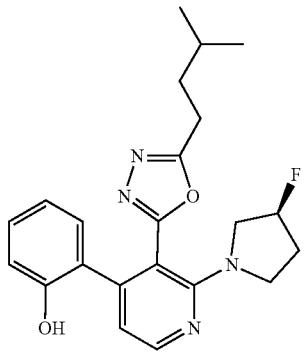 [SMILES: CC(C)CCc1nnc(-c2c(-c3ccccc3O)ccnc2N2CC[C@H](F)C2)o1]

To a solution of 2-(2-chloro-4-(2-fluorophenyl)pyridin-3-yl)-5-isopentyl-1,3,4-oxadiazole (0.044 g, 0.127 mmol) in anhydrous dimethyl sulfoxide (1.0 mL) was added potassium carbonate (0.070 g, 0.508 mmol), and (S)-3-fluoropyrrolidine hydrochloric acid salt (0.032 g, 0.254 mmol). The reaction mixture was stirred at 90° C. for 5 h. After cooling to ambient temperature, the reaction mixture was diluted with saturated aqueous sodium bicarbonate solution (20 mL), and extracted with ethyl acetate (2×20 mL). The combined organic phases were washed with brine (40 mL), dried over anhydrous sodium sulfate, and filtered. The filtrate was concentrated in vacuo to give a residue, which was purified by column chromatography, eluting with a gradient of 2% to 50% ethyl acetate in heptane, to provide the title compound as a yellow solid (0.009 g, 19% yield): $^1$H-NMR (300 MHz; DMSO-$d_6$) δ 10.72 (d, J=2.5 Hz, 1H), 8.38-8.33 (m, 2H), 7.66-7.58 (m, 2H), 7.41-7.29 (m, 2H), 5.50-5.30 (m, 1H), 4.17-3.84 (m, 2H), 3.43-3.13 (m, 2H), 2.46-2.38 (m, 2H), 2.29-2.00 (m, 2H), 1.70-1.48 (m, 3H), 0.95 (ddd, J=7.9, 6.4, 1.5 Hz, 6H); MS (ES+) m/z 397.2 (M+1).

Example 14

Synthesis of (S)-2-(4-(cyclopent-1-en-1-yl)-2-(3-fluoropyrrolidin-1-yl)pyridin-3-yl)-1H-benzo[d]imidazole

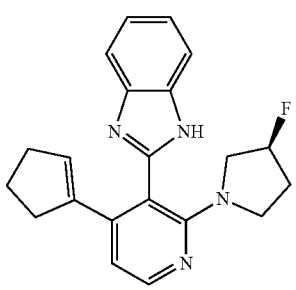 [SMILES: F[C@H]1CCN(c2nccc(C3=CCCC3)c2-c2nc3ccccc3[nH]2)C1]

Step 1. Preparation of 2-(2-chloro-4-(cyclopent-1-en-1-yl)pyridin-3-yl)-1-((2-(trimethylsilyl)ethoxy)methyl)-1H-benzo[d]imidazole

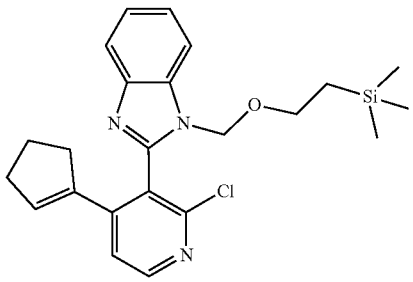 [SMILES: C[Si](C)(C)CCOCn1c(-c2c(C3=CCCC3)ccnc2Cl)nc2ccccc21]

A mixture of 2-(2-chloro-4-iodopyridin-3-yl)-1-((2-(trimethylsilyl)ethoxy)methyl)-1H-benzo[d]imidazole (0.486 g, 1.00 mmol), 2-(cyclopent-1-en-1-yl)-4,4,5,5-tetramethyl-1,3,2-dioxaborolane (0.213 g, 1.10 mmol), potassium carbonate (0.345 g, 1.10 mmol), dioxane (3.3 mL) and water (0.4 mL) was sparged with nitrogen for 10 min. To the reaction mixture was added [1,1'-bis(diphenylphosphino)ferrocene]dichloropalladium(II) complex with dichloromethane (0.086 g, 0.10 mmol). The reaction mixture was heated to reflux for 20 h. After cooling to ambient temperature, the reaction mixture was filtered through diatomaceous earth (i.e. Celite®), washing with ethyl acetate (20 mL), and concentrated in vacuo. Purification of the residue by column chromatography, eluting with a gradient of 5-60% of ethyl acetate in heptane, afforded the title compound as a yellow oil (0.376 g, 88% yield): $^1$H-NMR (300 MHz; CDCl$_3$) δ 8.56 (d, J=5.3 Hz, 1H), 7.78-7.74 (m, 2H), 7.61 (d, J=5.3 Hz, 1H), 7.42-7.27 (m 2H), 5.73-7.58 (m, 1H), 5.35 (d, J=11.3 Hz, 1H), 5.26 (d, J=11.3 Hz, 1H), 3.48-3.31 (m, 2H), 2.38-2.20 (m, 4H), 1.69-1.60 (m, 2H), 0.79-0.70 (m, 2H), −0.10-0.13 (m, 9H); MS (ES+) m/z 426.4, 428.4 (M+1).

Step 2. Preparation of (S)-2-(4-(cyclopent-1-en-1-yl)-2-(3-fluoropyrrolidin-1-yl)pyridin-3-yl)-1-((2-(trimethylsilyl)ethoxy)methyl)-1H-benzo[d]imidazole

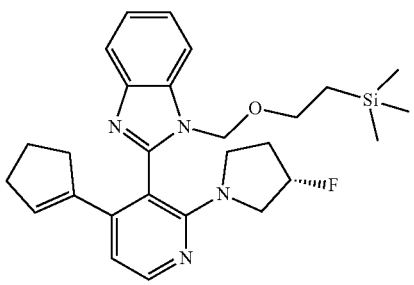 [SMILES: C[Si](C)(C)CCOCn1c(-c2c(C3=CCCC3)ccnc2N2CC[C@H](F)C2)nc2ccccc21]

A mixture of 2-(2-chloro-4-(cyclopent-1-en-1-yl)pyridin-3-yl)-1-((2-(trimethylsilyl)ethoxy)methyl)-1H-benzo[d]imidazole (0.38 g, 0.88 mmol), (S)-fluoropyrrolidine hydrochloride (0.17 g, 1.3 mmol), potassium carbonate (0.30 g, 2.2 mmol), and dimethylsulfoxide (4.4 mL) was heated at 90° C. for 11 h. After cooling to ambient temperature, the reaction mixture was diluted with ethyl acetate (15 mL) and water (10 mL). The layers were separated and the aqueous phase extracted with ethyl acetate (3×15 mL). The combined organic layers were washed with brine (20 mL). The organic phase was dried over anhydrous magnesium sulfate, filtered, and concentrated in vacuo. Purification of the residue by column chromatography, eluting with a gradient of 5-80% of ethyl acetate in heptane, afforded the title compound as a yellow oil (0.21 g, 50% yield): MS (ESI+) m/z 497.4 (M+1).

Step 3. Preparation of (S)-2-(4-(cyclopent-1-en-1-yl)-2-(3-fluoropyrrolidin-1-yl)pyridin-3-yl)-1H-benzo[d]imidazole

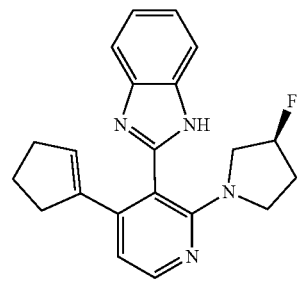 [SMILES: F[C@H]1CCN(c2nccc(C3=CCCC3)c2-c2nc3ccccc3[nH]2)C1]

A mixture of (S)-2-(4-(cyclopent-1-en-1-yl)-2-(3-fluoropyrrolidin-1-yl)pyridin-3-yl)-1-((2-(trimethylsilyl)ethoxy)methyl)-1H-benzo[d]imidazole (0.052 g, 0.11 mmol) and hydrochloric acid in dioxane (4.0 M, 0.56 mL) was heater at 85° C. for 4 hours. After cooling to ambient temperature, the mixture was diluted with ethyl acetate (20 mL) and washed with saturated potassium carbonate (3×15 mL). The organic phase was dried with magnesium sulfate, filtered, and concentrated in vacuo. Purification of the residue by column chromatography, eluting with a gradient of 5-70% of ethyl acetate (containing 10% triethylamine and 10% isopropanol) in heptane, afforded the title compound as a colorless solid (0.049 g, 12% yield): $^1$H-NMR (300 MHz; CDCl$_3$) δ 12.60 (broad singlet, 1H), 8.18 (d, J=5.2 Hz, 1H), 7.67-7.64 (m, 1H), 7.50-7.47 (m, 1H), 7.22-7.18 (m, 2H), 6.07 (d, J=5.2 Hz, 1H), 5.48-5.45 (m, 1H), 5.24-5.04 (m, 1H), 3.22-3.06 (m, 4H), 2.16-1.95 (m, 5H), 1.65-1.59 (m, 3H); MS (ESI+) m/z 349.2 (M+1).

Example 15

Synthesis of 2-(2'-(pyrrolidin-1-yl)-[2,4'-bipyridin]-3'-yl)-1H-benzo[d]imidazole

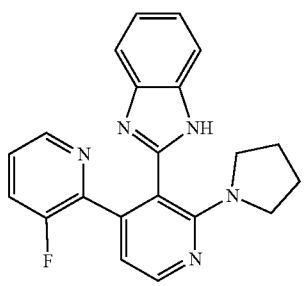 [SMILES: Fc1cccnc1-c1ccnc(N2CCCC2)c1-c1nc2ccccc2[nH]1]

Step 1. Preparation of 2-(2'-chloro-3-fluoro-[2,4'-bipyridin]-3'-yl)-1-((2-(trimethylsilyl)ethoxy)methyl)-1H-benzo[d]imidazole

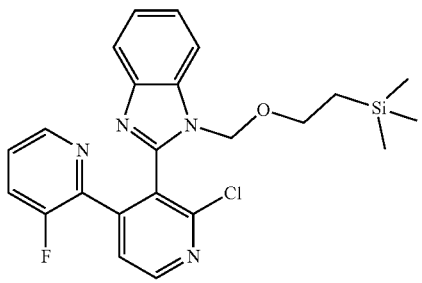 [SMILES: C[Si](C)(C)CCOCn1c(-c2c(-c3ncccc3F)ccnc2Cl)nc2ccccc21]

A mixture of 3-fluoro-2-iodopyridine (0.40 g, 1.8 mmol) and tetrahydrofuran (1 mL) was sparged with nitrogen for 1 min, and cooled in an ice/water bath. A 2.0 M solution of 2-propylmagnesium chloride (0.805 mL, 1.61 mmol) was added and the mixture was allowed to warm to ambient temperature. The reaction mixture was stirred for 4 h. The 3-fluoropyridyl-2-magensium chloride solution was added to a mixture of 2-(2-chloro-4-iodopyridin-3-yl)-1-((2-(trimethylsilyl)ethoxy)methyl)-1H-benzo[d]imidazole (0.391 g, 0.805 mmol), [1,1'-bis(diphenylphosphino)ferrocene]dichloropalladium(II), complex with dichloromethane (0.069 g, 0.080 mmol), and tetrahydrofuran (2 mL) under nitrogen. The reaction mixture was heated at 50° C. for 2 h. After cooling to ambient temperature, the reaction mixture was diluted with ethyl acetate (200 mL). The organic layer was washed with saturated ammonium chloride (2×100 mL) and brine (100 mL). The organic phase was dried over anhydrous magnesium sulfate, filtered, and concentrated in vacuo. Purification of the residue by column chromatography, eluting with a gradient of 20-100% of ethyl acetate in heptane, afforded the title compound as a yellow solid (0.40 g, 88% yield): $^1$H-NMR (300 MHz; DMSO-$d_6$) δ 8.79 (d, J=5.1 Hz, 1H), 8.11 (ddd, J=4.6, 1.8, 1.3 Hz, 1H), 7.88 (dd, J=5.1, 2.3 Hz, 1H), 7.81 (ddd, J=10.4, 8.5, 1.3 Hz, 1H), 7.70-7.67 (m, 1H), 7.55 (ddd, J=8.0, 1.1, 0.7 Hz, 1H), 7.41-7.36 (m, 1H), 7.29 (ddd, J=8.2, 7.1, 1.1 Hz, 1H), 7.20 (ddd, J=8.1, 7.1, 1.1 Hz, 1H), 5.52-5.43 (m, 2H), 3.55-3.50 (m, 2H), 0.85-0.79 (m, 2H), −0.09-0.11 (m, 9H); MS (ESI+) m/z 455 (M+1), 457 (M+1).

Step 2. Preparation of 2-(3-fluoro-2'-(pyrrolidin-1-yl)-[2,4'-bipyridin]-3'-yl)-1-((2-(trimethylsilyl)ethoxy)methyl)-1H-benzo[d]imidazole

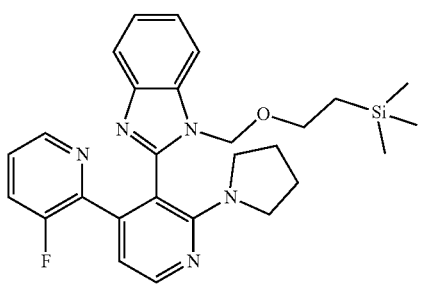 [SMILES: C[Si](C)(C)CCOCn1c(-c2c(-c3ncccc3F)ccnc2N2CCCC2)nc2ccccc21]

A mixture of 2-(2'-chloro-3-fluoro-[2,4'-bipyridin]-3'-yl)-1-((2-(trimethylsilyl)ethoxy)methyl)-1H-benzo[d]imidazole (0.40 g, 0.88 mmol), pyrrolidine (0.093 g, 1.3 mmol), potassium carbonate (0.241 g, 1.75 mmol), and dimethylsulfoxide (3 mL) was sparged with nitrogen for 2 min. The reaction vessel was sealed and heated at 95° C. for 4 h. After cooling to ambient temperature, the reaction mixture was diluted with ethyl acetate (250 mL). The organic layer was washed with saturated ammonium chloride (3×100 mL). The organic phase was dried over anhydrous magnesium sulfate, filtered, and concentrated in vacuo. Purification of the residue by column chromatography, eluting with a gradient of 5-100% of ethyl acetate in heptane, afforded the title compound as a colorless solid (0.32 g, 60% yield): MS (ESI+) 490 m/z (M+1).

Step 3. Preparation of 2-(3-fluoro-2'-(pyrrolidin-1-yl)-[2,4'-bipyridin]-3'-yl)-1H-benzo[d]imidazole

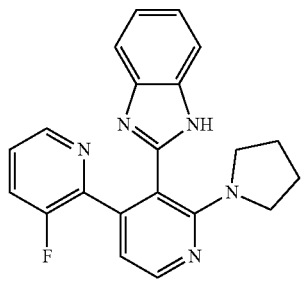

A mixture of 2-(3-fluoro-2'-(pyrrolidin-1-yl)-[2,4'-bipyridin]-3'-yl)-1-((2-(trimethylsilyl)ethoxy)methyl)-1H-benzo[d]imidazole (0.32 g, 0.52 mmol), and trifluoroacetic acid (20 mL) was heated at 50° C. for 1.5 h. After cooling to ambient temperature, the reaction mixture was concentrated in vacuo. Purification of the residue by column chromatography, eluting with a gradient of 20-100% of ethyl acetate in heptane followed by 0-25% methanol in dichloromethane, afforded the title compound as a colorless solid (0.16 g, 86% yield): $^1$H-NMR (300 MHz; DMSO-$d_6$) δ 8.45-8.43 (m, 1H), 8.06-8.02 (m, 1H), 7.78-7.69 (m, 1H), 7.62-7.57 (m, 2H), 7.38-7.31 (m, 3H), 6.93 (dt, J=5.2, 2.7 Hz, 1H), 3.09-3.02 (m, 4H), 1.72 (q, J=6.0 Hz, 4H), missing one N—H signal; MS (ESI+) m/z 360.2 (M+1).

Example 16

Synthesis of 2-(4-phenyl-2-(pyrrolidin-1-yl)pyridin-3-yl)-1H-benzo[d]imidazole

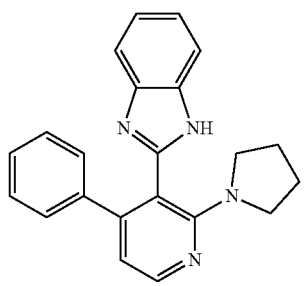 [SMILES: c1ccc(-c2ccnc(N3CCCC3)c2-c2nc3ccccc3[nH]2)cc1]

Step 1. Preparation of 2-chloro-4-phenylnicotinaldehyde

A mixture of 2-chloro-4-iodonicotinaldehyde (10.0 g, 37.4 mmol), 1,4-dioxane (124 mL), and water (14 mL) was sparged with nitrogen for 10 min. To this mixture was added phenylboronic acid (4.94 g, 41.1 mmol), potassium carbonate (12.9 g, 93.5 mmol), [1,1'-bis(diphenylphosphino)ferrocene]dichloropalladium(II), complex with dichloromethane (3.2 g, 3.7 mmol) and the reaction mixture was heated at 90° C. for 3 h. After cooling to ambient temperature, the reaction mixture was diluted with ethyl acetate (300 mL). The organic layer was washed with saturated ammonium chloride (2×100 mL). The organic phase was dried over anhydrous magnesium sulfate, filtered and concentrated in vacuo. The residue was purified by column chromatography, eluting with a gradient of 1-25% of ethyl acetate in heptane, to afford the title compound as a yellow solid (7.3 g, 90% yield): MS (ESI+) m/z 218 (M+1), 220 (M+1).

Step 2. Preparation of 2-(2-chloro-4-phenylpyridin-3-yl)-1H-benzo[d]imidazole

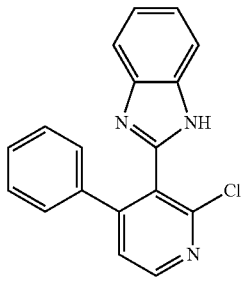 [SMILES: Clc1nccc(-c2ccccc2)c1-c1nc2ccccc2[nH]1]

A mixture of 2-chloro-4-phenylnicotinaldehyde (0.300 g, 1.38 mmol), benzene-1,2-diamine (0.164 g, 1.52 mmol), and methanol (14 mL) was heated to reflux for 12 h. After cooling to ambient temperature, the reaction mixture was concentrated in vacuo. Purification of the residue by column chromatography, eluting with a gradient of 25-100% of ethyl acetate in heptane, afforded the title compound as a colorless solid (0.35 g, 83% yield): MS (ESI+) m/z 306 (M+1), 308 (M+1).

Step 3. Preparation of 2-(4-phenyl-2-(pyrrolidin-1-yl)pyridin-3-yl)-1H-benzo[d]imidazole

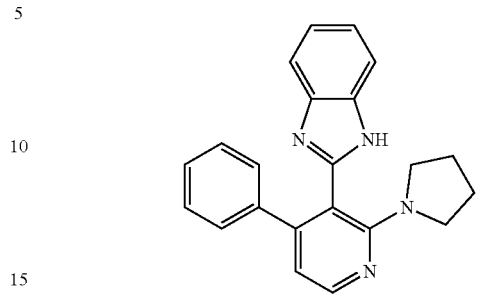

A mixture of 2-(2-chloro-4-phenylpyridin-3-yl)-1H-benzo[d]imidazole (0.115 g, 0.337 mmol), pyrrolidine (0.053 g, 0.75 mmol), potassium carbonate (0.156 g, 1.13 mmol), and dimethylsulfoxide (1.9 mL) was sparged with nitrogen for 2 min and heated at 110° C. for 2 h. After cooling to ambient temperature, the reaction mixture was concentrated in vacuo. Purification of the residue by preparative reverse phase HPLC, using acetonitrile in water containing 0.1% of trifluoroacetic acid as eluent, afforded the title compound as a colorless solid (0.059 g, 51% yield): $^1$H-NMR (300 MHz; DMSO-$d_6$) δ 8.45-8.42 (m, 1H), 7.75-7.69 (m, 2H), 7.52-7.46 (m, 2H), 7.29-7.20 (m, 3H), 7.13-7.07 (m, 2H), 6.84-6.82 (m, 1H), 3.13-3.02 (m, 4H), 1.81-1.71 (m, 4H); MS (ESI+) m/z 341.2 (M+1).

Example 17

Synthesis of (S)-2-(2-(3-fluoropyrrolidin-1-yl)-4-phenylpyridin-3-yl)-1H-benzo[d]imidazole

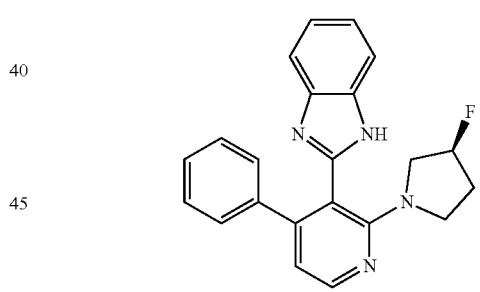

Step 1. Preparation of (S)-2-(2-(3-fluoropyrrolidin-1-yl)-4-phenylpyridin-3-yl)-1H-benzo[d]imidazole

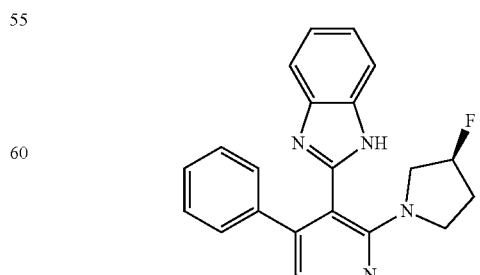

A mixture of 2-(2-chloro-4-phenylpyridin-3-yl)-1H-benzo[d]imidazole (0.115 g, 0.337 mmol), (S)-3-fluoropyrrolidine hydrochloride (0.095 g, 0.75 mmol), potassium carbonate (0.156 g, 1.13 mmol), and dimethylsulfoxide (1.9 mL) was sparged with nitrogen for 2 min and heated at 110° C. for 2 h. After cooling to ambient temperature, the reaction mixture was concentrated in vacuo. Purification of the residue by preparative reverse phase HPLC, using acetonitrile in water containing 0.1% of trifluoroacetic acid as eluent, afforded the title compound as a colorless solid (0.026 g, 19% yield): $^1$H-NMR (300 MHz; DMSO-d$_6$) δ 8.47-8.43 (m, 1H), 7.71-7.65 (m, 2H), 7.49-7.41 (m, 2H), 7.27-7.20 (m, 3H), 7.14-7.08 (m, 2H), 6.85 (t, J=3.9 Hz, 1H), 5.33-5.15 (m, 1H), 3.41-3.26 (m, 2H), 3.25-3.10 (m, 2H), 2.12-1.85 (m, 2H), missing one N—H signal; MS (ESI+) m/z 359.2 (M+1).

Example 18

Synthesis of (S)-2-(4-(2-fluorophenyl)-2-(3-fluoropyrrolidin-1-yl)pyridin-3-yl)-1H-benzo[d]imidazole

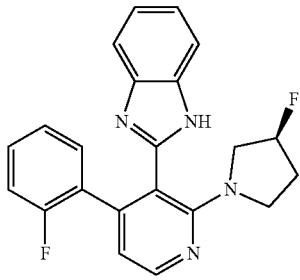 [SMILES: Fc1ccccc1-c1ccnc(N2CC[C@H](F)C2)c1-c1nc2ccccc2[nH]1]

Step 1. Preparation of (S)-2-(4-(2-fluorophenyl)-2-(3-fluoropyrrolidin-1-yl)pyridin-3-yl)-1-((2-(trimethylsilyl)ethoxy)methyl)-1H-benzo[d]imidazole

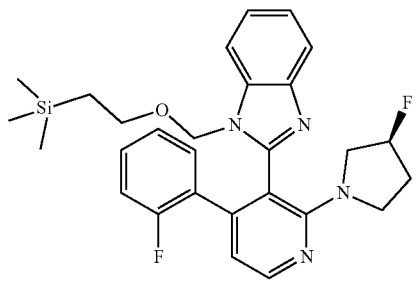 [SMILES: C[Si](C)(C)CCOCn1c(-c2c(-c3ccccc3F)ccnc2N2CC[C@H](F)C2)nc2ccccc21]

A mixture of 2-(2'-chloro-3-fluoro-[2,4'-bipyridin]-3'-yl)-1-((2-(trimethylsilyl)ethoxy)methyl)-1H-benzo[d]imidazole (0.51 g, 1.1 mmol), (S)-3-fluoropyrrolidine hydrochloride (0.42 g, 3.3 mmol), potassium carbonate (1.1 g, 7.8 mmol), and dimethylsulfoxide (5.6 mL) was sparged with nitrogen for 2 min. The reaction vessel was sealed and heated at 95° C. for 4 h. After cooling to ambient temperature, the reaction mixture was diluted with ethyl acetate (250 mL). The organic layer was washed with saturated ammonium chloride (3×100 mL). The organic phase was dried over anhydrous magnesium sulfate, filtered, and concentrated in vacuo. Purification of the residue by column chromatography, eluting with a gradient of 10-100% of ethyl acetate in heptane, afforded the title compound as a colorless solid (0.29 g, 52% yield): MS (ESI+) m/z 507 (M+1).

Step 2. Preparation of (S)-2-(4-(2-fluorophenyl)-2-(3-fluoropyrrolidin-1-yl)pyridin-3-yl)-1H-benzo[d]imidazole

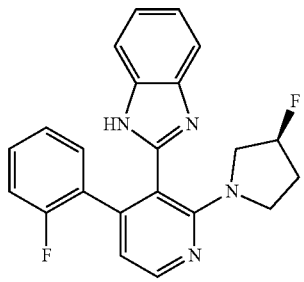 [SMILES: Fc1ccccc1-c1ccnc(N2CC[C@H](F)C2)c1-c1nc2ccccc2[nH]1]

A mixture of (S)-2-(4-(2-fluorophenyl)-2-(3-fluoropyrrolidin-1-yl)pyridin-3-yl)-1-((2-(trimethylsilyl)ethoxy)methyl)-1H-benzo[d]imidazole (0.29 g, 0.57 mmol), and trifluoroacetic acid (15 mL) was heated at 50° C. for 2 h. After cooling to ambient temperature, the reaction mixture was concentrated in vacuo. Purification of the residue by preparative reverse phase HPLC, using acetonitrile in water containing 0.1% of trifluoroacetic acid as eluent, afforded the title compound as a colorless solid (0.14 g, 66% yield): $^1$H-NMR (300 MHz; DMSO-d$_6$) δ 12.49-12.47 (m, 1H), 8.30 (d, J=5.0 Hz, 1H), 7.54-7.49 (m, 1H), 7.38-7.32 (m, 1H), 7.23-7.01 (m, 5H), 6.95-6.90 (m, 1H), 6.71 (d, J=5.0 Hz, 1H), 5.27-5.09 (m, 1H), 3.30-3.09 (m, 4H), 2.02-1.81 (m, 2H); MS (ESI+) m/z 377.2 (M+1).

Example 19

Synthesis of (S)-2-(3-fluoropyrrolidin-1-yl)-4-phenyl-3-(5-(pyridin-3-yl)-1H-pyrazol-3-yl)pyridine

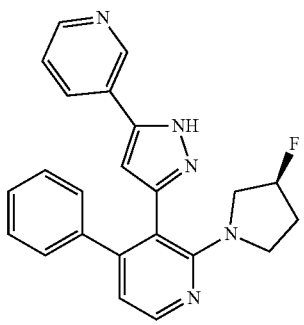 [SMILES: F[C@H]1CCN(c2nccc(-c3ccccc3)c2-c2cc(-c3cccnc3)[nH]n2)C1]

Step 1. Preparation of 2-chloro-4-phenyl-3-(5-(pyridin-3-yl)-1H-pyrazol-3-yl)pyridine

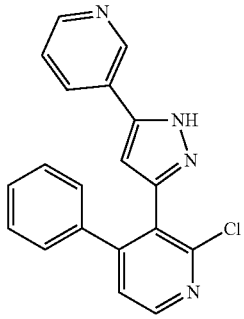 [SMILES: Clc1nccc(-c2ccccc2)c1-c1cc(-c2cccnc2)[nH]n1]

A mixture of 2-chloro-4-phenylnicotinaldehyde (0.50 g, 2.3 mmol), 1-(pyridine-3-yl)ethan-1-one (0.306 g, 2.53 mmol), piperidine (0.005 mL, 0.05 mmol), N-ethyl-N-isopropylpropan-2-amine (0.29 g, 2.3 mmol), and methanol (12 mL) was heated to reflux for 1 h. After cooling to ambient temperature, the reaction mixture was diluted with ethyl acetate (250 mL). The organic layer was washed with saturated ammonium chloride (2×100 mL). The organic phase was dried over anhydrous magnesium sulfate, filtered, and concentrated in vacuo. The residue was dissolved in ethanol (25 mL) and hydrazine hydrate (0.23 g, 4.6 mmol) was added. The mixture was heated to reflux for 1 h. After cooling to ambient temperature, the reaction mixture was diluted with ethyl acetate (250 mL). The organic layer was washed with saturated ammonium (2×100 mL). The organic phase was dried over anhydrous magnesium sulfate, filtered, and concentrated in vacuo. The residue was dissolved in dimethyl sulfoxide (23 mL) and potassium carbonate (0.38 g, 2.8 mmol), and [acetyloxy(phenyl)-λ³-iodanyl] acetate (0.89 g, 2.8 mmol) was added. The reaction mixture was stirred at ambient temperature for 1 h. The reaction mixture was diluted with ethyl acetate (200 mL), and washed with saturated ammonium chloride (2×100 mL). The organic phase was dried over anhydrous magnesium sulfate, filtered, and concentrated in vacuo. Purification of the residue by column chromatography, eluting with a gradient of 10-100% of ethyl acetate in heptane, afforded the title compound as a colorless solid (0.18 g, 24% yield): MS (ESI+) m/z 333 (M+1), 335 (M+1).

Step 2. Preparation of (S)-2-(3-fluoropyrrolidin-1-yl)-4-phenyl-3-(5-(pyridin-3-yl)-1H-pyrazol-3-yl)pyridine

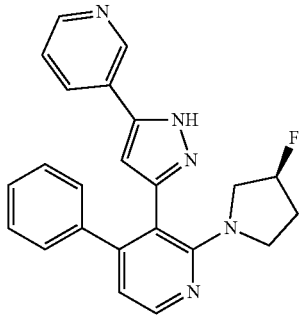 [SMILES: F[C@H]1CCN(c2nccc(-c3ccccc3)c2-c2cc(-c3cccnc3)[nH]n2)C1]

A mixture 2-chloro-4-phenyl-3-(5-(pyridin-3-yl)-1H-pyrazol-3-yl)pyridine (0.18 g, 0.50 mmol), potassium carbonate (0.41 g, 3.0 mmol), (S)-3-fluoropyrrolidine hydrochloride (0.16 g, 1.2 mmol), and dimethyl sulfoxide (2.5 mL) was sparged with nitrogen for 10 min, and heated at 120° C. for 8 h. After cooling to ambient temperature, the reaction mixture was diluted with ethyl acetate (220 mL). The organic layer was washed with saturated ammonium chloride (2×100 mL). The organic phase was dried over anhydrous magnesium sulfate, filtered, and concentrated in vacuo. Purification of the residue by preparative reverse phase HPLC, using acetonitrile in water containing 0.1% of trifluoroacetic acid as eluent, afforded the title compound as a colorless solid (0.023 g, 12% yield): $^1$H-NMR (300 MHz; DMSO-$d_6$) δ 13.15-13.03 (m, 1H), 8.97-8.91 (m, 1H), 8.51-8.46 (m, 1H), 8.26-8.20 (m, 1H), 8.14-8.06 (m, 1H), 7.47-7.40 (m, 1H), 7.28-7.13 (m, 5H), 6.73-6.66 (m, 2H), 5.33-5.14 (m, 1H), 3.44-3.18 (m, 4H), 2.09-1.80 (m, 2H); MS (ESI+) m/z 386.09 (M+1).

Example 20

Synthesis of (S)-2-(3-fluoropyrrolidin-1-yl)-3-(5-(4-isopropylphenyl)-1H-pyrazol-3-yl)-4-phenylpyridine

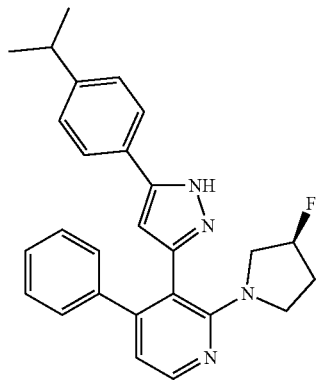 [SMILES: CC(C)c1ccc(-c2cc(-c3c(-c4ccccc4)ccnc3N3CC[C@H](F)C3)n[nH]2)cc1]

Step 1. Preparation of 2-chloro-3-(5-(4-isopropylphenyl)-1H-pyrazol-3-yl)-4-phenylpyridine

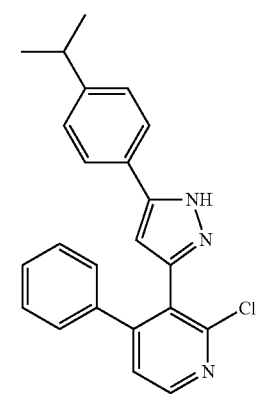 [SMILES: CC(C)c1ccc(-c2cc(-c3c(-c4ccccc4)ccnc3Cl)n[nH]2)cc1]

A mixture of 2-chloro-4-phenylnicotinaldehyde (0.69 g, 3.2 mmol), 1-(4-isopropylphenyl)ethan-1-one (0.515 g, 3.18 mmol), potassium hydroxide (0.357 g, 6.36 mmol), and tetrahydrofuran (21 mL) was heated to reflux for 2 h. After cooling to ambient temperature, hydrazine hydrate (0.23 g, 4.6 mmol) was added. The reaction mixture was heated at 50° C. for 18 h. After cooling to ambient temperature, the reaction mixture was diluted with ethyl acetate (250 mL). The organic layer was washed with saturated ammonium chloride (3×100 mL). The organic phase was dried over anhydrous magnesium sulfate, filtered, and concentrated in vacuo. Purification of the residue by column chromatography, eluting with a gradient of 15-100% of ethyl acetate in heptane, afforded the title compound as a colorless solid (0.71 g, 59% yield): MS (ESI+) m/z 374 (M+1), 376 (M+1).

Step 2. Preparation of (S)-2-(3-fluoropyrrolidin-1-yl)-3-(5-(4-isopropylphenyl)-1H-pyrazol-3-yl)-4-phenylpyridine

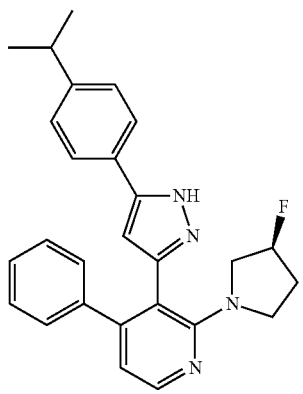 [SMILES: CC(C)c1ccc(-c2cc(-c3c(-c4ccccc4)ccnc3N3CC[C@H](F)C3)n[nH]2)cc1]

A mixture 2-chloro-3-(5-(4-isopropylphenyl)-1H-pyrazol-3-yl)-4-phenylpyridine (0.15 g, 0.40 mmol), potassium carbonate (0.22 g, 1.6 mmol), (S)-3-fluoropyrrolidine hydrochloride (0.10 g, 0.80 mmol), and dimethyl sulfoxide (1.5 mL) was sparged with nitrogen for 2 min. The reaction mixture was heated at 130° C. for 6 h. After cooling to ambient temperature, the reaction mixture was diluted with ethyl acetate (220 mL). The organic layer was washed with saturated ammonium chloride (2×100 mL). The organic phase was dried over anhydrous magnesium sulfate, filtered, and concentrated in vacuo. Purification of the residue by preparative reverse phase HPLC, using acetonitrile in water containing 0.1% of trifluoroacetic acid as eluent, afforded the title compound as a colorless solid (0.031 g, 18% yield): $^1$H-NMR (300 MHz; DMSO-$d_6$) δ 8.20 (d, J=5.5 Hz, 1H), 7.59 (d, J=8.3 Hz, 2H), 7.29-7.22 (m, 5H), 7.21-7.17 (m, 2H), 6.81-6.79 (m, 1H), 6.50 (s, 1H), 5.36-5.17 (m, 1H), 3.45-3.26 (m, 4H), 2.92-2.83 (m, 1H), 2.12-2.03 (m, 2H), 1.18 (t, J=6.4 Hz, 6H); MS (ESI+) m/z 427.1 (M+1).

Example 21

Synthesis of (S)-1-(6-chloropyridin-3-yl)-3-(4-(2-fluorophenyl)-2-(3-fluoropyrrolidin-1-yl)pyridin-3-yl)imidazolidin-2-one

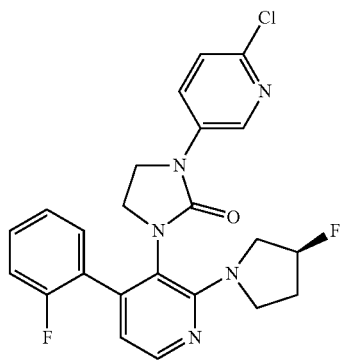 [SMILES: O=C1N(c2ccc(Cl)nc2)CCN1c1c(-c2ccccc2F)ccnc1N1CC[C@H](F)C1]

To a mixture of copper(I) iodide (0.004 g, 0.023 mmol), (1R,2R)-cyclohexane-1,2-diamine (0.008 g, 0.069 mmol), and tripotassium phosphate (0.122 g, 0.575 mmol) in 1,4-dioxane (2.7 mL) was added (S)-1-(4-(2-fluorophenyl)-2-(3-fluoropyrrolidin-1-yl)pyridin-3-yl)imidazolidin-2-one (0.080 g, 0.23 mmol), 2-chloro-5-iodopyridine (0.056 g, 0.23 mmol) under a nitrogen atmosphere. The reaction mixture was stirred at reflux for 20 h. After cooling to ambient temperature, the reaction mixture was diluted with dichloromethane (20 mL), and filtered through a layer of diatomaceous earth (i.e. Celite®). The filtrate was concentrated in vacuo to give a residue, which was purified by column chromatography, eluting with a gradient of 5% to 100% of ethyl acetate in heptane, to provide the title compound as a colorless solid (0.007 g, 6% yield): $^1$H-NMR (300 MHz; CDCl$_3$) δ 8.28-8.02 (m, 3H), 7.45-7.24 (m, 3H), 7.20-7.09 (m, 2H), 6.75-6.70 (m, 1H), 5.45-5.25 (m, 1H), 4.02-3.29 (m, 8H), 2.41-1.99 (m, 2H); MS (ES+) m/z 456.1 (M+1).

Example 22

Synthesis of (S)-1-(6-chloropyridin-3-yl)-3-(4-(2-fluorophenyl)-2-(3-fluoropyrrolidin-1-yl)pyridin-3-yl)-1,3-dihydro-2H-imidazol-2-one

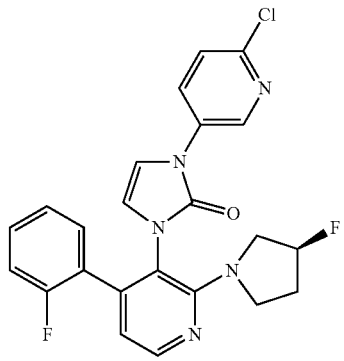 [SMILES: O=c1n(-c2ccc(Cl)nc2)ccn1-c1c(-c2ccccc2F)ccnc1N1CC[C@H](F)C1]

Step 1. Preparation of 2-chloro-4-phenylnicotinaldehyde

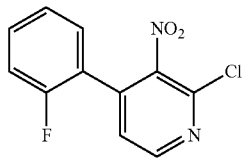 [SMILES: O=[N+]([O-])c1c(-c2ccccc2F)ccnc1Cl]

To a solution of 2,4-dichloro-3-nitropyridine (2.00 g, 10.4 mmol) in 1,4-dioxane (20 mL) was added 2-fluorophenylboronic acid (1.45 g, 10.4 mmol), [1,1'-bis(diphenylphosphino)ferrocene]dichloropalladium(II) complex with dichloromethane (0.849 g, 1.04 mmol), and potassium carbonate (2.15 g, 15.5 mmol). The mixture was degassed with argon for 15 minutes, then water (7 mL) was added. The reaction mixture was then heated to 60° C. for 4 h. After cooling to ambient temperature, the reaction mixture was diluted with brine (25 mL) and water (25 mL), and extracted with ethyl acetate (3×30 mL). The combined organic phases were washed with water (2×50 mL), dried over anhydrous sodium sulfate, and filtered. The filtrate was concentrated in vacuo and the residue was purified by column chromatography, eluting with a gradient of 0% to 22% of ethyl acetate (containing 10% triethylamine and 10% isopropanol) in heptane, to provide the title compound as a yellow solid (1.66 g, 64% yield): $^1$H-NMR (300 MHz; CDCl$_3$) δ 8.60 (d, J=5.1 Hz, 1H), 7.52 (dddd, J=8.3, 7.0, 5.2, 2.3 Hz, 1H), 7.43 (dd, J=5.0, 1.3 Hz, 1H), 7.35-7.29 (m, 3H); MS (ES+) m/z 253.2 (M+1), 255.2 (M+1).

Step 2. Preparation of (S)-4-(2-fluorophenyl)-2-(3-fluoropyrrolidin-1-yl)-3-nitropyridine

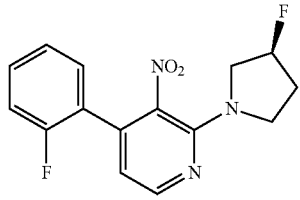 [SMILES: O=[N+]([O-])c1c(-c2ccccc2F)ccnc1N1CC[C@H](F)C1]

To a solution of 2-chloro-4-phenylnicotinaldehyde (1.00 g, 3.96 mmol) in anhydrous dimethyl sulfoxide (16 mL) was added potassium carbonate (1.37 g, 9.90), and (S)-3-fluoropyrrolidine hydrochloric acid salt (0.597 g, 4.75 mmol). The reaction mixture was stirred at 90° C. for 5 h. After cooling to ambient temperature, the reaction mixture was diluted with saturated aqueous sodium bicarbonate solution (50 mL), and extracted with ethyl acetate (2×50 mL). The combined organic phases were washed with brine (80 mL), dried over anhydrous sodium sulfate, and filtered. The filtrate was concentrated in vacuo to give a residue, which was purified by column chromatography, eluting with a gradient of 2% to 40% ethyl acetate in heptane, to provide the title compound as a yellow solid (1.13 g, 93% yield): $^1$H-NMR (300 MHz; DMSO-d$_6$) δ 8.50 (d, J=5.1 Hz, 1H), 7.60-7.55 (m, 2H), 7.54-7.52 (m, 1H), 7.48-7.44 (m, 3H), 7.13-7.09 (m, 1H), 2.82-2.72 (m, 1H), 2.47-2.38 (m, 1H), 2.09-1.99 (m, 2H), 1.74-1.67 (m, 2H), 1.36-1.17 (m, 4H); MS (ES+) m/z 306.4 (M+1).

Step 3. Preparation of (S)-4-(2-fluorophenyl)-2-(3-fluoropyrrolidin-1-yl)pyridin-3-amine

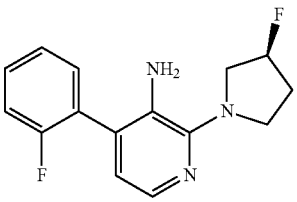 [SMILES: Nc1c(-c2ccccc2F)ccnc1N1CC[C@H](F)C1]

To a solution of (S)-4-(2-fluorophenyl)-2-(3-fluoropyrrolidin-1-yl)-3-nitropyridine (1.125 g, 3.69 mmol) in glacial acetic acid (7.5 mL) was added iron power (0.659 g, 11.8 mmol). The reaction mixture was heated to 40° C. for 9 h. Then the reaction mixture was poured onto ice and was neutralized with saturated sodium bicarbonate and sodium carbonate solution till the pH reached 6.5. The mixture was extracted with ethyl acetate (3×50 mL). The combined organic phases were washed with saturated aqueous sodium bicarbonate (100 mL), dried over anhydrous sodium sulfate, and filtered. The filtrate was concentrated in vacuo to give the title compound (1.00 g, 99% yield): $^1$H-NMR (300 MHz; CDCl$_3$) δ 7.80 (d, J=5.2 Hz, 1H), 7.46-7.35 (m, 2H), 7.29-7.17 (m, 2H), 6.78 (dd, J=5.2, 0.8 Hz, 1H), 5.48-5.26 (m, 1H), 3.80-3.66 (m, 4H), 2.32-2.15 (m, 2H); MS (ES+) m/z 276.4 (M+1).

Step 4. Preparation of (S)-1-(4-(2-fluorophenyl)-2-(3-fluoropyrrolidin-1-yl)pyridin-3-yl)imidazolidin-2-one

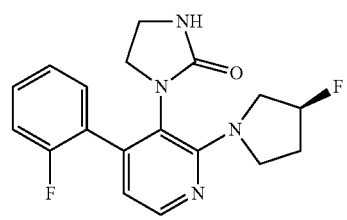 [SMILES: O=C1NCCN1c1c(-c2ccccc2F)ccnc1N1CC[C@H](F)C1]

To a solution of (S)-4-(2-fluorophenyl)-2-(3-fluoropyrrolidin-1-yl)pyridin-3-amine (0.493 g, 1.79 mmol) in anhydrous toluene (2.0 mL) was dropwise added 1-chloro-2-isocyanatoethane (0.23 mL, 2.69 mmol) at 0° C. The reaction mixture was warmed up to ambient temperature and stirred for 16 h. After dilution with toluene (2.0 mL), the reaction mixture was filtered and the solid was rinsed with toluene (2.0 mL) and dried under reduced pressure to afford a residue. Then this residue was dissolved in anhydrous N,N-dimethylformamide (3.0 mL) to form a solution, which was added to a stirred mixture of sodium hydride (60% in a mixture with mineral oil, 0.067 g, 1.66 mmol) in anhydrous tetrahydrofuran (3.0 mL) at 0° C. The reaction mixture was stirred at ambient temperature for 16 h. Then the reaction mixture was quenched with water (1.0 mL), diluted with saturated aqueous sodium bicarbonate solution (10 mL), and extracted with ethyl acetate (3×50 mL). The combined organic phases were washed brine (50 mL), dried over anhydrous sodium sulfate, and filtered. The filtrate was concentrated in vacuo to give a residue, which was purified by column chromatography, eluting with a gradient of 25% to 100% of ethyl acetate in heptane, to provide the title compound as a light yellow solid (0.443 g, 72% yield): ¹H-NMR (300 MHz; DMSO-d₆) δ 8.10 (dd, J=4.9, 2.4 Hz, 1H), 7.52-7.41 (m, 1H), 7.38-7.31 (m, 1H), 7.30-7.20 (m, 2H), 6.61 (dd, J=4.9, 1.0 Hz, 1H), 6.41 (d, J=12.9 Hz, 1H), 5.50-5.30 (m, 1H), 3.85-3.45 (m, 6H), 3.21-2.82 (m, 2H), 2.28-2.01 (m, 2H); MS (ES+) m/z 345.4 (M+1).

Step 5. Preparation of (S)-1-(6-chloropyridin-3-yl)-3-(4-(2-fluorophenyl)-2-(3-fluoropyrrolidin-1-yl)pyridin-3-yl)imidazolidin-2-one

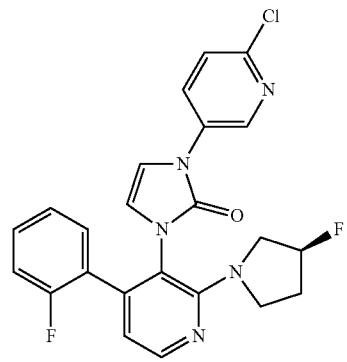 [SMILES: O=c1n(-c2ccc(Cl)nc2)ccn1-c1c(-c2ccccc2F)ccnc1N1CC[C@H](F)C1]

To a mixture of copper(I) iodide (0.004 g, 0.023 mmol), (1R,2R)-cyclohexane-1,2-diamine (0.008 g, 0.069 mmol), and tripotassium phosphate (0.122 g, 0.575 mmol) in 1,4-dioxane (2.7 mL) was added (S)-1-(4-(2-fluorophenyl)-2-(3-fluoropyrrolidin-1-yl)pyridin-3-yl)imidazolidin-2-one (0.080 g, 0.23 mmol), 2-chloro-5-iodopyridine (0.056 g, 0.23 mmol) under a nitrogen atmosphere. The reaction mixture was stirred at reflux for 20 h. After cooling to ambient temperature, the reaction mixture was diluted with dichloromethane (20 mL), and filtered through a layer of diatomaceous earth (i.e. Celite®). The filtrate was concentrated in vacuo to give a residue, which was purified by column chromatography, eluting with a gradient of 5% to 100% of ethyl acetate in heptane, to provide the title compound as a colorless solid (0.002 g, 2% yield): ¹H-NMR (300 MHz; CDCl₃) δ 8.44-8.36 (m, 1H), 8.33-8.29 (m, 1H), 7.97 (ddd, J=40.4, 8.7, 2.9 Hz, 1H), 7.41-7.31 (m, 3H), 7.15-7.02 (m, 2H), 6.75-6.69 (m, 1H), 6.75-6.69 (m, 1H), 6.53 (dd, J=14.6, 3.1 Hz, 1H), 6.48-6.32 (m, 1H), 5.40-5.16 (m, 1H), 3.86-3.47 (m, 4H), 2.40-1.93 (m, 2H); MS (ES+) m/z 454.0 (M+1).

Example 23

Synthesis of 2-(4-(3,5-difluorophenyl)-2-(pyrrolidin-1-yl)pyridin-3-yl)-1H-benzo[d]imidazole

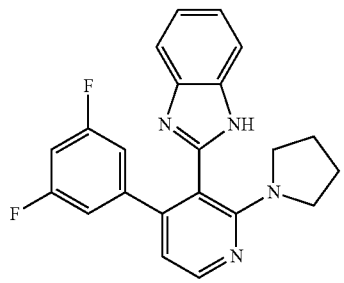 [SMILES: Fc1cc(F)cc(-c2ccnc(N3CCCC3)c2-c2nc3ccccc3[nH]2)c1]

Step 1. Preparation of 2-(2-chloro-4-(3,5-difluorophenyl)pyridin-3-yl)-1-((2-(trimethylsilyl)ethoxy)methyl)-1H-benzo[d]imidazole

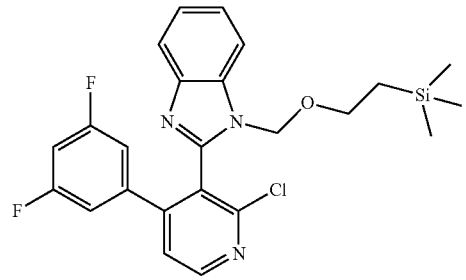 [SMILES: C[Si](C)(C)CCOCn1c(-c2c(-c3cc(F)cc(F)c3)ccnc2Cl)nc2ccccc21]

A mixture of 2-(2-chloro-4-iodopyridin-3-yl)-1-((2-(trimethylsilyl)ethoxy)methyl)-1H-benzo[d]imidazole (0.32 g, 0.65 mmol), [1,1'bis(diphenylphosphino)ferrocene]dichloropalladium(II)] complex with dichloromethane (0.056 g, 0.065 mmol), potassium carbonate (0.225 g, 1.63 mmol), 3,5-difluorophenylboronic acid (0.113 g, 0.717 mmol), 1,4-dioxane (2.2 mL), and water (0.24 mL) were sparged with nitrogen for 10 min. The reaction vial was sealed and heated at 95° C. for 3 h. After cooling to ambient temperature, the reaction mixture was diluted with ethyl acetate (100 mL), filtered, and concentrated in vacuo. Purification of the residue by column chromatography, eluting with a gradient of 10-80% of ethyl acetate in heptane, afforded the title compound as a yellow solid (0.25 g, 81% yield): MS (ESI+) m/z 472 (M+1), 474 (M+1).

Step 2. Preparation of 2-(4-(3,5-difluorophenyl)-2-(pyrrolidin-1-yl)pyridin-3-yl)-1H-benzo[d]imidazole

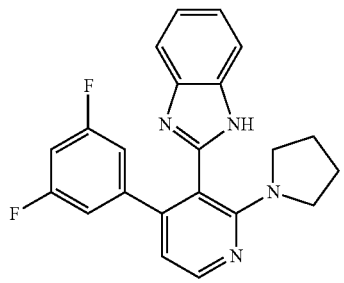 [SMILES: Fc1cc(F)cc(-c2ccnc(N3CCCC3)c2-c2nc3ccccc3[nH]2)c1]

A mixture of 2-(2-chloro-4-(3,5-difluorophenyl)pyridin-3-yl)-1-((2-(trimethylsilyl)ethoxy)methyl)-1H-benzo[d]imidazole (0.25 g, 0.53 mmol), pyrrolidine (0.075 g, 1.1 mmol), potassium carbonate (0.22 g, 1.6 mmol), and dimethylsulfoxide (5.3 mL) was sparged with nitrogen for 2 min. The reaction vessel was sealed and heated at 120° C. for 6 h. After cooling to ambient temperature, the reaction mixture was diluted with ethyl acetate (200 mL). The organic layer was washed with saturated ammonium chloride (2×100 mL). The organic phase was dried over anhydrous magnesium sulfate, filtered, and concentrated in vacuo. The residue was dissolved in trifluoroacetic acid (15 mL) was heated at 50° C. for 1.5 h. After cooling to ambient temperature, the reaction mixture was concentrated in vacuo. Purification of the residue by preparative reverse phase HPLC, using acetonitrile in water containing 0.1% of trifluoroacetic acid as eluent, afforded the title compound as a colorless solid (0.146 g, 73% yield): $^1$H-NMR (300 MHz; DMSO-$d_6$) δ 8.41 (d, J=5.1 Hz, 1H), 7.72-7.65 (m, 2H), 7.45-7.39 (m, 2H), 7.16 (tt, J=9.4, 2.3 Hz, 1H), 6.86-6.78 (m, 3H), 3.08-3.02 (m, 4H), 1.77-1.69 (m, 4H); MS (ESI+) m/z 377.2 (M+1).

Example 24

Synthesis of (3aR,7aR)-2-(2-((S)-3-fluoropyrrolidin-1-yl)-4-phenylpyridin-3-yl)-3a,4,5,6,7,7a-hexahydro-1H-benzo[d]imidazole

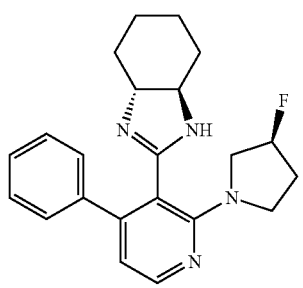 [SMILES: F[C@H]1CCN(c2nccc(-c3ccccc3)c2C2=N[C@@H]3CCCC[C@H]3N2)C1]

Step 1. Preparation of (3aR,7aR)-2-(2-((S)-3-fluoropyrrolidin-1-yl)-4-phenylpyridin-3-yl)-3a,4,5,6,7,7a-hexahydro-1H-benzo[d]imidazole

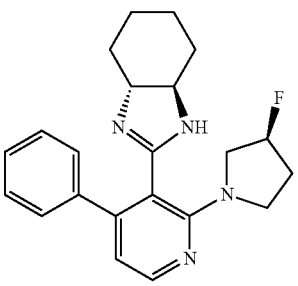 [SMILES: F[C@H]1CCN(c2nccc(-c3ccccc3)c2C2=N[C@@H]3CCCC[C@H]3N2)C1]

A microwave vial was charged with (3aS,7aS)-2-(2-chloro-4-phenylpyridin-3-yl)-3a,4,5,6,7,7a-hexahydro-1H-benzo[d]imidazole (0.039 g, 0.125 mmol), n-butanol (3.0 mL), (S)-3-fluoropyrrolidine hydrochloric acid salt (0.126 g, 1.00 mmol), and N,N-diisopropylethylamine (0.87 mL, 5.0 mmol). The vial was capped and heated to 180° C. for 20 minutes under a microwave. After cooling to ambient temperature, the reaction mixture was concentrated in vacuo to give a residue, which was purified by column chromatography, eluting with a gradient of 2% to 40% of ethyl acetate (containing 10% trimethylamine and 10% isopropanol) in heptane, to provide the title compound as a colorless solid (0.010 g, 21% yield): $^1$H-NMR (300 MHz; CD$_3$CN) δ 8.21-8.14 (m, 1H), 7.46-7.35 (m, 3H), 7.34-7.25 (m, 2H), 6.64-6.57 (m, 1H), 5.42-5.23 (m, 1H), 3.89-3.54 (m, 4H), 2.30-2.11 (m, 2H), 2.02-1.99 (m, 2H), 1.74-1.71 (m, 2H), 1.31-1.24 (m, 4H); MS (ES+) m/z 365.1 (M+1).

Example 25

Synthesis of 4-(3-((3aR,7aR)-3a,4,5,6,7,7a-hexahydro-1H-benzo[d]imidazol-2-yl)-4-phenylpyridin-2-yl)morpholine

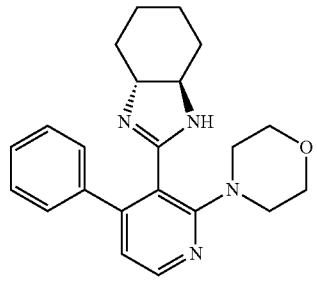 [SMILES: c1ccc(-c2ccnc(N3CCOCC3)c2C2=N[C@@H]3CCCC[C@H]3N2)cc1]

Step 1. Preparation of 4-(3-((3aR,7aR)-3a,4,5,6,7,7a-hexahydro-1H-benzo[d]imidazol-2-yl)-4-phenylpyridin-2-yl)morpholine

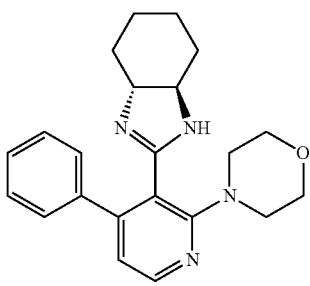 [SMILES: c1ccc(-c2ccnc(N3CCOCC3)c2C2=N[C@@H]3CCCC[C@H]3N2)cc1]

A microwave vial was charged with (3aS,7aS)-2-(2-chloro-4-phenylpyridin-3-yl)-3a,4,5,6,7,7a-hexahydro-1H-benzo[d]imidazole (0.039 g, 0.125 mmol), n-butanol (3.0 mL), and morpholine (0.22 mL, 2.50 mmol). The vial was capped and heated to 180° C. for 20 minutes under a microwave. After cooling to ambient temperature, the reaction mixture was concentrated in vacuo to give a residue, which was purified by column chromatography, eluting with a gradient of 2% to 40% of ethyl acetate (containing 10% trimethylamine and 10% isopropanol) in heptane, to provide the title compound as a colorless solid (0.017 g, 40% yield): $^1$H-NMR (300 MHz; CD$_3$CN) δ 8.31 (d, J=5.1 Hz, 1H), 7.48-7.38 (m, 5H), 6.98 (d, J=5.1 Hz, 1H), 3.81-3.70 (m, 4H), 3.47-3.39 (m, 2H), 3.17-3.09 (m, 2H), 2.82-2.78 (m, 2H), 2.13-2.08 (m, 2H), 1.78-1.73 (m, 2H), 1.42-1.26 (m, 4H); MS (ES+) m/z 363.1 (M+1).

Example 26

Synthesis of 2-((S)-3-fluoropyrrolidin-1-yl)-3-(5-methyl-4,5-dihydro-1H-imidazol-2-yl)-4-phenylpyridine

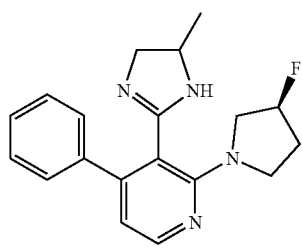 [SMILES: CC1CN=C(c2c(-c3ccccc3)ccnc2N2CC[C@H](F)C2)N1]

Step 1. Preparation of 2-chloro-3-(5-methyl-4,5-dihydro-1H-imidazol-2-yl)-4-phenylpyridine

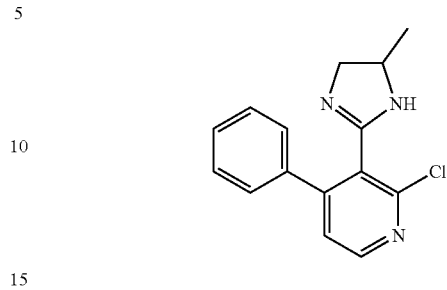

To a solution of 2-chloro-4-phenylnicotinaldehyde (0.425 g, 1.95 mmol) in dichloromethane (10 mL) was added 1,2-diaminopropane (0.18 mL, 1.97 mmol). The reaction mixture was stirred at ambient temperature for 40 minutes prior to the addition of N-bromosuccinimide (1.04, 5.85 mmol). After stirring at ambient temperature for 16 h, the reaction was quenched by dropwise addition of saturated aqueous sodium metabisulfite solution (20 mL), diluted with saturated aqueous sodium bicarbonate solution (50 mL), and extracted with dichloromethane (3×40 mL). The combined organic phases were washed with brine (100 mL), dried over anhydrous sodium sulfate, and filtered. Concentration of the filtrate in vacuo gave a residue, which was purified by column chromatography, eluting with a gradient of 4% to 40% of ethyl acetate (containing 10% trimethylamine and 10% isopropanol) in heptane, to provide the title compound as a light yellow liquid (0.214 g, 40% yield): $^1$H-NMR (300 MHz; DMSO-d$_6$) δ 8.50 (d, J=5.1 Hz, 1H), 7.60-7.55 (m, 2H), 7.54-7.52 (m, 1H), 7.48-7.44 (m, 3H), 7.13-7.09 (m, 1H), 2.82-2.72 (m, 1H), 2.47-2.38 (m, 1H), 2.09-1.99 (m, 2H), 1.74-1.67 (m, 2H), 1.36-1.17 (m, 4H); MS (ES+) m/z 272.0 (M+1), 274.0 (M+1).

Step 2. Preparation of 2-((S)-3-fluoropyrrolidin-1-yl)-3-(5-methyl-4,5-dihydro-1H-imidazol-2-yl)-4-phenylpyridine

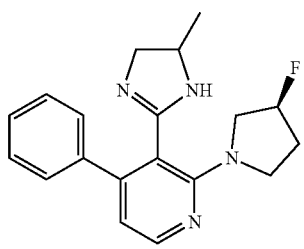 [SMILES: CC1CN=C(c2c(-c3ccccc3)ccnc2N2CC[C@H](F)C2)N1]

A microwave vial was charged with 2-chloro-3-(5-methyl-4,5-dihydro-1H-imidazol-2-yl)-4-phenylpyridine (0.082 g, 0.30 mmol), n-butanol (6.0 mL), (S)-3-fluoropyrrolidine hydrochloric acid salt (0.304 g, 2.4 mmol), and N,N-diisopropylethylamine (2.1 mL, 12 mmol). The vial was capped and heated to 180° C. for 20 minutes under a microwave. After cooling to ambient temperature, the reaction mixture was diluted with saturated aqueous sodium bicarbonate solution (40 mL), and extracted with ethyl acetate (40 mL). The organic phase was washed with brine (40 mL), dried over anhydrous sodium sulfate, and filtered. Concentration of the filtrate gave a residue, which was purified by column chromatography, eluting with a gradient of 8% to 61% of ethyl acetate (containing 10% trimethylamine and 10% isopropanol) in heptane, to provide the title compound as a colorless solid (0.005 g, 5% yield): $^1$H-NMR (300 MHz; CD3CN) δ 8.15 (m, 1H), 7.47-7.37 (m, 5H), 6.57 (m 1H), 5.43-5.23 (m, 1H), 3.87-3.82 (m, 1H), 3.77-3.68 (m, 4H), 3.67-3.56 (m, 1H), 2.11-2.01 (m, 2H), 1.05-0.78 (m, 3H); MS (ES+) m/z 325.1 (M+1).

Example 27

Synthesis of (S)-3-(4-bromo-5-methyl-1H-imidazol-2-yl)-2-(3-fluoropyrrolidin-1-yl)-4-phenylpyridine

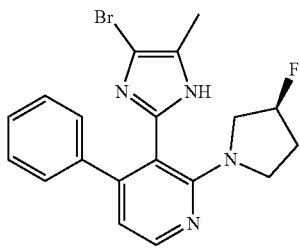 [SMILES: Cc1[nH]c(-c2c(-c3ccccc3)ccnc2N2CC[C@H](F)C2)nc1Br]

Step 1. Preparation of 3-(4-bromo-5-methyl-1H-imidazol-2-yl)-2-chloro-4-phenylpyridine

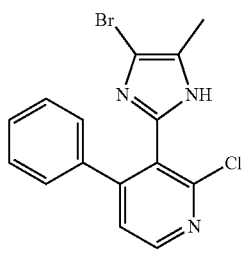 [SMILES: Cc1[nH]c(-c2c(-c3ccccc3)ccnc2Cl)nc1Br]

To a solution of 2-chloro-4-phenylnicotinaldehyde (0.425 g, 1.95 mmol) in dichloromethane (10 mL) was added 1,2-diaminopropane (0.18 mL, 1.97 mmol). The reaction mixture was stirred at ambient temperature for 40 minutes prior to the addition of N-bromosuccinimide (1.04, 5.85 mmol). After stirring at ambient temperature for 16 h, the reaction was quenched by dropwise addition of saturated aqueous sodium metabisulfite solution (20 mL), diluted with saturated aqueous sodium bicarbonate solution (50 mL), and extracted with dichloromethane (3×40 mL). The combined organic phases were washed with brine (100 mL), dried over anhydrous sodium sulfate, and filtered. Concentration of the filtrate in vacuo gave a residue, which was purified by column chromatography, eluting with a gradient of 4% to 40% of ethyl acetate (containing 10% trimethylamine and 10% isopropanol) in heptane, to provide the title compound as a light yellow liquid (0.179 g, 26% yield): $^1$H-NMR (300 MHz; CDCl$_3$): δ 8.42-8.40 (m, 1H), 7.39-7.26 (m, 5H), 7.09-7.05 (m, 2H), 2.10 (d, J=0.9 Hz, 3H); MS (ES+) m/z 348.0 (M+1), 350.0 (M+1).

Step 2. Preparation of (S)-3-(4-bromo-5-methyl-1H-imidazol-2-yl)-2-(3-fluoropyrrolidin-1-yl)-4-phenylpyridine

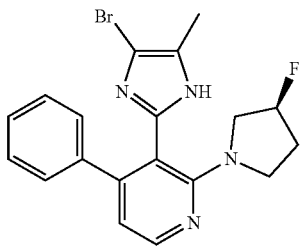 [SMILES: Cc1[nH]c(-c2c(-c3ccccc3)ccnc2N2CC[C@H](F)C2)nc1Br]

A microwave vial was charged with 2-chloro-3-(5-methyl-4,5-dihydro-1H-imidazol-2-yl)-4-phenylpyridine (0.080 g, 0.30 mmol), n-butanol (3.0 mL), (S)-3-fluoropyrrolidine hydrochloric acid salt (0.230 g, 1.84 mmol), and N,N-diisopropylethylamine (1.6 mL, 9.2 mmol). The vial was capped and heated to 180° C. for 15 minutes under a microwave. After cooling to ambient temperature, the reaction mixture was diluted with saturated aqueous sodium bicarbonate solution (40 mL), and extracted with ethyl acetate (40 mL). The organic phase was washed with brine (40 mL), dried over anhydrous sodium sulfate, and filtered. Concentration of the filtrate gave a residue, which was purified by column chromatography, eluting with a gradient of 4% to 40% of ethyl acetate (containing 10% trimethylamine and 10% isopropanol) in dichloromethane, to provide the title compound as a colorless solid (0.005 g, 5% yield): $^1$H-NMR (300 MHz; MeOD) δ 8.24-8.18 (m, 1H), 7.33-7.27 (m, 3H), 7.14-7.12 (m, 2H), 6.74-6.70 (m, 1H), 5.30-5.11 (m, 1H), 3.38-3.28 (m, 4H), 2.24-1.91 (m, 5H); MS (ES+) m/z 401.0 (M+1), 403.0 (M+1).

Example 28

Synthesis of 2-(5-phenyl-3-(pyrrolidin-1-yl)pyridazin-4-yl)-1H-benzo[d]imidazole

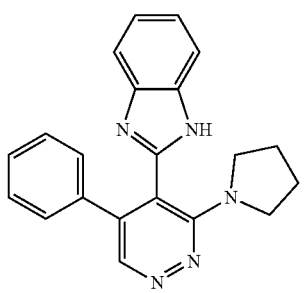 [SMILES: c1ccc(-c2cnnc(N3CCCC3)c2-c2nc3ccccc3[nH]2)cc1]

Step 1. Preparation of 2-(3-chloro-5-phenylpyridazin-4-yl)-1H-benzo[d]imidazole

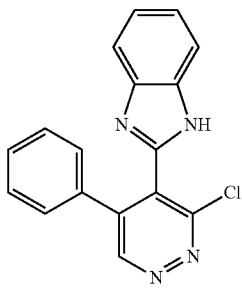 [SMILES: Clc1nncc(-c2ccccc2)c1-c1nc2ccccc2[nH]1]

To a mixture of 3-oxo-5-phenyl-2,3-dihydropyridazine-4-carboxylic acid (0.474 g, 2.19 mmol), benzene-1,2-diamine (0.24 g, 2.2 mmol), and 1,4-dioxane (5.5 mL) was added phosphoryl trichloride (2.67 g, 17.5 mmol) at ambient temperature. The reaction vessel was sealed and heated at 110° C. for 1.5 h. After cooling to ambient temperature, the reaction mixture was diluted with ethyl acetate (200 mL). The organic layer was washed with saturated ammonium chloride (2×100 mL). The organic phase was dried over anhydrous magnesium sulfate, filtered, and concentrated in vacuo. Purification of the residue by column chromatography, eluting with a gradient of 10-100% of ethyl acetate in heptane, then 10-50% methanol in dichloromethane, afforded the title compound as a brown oil (0.48 g, 71% yield): MS (ESI+) m/z 307 (M+1), 309 (M+1).

Step 2. Preparation of 2-(5-phenyl-3-(pyrrolidin-1-yl)pyridazin-4-yl)-1H-benzo[d]imidazole

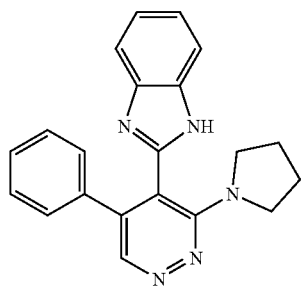 [SMILES: c1ccc(-c2cnnc(N3CCCC3)c2-c2nc3ccccc3[nH]2)cc1]

A mixture of 2-(3-chloro-5-phenylpyridazin-4-yl)-1H-benzo[d]imidazole (0.16 g, 0.52 mmol), potassium carbonate (0.36 g, 2.6 mmol), pyrrolidine (0.15 g, 2.1 mmol), and dimethylsulfoxide (5.2 mL) was sparged with nitrogen for 2 min. The reaction vessel was sealed and heated at 115° C. for 4 h. After cooling to ambient temperature, the reaction mixture was diluted with dimethylsulfoxide (2 mL) and filtered. Purification of the residue by preparative reverse phase HPLC, using acetonitrile in water containing 0.1% of trifluoroacetic acid as eluent, afforded the title compound as a colorless solid (0.012 g, 7% yield): $^1$H-NMR (300 MHz; DMSO-$d_6$) δ 12.67-12.64 (m, 1H), 8.64 (s, 1H), 7.63-7.59 (m, 1H), 7.45-7.37 (m, 1H), 7.26-7.14 (m, 7H), 3.08 (q, J=5.9 Hz, 4H), 1.76-1.67 (m, 4H); MS (ESI+) m/z 342.05 (M+1).

Example 29

Synthesis of (S)-2-(2-(3-fluoropyrrolidin-1-yl)-4-phenylpyridin-3-yl)-4,5,6,7-tetrahydro-1H-benzo[d]imidazole

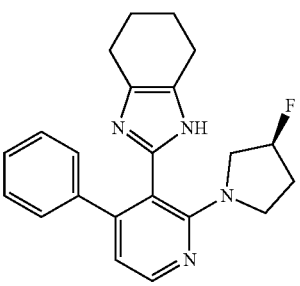 [SMILES: F[C@H]1CCN(c2nccc(-c3ccccc3)c2-c2nc3c([nH]2)CCCC3)C1]

Step 1. Preparation of 2-chloro-4-phenylnicotinaldehyde

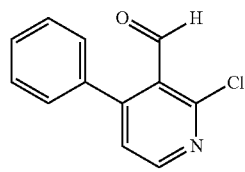 [SMILES: O=Cc1c(-c2ccccc2)ccnc1Cl]

To a solution of 2-chloro-4-iodonicotinaldehyde (10.0 g, 37.4 mmol) in 1,4-dioxane (125 mL) was added phenylboronic acid (5.0 g, 41 mmol), [1,1′-bis(diphenylphosphino)ferrocene]dichloropalladium(II) complex with dichloromethane (3.05 g, 3.74 mmol), and potassium carbonate (12.9 g, 93.3 mmol). The mixture was degassed with argon for 15 minutes, then water (14 mL) was added. The reaction mixture was then heated to 90° C. for 195 minutes. After cooling to ambient temperature, the reaction mixture was filtered through a layer of diatomaceous earth (i.e. Celite®), and then diluted with water (200 mL). The organic phase was collected and the aqueous phase was extracted with ethyl acetate (100 mL). The combined organic phases were washed with brine (200 mL), dried over anhydrous sodium sulfate, and filtered. The filtrate was concentrated in vacuo and the residue was purified by trituration with a solvent mixture of methanol (10 mL), ethanol (10 mL), and isopropanol (10 mL), to provide the title compound as a yellow solid (6.23 g, 77% yield): $^1$H-NMR (300 MHz; CDCl$_3$) δ 10.20 (s, 1H), 8.56 (d, J=5.0 Hz, 1H), 7.53-7.49 (m, 3H), 7.35-7.32 (m, 3H); MS (ES+) m/z 218.0 (M+1), 220.0 (M+1).

Step 2. Preparation of (3aS,7aS)-2-(2-chloro-4-phenylpyridin-3-yl)-3a,4,5,6,7,7a-hexahydro-1H-benzo[d]imidazole

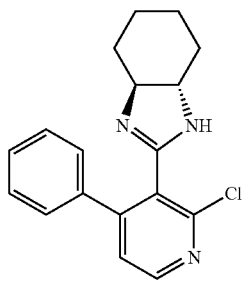 [SMILES: Clc1nccc(-c2ccccc2)c1C1=N[C@H]2CCCC[C@@H]2N1]

To a solution of 2-chloro-4-phenylnicotinaldehyde (0.41 g, 1.88 mmol) in dichloromethane (9.4 mL) was added a solution of (1S,2S)-cyclohexane-1,2-diamine (0.226 g, 1.97 mmol) in dichloromethane (2.0 mL). The mixture was stirred at ambient temperature for 30 minutes prior to the addition of N-bromosuccinimide (0.356 g, 2.00 mmol), and then the mixture was stirred at ambient temperature for 16 h. To the reaction mixture was added N-bromosuccinimide (0.702 g, 4.00 mmol), and the reaction was heated to 40° C. for 16 h. After cooling to ambient temperature, the reaction mixture was quenched by dropwise addition of saturated aqueous sodium metabisulfite solution (20 mL), diluted with saturated aqueous sodium bicarbonate solution (50 mL), and extracted with dichloromethane (3×40 mL). The combined organic phases were washed with brine (100 mL), dried over anhydrous sodium sulfate, and filtered. Concentration of the filtrate in vacuo gave a residue, which was purified by column chromatography, eluting with a gradient of 0% to 10% of ethyl acetate (containing 10% trimethylamine and 10% isopropanol) in dichloromethane, to provide the title compound as a light yellow liquid (0.306 g, 52% yield): $^1$H-NMR (300 MHz; DMSO-$d_6$) δ 8.50 (d, J=5.1 Hz, 1H), 7.60-7.55 (m, 2H), 7.54-7.52 (m, 1H), 7.48-7.44 (m, 3H), 7.13-7.09 (m, 1H), 2.82-2.72 (m, 1H), 2.47-2.38 (m, 1H), 2.09-1.99 (m, 2H), 1.74-1.67 (m, 2H), 1.36-1.17 (m, 4H); MS (ES+) m/z 312.4.0 (M+1), 314.4 (M+1).

Step 3. Preparation of 2-(2-chloro-4-phenylpyridin-3-yl)-4,5,6,7-tetrahydro-1H-benzo[d]imidazole

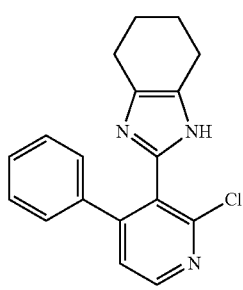 [SMILES: Clc1nccc(-c2ccccc2)c1-c1nc2c([nH]1)CCCC2]

To a solution of oxalyl chloride (0.025 mL, 0.29 mmol) in anhydrous dichloromethane (1.0 mL) was added anhydrous dimethyl sulfoxide (0.04 mL, 0.6 mmol) dropwise at −78° C. The mixture was stirred at −78° C. for 13 minutes, followed by dropwise addition of a solution of (3aS,7aS)-2-(2-chloro-4-phenylpyridin-3-yl)-3a,4,5,6,7,7a-hexahydro-1H-benzo[d]imidazole (0.06 g, 0.2 mmol) in anhydrous dichloromethane (1.8 mL). After 20 minutes, triethylamine (0.13 mL, 0.94 mmol) was added dropwise. After warming to ambient temperature and stirring for 16 h, the reaction mixture was diluted with dichloromethane (30 mL). The mixture was washed with water (40 mL) and brine (40 mL), dried over anhydrous sodium sulfate, and filtered. Concentration of the filtrate in vacuo gave a residue, which was purified by column chromatography, eluting with a gradient of 8% to 50% of ethyl acetate (10% trimethylamine and 10% isopropanol) in heptane, to provide the title compound as light yellow solid (0.029 g, 49% yield): $^1$H-NMR (300 MHz; CDCl$_3$) δ 8.37 (d, J=5.1 Hz, 1H), 7.32-7.19 (m, 5H), 7.00-6.97 (m, 2H), 2.38 (br s, 4H), 1.76 (br s, 4H); MS (ES+) m/z 310.0 (M+1), 312.0 (M+1).

Step 4. Preparation of (S)-2-(2-(3-fluoropyrrolidin-1-yl)-4-phenylpyridin-3-yl)-4,5,6,7-tetrahydro-1H-benzo[d]imidazole

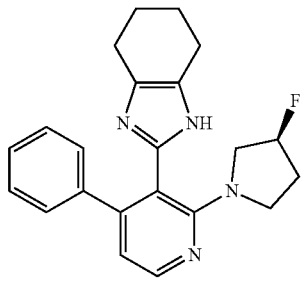 [SMILES: F[C@H]1CCN(c2nccc(-c3ccccc3)c2-c2nc3c([nH]2)CCCC3)C1]

A mixture of 2-(2-chloro-4-phenylpyridin-3-yl)-4,5,6,7-tetrahydro-1H-benzo[d]imidazole (0.029 g, 0.094 mmol), n-butanol (4.0 mL), (S)-3-fluoropyrrolidine hydrochloric acid salt (0.094 g, 0.75 mmol), and N,N-diisopropylethylamine (0.65 mL, 3.74 mmol) was heated to 180° C. for 70 minutes under microwave irradiation. After cooling to ambient temperature, the reaction mixture was concentrated in vacuo to give a residue, which was purified by column chromatography, eluting with a gradient of 2% to 40% of ethyl acetate (containing 10% trimethylamine and 10% isopropanol) in heptane, to provide the title compound as a colorless solid (0.017 g, 50% yield): $^1$H-NMR (300 MHz; DMSO-$d_6$) δ 11.38 (t, J=0.3 Hz, 1H), 8.19 (d, J=5.1 Hz, 1H), 7.26-7.23 (m, 3H), 7.11 (tdd, J=3.3, 2.0, 1.3 Hz, 2H), 6.65 (d, J=5.1 Hz, 1H), 5.33-5.14 (m, 1H), 3.26-3.14 (m, 4H), 2.43-2.34 (m, 4H), 2.08-1.85 (m, 2H), 1.68 (d, J=2.4 Hz, 4H); MS (ES+) m/z 363.1 (M+1).

Example 30

Synthesis of (S)-2-(2-(3-fluoropyrrolidin-1-yl)-4-phenylpyridin-3-yl)-5-(4-isopropylphenyl)-1,3,4-oxadiazole

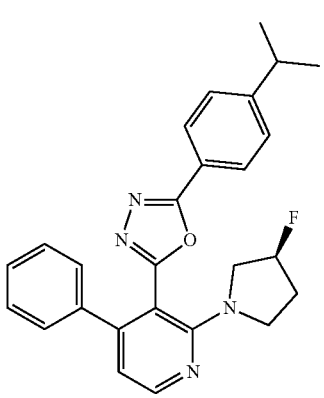 [SMILES: CC(C)c1ccc(-c2nnc(-c3c(-c4ccccc4)ccnc3N3CC[C@H](F)C3)o2)cc1]

Step 1. Preparation of 2-(2-chloro-4-phenylpyridin-3-yl)-5-(4-isopropylphenyl)-1,3,4-oxadiazole

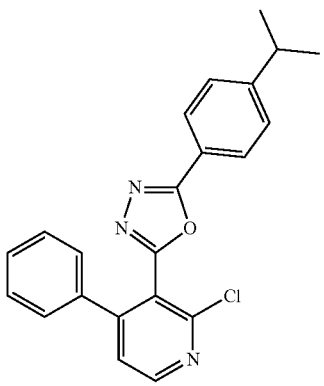 [SMILES: CC(C)c1ccc(-c2nnc(-c3c(-c4ccccc4)ccnc3Cl)o2)cc1]

To a mixture of 2-chloro-4-phenylnicotinaldehyde (0.45 g, 2.0 mmol), and acetic acid (3 mL) was added ammonium acetate (0.24 g, 3.0 mmol) and 4-isopropylbenzohydrazide (0.36 g, 2.0 mmol). The reaction vessel was sealed and stirred at ambient temperature for 1 h. The reaction mixture was diluted with ethyl acetate (200 mL) and washed with saturated ammonium chloride (2×100 mL). The organic phase was dried over anhydrous magnesium sulfate, filtered, and concentrated in vacuo. The residue was dissolved in tert-butylalcohol (22 mL) and tert-butyl hypochlorite (0.25 g, 3.0 mmol) was added at ambient temperature. The reaction mixture was stirred at ambient temperature for 30 min. The reaction mixture was diluted with ethyl acetate (250 mL) and the organic layer was washed with saturated sodium thiosulfate solution (100 mL) and saturated ammonium chloride (100 mL). The organic phase was dried over anhydrous magnesium sulfate, filtered, and concentrated in vacuo. Purification of the residue by column chromatography, eluting with a gradient of 5-65% of ethyl acetate in heptane, afforded the title compound as a colorless oil (0.25 g, 33% yield): MS (ESI+) m/z 376 (M+1), 378 (M+1).

Step 2. Preparation of (S)-2-(2-(3-fluoropyrrolidin-1-yl)-4-phenylpyridin-3-yl)-5-(4-isopropylphenyl)-1,3,4-oxadiazole

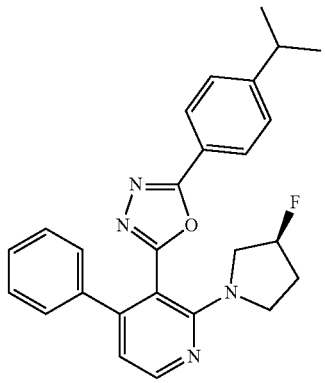 [SMILES: CC(C)c1ccc(-c2nnc(-c3c(-c4ccccc4)ccnc3N3CC[C@H](F)C3)o2)cc1]

A mixture of 2-(2-chloro-4-phenylpyridin-3-yl)-5-(4-isopropylphenyl)-1,3,4-oxadiazole (0.23 g, 0.62 mmol), potassium carbonate (0.43 g, 3.1 mmol), (S)-3-fluoropyrrolidine hydrochloride (0.19 g, 1.5 mmol), and dimethylsulfoxide (6.1 mL) was sparged with nitrogen for 2 min. The reaction vessel was sealed and heated at 100° C. for 4 h. After cooling to ambient temperature, the reaction mixture was diluted with ethyl acetate (250 mL). The organic layer was washed with saturated ammonium chloride (2×50 mL). The organic phase was dried over anhydrous magnesium sulfate, filtered, and concentrated in vacuo. Purification of the residue by column chromatography, eluting with a gradient of 10-100% of ethyl acetate in heptane, afforded the title compound as a colorless solid (0.142 g, 53% yield): $^1$H-NMR (300 MHz; DMSO-$d_6$) δ 8.41 (d, J=5.0 Hz, 1H), 7.79-7.75 (m, 2H), 7.45-7.41 (m, 2H), 7.35-7.27 (m, 3H), 7.21-7.17 (m, 2H), 6.81 (d, J=5.0 Hz, 1H), 5.38-5.20 (m, 1H), 3.53-3.25 (m, 4H), 2.95 (hept, J=6.9 Hz, 1H), 2.14-2.11 (m, 2H), 1.21 (d, J=6.9 Hz, 6H); MS (ESI+) m/z 429.0 (M+1).

Example 31

Synthesis of 6-(tert-butyl)-2-(4-phenyl-6-(pyrrolidin-1-yl)pyrimidin-5-yl)-1H-benzo[d]imidazole

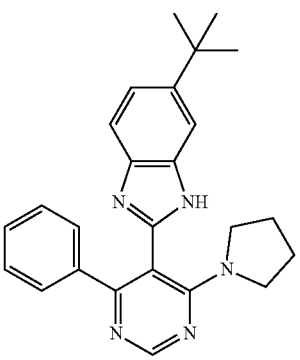 [SMILES: CC(C)(C)c1ccc2nc(-c3c(-c4ccccc4)ncnc3N3CCCC3)[nH]c2c1]

Step 1. Preparation of 4-chloro-6-(pyrrolidin-1-yl)pyrimidine-5-carbaldehyde

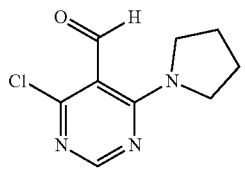 [SMILES: O=Cc1c(Cl)ncnc1N1CCCC1]

A mixture of 4,6-dichloropyrimidine-5-carbaldehyde (5.0 g, 28 mmol), and N,N-dimethylformamide (142 mL) was cooled in an ice/water bath. To the cooled solution was added N-ethyl-N-isopropylpropan-2-amine (7.3 g, 57 mmol), followed by an N,N-dimethylformamide (10 mL) solution of pyrrolidine (1.9 g, 27 mmol) dropwise. The reaction mixture was stirred in the ice/water bath for 1 h. The reaction mixture was diluted with ethyl acetate (400 mL), and washed with saturated ammonium chloride (2×100 mL). The organic phase was dried over anhydrous magnesium sulfate, filtered, and concentrated in vacuo. Purification of the residue by column chromatography, eluting with a gradient of 5-100% of ethyl acetate in heptane, afforded the title compound as a colorless solid (1.36 g, 23% yield): MS (ESI+) m/z 212 (M+1), 214 (M+1).

Step 2. Preparation of 6-(tert-butyl)-2-(4-chloro-6-(pyrrolidin-1-yl)pyrimidin-5-yl)-1H-benzo[d]imidazole

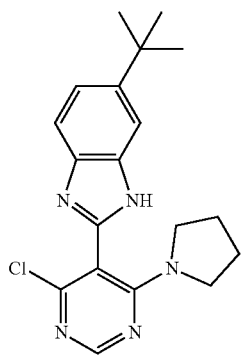 [SMILES: CC(C)(C)c1ccc2nc(-c3c(Cl)ncnc3N3CCCC3)[nH]c2c1]

A mixture of 4-chloro-6-(pyrrolidin-1-yl)pyrimidine-5-carbaldehyde (0.73 g, 3.4 mmol), and N,N-dimethylformamide (32 mL) was cooled in an ice/water bath. To the cooled solution was added 4-(tert-butyl)benzene-1,2-diamine (0.56 g, 3.4 mmol), followed by potassium peroxymonosulfate (1.5 g, 2.4 mmol) and water (1.7 mL). After stirring for 1 h the reaction mixture was charged with potassium peroxymonosulfate (1.5 g, 2.4 mmol) and water (1 mL). The reaction mixture was stirred at ambient temperature for 6 h. The reaction mixture was diluted with ethyl acetate (250 mL) and the organic layer was washed with saturated sodium thiosulfate solution (100 mL) and saturated ammonium chloride (100 mL). The organic phase was dried over anhydrous magnesium sulfate, filtered, and concentrated in vacuo. Purification of the residue by column chromatography, eluting with a gradient of 40-100% of ethyl acetate in heptane, afforded the title compound as a brown oil (0.61 g, 50% yield): $^1$H-NMR (300 MHz; CDCl$_3$) δ 8.36 (s, 1H), 7.69 (t, J=2.1 Hz, 1H), 7.64 (d, J=8.6 Hz, 1H), 7.44 (dd, J=8.6, 1.8 Hz, 1H), 3.20 (br s, 4H), 1.80-1.76 (m, 4H), 1.42 (s, 9H); MS (ESI+) m/z 356 (M+1), 358 (M+1).

Step 3. Preparation of 6-(tert-butyl)-2-(4-phenyl-6-(pyrrolidin-1-yl)pyrimidin-5-yl)-1H-benzo[d]imidazole

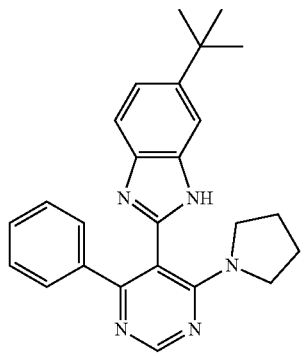 [SMILES: CC(C)(C)c1ccc2nc(-c3c(-c4ccccc4)ncnc3N3CCCC3)[nH]c2c1]

A mixture of 6-(tert-butyl)-2-(4-chloro-6-(pyrrolidin-1-yl)pyrimidin-5-yl)-1H-benzo[d]imidazole (0.40 g, 1.1 mmol) and 1,4-dioxane (11.4 mL) was sparged with nitrogen for 10 min. To the solution was added phenylboronic acid (0.55 g, 4.5 mmol), tripotassium phosphate (0.97 g, 4.6 mmol), palladium(II) acetate (0.051 g, 0.23 mmol), and tricyclohexylphosphine tetrafluoroborate (0.17 g, 0.46 mmol). The vial was sealed and the reaction mixture was heated in a microwave at 120° C. for 2 h. After cooling to ambient temperature, the reaction mixture was diluted with ethyl acetate (250 mL). The organic layer was washed with saturated ammonium chloride (2×100 mL). The organic phase was dried over anhydrous magnesium sulfate, filtered, and concentrated in vacuo. Purification of the residue by column chromatography, eluting with a gradient of 25-100% of ethyl acetate in heptane then 0-20% methanol in dichloromethane, followed by purification by preparative reverse phase HPLC, using acetonitrile in water containing 0.5% of formic acid as eluent, afforded the title compound as a colorless solid (0.83 g, 19% yield): $^1$H-NMR (300 MHz; DMSO-d$_6$) δ 8.82 (s, 1H), 7.57 (t, J=7.6 Hz, 2H), 7.48 (dd, J=8.6, 1.6 Hz, 1H), 7.32-7.26 (m, 5H), 3.17-3.12 (m, 4H), 1.77-1.73 (m, 4H), 1.33 (s, 9H); MS (ESI+) m/z 398.1 (M+1).

Example 32

Synthesis of (S)-2-(3-fluoropyrrolidin-1-yl)-4-phenyl-3-(1H-tetrazol-5-yl)pyridine

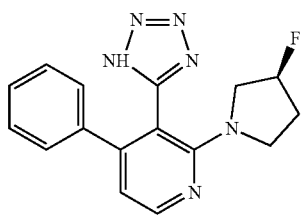 [SMILES: F[C@H]1CCN(c2nccc(-c3ccccc3)c2-c2nnn[nH]2)C1]

Step 1. Preparation of 2-chloro-4-phenylnicotinonitrile

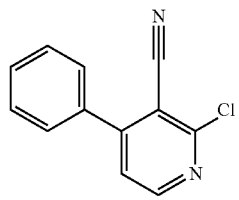 [SMILES: N#Cc1c(-c2ccccc2)ccnc1Cl]

To a solution of 2-chloro-4-iodonicotinonitrile (0.50 g, 1.9 mmol) in anhydrous dioxane (15 mL) and water (1.5 mL) was added phenylboronic acid (0.23 g, 1.9 mmol), potassium phosphate tribasic (1.20 g, 5.67 mmol) and the mixture was purged with nitrogen for 10 minutes. To the mixture was added dichloro[1,1'-bis(diphenyl-phosphino) ferrocene]palladium(II) dichloromethane adduct (0.15 g, 0.19 mmol) and the reaction mixture was heated to 80° C. for 3 h. After cooling to ambient temperature, the reaction mixture was filtered through a bed of diatomaceous earth (i.e. Celite®) and the filtrate concentrated under reduced pressure. Purification of the residue by column chromatography, eluting with a gradient of 0 to 30% of ethyl acetate in heptane, afforded the title compound as an off-white solid (0.39 g, 95% yield): $^1$H-NMR (300 MHz; DMSO-$d_6$) δ 8.73 (d, J=5.2 Hz, 1H), 7.75 (d, J=4.5 Hz, 1H), 7.73-7.70 (m, 2H), 7.62-7.60 (m, 3H).

Step 2. Preparation of (S)-2-(3-fluoropyrrolidin-1-yl)-4-phenylnicotinonitrile

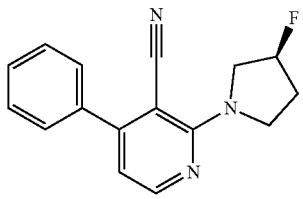 [SMILES: N#Cc1c(-c2ccccc2)ccnc1N1CC[C@H](F)C1]

To a solution of 2-chloro-4-phenylnicotinonitrile (0.10 g, 0.47 mmol) and (S)-3-fluoropyrrolidine hydrochloride (0.12 g, 0.94 mmol) in anhydrous N,N-dimethylformamide (2 mL) was added cesium carbonate (0.46 g, 1.4 mmol) and the reaction mixture was heated at 120° C. for 20 h. After cooling to ambient temperature, the reaction mixture was diluted with ethyl acetate (25 mL) and washed with water (25 mL) and brine (40 mL). The organic phase was dried over anhydrous sodium sulfate, filtered, and the filtrate concentrated in vacuo. The residue was purified by column chromatography, eluting with a gradient of 0 to 35% of ethyl acetate in heptane, to provide the title compound as a colorless solid (0.112 g, 89% yield): $^1$H-NMR (300 MHz; DMSO-$d_6$) δ 8.36 (d, J=5.0 Hz, 1H), 7.63-7.58 (m, 2H), 7.56-7.51 (m, 3H), 6.84 (d, J=5.0 Hz, 1H), 5.56-5.37 (m, 1H), 4.09-3.80 (m, 4H), 2.39-2.04 (m, 2H); MS (ES+) m/z 268.2 (M+1).

Step 3. Preparation of (S)-2-(3-fluoropyrrolidin-1-yl)-4-phenyl-3-(1H-tetrazol-5-yl)pyridine

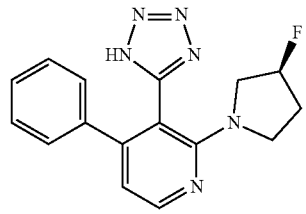 [SMILES: F[C@H]1CCN(c2nccc(-c3ccccc3)c2-c2nnn[nH]2)C1]

To a solution of (S)-2-(3-fluoropyrrolidin-1-yl)-4-phenylnicotinonitrile (0.088 g, 0.33 mmol), trimethylsilyl azide (0.11 mL, 0.76 mmol) in toluene (3 mL) was added dibutyltin oxide (0.014 g, 0.056 mmol) in portions. The reaction mixture was stirred at 120° C. for 24 h and then concentrated in vacuo. The residue was purified by preparative reverse phase HPLC, using acetonitrile in water containing 0.2% of formic acid as eluent, to afford the title compound as a colorless solid (0.0086 g, 7.2% yield) $^1$H-NMR (300 MHz; DMSO-$d_6$) δ 8.32 (d, J=5.0 Hz, 1H), 7.25 (quintet, J=3.2 Hz, 3H), 7.05-7.01 (m, 2H), 6.74 (d, J=5.0 Hz, 1H), 5.31-5.12 (m, 1H), 3.16-2.93 (m, 4H), 2.10-1.80 (m, 2H); MS (ES+) m/z 311.2 (M+1).

Example 33

Synthesis of (S)-2-(3-fluoropyrrolidin-1-yl)-3-(4-methyl-5-(trifluoromethyl)-1H-imidazol-2-yl)-4-phenylpyridine

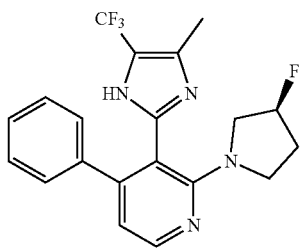 [SMILES: Cc1nc(-c2c(-c3ccccc3)ccnc2N2CC[C@H](F)C2)[nH]c1C(F)(F)F]

Step 1. Preparation of (S)-2-(3-fluoropyrrolidin-1-yl)-4-phenylnicotinaldehyde

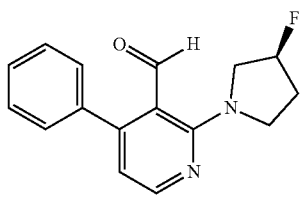 [SMILES: O=Cc1c(-c2ccccc2)ccnc1N1CC[C@H](F)C1]

To a solution of 2-chloro-4-phenylnicotinaldehyde (0.20 g, 0.92 mmol) and (S)-3-fluoropyrrolidine hydrochloride (0.24 g, 1.1 mmol) in anhydrous N,N-dimethylformamide (2 mL) was added cesium carbonate (0.46 g, 1.4 mmol) and the reaction mixture was heated at 120° C. for 20 h. After cooling to ambient temperature, the reaction mixture was diluted with ethyl acetate (25 mL) and the organic phase was washed with water (25 mL) and brine (40 mL). The organic phase was dried over anhydrous sodium sulfate, filtered, and concentrated in vacuo. Purification of the residue by column chromatography, eluting with a gradient of 0 to 40% of ethyl acetate in heptane, provided the title compound as a colorless solid (0.64 g, 25% yield): $^1$H-NMR (300 MHz; CDCl$_3$) δ 9.85 (s, 1H), 8.34 (d, J=4.8 Hz, 1H), 7.51-7.44 (m, 5H), 6.68-6.67 (m, 1H), 5.48-5.28 (m, 1H), 4.12-3.93 (m, 2H), 3.66-3.59 (m, 1H), 3.29-3.16 (m, 1H), 2.44-2.33 (m, 1H), 2.26-2.07 (m, 1H).

Step 2. Preparation of (S)-2-(3-fluoropyrrolidin-1-yl)-3-(4-methyl-5-(trifluoromethyl)-1H-imidazol-2-yl)-4-phenylpyridine

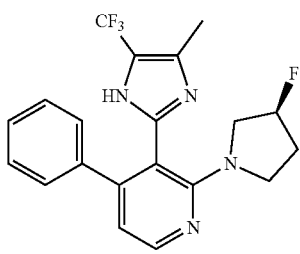 [SMILES: Cc1nc(-c2c(-c3ccccc3)ccnc2N2CC[C@H](F)C2)[nH]c1C(F)(F)F]

To a solution of (S)-2-(3-fluoropyrrolidin-1-yl)-4-phenylnicotinaldehyde (0.11 g, 0.41 mmol), 3-bromo-1,1,1-trifluorobutan-2-one (0.11 mL, 0.82 mmol) and concentrated ammonium hydroxide (0.17 mL, 1.2 mmol) in anhydrous N,N-dimethylformamide (1.6 mL) was added ammonium acetate (0.14 g, 1.85 mmol) in portions. The reaction mixture was stirred at 120° C. for 24 h. After cooling to ambient temperature, the reaction mixture was diluted with ethyl acetate, extracted with water and washed with brine (30 mL). The organic phase was dried over anhydrous sodium sulfate, concentrated in vacuo, and purified by preparative reverse phase HPLC, using acetonitrile in water containing 0.2% of formic acid as eluent, to afford the title compound as a beige solid (0.0038 g, 2% yield)$^1$H-NMR (300 MHz; CDCl$_3$) δ 8.26 (d, J=5.1 Hz, 1H), 8.07 (s, 1H), 7.33-7.29 (m, 3H), 7.15-7.12 (m, 2H), 6.70 (d, J=5.1 Hz, 1H), 5.30-5.12 (m, 1H), 3.53-3.46 (m, 2H), 3.42-3.11 (m, 3H), 2.23 (m, 3H), 2.09-1.89 (m, 2H); MS (ES+) m/z 391.2 (M+1).

Example 34

Synthesis of Tert-Butyl (S)-2-(2-(3-fluoropyrrolidin-1-yl)-4-phenylpyridin-3-yl)-3,4,6,7-tetrahydro-5H-imidazo[4,5-c]pyridine-5-carboxylate

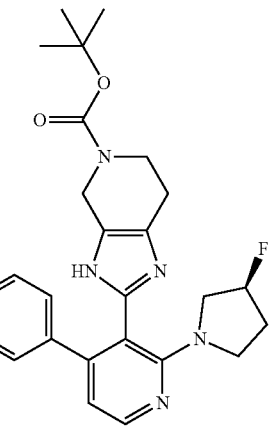

Step 1. Preparation of Tert-Butyl 2-(2-chloro-4-phenylpyridin-3-yl)-3,4,6,7-tetrahydro-5H-imidazo[4,5-c]pyridine-5-carboxylate

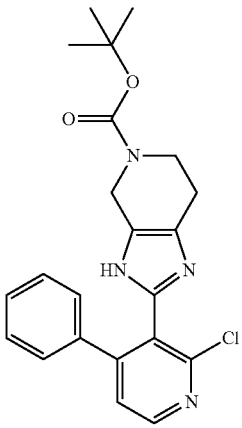 [SMILES: CC(C)(C)OC(=O)N1CCc2nc(-c3c(-c4ccccc4)ccnc3Cl)[nH]c2C1]

To a solution of 2-chloro-4-phenylnicotinaldehyde (1.0 g, 4.6 mmol), 3-bromo-4-oxo-piperidine-1-carboxylic acid tert-butyl ester (2.6 g, 9.2 mmol) and concentrated ammonium hydroxide (2.0 mL, 14 mmol) in anhydrous N,N-dimethylformamide (10 mL) was added ammonium acetate (1.6 g, 21 mmol) in portions. The reaction mixture was stirred at ambient temperature for 45 minutes, and oxone (1.4 g, 4.6 mmol) was added to it. The reaction mixture was stirred at 65° C. for another 24 h. After cooling to ambient temperature, the reaction mixture was diluted with ethyl acetate (100 mL) and extracted with water (100 mL×3). The combined organic layers were washed with brine (400 mL), dried over anhydrous sodium sulfate, filtered and concentrated in vacuo. Purification of the residue by column chromatography, eluting with a gradient of 0 to 95% of ethyl acetate in heptane, provided the title compound as a yellow solid (0.39 g, 21% yield): $^1$H-NMR (300 MHz; DMSO-d$_6$)

δ 8.54 (d, J=5.1 Hz, 1H), 8.33-8.29 (m, 1H), 7.56 (d, J=5.1 Hz, 1H), 7.36-7.29 (m, 3H), 7.24-7.19 (m, 2H), 4.25-4.24 (m, 2H), 3.61-3.57 (m, 2H), 3.48-3.28 (m, 2H), 1.42 (s, 9H); MS (ES+) m/z 411.2 (M+1), 413.2 (M+1).

Step 2. Preparation of Tert-Butyl (S)-2-(2-(3-fluoropyrrolidin-1-yl)-4-phenylpyridin-3-yl)-3,4,6,7-tetrahydro-5H-imidazo[4,5-c]pyridine-5-carboxylate

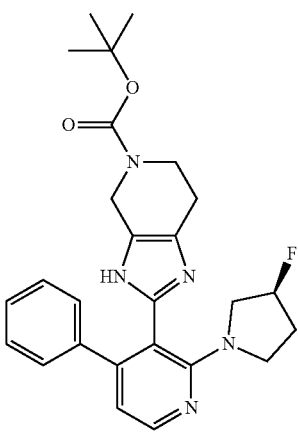 [SMILES: CC(C)(C)OC(=O)N1CCc2nc(-c3c(-c4ccccc4)ccnc3N3CC[C@H](F)C3)[nH]c2C1]

To a solution of tert-butyl 2-(2-chloro-4-phenylpyridin-3-yl)-3,4,6,7-tetrahydro-5H-imidazo[4,5-c]pyridine-5-carboxylate (0.39 g, 0.95 mmol) and (S)-3-fluoropyrrolidine hydrochloride (0.36 g, 2.9 mmol) in anhydrous dimethylsulfoxide (4.8 mL) was added potassium carbonate (0.59 g, 4.3 mmol) and the reaction mixture was heated at 130° C. for 20 h. After cooling to ambient temperature, the reaction mixture was diluted with ethyl acetate (25 mL) and the organic phase was washed with water (25 mL) and brine (40 mL). The organic phase was dried over anhydrous sodium sulfate, filtered, and concentrated in vacuo. Purification of the residue by column chromatography, eluting with a gradient of 0 to 90% of ethyl acetate in heptane, provided the title compound as a pale yellow solid (0.21 g, 47% yield): ¹H-NMR (300 MHz; DMSO-d₆) δ 11.70 (s, 1H), 8.21 (d, J=5.0 Hz, 1H), 7.27-7.22 (m, 3H), 7.14-7.08 (m, 2H), 6.66 (d, J=5.1 Hz, 1H), 5.32-5.14 (m, 1H), 4.29-4.15 (m, 2H), 3.62-3.47 (m, 2H), 3.28-3.13 (m, 4H), 2.47-2.39 (m, 2H), 2.12-1.93 (m, 2H), 1.41 (s, 9H); MS (ES+) m/z 464.3 (M+1).

Example 35

Synthesis of (S)-2-(2-(3-fluoropyrrolidin-1-yl)-4-phenylpyridin-3-yl)-4,5,6,7-tetrahydro-3H-imidazo[4,5-c]pyridine 2,2,2-trifluoroacetic Acid Salt (Free Acid)

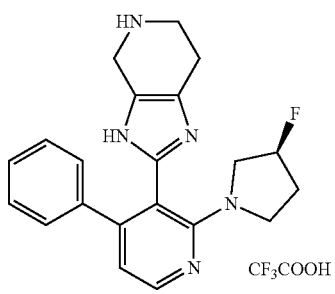 [SMILES: F[C@H]1CCN(c2nccc(-c3ccccc3)c2-c2nc3c([nH]2)CNCC3)C1 ; "CF3COOH"]

To a solution of tert-butyl (S)-2-(2-(3-fluoropyrrolidin-1-yl)-4-phenylpyridin-3-yl)-3,4,6,7-tetrahydro-5H-imidazo[4,5-c]pyridine-5-carboxylate (0.21 g, 0.45 mmol) in dichloromethane (2.3 mL) was added trifluoroacetic acid (1.1 mL) and the mixture was stirred at ambient temperature for 2.5 h. The reaction was concentrated in vacuo to afford the title compound as a yellow foam (0.19 g, 87% yield): ¹H-NMR (300 MHz; DMSO-d₆+D₂O) δ 8.35 (d, J=5.1 Hz, 1H), 7.35-7.28 (m, 3H), 7.11-7.06 (m, 2H), 6.78 (d, J=5.1 Hz, 1H), 5.36-5.18 (m, 1H), 4.30-4.17 (m, 2H), 3.44-3.36 (m, 3H), 3.32-3.27 (m, 1H), 3.22-3.17 (m, 2H), 2.90-2.76 (m, 2H), 2.19-1.87 (m, 2H): MS (ES+) m/z 364.0 (M+1).

Example 36

Synthesis of (S)-2-(2-(3-fluoropyrrolidin-1-yl)-4-phenylpyridin-3-yl)-5-methyl-4,5,6,7-tetrahydro-3H-imidazo[4,5-c]pyridine

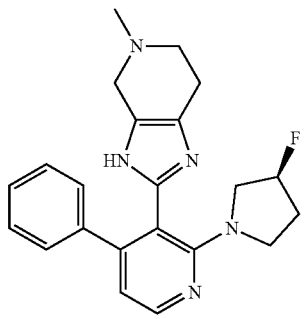 [SMILES: CN1CCc2nc(-c3c(-c4ccccc4)ccnc3N3CC[C@H](F)C3)[nH]c2C1]

To a solution of (S)-2-(2-(3-fluoropyrrolidin-1-yl)-4-phenylpyridin-3-yl)-4,5,6,7-tetrahydro-3H-imidazo[4,5-c]pyridine 2,2,2-trifluoroacetic acid salt (0.10 g, 0.22 mmol) in anhydrous THF (2.5 mL) were added sodium triacetoxyborohydride (0.14 g, 0.65 mmol) and formaldehyde (1.2 mL, 0.43 mmol). The resulting mixture was stirred for 2 h at 40° C. and then concentrated under reduced pressure. The residue was diluted with DCM (20 mL) and washed with saturated sodium bicarbonate solution and brine. The combined organic layers were dried over sodium sulfate, filtered and concentrated in vacuo. Purification of the residue by column chromatography, eluting with a gradient of 0-20% of methanol in dichloromethane, provided the title compound as an off-white solid (0.038 g, 43% yield): ¹H-NMR (300 MHz; DMSO-d₆) δ 11.60-11.52 (m, 1H), 8.19 (d, J=5.1 Hz, 1H), 7.26-7.23 (m, 3H), 7.13-7.10 (m, 2H), 6.65 (d, J=5.1 Hz, 1H), 5.33-5.14 (m, 1H), 3.30-3.10 (m, 8H), 2.64-2.59 (m, 2H), 2.34 (s, 3H), 2.07-1.84 (m, 2H): MS (ES+) m/z 378.2 (M+1).

Example 37

Synthesis of (S)-1-(2-(2-(3-fluoropyrrolidin-1-yl)-4-phenylpyridin-3-yl)-3,4,6,7-tetrahydro-5H-imidazo[4,5-c]pyridin-5-yl)ethan-1-one

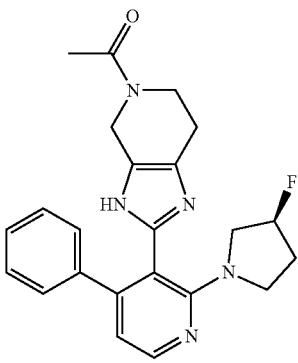 [SMILES: CC(=O)N1CCc2nc(-c3c(-c4ccccc4)ccnc3N3CC[C@H](F)C3)[nH]c2C1]

To a solution of (S)-2-(2-(3-fluoropyrrolidin-1-yl)-4-phenylpyridin-3-yl)-4,5,6,7-tetrahydro-3H-imidazo[4,5-c]pyridine 2,2,2-trifluoroacetic acid salt (0.10 g, 0.21 mmol) in anhydrous THF (2.1 mL) under nitrogen was added N,N-diisopropylethylamine (0.11 mL, 0.63 mmol) and stirred for 5 minutes. And to a mixture was then added a solution of isobutyric anhydride (0.027 mL, 0.19 mmol) at 0° C. The resulting solution was stirred at 0-3° C. in a water/ice bath. The reaction mixture was concentrated under reduced pressure. Purification of the residue by column chromatography, eluting with a gradient of 0-10% of methanol in dichloromethane, provided the title compound as a colorless solid (0.032 g, 37% yield): $^1$H-NMR (300 MHz; DMSO-$d_6$) δ 11.73-11.69 (m, 1H), 8.21 (d, J=5.1 Hz, 1H), 7.25-7.18 (m, 3H), 7.14-7.09 (m, 2H), 6.66 (d, J=5.1 Hz, 1H), 5.32-5.12 (m, 1H), 4.47-4.25 (m, 2H), 3.77-3.61 (m, 2H), 3.31-3.14 (m, 4H), 2.99-2.86 (m, 1H), 2.58-2.53 (m, 1H), 2.47-2.36 (m, 1H), 2.07-1.84 (m, 2H), 1.02 (d, J=6.7 Hz, 3H), 0.96-0.88 (m, 3H): MS (ES+) m/z 434.2 [M+1].

Example 38

Synthesis of (S)-2-(2-(3-fluoropyrrolidin-1-yl)-4-phenylpyridin-3-yl)-5-isopropyl-4,5,6,7-tetrahydro-3H-imidazo[4,5-c]pyridine

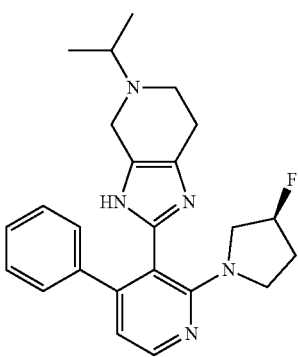 [SMILES: CC(C)N1CCc2nc(-c3c(-c4ccccc4)ccnc3N3CC[C@H](F)C3)[nH]c2C1]

To a solution of (S)-2-(2-(3-fluoropyrrolidin-1-yl)-4-phenylpyridin-3-yl)-4,5,6,7-tetrahydro-3H-imidazo[4,5-c]pyridine 2,2,2-trifluoroacetic acid salt (0.12 g, 0.25 mmol) in anhydrous THF (2.5 mL) were added sodium triacetoxyborohydride (0.16 g, 0.75 mmol) and acetone (0.038 mL, 0.50 mmol). The resulting mixture was stirred for 2 h at 40° C. and then concentrated under reduced pressure. The residue was diluted with dichloromethane (20 mL) and washed with saturated sodium bicarbonate solution and brine. The combined organic layers were dried over sodium sulfate, filtered and concentrated in vacuo. Purification of the residue by column chromatography, eluting with a gradient of 0-20% of methanol in dichloromethane, provided the title compound as a yellow solid (0.016 g, 16% yield): $^1$H-NMR (300 MHz; DMSO-$d_6$) δ 8.20 (d, J=5.1 Hz, 1H), 7.28-7.23 (m, 3H), 7.16-7.11 (m, 2H), 6.65 (d, J=5.1 Hz, 1H), 5.33-5.15 (m, 1H), 3.60-3.48 (m, 3H), 3.28-2.99 (m, 6H), 2.88-2.80 (m, 2H), 2.08-1.84 (m, 2H), 1.10-1.00 (m, 6H): MS (ES+) m/z 406.2 (M+1).

Example 39

Synthesis of (S)-2-(2-(3-fluoropyrrolidin-1-yl)-4-phenylpyridin-3-yl)-5-(oxetan-3-yl)-4,5,6,7-tetrahydro-3H-imidazo[4,5-c]pyridine

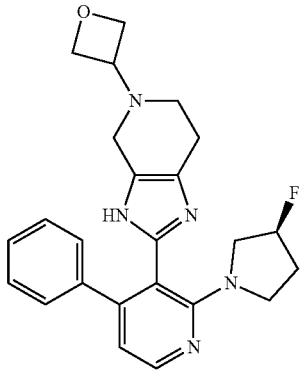 [SMILES: F[C@H]1CCN(c2nccc(-c3ccccc3)c2-c2nc3c([nH]2)CN(C2COC2)CC3)C1]

To a solution of (S)-2-(2-(3-fluoropyrrolidin-1-yl)-4-phenylpyridin-3-yl)-4,5,6,7-tetrahydro-3H-imidazo[4,5-c]pyridine 2,2,2-trifluoroacetic acid salt (0.10 g, 0.21 mmol), 3-oxetanone (0.035 mL, 0.54 mmol) in MeOH/THF (1:1 v/v) were added sodium cyanoborohydride (0.035 g, 0.56 mmol) and glacial acetic acid (0.0016 mL, 0.028 mmol). The resulting mixture was stirred for 24 h at ambient temperature and then diluted with dichloromethane. The organic layer was washed with saturated sodium bicarbonate solution followed by brine and concentrated in vacuo. Purification of the residue by column chromatography, eluting with a gradient of 0-20% of methanol in dichloromethane, provided the title compound as a colorless solid (0.016 g, 16% yield): $^1$H-NMR (300 MHz; DMSO-$d_6$) δ 11.95-11.60 (m, 1H), 8.21 (d, J=5.1 Hz, 1H), 7.29-7.24 (m, 3H), 7.14-7.10 (m, 2H), 6.66 (d, J=5.1 Hz, 1H), 5.34-5.15 (m, 1H), 4.58-4.45 (m, 4H), 3.71-3.62 (m, 1H), 3.28-3.16 (m, 6H), 2.57-2.53 (m, 2H), 2.47-2.43 (m, 1H), 2.08-1.90 (m, 2H): MS (ES+) m/z 420.2 (M+1).

Example 40

Synthesis of diethyl (S)-2-(2-(3-fluoropyrrolidin-1-yl)-4-phenylpyridin-3-yl)-6,7-dihydro-3H-imidazo[4,5-c]pyridine-3,5(4H)-dicarboxylate

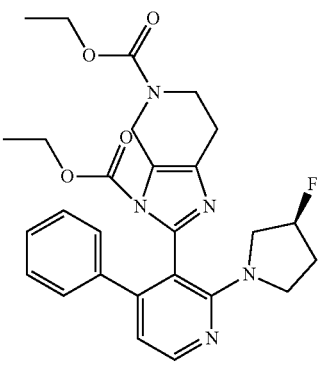 [SMILES: CCOC(=O)N1CCc2nc(-c3c(-c4ccccc4)ccnc3N3CC[C@H](F)C3)n(C(=O)OCC)c2C1]

To a solution of (S)-2-(2-(3-fluoropyrrolidin-1-yl)-4-phenylpyridin-3-yl)-4,5,6,7-tetrahydro-3H-imidazo[4,5-c]pyridine 2,2,2-trifluoroacetic acid salt (0.10 g, 0.21 mmol) in anhydrous THF (1 mL) under nitrogen was added N,N-diisopropylethylamine (0.11 mL, 0.63 mmol) and diethylpyrocarbonate (0.037 mL, 0.25 mmol). The resulting solution was stirred at ambient temperature for 18 h. The reaction mixture was then concentrated under reduced pressure. Purification of the residue by column chromatography, eluting with a gradient of 20-90% of ethyl acetate in heptane, provided the title compound as a colorless solid (0.052 g, 49% yield): $^1$H-NMR (300 MHz; DMSO-$d_6$) δ 8.22 (m, 1H), 7.32-7.21 (m, 3H), 7.02-6.99 (m, 1H), 6.89 (m, 1H), 6.66 (m, 1H), 5.25 (m, 1H), 4.58-4.39 (m, 1H), 4.33-4.18 (m, 1H), 4.13-4.02 (m, 3H), 4.01-3.93 (m, 1H), 3.78-3.46 (m, 3H), 3.31-3.02 (m, 3H), 2.83-2.55 (m, 2H), 2.12-1.88 (m, 2H), 1.24-1.18 (m, 3H), 1.00-0.94 (m, 3H); MS (ES+) m/z 508.2 (M+1).

Example 41

Synthesis of (S)-1-(2-(2-(3-fluoropyrrolidin-1-yl)-4-phenylpyridin-3-yl)-3,4,6,7-tetrahydro-5H-imidazo[4,5-c]pyridin-5-yl)-2-methylpropan-1-one

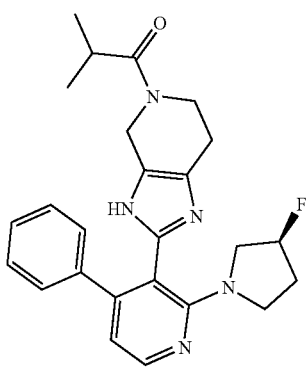 [SMILES: CC(C)C(=O)N1CCc2nc(-c3c(-c4ccccc4)ccnc3N3CC[C@H](F)C3)[nH]c2C1]

To a solution of (S)-2-(2-(3-fluoropyrrolidin-1-yl)-4-phenylpyridin-3-yl)-4,5,6,7-tetrahydro-3H-imidazo[4,5-c]pyridine 2,2,2-trifluoroacetic acid salt (0.11 g, 0.24 mmol) in anhydrous N,N-dimethylformamide (2.4 mL) under nitrogen was added N,N-diisopropylethylamine (0.25 mL, 1.43 mmol) and stirred for 5 minutes. And to a mixture was then added a solution of acetic anhydride (0.025 mL, 0.26 mmol) in N,N-dimethylformamide (0.2 mL) dropwise at 0° C. The resulting solution was stirred at 0-3° C. in a water/ice bath. The reaction mixture was then diluted with 50 ml, of ethyl acetate and washed with 2×20 mL of brine. The organic phase was dried over sodium sulfate, filter and concentrated in vacuo. Purification of the residue by column chromatography, eluting with a gradient of 0-15% of methanol in dichloromethane, provided the title compound as off-white solid (0.027 g, 27% yield): $^1$H-NMR (300 MHz; DMSO-$d_6$) δ 11.73-11.69 (m, 1H), 8.21 (d, J=5.1 Hz, 1H), 7.25-7.18 (m, 3H), 7.14-7.09 (m, 2H), 6.66 (d, J=5.1 Hz, 1H), 5.32-5.12 (m, 1H), 4.47-4.25 (m, 2H), 3.77-3.61 (m, 2H), 3.31-3.14 (m, 4H), 2.99-2.86 (m, 1H), 2.58-2.53 (m, 1H), 2.47-2.36 (m, 1H), 2.07-1.84 (m, 2H), 1.02 (d, J=6.7 Hz, 3H), 0.96-0.88 (m, 3H); MS (ES+) m/z 434.2 (M+1).

Example 42

Synthesis of (S)-5-benzyl-2-(2-(3-fluoropyrrolidin-1-yl)-4-phenylpyridin-3-yl)-4,5,6,7-tetrahydro-3H-imidazo[4,5-c]pyridine

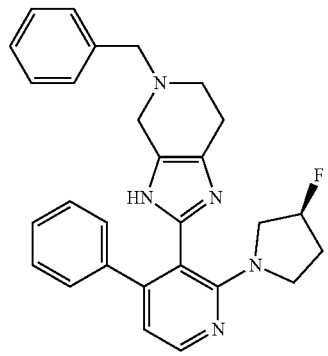 [SMILES: F[C@H]1CCN(c2nccc(-c3ccccc3)c2-c2nc3c([nH]2)CN(Cc2ccccc2)CC3)C1]

To a solution of (S)-2-(2-(3-fluoropyrrolidin-1-yl)-4-phenylpyridin-3-yl)-4,5,6,7-tetrahydro-3H-imidazo[4,5-c]pyridine 2,2,2-trifluoroacetic acid salt (0.090 g, 0.19 mmol) in anhydrous THF (1 mL) were added sodium triacetoxyborohydride (0.12 g, 0.57 mmol) and benzaldehyde (0.036 mL, 0.38 mmol). The resulting mixture was stirred for 3 h at 40° C. and then concentrated under reduced pressure. Purification of the residue by preparative reverse phase HPLC using acetonitrile in water containing 0.5% of formic acid as eluent afforded the title compound as off-white solid (0.013 g, 14% yield): $^1$H-NMR (300 MHz; DMSO-$d_6$) δ 8.36 (d, J=5.1 Hz, 1H), 7.51-7.46 (m, 5H), 7.36-7.32 (m, 3H), 7.13-7.08 (m, 2H), 6.79 (d, J=5.1 Hz, 1H), 5.37-5.19 (m, 1H), 4.45-4.35 (m, 2H), 4.22-4.10 (m, 2H), 3.59-3.11 (m, 6H), 3.01-2.82 (m, 2H), 2.17-1.90 (m, 2H): MS (ES+) m/z 454.2 (M+1).

Example 43

Synthesis of 2-(2-(3,3-difluoropyrrolidin-1-yl)-4-phenylpyridin-3-yl)-3,4,6,7-tetrahydropyrano[3,4-d]imidazole

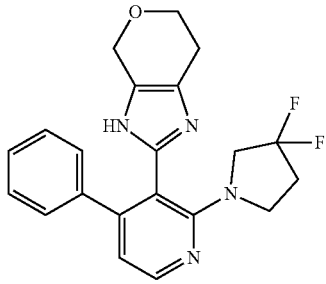 [SMILES: FC1(F)CCN(c2nccc(-c3ccccc3)c2-c2nc3c([nH]2)COCC3)C1]

Step 1. Preparation of 2-(2-chloro-4-phenylpyridin-3-yl)-3,4,6,7-tetrahydropyrano[3,4-d]imidazole

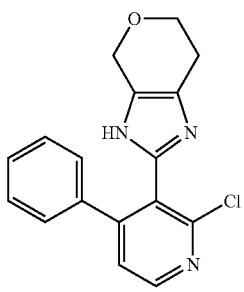 [SMILES: Clc1nccc(-c2ccccc2)c1-c1nc2c([nH]1)COCC2]

To a solution of 2-chloro-4-phenylnicotinaldehyde (0.30 g, 1.4 mmol), 3-bromooxan-4-one (0.51 g, 2.8 mmol) and concentrated ammonium hydroxide (0.65 mL, 4.1 mmol) in anhydrous N,N-dimethylformamide (2.8 mL) was added ammonium acetate (0.48 g, 6.2 mmol) in portions. The reaction mixture was stirred at ambient temperature for 45 minutes, and oxone (0.42 g, 1.4 mmol) was added to it. The reaction mixture was stirred at 65° C. for another 24 h. After cooling to ambient temperature, the reaction mixture was diluted with ethyl acetate (30 mL) and extracted with water (30 mL×3). The combined organic layers were washed with brine (50 mL), dried over anhydrous sodium sulfate, filtered and concentrated in vacuo. Purification of the residue by column chromatography, eluting with a gradient of 0 to 10% of methanol in dichloromethane, provided the title compound as a yellow solid (0.097 g, 23% yield): $^1$H-NMR (300 MHz; MeOD) δ 8.46 (d, J=5.2 Hz, 1H), 7.49 (d, J=5.2 Hz, 1H), 7.31-7.28 (m, 3H), 7.19 (d, J=1.8 Hz, 2H), 4.54 (t, J=1.5 Hz, 2H), 3.90 (t, J=5.5 Hz, 2H), 2.62 (ddd, J=5.5, 3.9, 1.5 Hz, 2H); MS (ESI+) m/z=312.0 (M+1), 314.2 (M+1).

Step 2. Preparation of 2-(2-(3,3-difluoropyrrolidin-1-yl)-4-phenylpyridin-3-yl)-3,4,6,7-tetrahydropyrano[3,4-d]imidazole

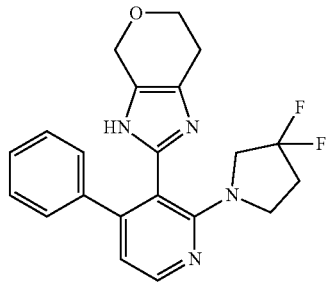 [SMILES: FC1(F)CCN(c2nccc(-c3ccccc3)c2-c2nc3c([nH]2)COCC3)C1]

To a solution of 2-(2-chloro-4-phenylpyridin-3-yl)-3,4,6,7-tetrahydropyrano[3,4-d]imidazole (0.079 g, 0.25 mmol) and 3,3-difluoropyrrolidine hydrochloride (0.073 g, 0.50 mmol) in anhydrous dimethylsulfoxide (1.2 mL) was added potassium carbonate (0.11 g, 0.75 mmol) and the reaction mixture was heated at 130° C. for 20 h. After cooling to ambient temperature, the reaction mixture was diluted with ethyl acetate (25 mL) and the organic phase was washed with water (25 mL) and brine (40 mL). The organic phase was dried over anhydrous sodium sulfate, filtered, and concentrated in vacuo. Purification of the residue by preparative reverse phase HPLC using acetonitrile in water containing 0.5% of formic acid as eluent afforded the title compound as a colorless solid (0.017 g, 18% yield): $^1$H-NMR (300 MHz; DMSO-d$_6$) δ 11.76 (s, 1H), 8.25 (d, J=5.1 Hz, 1H), 7.29-7.25 (m, 3H), 7.16-7.11 (m, 2H), 6.77 (d, J=5.1 Hz, 1H), 4.45 (s, 2H), 3.80 (t, J=5.3 Hz, 2H), 3.33-3.27 (m, 4H), 2.54-2.52 (m, 2H), 2.42-2.27 (m, 2H); MS (ES+) m/z 382.9 (M+1).

Example 44

Synthesis of 2-(4-phenyl-2-(pyrrolidin-1-yl)pyridin-3-yl)-3,4,6,7-tetrahydropyrano[3,4-d]imidazole

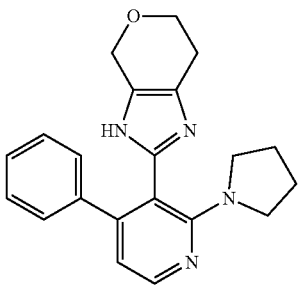 [SMILES: c1ccc(-c2ccnc(N3CCCC3)c2-c2nc3c([nH]2)COCC3)cc1]

To a solution of 2-(2-chloro-4-phenylpyridin-3-yl)-3,4,6,7-tetrahydropyrano[3,4-d]imidazole (0.065 g, 0.21 mmol) and pyrrolidine (0.052 mL, 0.63 mmol) in anhydrous dimethylsulfoxide (1 mL) was added potassium carbonate (0.13 g, 0.94 mmol) and the reaction mixture was heated at 130° C. for 12 h. After cooling to ambient temperature, the reaction mixture was diluted with ethyl acetate (25 mL) and the organic phase was washed with water (25 mL) and brine (40 mL). The organic phase was dried over anhydrous sodium sulfate, filtered, and concentrated in vacuo. Purification of the residue by preparative reverse phase HPLC using acetonitrile in water containing 0.5% of formic acid as eluent, to afford the title compound as a colorless solid (0.012 g, 16% yield): $^1$H-NMR (300 MHz; DMSO-d$_6$) δ 11.64 (s, 1H), 8.17 (d, J=5.0 Hz, 1H), 7.27-7.22 (m, 3H), 7.13-7.07 (m, 2H), 6.58 (d, J=5.0 Hz, 1H), 4.43 (s, 2H), 3.78 (t, J=5.3 Hz, 2H), 3.03 (t, J=6.6 Hz, 4H), 2.49-2.48 (m, 2H), 1.76-1.68 (m, 4H); MS (ESI+) m/z 347.2 (M+1).

Example 45

Synthesis of 2-(2-(6,6-difluoro-3-azabicyclo[3.1.0] hexan-3-yl)-4-phenylpyridin-3-yl)-3,4,6,7-tetrahydropyrano[3,4-d]imidazole

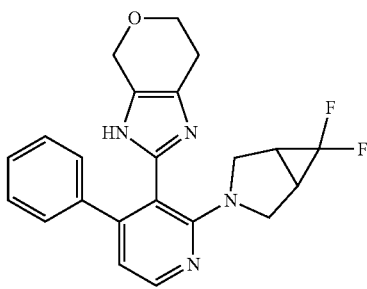 [SMILES: FC1(F)C2CN(c3nccc(-c4ccccc4)c3-c3nc4c([nH]3)COCC4)CC21]

To a solution of 2-(2-chloro-4-phenylpyridin-3-yl)-3,4,6,7-tetrahydropyrano[3,4-d]imidazole (0.065 g, 0.21 mmol) and 6,6-difluoro-3-azabicyclo[3.1.0]hexane (0.075 g, 0.63 mmol) in anhydrous dimethylsulfoxide (1 mL) was added potassium carbonate (0.13 g, 0.94 mmol) and the reaction mixture was heated at 130° C. for 12 h. After cooling to ambient temperature, the reaction mixture was diluted with ethyl acetate (25 mL) and the organic phase was washed with water (25 mL) and brine (40 mL). The organic phase was dried over anhydrous sodium sulfate, filtered, and concentrated in vacuo. Purification of the residue by preparative reverse phase HPLC using acetonitrile in water containing 0.5% of formic acid as eluent, to afford the title compound as the title compound (0.0075 g, 8.9% yield): $^1$H-NMR (300 MHz; CDCl$_3$) δ 8.22 (d, J=5.1 Hz, 1H), 7.25-7.23 (m, 3H), 7.11-7.05 (m, 2H), 6.70 (d, J=5.1 Hz, 1H), 4.60 (s, 2H), 3.94 (t, J=5.5 Hz, 2H), 3.57 (dtd, J=11.2, 3.4, 1.8 Hz, 2H), 3.42 (m, 2H), 2.64-2.60 (m, 2H), 2.22 (ddd, J=12.1, 3.3, 1.6 Hz, 2H); MS (ESI+) m/z 395.2 (M+1).

Example 46

Synthesis of 2-(2-(6,6-difluoro-3-azabicyclo[3.1.0] hexan-3-yl)-4-phenylpyridin-3-yl)-3,4,6,7-tetrahydropyrano[3,4-d]imidazole

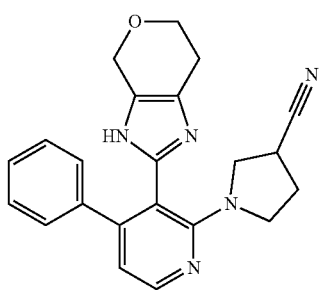 [SMILES: N#CC1CCN(c2nccc(-c3ccccc3)c2-c2nc3c([nH]2)COCC3)C1]

To a solution of 2-(2-chloro-4-phenylpyridin-3-yl)-3,4,6,7-tetrahydropyrano[3,4-d]imidazole (0.067 g, 0.22 mmol) and pyrrolidine-3-carbonitrile (0.041 g, 0.43 mmol) in anhydrous dimethylsulfoxide (1 mL) was added potassium carbonate (0.13 g, 0.97 mmol) and the reaction mixture was heated at 130° C. for 12 h. After cooling to ambient temperature, the reaction mixture was diluted with ethyl acetate (25 mL) and the organic phase was washed with water (25 mL) and brine (40 mL). The organic phase was dried over anhydrous sodium sulfate, filtered, and concentrated in vacuo. Purification of the residue by preparative reverse phase HPLC using 4-50% acetonitrile in water containing 0.5% of formic acid as eluent, to afford the title compound as the light yellow solid (0.022 g, 25% yield): $^1$H-NMR (300 MHz; CDCl$_3$) δ 8.27 (d, J=5.1 Hz, 1H), 8.02 (s, 1H, N—H), 7.34-7.29 (m, 3H), 7.10-7.06 (m, 2H), 6.74 (d, J=5.0 Hz, 1H), 4.58 (s, 2H), 3.94-3.90 (m, 2H), 3.62-3.43 (m, 2H), 3.25-3.21 (m, 2H), 3.14-3.08 (m, 1H), 2.66-2.62 (m, 2H), 2.28-2.12 (m, 2H); MS (ESI+) m/z 372.2 (M+1).

Example 47

Synthesis of 2-(4-phenyl-2-(3-(trifluoromethyl)pyrrolidin-1-yl)pyridin-3-yl)-3,4,6,7-tetrahydropyrano[3,4-d]imidazole

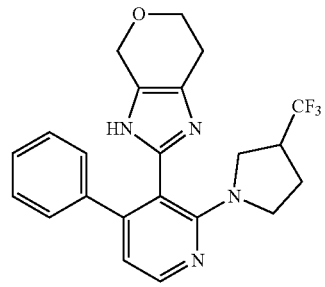 [SMILES: FC(F)(F)C1CCN(c2nccc(-c3ccccc3)c2-c2nc3c([nH]2)COCC3)C1]

To a solution of 2-(2-chloro-4-phenylpyridin-3-yl)-3,4,6,7-tetrahydropyrano[3,4-d]imidazole (0.070 g, 0.23 mmol) and 3-(trifluoromethyl)pyrrolidine hydrochloride (0.12 g, 0.67 mmol) in anhydrous dimethylsulfoxide (1.5 mL) was added potassium carbonate (0.14 g, 1.1 mmol) and the reaction mixture was heated at 130° C. for 12 h. After cooling to ambient temperature, the reaction mixture was diluted with ethyl acetate (25 mL) and the organic phase was washed with water (25 mL) and brine (40 mL). The organic phase was dried over anhydrous sodium sulfate, filtered, and concentrated in vacuo. Purification of the residue by preparative reverse phase HPLC using 5-45% acetonitrile in water containing 0.5% of formic acid as eluent, to afford the title compound as an off-white solid (0.045 g, 43% yield): $^1$H-NMR (300 MHz; CDCl$_3$) δ 8.25 (d, J=5.1 Hz, 1H), 7.32-7.24 (m, 3H), 7.08-7.05 (m, 2H), 6.70 (d, J=5.0 Hz, 1H), 4.57 (s, 2H), 3.92 (t, J=5.3 Hz, 2H), 3.52-3.30 (m, 2H), 3.15 (t, J=6.9 Hz, 2H), 2.95-2.81 (m, 1H), 2.61-2.58 (m, 2H), 2.15-1.95 (m, 2H); MS (ESI+) m/z 415.2 (M+1)

Example 48

Synthesis of 2-(2-((3S,4R)-3,4-difluoropyrrolidin-1-yl)-4-phenylpyridin-3-yl)-3,4,6,7-tetrahydropyrano[3,4-d]imidazole

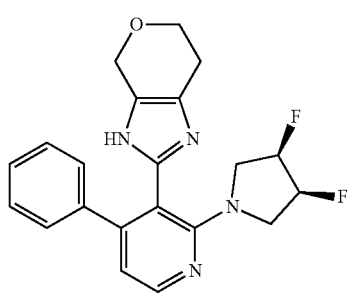 [SMILES: F[C@@H]1CN(c2nccc(-c3ccccc3)c2-c2nc3c([nH]2)COCC3)C[C@@H]1F]

To a solution of 2-(2-chloro-4-phenylpyridin-3-yl)-3,4,6,7-tetrahydropyrano[3,4-d]imidazole (0.041 g, 0.13 mmol) and (3S,4R)-3,4-difluoropyrrolidine; hydrochloride (0.057 g, 0.40 mmol) in anhydrous dimethylsulfoxide (0.85 mL) was added potassium carbonate (0.082 g, 0.59 mmol) and the reaction mixture was heated at 130° C. for 12 h. After cooling to ambient temperature, the reaction mixture was diluted with ethyl acetate (25 mL) and the organic phase was washed with water (25 mL) and brine (40 mL). The organic phase was dried over anhydrous sodium sulfate, filtered, and concentrated in vacuo. Purification of the residue by preparative reverse phase HPLC using 5-45% acetonitrile in water containing 0.5% of formic acid as eluent, to afford the title compound as an off-white solid (0.045 g, 43% yield): $^1$H-NMR (300 MHz; CDCl$_3$) δ 8.27 (d, J=5.1 Hz, 1H), 7.30 (m, 3H), 7.10-7.06 (m, 2H), 6.75 (d, J=5.1 Hz, 1H), 5.21-5.14 (m, 1H), 5.04-4.97 (m, 1H), 4.62 (s, 2H), 3.95 (t, J=5.5 Hz, 2H), 3.68-3.55 (m, 2H), 3.48-3.35 (m, 2H), 2.63-2.58 (m, 2H); m/z (ESI+) 383.2 (M+1).

Example 49

Synthesis of 2-(2-(3,3-difluoropiperidin-1-yl)-4-phenylpyridin-3-yl)-3,4,6,7-tetrahydropyrano[3,4-d]imidazole

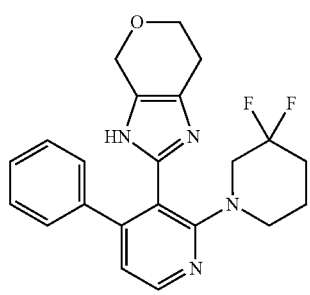 [SMILES: FC1(F)CCCN(c2nccc(-c3ccccc3)c2-c2nc3c([nH]2)COCC3)C1]

To a solution of 2-(2-chloro-4-phenylpyridin-3-yl)-3,4,6,7-tetrahydropyrano[3,4-d]imidazole (0.050 g, 0.16 mmol) and 3,3-difluoropiperidine hydrochloride (0.075 g, 0.48 mmol) in anhydrous dimethylsulfoxide (1.5 mL) was added potassium carbonate (0.10 g, 0.72 mmol) and the reaction mixture was heated at 130° C. for 12 h. After cooling to ambient temperature, the reaction mixture was diluted with ethyl acetate (25 mL) and the organic phase was washed with water (25 mL) and brine (40 mL). The organic phase was dried over anhydrous sodium sulfate, filtered, and concentrated in vacuo. Purification of the residue by preparative reverse phase HPLC using acetonitrile in water containing 0.5% of formic acid as eluent, to afford the title compound as a colorless solid (0.010 g, 15% yield): $^1$H-NMR (300 MHz; CDCl$_3$) δ 8.32 (d, J=5.1 Hz, 1H), 7.33-7.29 (m, 3H), 7.11 (dtd, J=5.8, 3.0, 1.7 Hz, 2H), 7.03 (d, J=5.1 Hz, 1H), 4.57 (t, J=1.4 Hz, 2H), 3.97 (t, J=5.5 Hz, 2H), 3.36-3.28 (m, 2H), 2.99-2.95 (m, 2H), 2.73 (m, 2H), 2.06-1.92 (m, 2H), 1.71-1.63 (m, 2H); MS (ESI+) m/z 397.2 (M+1).

Example 50

Synthesis of 2-(2-(6,6-difluoro-2-azaspiro[3.3]heptan-2-yl)-4-phenylpyridin-3-yl)-3,4,6,7-tetrahydropyrano[3,4-d]imidazole

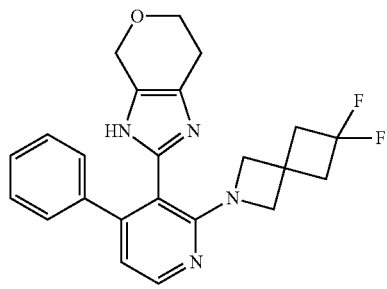 [SMILES: FC1(F)CC2(CN(c3nccc(-c4ccccc4)c3-c3nc4c([nH]3)COCC4)C2)C1]

To a solution of 2-(2-chloro-4-phenylpyridin-3-yl)-3,4,6,7-tetrahydropyrano[3,4-d]imidazole (0.050 g, 0.16 mmol) and 6,6-difluoro-2-aza-spiro[3.3]heptane trifluoroacetate (0.079 g, 0.32 mmol) in anhydrous dimethylsulfoxide (1.5 mL) was added potassium carbonate (0.10 g, 0.72 mmol) and the reaction mixture was heated at 130° C. for 12 h. After cooling to ambient temperature, the reaction mixture was diluted with ethyl acetate (25 mL) and the organic phase was washed with water (25 mL) and brine (40 mL). The organic phase was dried over anhydrous sodium sulfate, filtered, and concentrated in vacuo. Purification of the residue by preparative reverse phase HPLC using acetonitrile in water containing 0.5% of formic acid as eluent, to afford the title compound as a colorless solid (0.014 g, 21% yield): $^1$H-NMR (300 MHz; CDCl$_3$) δ 8.23 (d, J=5.2 Hz, 1H), 7.32-7.29 (m, 3H), 7.11-7.07 (m, 2H), 6.73 (d, J=5.2 Hz, 1H), 4.66 (s, 2H), 3.98 (t, J=5.5 Hz, 2H), 3.81 (s, 4H), 2.74-2.65 (m, 6H); MS (ESI+) m/z 409.2 (M+1).

Example 51

Synthesis of 4-phenyl-3-(3,4,6,7-tetrahydropyrano[3,4-d]imidazol-2-yl)-N-((1-(trifluoromethyl)cyclobutyl)methyl)pyridin-2-amine

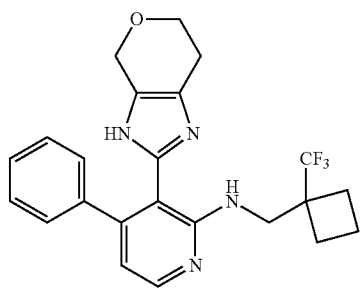 [SMILES: FC(F)(F)C1(CNc2nccc(-c3ccccc3)c2-c2nc3c([nH]2)COCC3)CCC1]

To a solution of 2-(2-chloro-4-phenylpyridin-3-yl)-3,4,6,7-tetrahydropyrano[3,4-d]imidazole (0.14 g, 0.43 mmol) and (1-(trifluoromethyl)cyclobutyl)methanamine hydrochloride (0.16 g, 0.86 mmol) in anhydrous dimethylsulfoxide (2.1 mL) was added N,N-diisopropylethylamine (0.75 mL, 4.3 mmol) and the reaction mixture was heated at 130° C. for 12 h. After cooling to ambient temperature, the reaction mixture was diluted with ethyl acetate (25 mL) and the organic phase was washed with water (25 mL) and brine (40 mL). The organic phase was dried over anhydrous sodium sulfate, filtered, and concentrated in vacuo. Purification of the residue by preparative reverse phase HPLC using acetonitrile in water containing 0.5% of formic acid as eluent, afforded the title compound as a colorless solid (0.55 g, 30% yield): $^1$H-NMR (300 MHz; CDCl$_3$) δ 9.76 (s, 1H), 8.13 (d, J=5.3 Hz, 1H), 7.51-7.47 (m, 3H), 7.38-7.33 (m, 2H), 6.54 (d, J=5.3 Hz, 1H), 4.60 (s, 2H), 4.05-4.04 (m, 2H), 3.91 (t, J=5.5 Hz, 2H), 2.51 (s, 2H), 2.39-2.29 (m, 2H), 2.18-2.03 (m, 4H); MS (ESI+) m/z 429.2 (M+1).

Example 52

Synthesis of 2-(2-(3,3-difluoropyrrolidin-1-yl)-4-phenylpyridin-3-yl)-6,6-dimethyl-3,4,6,7-tetrahydropyrano[3,4-d]imidazole

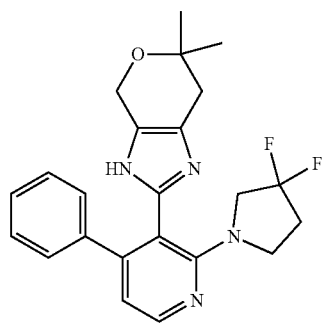 [SMILES: CC1(C)Cc2nc(-c3c(-c4ccccc4)ccnc3N3CCC(F)(F)C3)[nH]c2CO1]

Step 1. Preparation of 5-bromo-2,2-dimethyltetrahydro-4H-pyran-4-one

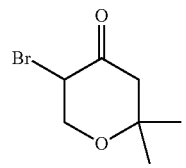

To a solution of tetrahydro-2,2-dimethyl-4H-pyran-4-one (0.50 g, 3.9 mmol) in diethyl ether (14 mL) was added N-bromosuccinimide (2.1 g, 11.7 mmol) and ammonium acetate (0.030 g, 0.39 mmol). The reaction mixture was stirred at ambient temperature for 18 h. Purification of the residue by column chromatography, eluting with a gradient of 0 to 8% of ethyl acetate in heptane, afforded the title compound as an yellow oil (1.02 g, 25% yield): $^1$H-NMR (300 MHz; CDCl$_3$) δ 4.45 (ddd, J=7.9, 5.8, 1.3 Hz, 1H), 4.29 (ddd, J=12.5, 5.7, 0.8 Hz, 1H), 3.98 (ddd, J=12.5, 7.9, 0.9 Hz, 1H), 2.87 (d, J=13.7 Hz, 1H), 2.54-2.49 (m, 1H), 1.33 (s, 3H), 1.30 (s, 3H).

Step 2. Preparation of 2-(2-chloro-4-phenylpyridin-3-yl)-6,6-dimethyl-3,4,6,7-tetrahydropyrano[3,4-d]imidazole

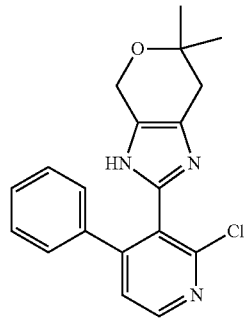 [SMILES: CC1(C)Cc2nc(-c3c(-c4ccccc4)ccnc3Cl)[nH]c2CO1]

To a solution of 2-chloro-4-phenylnicotinaldehyde (0.073 g, 0.34 mmol) in N,N-dimethylformamide (1.9 mL) was added 5-bromo-2,2-dimethyltetrahydro-4H-pyran-4-one (0.14 mg, 0.67 mmol), ammonium hydroxide (0.15 mL, 3.7 mmol, 28-30%) and ammonium acetate (0.12 g, 1.5 mmol). The reaction mixture was stirred at ambient temperature for 15 minutes and stirred at 65° C. for another 20 h. After cooling to ambient temperature, the reaction mixture was diluted with ethyl acetate (20 mL) and extracted with water (20 mL×3). The combined organic layers were washed with brine (40 mL), dried over anhydrous sodium sulfate, filtered and concentrated in vacuo. Purification of the residue by column chromatography, eluting with a gradient of 30 to 80% of ethyl acetate in heptane, provided the title compound as a yellow solid (0.028 g, 24% yield).

Step 3. Preparation of 2-(2-(3,3-difluoropyrrolidin-1-yl)-4-phenylpyridin-3-yl)-6,6-dimethyl-3,4,6,7-tetrahydropyrano[3,4-d]imidazole

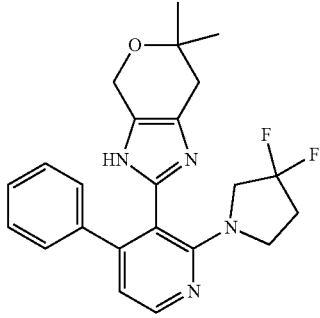 [SMILES: CC1(C)Cc2nc(-c3c(-c4ccccc4)ccnc3N3CCC(F)(F)C3)[nH]c2CO1]

To a solution of 2-(2-chloro-4-phenylpyridin-3-yl)-3,4,6,7-tetrahydropyrano[3,4-d]imidazole (0.028 g, 0.083 mmol) and 3,3-difluoropyrrolidine hydrochloride (0.026 g, 0.25 mmol) in anhydrous dimethyl sulfoxide (0.5 mL) was added potassium carbonate (0.052 g, 0.37 mmol) and the reaction mixture was heated at 130° C. for 20 h. After cooling to ambient temperature, the reaction mixture was diluted with ethyl acetate (15 mL) and the organic phase was washed with water (15 mL) and brine (30 mL). The organic phase was dried over anhydrous sodium sulfate, filtered, and concentrated in vacuo. Purification of the residue by preparative reverse phase HPLC using acetonitrile in water containing 0.5% of formic acid as eluent afforded the title compound as a colorless solid (0.0042 g, 12% yield): $^1$H-NMR (300 MHz; CDCl$_3$) δ 8.28 (d, J=5.1 Hz, 1H), 8.03 (s, 1H), 7.27-7.24 (m, 3H), 7.08-7.05 (m, 2H), 6.76 (d, J=5.1 Hz, 1H), 4.60 (s, 2H), 3.53-3.49 (m, 2H), 3.39 (t, J=13.3 Hz, 2H), 2.48 (s, 2H), 2.31 (tt, J=13.7, 7.0 Hz, 2H), 1.29 (s, 6H); MS (ESI+) m/z 411.2 (M+1).

Example 53

Synthesis of 2'-(2-(3,3-difluoropyrrolidin-1-yl)-4-phenylpyridin-3-yl)-4',7'-dihydro-3'H-spiro[cyclobutane-1,6'-pyrano[3,4-d]imidazole]

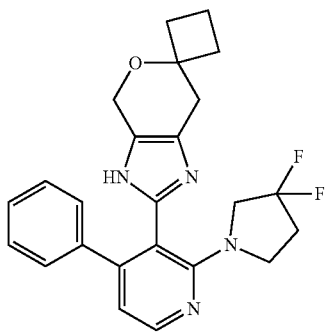 [SMILES: FC1(F)CCN(c2nccc(-c3ccccc3)c2-c2nc3c([nH]2)COC2(CCC2)C3)C1]

Step 1. Preparation of 7-bromo-5-oxaspiro[3.5]nonan-8-one

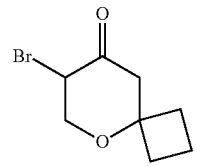

To a solution of 5-oxaspiro[3.5]nonan-8-one (1.0 g, 3.9 mmol) in diethyl ether (20 mL) was added N-bromosuccinimide (4.1 g, 23 mmol) and ammonium acetate (0.055 g, 0.71 mmol). The reaction mixture was stirred at ambient temperature for 18 h, then diluted with ethyl acetate (20 mL). The resulting mixture was washed brine (2×40 mL), dried over sodium sulfate, filtered and concentrated in vacuo. Purification of the residue by column chromatography, eluting with a gradient of 0 to 10% of ethyl acetate in heptane, afforded the title compound as a yellow oil (0.55 g, 35% yield): $^1$H-NMR (300 MHz; CDCl$_3$): δ 5.39 (dd, J=11.2, 6.9 Hz, 1H), 4.55 (s, 1H), 4.25 (dd, J=11.6, 6.9 Hz, 1H), 3.69 (t, J=11.4 Hz, 1H), 2.32-2.17 (m, 3H), 2.13-2.04 (m, 1H), 1.97-1.84 (m, 1H), 1.77-1.60 (m, 2H).

Step 2. Preparation of 2'-(2-chloro-4-phenylpyridin-3-yl)-4',7'-dihydro-3'H-spiro[cyclobutane-1,6'-pyrano[3,4-d]imidazole]

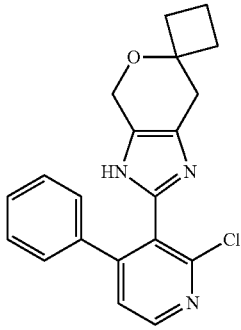 [SMILES: Clc1nccc(-c2ccccc2)c1-c1nc2c([nH]1)COC1(CCC1)C2]

To a solution of 2-chloro-4-phenylnicotinaldehyde (0.15 g, 0.69 mmol) in N,N-dimethylformamide (1.4 mL) was added 7-bromo-5-oxaspiro[3.5]nonan-8-one (0.31 g, 1.0 mmol), ammonium hydroxide (0.38 mL, 9.5 mmol, 28-30%) and ammonium acetate (0.24 g, 3.1 mmol). The reaction mixture was stirred at ambient temperature for 90 minutes and oxone (0.38 g, 0.62 mmol) was added to it. The reaction mixture was stirred at 65° C. for another 12 h. After cooling to ambient temperature, the reaction mixture was diluted with ethyl acetate (20 mL) and extracted with water (20 mL×3). The combined organic layers were washed with brine (40 mL), dried over anhydrous sodium sulfate, filtered and concentrated in vacuo. Purification of the residue by column chromatography, eluting with a gradient of 20 to 100% of ethyl acetate in heptane, provided the title compound as a yellow solid (0.124 g, 51% yield); MS (ESI+) m/z 352.2 (M+1), 354.2 (M+1).

139

Step 3. Preparation of 2'-(2-(3,3-difluoropyrrolidin-1-yl)-4-phenylpyridin-3-yl)-4',7'-dihydro-3'H-spiro[cyclobutane-1,6'-pyrano[3,4-d]imidazole]

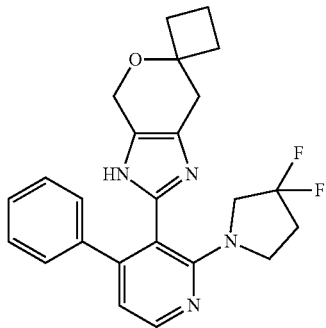 [SMILES: FC1(F)CCN(c2nccc(-c3ccccc3)c2-c2nc3c([nH]2)COC2(CCC2)C3)C1]

To a solution of 2'-(2-(3,3-difluoropyrrolidin-1-yl)-4-phenylpyridin-3-yl)-4',7'-dihydro-3'H-spiro[cyclobutane-1,6'-pyrano[3,4-d]imidazole] (0.070 g, 0.20 mmol) and 3,3-difluoropyrrolidine hydrochloride (0.086 g, 0.60 mmol) in anhydrous dimethyl sulfoxide (1.5 mL) was added potassium carbonate (0.12 g, 0.90 mmol) and the reaction mixture was heated at 130° C. for 20 h. After cooling to ambient temperature, the reaction mixture was diluted with ethyl acetate (15 mL) and the organic phase was washed with water (15 mL) and brine (30 mL). The organic phase was dried over anhydrous sodium sulfate, filtered, and concentrated in vacuo. Purification of the residue by preparative reverse phase HPLC using acetonitrile in water containing 0.5% of formic acid as eluent afforded the title compound as a colorless solid (0.0081 g, 8.9% yield); $^1$H-NMR (300 MHz; CDCl$_3$) δ 8.28 (d, J=5.1 Hz, 1H), 8.04 (s, 1H) 7.26 (m, 3H), 7.11 (m, 2H), 6.77-6.75 (m, 1H), 3.87 (t, J=5.4 Hz, 2H), 3.52 (t, J=7.3 Hz, 2H), 3.43 (t, J=13.3 Hz, 2H), 2.59 (t, J=5.4 Hz, 2H), 2.38-2.23 (m, 6H), 2.03-1.85 (m, 2H); MS (ESI+) m/z 423.2 (M+1).

Example 54

Synthesis of 2-(2-(3,3-difluoropyrrolidin-1-yl)-4-phenylpyridin-3-yl)-4,4-dimethyl-3,4,6,7-tetrahydropyrano[3,4-d]imidazole

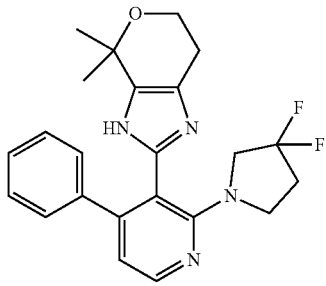 [SMILES: CC1(C)OCCc2nc(-c3c(-c4ccccc4)ccnc3N3CCC(F)(F)C3)[nH]c21]

140

Step 1. Preparation of 5-bromo-3,3-dimethyltetrahydro-4H-pyran-4-one

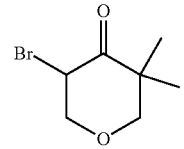

A solution of lithium diisopropylamide (5.0 mL, 10 mmol) in tetrahydrofuran (20 mL) was cooled to −78° C. under a nitrogen atmosphere. To the solution was added chlorotrimethylsilane (5.0 mL, 39 mmol) followed by 3,3-dimethyloxan-4-one (1.0 g, 7.8 mmol) in THF (10 mL) and triethylamine (16 mL, 115 mmol). The resulting mixture was stirred at −78° C. for 5 minutes and then quenched with saturated sodium bicarbonate (40 mL). The mixture was extracted with ether (50 mL) and the organic phase was washed with 1M hydrochloric acid (50 mL), dried over anhydrous sodium sulfate, filtered and concentrated in vacuo. The residue was dissolved in tetrahydrofuran (10 mL) and cooled to 0° C. To the mixture was added N-bromosuccinimide (1.4 g, 7.8 mmol), and the resulting mixture was stirred at ambient temperature for 2 h and then quenched with saturated sodium bicarbonate (20 mL). The mixture was extracted with ether twice and the organic phases were washed with brine, dried over anhydrous sodium sulfate, filtered and concentrated in vacuo. Purification of the residue by column chromatography, eluting with a gradient of 0 to 15% of ethyl acetate in heptane, afforded the title compound as a colorless oil (0.84 g, 52% yield); $^1$H-NMR (300 MHz; CDCl$_3$): δ 4.90 (dd, J=11.2, 6.8 Hz, 1H), 4.45 (ddd, J=11.2, 6.8, 1.8 Hz 1H), 3.78 (dd, J=11.5, 1.8 Hz, 1H), 3.72 (t, J=11.2 Hz, 1H), 3.50 (dd, J=11.5, 0.5 Hz, 1H), 1.35 (s, 3H), 1.11 (s, 3H).

Step 2. Preparation of 2-(2-chloro-4-phenylpyridin-3-yl)-4,4-dimethyl-3,4,6,7-tetrahydropyrano[3,4-d]imidazole

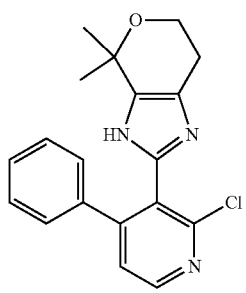 [SMILES: CC1(C)OCCc2nc(-c3c(-c4ccccc4)ccnc3Cl)[nH]c21]

To a solution of 2-chloro-4-phenylnicotinaldehyde (0.20 g, 0.92 mmol) in N,N-dimethylformamide (1.8 mL) were added 5-bromo-3,3-dimethyltetrahydro-4H-pyran-4-one (0.29 g, 1.4 mmol), ammonium hydroxide (0.51 mL, 13 mmol, 28-30%) and ammonium acetate (0.32 g, 4.1 mmol). The reaction mixture was stirred at ambient temperature for 90 minutes and oxone (0.51 g, 0.83 mmol) was added to it. The reaction mixture was stirred at 65° C. for another 12 h. After cooling to ambient temperature, the reaction mixture was diluted with ethyl acetate (20 mL), extracted with water (20 mL×3). The combined organic layers were washed with brine (40 mL), dried over anhydrous sodium sulfate, filtered and concentrated in vacuo. Purification of the residue by column chromatography, eluting with a gradient of 40 to 100% of ethyl acetate in heptane, provided the title compound as a yellow solid (0.065 g, 21% yield): MS (ESI+) m/z 340.2 (M+1), 342.2 (M+1).

Step 3. Preparation of 2-(2-(3,3-difluoropyrrolidin-1-yl)-4-phenylpyridin-3-yl)-4,4-dimethyl-3,4,6,7-tetrahydropyrano[3,4-d]imidazole

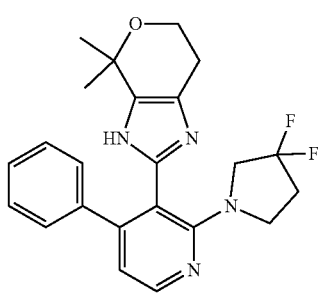 [SMILES: CC1(C)OCCc2nc(-c3c(-c4ccccc4)ccnc3N3CCC(F)(F)C3)[nH]c21]

To a solution of 2'-(2-(3,3-difluoropyrrolidin-1-yl)-4-phenylpyridin-3-yl)-4',7'-dihydro-3'H-spiro[cyclobutane-1,6'-pyrano[3,4-d]imidazole] (0.065 g, 0.19 mmol) and 3,3-difluoropyrrolidine hydrochloride (0.082 g, 0.57 mmol) in anhydrous dimethyl sulfoxide (1.5 mL) was added potassium carbonate (0.12 g, 0.86 mmol) and the reaction mixture was heated at 130° C. for 20 h. After cooling to ambient temperature, the reaction mixture was diluted with ethyl acetate (15 mL) and the organic phase was washed with water (15 mL) and brine (30 mL). The organic phase was dried over anhydrous sodium sulfate, filtered, and concentrated in vacuo. Purification of the residue by preparative reverse phase HPLC using 5-40% acetonitrile in water containing 0.5% of formic acid as eluent afforded the title compound as a light brown solid (0.0016 g, 20% yield): $^1$H-NMR (300 MHz; CDCl$_3$) δ 8.28 (d, J=5.0 Hz, 1H), 7.27-7.22 (m, 3H), 7.07-7.04 (m, 2H), 6.74 (d, J=5.0 Hz, 1H), 4.55 (s, 2H), 3.56-3.36 (m, 6H), 2.31 (qd, J=13.6, 6.7 Hz, 2H), 1.11 (s, 6H). MS (ESI+) m/z 411.2 (M+1).

Example 55

Synthesis of Tert-Butyl 2-[2-(3,3-difluoropyrrolidin-1-yl)-4-phenyl-3-pyridyl]-3,4,6,7-tetrahydroimidazo[4,5-c]pyridine-5-carboxylate

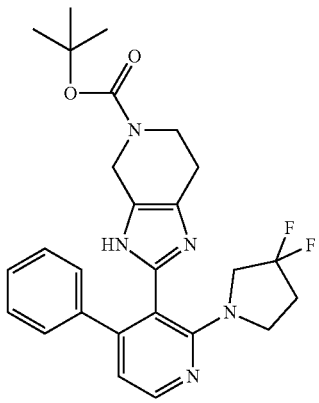 [SMILES: CC(C)(C)OC(=O)N1CCc2nc(-c3c(-c4ccccc4)ccnc3N3CCC(F)(F)C3)[nH]c2C1]

Step 1. Preparation of 2-(3,3-difluoropyrrolidin-1-yl)-4-iodonicotinaldehyde

To a solution of 3,3-difluoropyrrolidine (0.24 g, 2.2 mmol), 3,3-difluoropyrrolidine (0.24 g, 2.2 mmol) in dimethylsulfoxide (13 mL) was added potassium carbonate (0.55 g, 4.0 mmol) and stirred at 120° C. for 12 h. The reaction mixture was then diluted with EtOAc and water. The combined organic layers were washed with brine, dried over sodium sulfate, and concentrated in vacuo. Purification of the residue by column chromatography, eluting with a gradient of 20 to 90% of ethyl acetate in heptane, afforded the title compound as an off-white solid (0.29 g, 43% yield): MS (ES+) m/z 339.2 (M+1).

Step 2. Preparation of Tert-Butyl 2-(2-(3,3-difluoro-pyrrolidin-1-yl)-4-iodopyridin-3-yl)-3,4,6,7-tetrahydro-5H-imidazo[4,5-c]pyridine-5-carboxylate

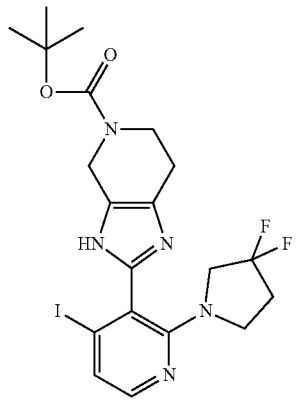 [SMILES: CC(C)(C)OC(=O)N1CCc2nc(-c3c(I)ccnc3N3CCC(F)(F)C3)[nH]c2C1]

To a solution of 2-(3,3-difluoropyrrolidin-1-yl)-4-iodopyridine-3-carbaldehyde (0.29 g, 0.86 mmol), ammonium hydroxide, 28-30% (0.37 mL, 9.2 mmol) in N,N-dimethylformamide (1.8 mL) were added ammonium acetate (0.30 g, 3.9 mmol) and tert-Butyl 3-bromo-4-oxopiperidine-1-carboxylate (0.36 g, 1.3 mmol). The reaction mixture was stirred at ambient temperature for 45 minutes and stirred at 60° C. for another 20 h. After cooling to ambient temperature, the reaction mixture was diluted with ethyl acetate (20 mL), extracted with water (20 mL×3). The combined organic layers were washed with brine (40 mL), dried over anhydrous sodium sulfate, filtered and concentrated in vacuo. Purification of the residue by column chromatography, eluting with a gradient of 0 to 30% of ethyl acetate in heptane, provided the title compound as a yellow solid (0.12 g, 26% yield): MS (ES+) m/z 532.2 (M+1).

Step 3. Preparation of Tert-Butyl 2-[2-(3,3-difluoro-pyrrolidin-1-yl)-4-phenyl-3-pyridyl]-3,4,6,7-tetrahydroimidazo[4,5-c]pyridine-5-carboxylate

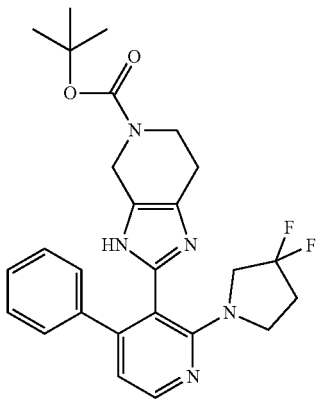 [SMILES: CC(C)(C)OC(=O)N1CCc2nc(-c3c(-c4ccccc4)ccnc3N3CCC(F)(F)C3)[nH]c2C1]

A mixture of tert-butyl 2-(2-(3,3-difluoropyrrolidin-1-yl)-4-iodopyridin-3-yl)-3,4,6,7-tetrahydro-5H-imidazo[4,5-c]pyridine-5-carboxylate (0.12 g, 0.22 mmol), phenylboronic acid (0.029 g, 0.24 mmol) and [1,1'-bis(diphenylphosphino)ferrocene]dichloropalladium(II), complex with $CH_2Cl_2$ (1:1) (0.018, 0.022 mmol) and potassium carbonate (0.076 g, 0.55 mmol) in 1,4-Dioxane (1.0 mL) was stirred for 5 min under nitrogen (purging). To this was added Water (0.08 mL) and stirred at 85 degree for 4 h under nitrogen. The mixture was filtered through diatomaceous earth (i.e. Celite®) to remove the solid impurities, and the filtrate was concentrated to remove the solvent. Purification by reverse phase preparative HPLC, using acetonitrile in water containing 0.5% formic acid as eluent afforded the title compound as an off-white solid (0.007 g, 6.5% yield): $^1$H-NMR (300 MHz; DMSO-$d_6$) δ 11.75 (s, 1H), 8.25 (d, J=5.1 Hz, 1H), 7.28-7.24 (m, 3H), 7.14-7.10 (m, 2H), 6.77 (d, J=5.1 Hz, 1H), 4.23 (t, J=0.3 Hz, 2H), 3.56 (dd, J=5.5, 0.5 Hz, 2H), 3.32-3.27 (m, 6H), 2.39-2.29 (m, 2H), 1.46-1.35 (m, 9H); MS (ES+) m/z 482.2 (M+1).

Example 56

Synthesis of (S)-2-(4-(2,5-difluorophenyl)-2-(3-fluoropyrrolidin-1-yl)pyridin-3-yl)-3,4,6,7-tetrahydropyrano[3,4-d]imidazole

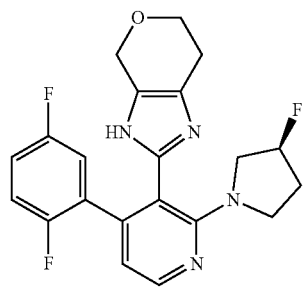 [SMILES: Fc1ccc(F)c(-c2ccnc(N3CC[C@H](F)C3)c2-c2nc3c([nH]2)COCC3)c1]

Step 1. Preparation of 2-[2-[(3S)-3-fluoropyrrolidin-1-yl]-4-iodo-3-pyridyl]-3,4,6,7-tetrahydropyrano[3,4-d]imidazole

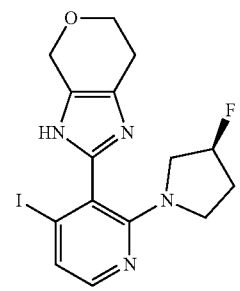 [SMILES: F[C@H]1CCN(c2nccc(I)c2-c2nc3c([nH]2)COCC3)C1]

To a solution of 2-(3,3-difluoropyrrolidin-1-yl)-4-iodopyridine-3-carbaldehyde (0.40 g, 1.2 mmol), ammonium hydroxide, 28-30% (0.52 mL, 13 mmol) in N,N-dimethylformamide (3.6 mL) was added ammonium acetate (0.41 g, 5.3 mmol) and 5-bromo-2,2-dimethyltetrahydro-4H-pyran-4-one (0.43 g, 5.6 mmol). The reaction mixture was stirred at ambient temperature for 90 minutes and stirred at 65° C. for another 12 h. After cooling to ambient temperature, the reaction mixture was diluted with ethyl acetate (20 mL) and extracted with water (20 mL×3). The combined layers were washed with brine (40 mL), dried over anhydrous sodium sulfate, filtered and concentrated in vacuo.

Purification of the residue by column chromatography, eluting with a gradient of 0-4% of methanol in dichloromethane, afforded the title compound as a yellow solid (0.15 g, 22% yield): MS (ES+) m/z 415.2 (M+1).

Step 2. Preparation of (S)-2-(4-(2,5-difluorophenyl)-2-(3-fluoropyrrolidin-1-yl)pyridin-3-yl)-3,4,6,7-tetrahydropyrano[3,4-d]imidazole

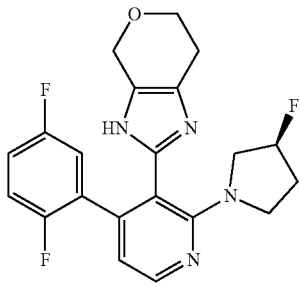 [SMILES: Fc1ccc(F)c(-c2ccnc(N3CC[C@H](F)C3)c2-c2nc3c([nH]2)COCC3)c1]

A mixture of 2-[2-[(3S)-3-fluoropyrrolidin-1-yl]-4-iodo-3-pyridyl]-3,4,6,7-tetrahydropyrano[3,4-d]imidazole (0.058 g, 0.14 mmol), 2,5-difluorophenylboronic acid (0.033 g, 0.21 mmol) and [1,1'-bis(diphenylphosphino)ferrocene]dichloropalladium(II), complex with dichloromethane (1:1) (0.011 g, 0.014 mmol) and potassium carbonate (0.058 g, 0.42 mmol) in 1,4-dioxane (0.53 mL) was stirred for 5 min under a nitrogen atmosphere. To this was added water (0.060 mL) and stirred at 85° C. for 4 h. The mixture was filtered through diatomaceous earth (i.e. Celite®) and the concentrated in vacuo. Purification by reverse phase preparative HPLC, using acetonitrile in water containing 0.5% formic acid as eluent, afforded the title compound as a yellow solid (0.0075 g, 13% yield): $^1$H-NMR (500 MHz; DMSO-$d_6$) δ 11.89-11-83 (m, 1H), 8.23-8.22 (m, 1H), 8.16-8.15 (m, 1H), 7.40-7.30 (m, 1H), 7.24-7.14 (m, 2H), 4.68 (d, J=9.0 Hz, 4H) 4.47-4.34 (m, 2H), 4.02-4.00 (m, 3H), 2.24-1.91 (m, 4H); MS (ES+) m/z 401.2 (M+1).

Example 57

Synthesis of 2-(4-(2,5-difluorophenyl)-2-(3,3-difluoropyrrolidin-1-yl)pyridin-3-yl)-6,6-dimethyl-3,4,6,7-tetrahydropyrano[3,4-d]imidazole

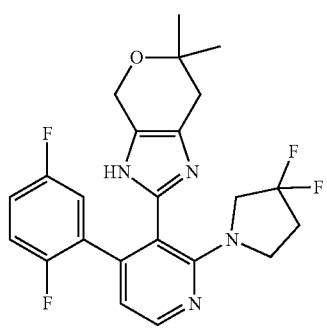 [SMILES: CC1(C)Cc2nc(-c3c(-c4cc(F)ccc4F)ccnc3N3CCC(F)(F)C3)[nH]c2CO1]

Step 1. Preparation of 2-(2-(3,3-difluoropyrrolidin-1-yl)-4-iodopyridin-3-yl)-6,6-dimethyl-3,4,6,7-tetrahydropyrano[3,4-d]imidazole

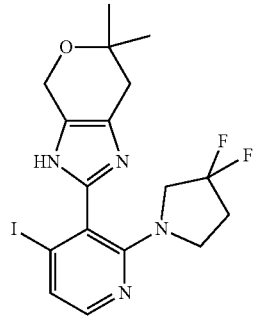 [SMILES: CC1(C)Cc2nc(-c3c(I)ccnc3N3CCC(F)(F)C3)[nH]c2CO1]

To a solution of 2-(3,3-difluoropyrrolidin-1-yl)-4-iodopyridine-3-carbaldehyde (0.40 g, 1.2 mmol), 28-30% ammonium hydroxide (0.65 mL, 16 mmol) in N,N-dimethylformamide (1.8 mL) were added ammonium acetate (0.41 g, 5.3 mmol) and 5-bromo-2,2-dimethyltetrahydro-4H-pyran-4-one (0.37 g, 1.8 mmol). The reaction mixture was stirred at ambient temperature for 90 minutes and stirred at 65° C. for another 12 h. After cooling to ambient temperature, the reaction mixture was diluted with ethyl acetate (20 mL), extracted with water (20 mL×3). The combined organic layers were washed with brine (40 mL), dried over anhydrous sodium sulfate, filtered and concentrated in vacuo. Purification of the residue by column chromatography, eluting with a gradient of 10-50% of ethyl acetate (containing 10% triethylamine) in heptane, afforded the title compound as a yellow solid (0.18 g, 32% yield): MS (ES+) m/z 461.2 (M+1).

Step 2. Preparation of 2-(4-(2,5-difluorophenyl)-2-(3,3-difluoropyrrolidin-1-yl)pyridin-3-yl)-6,6-dimethyl-3,4,6,7-tetrahydropyrano[3,4-d]imidazole

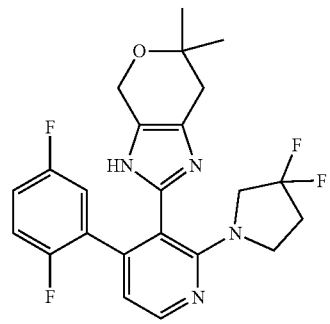 [SMILES: CC1(C)Cc2nc(-c3c(-c4cc(F)ccc4F)ccnc3N3CCC(F)(F)C3)[nH]c2CO1]

A mixture of 2-(2-(3,3-difluoropyrrolidin-1-yl)-4-iodopyridin-3-yl)-6,6-dimethyl-3,4,6,7-tetrahydropyrano[3,4-d]imidazole (0.16 g, 0.34 mmol), 2,5-difluorophenylboronic acid (0.080 g, 0.51 mmol) and [1,1'-bis(diphenylphosphino)ferrocene]dichloropalladium(II), complex with CH$_2$Cl$_2$ (1:1) (0.028 g, 0.034 mmol) and potassium carbonate (0.14 g, 1.0 mmol) in 1,4-Dioxane (1.4 mL) was stirred for 5 min under nitrogen (purging). To this was added Water (0.15 mL) and stirred at 85 degree for 4 h under nitrogen. The mixture was filtered through diatomaceous earth (i.e. Celite®) to remove the solid impurities, and the filtrate was concentrated to remove the solvent. Purification by reverse phase preparative HPLC, using acetonitrile in water containing 0.5% formic acid as eluent afforded the title compound as a yellow solid (0.17 g, 12% yield): $^1$H-NMR (300 MHz; CDCl$_3$) δ 8.31 (d, J=5.0 Hz, 1H), 6.98-6.93 (m, 2H), 6.86-6.80 (m, 1H), 6.74 (m, 1H), 4.58 (s, 2H), 3.46 (m, 4H), 2.53 (s, 2H), 2.38-2.24 (m, 2H), 1.27 (s, 6H); MS (ES+) m/z 447.2 (M+1).

Example 58

Synthesis of 2-(2-((S)-3-fluoropyrrolidin-1-yl)-4-phenylpyridin-3-yl)-6-methoxy-4,5,6,7-tetrahydro-1H-benzo[d]imidazole

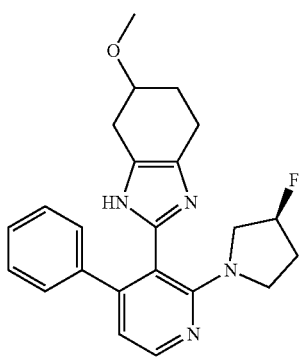 [SMILES: COC1CCc2nc(-c3c(-c4ccccc4)ccnc3N3CC[C@H](F)C3)[nH]c2C1]

Step 1. Preparation of 1,4-dimethoxycyclohexene

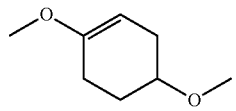

To a solution of 4-methoxycyclohex-3-enol (0.35 g, 2.7 mmol) in tetrahydrofuran (5.3 mL) was added sodium hydride (0.29 g, 12 mmol) at 0° C. and the solution was stirred for 10 min. Then iodomethane (0.51 mL, 8.2 mmol) was added dropwise with an evolution of gas (hydrogen) was observed. After 1 h at 25° C., the solution was diluted with diethyl ether (45 mL) and washed with water (20 mL). The aqueous phase was extracted with ether (20 mL×2), the combined organic phases were dried over magnesium sulfate and concentrated in vacuo. Purification of the residue by column chromatography, eluting with a gradient of 0 to 30% of ethyl acetate in heptane, provided the title compound as a yellow solid (0.57 g, quantitative). $^1$H-NMR (300 MHz; CDCl$_3$) δ 4.50 (m, 1H), 3.52 (s, 3H), 3.50-3.44 (m, 1H), 3.39 (s, 3H), 2.46-2.36 (m, 1H), 2.19-2.08 (m, 3H), 1.95-1.88 (m, 1H), 1.78-1.72 (m, 1H).

Step 2. Preparation of 2-bromo-4-methoxycyclohexan-1-one

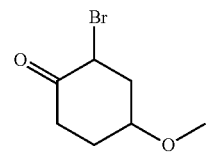

A solution N-bromosuccinimide (0.64 g, 3.6 mmol) and sodium acetate (0.029 g, 0.36 mmol) in tetrahydrofuran: water (1:1) was added dropwise to the 1,4-dimethoxycyclohexene (0.39 g, 2.7 mmol) at 0° C. The resulting mixture was warmed to ambient temperature and stirred at 22° C. for 3 h, then diluted with diethyl ether and washed with saturated sodium bicarbonate and brine. The mixture was dried over sodium sulfate, filtered and concentrated in vacuo. Purification of the residue by column chromatography, eluting with a gradient of 0 to 20% of ethyl acetate in heptane, provided the title compound as a yellow oil (0.15 g, 26%).

Step 3. Preparation of 2-(2-chloro-4-phenylpyridin-3-yl)-6-methoxy-4,5,6,7-tetrahydro-1H-benzo[d]imidazole

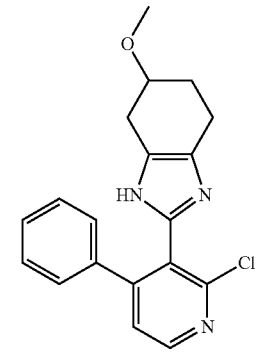 [SMILES: COC1CCc2nc(-c3c(-c4ccccc4)ccnc3Cl)[nH]c2C1]

To a solution of 2-chloro-4-phenyl-pyridine-3-carbaldehyde (0.15 g, 0.69 mmol) in N,N-dimethylformamide (3.3 mL) were added 2-bromo-4-methoxy-cyclohexanone (0.16 g, 0.76 mmol), ammonium hydroxide, 28-30% (0.29 mL, 7.2 mmol) and ammonium acetate (0.24 g, 3.1 mmol). The reaction mixture was stirred at ambient temperature for 30 minutes and stirred at 60° C. for another 20 h. After cooling to ambient temperature, the reaction mixture was diluted with ethyl acetate (20 mL) and extracted with water (20 mL×3). The combined organic layers were washed with brine (40 mL), dried over anhydrous sodium sulfate, filtered and concentrated in vacuo. Purification of the residue by column chromatography, eluting with a gradient of 20 to 100% of ethyl acetate in heptane, provided the title compound as a yellow solid (0.048 g, 20% yield).

Step 4. Preparation of 2-(2-((S)-3-fluoropyrrolidin-1-yl)-4-phenylpyridin-3-yl)-6-methoxy-4,5,6,7-tetrahydro-1H-benzo[d]imidazole

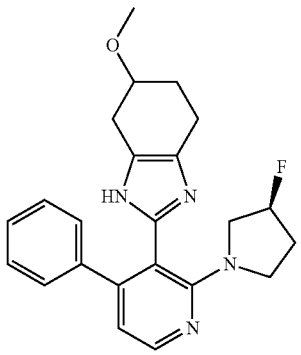 [SMILES: COC1CCc2nc(-c3c(-c4ccccc4)ccnc3N3CC[C@H](F)C3)[nH]c2C1]

To a solution of 2-(2-chloro-4-phenyl-3-pyridyl)-6-methoxy-4,5,6,7-tetrahydro-1H-benzimidazole (0.025 g, 0.074 mmol), rac-(3S)-3-fluoropyrrolidine; hydrochloride (0.028 g, 0.22 mmol) in DMSO (1.3 mL) was added potassium carbonate potassium carbonate (0.046, 0.33 mmol) in one portion. The reaction mixture was heated to 130° C. for 12 h. The mixture was diluted with ethyl acetate and water. The combined organic layers were washed with brine, dried over anhydrous sodium sulfate and concentrated in vacuo. Purification by preparative reverse phase HPLC, using acetonitrile in water containing 0.5% of formic acid as eluent, to afford the title compound as a colorless solid (0.0056 g, 19% yield): $^1$H-NMR (300 MHz; CDCl$_3$) δ 8.23 (d, J=5.1 Hz, 1H), 8.10 (s, 1H), 7.27-7.22 (m, 3H), 7.07-7.03 (m, 2H), 6.66 (d, J=5.1 Hz, 1H), 5.29-5.08 (m, 1H), 3.71-3.63 (m, 1H), 3.55-3.43 (m, 2H), 3.40 (m, 3H), 2.93-2.77 (m, 2H), 2.63-2.40 (m, 4H), 2.10-1.84 (m, 4H); MS (ESI+) m/z 393.2 (M+1).

Example 59

Synthesis of 2-(2-(3,3-difluoropyrrolidin-1-yl)-4-phenylpyridin-3-yl)-6-methoxy-4,5,6,7-tetrahydro-1H-benzo[d]imidazole

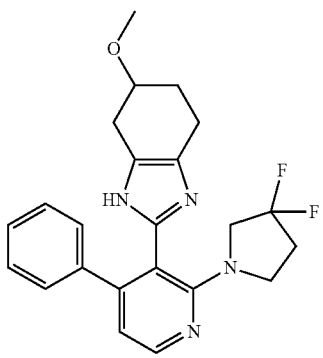 [SMILES: COC1CCc2nc(-c3c(-c4ccccc4)ccnc3N3CCC(F)(F)C3)[nH]c2C1]

To a solution of 2-(2-chloro-4-phenyl-3-pyridyl)-6-methoxy-4,5,6,7-tetrahydro-1H-benzimidazole (0.048 g, 0.14 mmol), 3,3-difluoropyrrolidine hydrochloride (0.061 g, 0.42 mmol) in dimethylsulfoxide (1.2 mL) was added potassium carbonate potassium carbonate (0.088 g, 0.64 mmol) in one portion. The reaction mixture was heated to 130° C. for 12 h. The mixture was then diluted with ethyl acetate and water. The combined organic layers were washed with brine, dried over anhydrous sodium sulfate and concentrated in vacuo. Purification by preparative reverse phase HPLC, using acetonitrile in water containing 0.5% of formic acid as eluent, to afford the title compound as a colorless solid (0.0096 g, 17% yield): $^1$H-NMR (500 MHz; DMSO-d$_6$) δ 11.49 (s, 1H), 8.23 (d, J=5.1 Hz, 1H), 7.28-7.25 (m, 3H), 7.14-7.12 (m, 2H), 6.76 (d, J=5.1 Hz, 1H), 4.30-4.26 (m, 2H), 4.02-3.87 (m, 1H), 3.77-3.65 (m, 2H), 3.60-3.55 (m, 1H), 3.28 (s, 3H), 2.40-2.31 (m, 4H), 2.09-1.93 (m, 2H); MS (ESI+) m/z 411.2 (M+1).

Example 60

Synthesis of 2-(2-(3,3-difluoropyrrolidin-1-yl)-4-phenylpyridin-3-yl)-4,5,6,7-tetrahydro-1H-benzo[d]imidazole

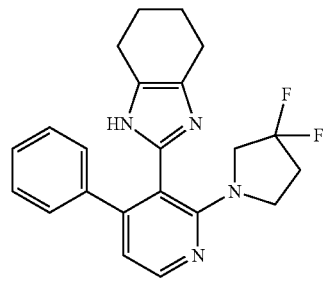 [SMILES: FC1(F)CCN(c2nccc(-c3ccccc3)c2-c2nc3c([nH]2)CCCC3)C1]

Step 1. Preparation of 2-(2-chloro-4-phenylpyridin-3-yl)-4,5,6,7-tetrahydro-1H-benzo[d]imidazole

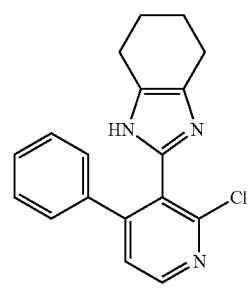 [SMILES: Clc1nccc(-c2ccccc2)c1-c1nc2c([nH]1)CCCC2]

To a solution of 2-chloro-4-phenyl-pyridine-3-carbaldehyde (0.10 g, 0.46 mmol), 1,2-cyclohexanedione (0.077 g, 0.69 mmol) in methanol (1.5 mL) was added ammonium hydroxide, 28-30% (0.19 mL, 4.8 mmol) in one portion. The reaction mixture was stirred at ambient temperature for 16 h. Upon completion, the solvent was concentrated in vacuo. Purification of the residue by column chromatography, eluting with a gradient of 0 to 100% of ethyl acetate in heptane, provided the title compound as a yellow solid (0.060 g, 42% yield). $^1$H-NMR (500 MHz; DMSO-d$_6$): δ 11.69 (s, 1H), 8.52 (d, J=5.1 Hz, 1H), 7.54 (d, J=5.1 Hz, 1H), 7.33 (dd, J=4.9, 2.3 Hz, 3H), 7.22-7.20 (m, 2H), 2.45 (m, 2H), 2.39 (m, 2H), 1.71 (m, 4H); MS (ESI+) m/z 310.2 (M+1), 312.2 (M+1).

Step 2. Preparation of 2-(2-(3,3-difluoropyrrolidin-1-yl)-4-phenylpyridin-3-yl)-4,5,6,7-tetrahydro-1H-benzo[d]imidazole

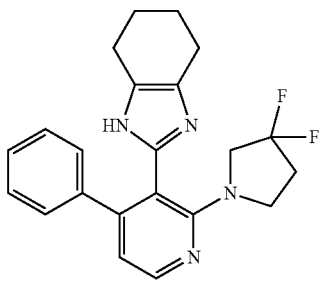 [SMILES: FC1(F)CCN(c2nccc(-c3ccccc3)c2-c2nc3c([nH]2)CCCC3)C1]

To a solution of 2-(2-chloro-4-phenyl-3-pyridyl)-4,5,6,7-tetrahydro-1H-benzimidazole (50 mg, 0.16 mmol), 3,3-difluoropyrrolidine hydrochloride (70 mg, 0.48 mmol) in DMSO (0.80 mL) was added potassium carbonate (0.10 g, 0.73 mmol). The reaction mixture was heated to 120° C. for 8 h. Reaction was then diluted with EtOAc and water. The combined organic layer was washed with brine, dried over sodium sulfate, and concentrated in vacuo to obtain the crude product. Purification by preparative reverse phase HPLC, using acetonitrile in water containing 0.5% of formic acid as eluent, to afford the title compound as a colorless solid (16 mg, 26% yield): $^1$H-NMR (500 MHz; DMSO-$d_6$) δ 8.44 (d, J=5.0 Hz, 1H), 7.41-7.35 (m, 3H), 7.06 (m, 2H), 6.92 (d, J=5.0 Hz, 1H), 3.60 (t, J=13.0 Hz, 2H), 3.20 (t, J=7.3 Hz, 2H), 2.49-2.40 (m, 4H), 1.74 (s, 4H); MS (ESI+) m/z 381.3 (M+1).

Example 61

Synthesis of 2-(3,3-difluoropyrrolidin-1-yl)-3-(5-methyl-4-phenyl-1H-imidazol-2-yl)-4-phenylpyridine

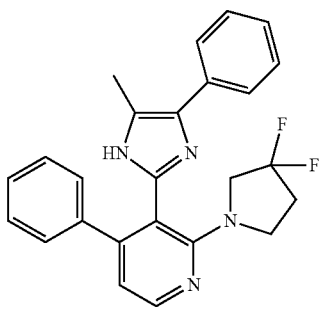 [SMILES: Cc1[nH]c(-c2c(-c3ccccc3)ccnc2N2CCC(F)(F)C2)nc1-c1ccccc1]

Step 1. Preparation of 2-chloro-3-(5-methyl-4-phenyl-1H-imidazol-2-yl)-4-phenylpyridine

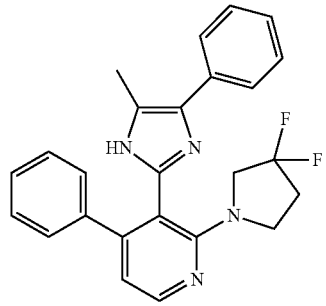 [SMILES: Cc1[nH]c(-c2c(-c3ccccc3)ccnc2N2CCC(F)(F)C2)nc1-c1ccccc1]

To a solution of 2-chloro-4-phenyl-pyridine-3-carbaldehyde (0.10 g, 0.46 mmol), 1,2-cyclohexanedione (0.077 g, 0.69 mmol) in methanol (1.5 mL) was added 28-30% ammonium hydroxide (0.19 mL, 4.82 mmol) in one portion. The reaction mixture was stirred at ambient temperature for 12 h. The mixture was concentrated in vacuo. The residue was purified by column chromatography, eluting with a gradient of 5-100% of ethyl acetate in heptane, to afford the title compound as a colorless solid (0.090 g, 57% yield); MS (ESI+) m/z 346.2 (M+1), 348.2 (M+1).

Step 2. 2-(3,3-difluoropyrrolidin-1-yl)-3-(5-methyl-4-phenyl-1H-imidazol-2-yl)-4-phenylpyridine To a solution of 2-chloro-3-(5-methyl-4-phenyl-1H-imidazol-2-yl)-4-phenyl-pyridine (0.080 g, 0.23 mmol), 3,3-difluoropyrrolidine hydrochloride (0.10 g, 0.69 mmol) in dimethylsulfoxide (1.0 mL) was added potassium carbonate (0.14 g, 1.0 mmol) and stirred at 120° C. for 8 h. After the mixture was cooled to ambient temperature, the reaction mixture was then diluted with ethyl acetate (15 mL) and washed with water (15 mL) and brine (25 mL). The combined organic layers were dried over sodium sulfate, and concentrated in vacuo. Purification by preparative reverse phase HPLC, using acetonitrile in water containing 0.5% of formic acid as eluent, afforded the title compound as an off-white solid (0.0095 g, 9.9% yield): $^1$H-NMR (500 MHz; DMSO-$d_6$) δ 8.48 (d, J=5.1 Hz, 1H), 7.53 (m, 2H), 7.46 (m, 3H), 7.38-7.35 (m, 3H), 7.16-7.14 (m, 2H), 6.95 (d, J=5.0 Hz, 1H), 4.24-3.99 (m, 3H), 3.69-3.64 (m, 2H), 2.48-2.43 (m, 2H), 2.36 (s, 3H); MS (ES+) m/z 417.3 (M+1).

Example 62

Synthesis of 5-(tert-butyl)-3-(2-(3,3-difluoropyrrolidin-1-yl)-4-phenylpyridin-3-yl)-1,2,4-oxadiazole

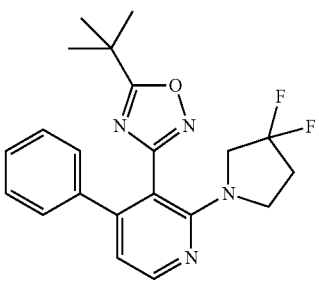 [SMILES: CC(C)(C)c1nc(-c2c(-c3ccccc3)ccnc2N2CCC(F)(F)C2)no1]

Step 1. Preparation of 2-(3,3-difluoropyrrolidin-1-yl)-4-phenylnicotinonitrile

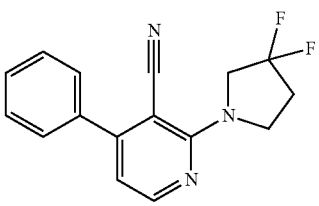 [SMILES: N#Cc1c(-c2ccccc2)ccnc1N1CCC(F)(F)C1]

To a solution of 2-chloro-4-phenyl-pyridine-3-carbonitrile (2.0 g, 9.3 mmol) and 3,3-difluoropyrrolidine hydrochloride (1.7 g, 12 mmol) in anhydrous DMSO (25 mL) was added potassium carbonate (3.9 g, 28 mmol) and the reaction mixture was heated at 120° C. for 20 h. After cooling to ambient temperature, the reaction mixture was diluted with ethyl acetate (100 mL) and washed with water (100 mL) and brine (120 mL). The organic phase was dried over anhydrous sodium sulfate, filtered, and the filtrate concentrated in vacuo. The residue was purified by column chromatography, eluting with a gradient of 0 to 35% of ethyl acetate in heptane, to provide the title compound as a colorless solid (2.0 g, 75% yield): MS (ES+) m/z 286.2 (M+1).

Step 2. Preparation of 2-(3,3-difluoropyrrolidin-1-yl)-4-phenylnicotinonitrile

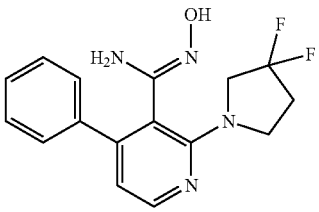 [SMILES: N/C(=N\O)c1c(-c2ccccc2)ccnc1N1CCC(F)(F)C1]

A solution of 2-(3,3-difluoropyrrolidin-1-yl)-4-phenyl-pyridine-3-carbonitrile (2.0 g, 7.0 mmol) and hydroxylamine (2.1 mL, 70 mmol) in ethanol (7 mL) was stirred at 100° C. After stirring at ambient temperature for 3 h, the mixture was cooled to ambient temperature and concentrated in vacuo. The residue was diluted with ethyl acetate, washed with brine, dried over sodium sulfate and concentrated under reduced pressure to yield the title compound as a colorless solid (1.8 g, 79% yield); MS (ESI+) m/z 319.2 (M+1).

Step 3. Preparation of 5-(tert-butyl)-3-(2-(3,3-difluoropyrrolidin-1-yl)-4-phenylpyridin-3-yl)-1,2,4-oxadiazole

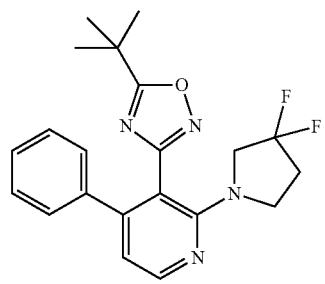 [SMILES: CC(C)(C)c1nc(-c2c(-c3ccccc3)ccnc2N2CCC(F)(F)C2)no1]

To a stirred solution of 2-(3,3-difluoropyrrolidin-1-yl)-N'-hydroxy-4-phenyl-pyridine-3-carboxamidine (0.080 g, 0.25 mmol) in anhydrous dichloromethane (1 mL) was added trimethylacetyl chloride (0.028 mL, 0.23 mmol) and triethylamine (0.053 mL, 0.38 mmol). The reaction mixture was stirred at ambient temperature for 10 h then poured into a saturated aqueous solution of sodium bicarbonate (10 mL). The mixture was extracted with ethyl acetate (5×5 mL) and the extract was dried over magnesium sulfate then concentrated under reduced pressure. To a suspension of the residue in anhydrous acetonitrile (1 mL) was added tetrabutylammonium fluoride (0.25 mL, 0.87 mmol). The reaction mixture was stirred at ambient temperature for 3 h then concentrated in vacuo. Purification by column chromatography, eluting with a gradient of 0-60% of ethyl acetate in heptane, afforded the title compound as a colorless solid: $^1$H-NMR (500 MHz; DMSO-$d_6$) δ 8.36 (d, J=5.0 Hz, 1H), 7.32-7.29 (m, 3H), 7.11-7.08 (m, 2H), 6.84 (d, J=5.0 Hz, 1H), 3.59 (t, J=13.2 Hz, 2H), 3.32 (m, 2H), 2.44-2.36 (m, 2H), 1.29 (s, 9H). MS (ESI+) m/z 385.2 (M+1).

Example 63

Synthesis of 2-(2-(3,3-difluoropyrrolidin-1-yl)-4-phenylpyridin-3-yl)-1,4,5,6-tetrahydrocyclopenta[d]imidazol-5-ol

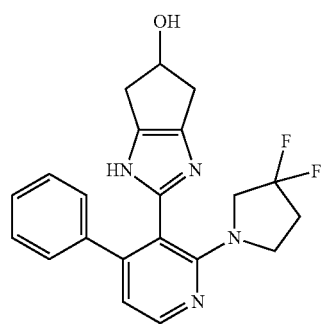 [SMILES: OC1Cc2nc(-c3c(-c4ccccc4)ccnc3N3CCC(F)(F)C3)[nH]c2C1]

Step 1. Preparation of 2-(3,3-difluoropyrrolidin-1-yl)-4-phenylnicotinimidamide hydrochloride

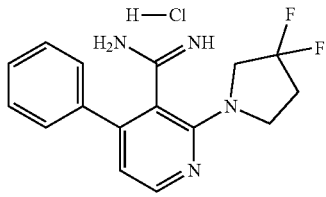

A solution of 2-(3,3-difluoropyrrolidin-1-yl)-N'-hydroxy-4-phenyl-pyridine-3-carboxamidine (0.29 g, 0.91 mmol) and acetic anhydride (0.095 mL, 1.0 mmol) in glacial acetic acid (1.1 mL, 0.91 mmol) was stirred at ambient temperature. After 5 minutes, the flask was purged with nitrogen then sodium formate (0.31 g, 4.6 mmol) and palladium on carbon (10%, wet support) (0.14 mg, 1.4 mmol) were added. The flask was purged with nitrogen followed by hydrogen. The mixture was stirred under a hydrogen atmosphere (balloon) at ambient temperature for 4 h. After purging the system with nitrogen, the solids were removed by filtration, and the filtrate was concentrated in vacuo. The residue was dissolved in 10 mL of ethanol and the pH was adjusted to 5-6 with hydrogen chloride (aq., 5 M). The resulting solids were then removed by filtration and the filtrate was concentrated under reduced pressure to afford the title compound as a colorless solid (0.36 g, quantitative): MS (ESI+) m/z 303.1 (M+1).

Step 2. Preparation of 2-(2-(3,3-difluoropyrrolidin-1-yl)-4-phenylpyridin-3-yl)-1,4,5,6-tetrahydrocyclopenta[d]imidazol-5-ol

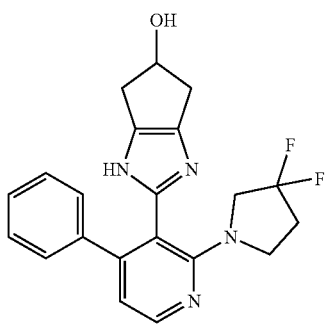 [SMILES: OC1Cc2nc(-c3c(-c4ccccc4)ccnc3N3CCC(F)(F)C3)[nH]c2C1]

To a solution of 4-benzyloxy-2-bromo-cyclopentanone (0.16 g, 0.59 mmol) in acetonitrile (2.5 mL, 0.31 mmol) was added 2-(3,3-difluoropyrrolidin-1-yl)-4-phenyl-pyridine-3-carboxamidine hydrochloride (0.10 g, 0.30 mmol) and potassium carbonate (0.12 g, 0.89 mmol) and the mixture was stirred at 80° C. for 12 h. The mixture was concentrated in vacuo and the residue was diluted with ethyl acetate (20 mL). The solution was washed with brine (2×10 mL), dried over sodium sulfate, filtered and concentrated in vacuo. Purification by reverse phase preparative HPLC, using acetonitrile in water containing 0.5% formic acid as eluent, afforded the title compound (0.0047 g, 4.2% yield): $^1$H-NMR (500 MHz; DMSO-$d_6$) δ 8.22 (s, 1H), 8.18 (d, J=5.0 Hz, 1H), 7.41-7.22 (m, 5H), 6.59 (d, J=5.0 Hz, 1H), 4.07-4.00 (m, 1H), 3.89-3.80 (m, 4H), 3.75-3.65 (m, 5H), 2.48-2.44 (m, 2H); MS (ESI+) m/z 383.2 (M+1).

Example 64

Synthesis of 2-(2-morpholino-4-phenylpyridin-3-yl)-3,4,6,7-tetrahydropyrano[3,4-d]imidazole

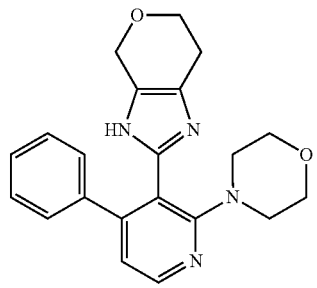 [SMILES: c1ccc(-c2ccnc(N3CCOCC3)c2-c2nc3c([nH]2)COCC3)cc1]

Step 1. Preparation of 2-fluoro-4-phenylnicotinaldehyde

To a mixture of 2-fluoro-4-iodonicotinaldehyde (10 g, 39.8 mmol) in anhydrous dioxane (135 mL) and water (15 mL) was added phenylboronic acid (5.3 g, 44 mmol) and potassium carbonate (6.5 g, 47 mmol). The mixture was purged with nitrogen for 10 minutes. To the mixture was then added dichloro[1,1'-bis(diphenyl-phosphino)ferrocene]palladium(II) dichloromethane adduct (3.37 g, 3.98 mmol) and the reaction mixture was heated to 90° C. for 3 h. After cooling to ambient temperature, the reaction mixture was filtered through a bed of diatomaceous earth (i.e. Celite®) and the filtrate concentrated under reduced pressure. Purification of the residue by column chromatography, eluting with a gradient of 0 to 30% of ethyl acetate in heptane, afforded the title compound as an off-white solid (7.6 g, 95% yield).

Step 2. Preparation of 2-morpholino-4-phenylnicotinaldehyde

To a solution of 2-fluoro-4-phenylnicotinaldehyde (0.50 g, 2.5 mmol) and morpholine (0.43 mL, 5.0 mmol) in anhydrous dimethylsulfoxide (6.2 mL) was added potassium carbonate (1.4 g, 9.9 mmol) and the reaction mixture was heated at 130° C. for 20 h. After cooling to ambient temperature, the reaction mixture was diluted with ethyl acetate (100 mL) and washed with water (100 mL) and brine (120 mL). The organic phase was dried over anhydrous sodium sulfate, filtered, and the filtrate concentrated in vacuo. The residue was purified by column chromatography, eluting with a gradient of 5 to 70% of ethyl acetate in heptane, to provide the title compound as a colorless solid (0.61 g, 91% yield): MS (ES+) m/z 269.0 (M+1).

Step 3. Preparation of 2-(2-morpholino-4-phenylpyridin-3-yl)-3,4,6,7-tetrahydropyrano[3,4-d]imidazole

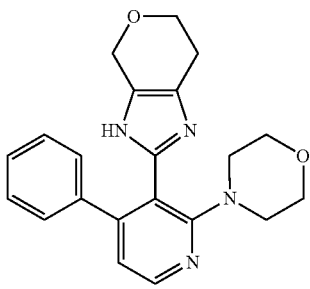 [SMILES: c1ccc(-c2ccnc(N3CCOCC3)c2-c2nc3c([nH]2)COCC3)cc1]

To a solution of 2-morpholino-4-phenylnicotinaldehyde (0.20 g, 0.75 mmol) in N,N-dimethylformamide (6.0 mL) was added 3-bromooxan-4-one (0.20 g, 1.1 mmol), 28-30% ammonium hydroxide (0.31 mL, 7.8 mmol) and ammonium acetate (0.25 g, 3.3 mmol). The reaction mixture was stirred at ambient temperature for 30 minutes and stirred at 75° C. for another 20 h. After cooling to ambient temperature, the reaction mixture was diluted with ethyl acetate (20 mL) and extracted with water (20 mL×3). The combined organic layers were washed with brine (40 mL), dried over anhydrous sodium sulfate, filtered and concentrated in vacuo. Purification by reverse phase preparative HPLC, using acetonitrile in water containing 0.5% formic acid as eluent afforded the title compound (0.051 g, 19% yield): $^1$H-NMR (500 MHz; DMSO-$d_6$) δ 8.29 (d, J=5.1 Hz, 1H), 8.22 (s, 1H), 7.29-7.27 (m, 3H), 7.12-7.11 (m, 2H), 6.94 (d, J=5.1 Hz, 1H), 4.42-4.41 (m, 2H), 3.81-3.79 (m, 3H), 3.56-3.48 (m, 9H), 2.95 (m, 4H); MS (ESI+) m/z 363.2 (M+1).

Example 65

Synthesis of 2-(2-(3,3-difluoroazetidin-1-yl)-4-phenylpyridin-3-yl)-3,4,6,7-tetrahydropyrano[3,4-d]imidazole

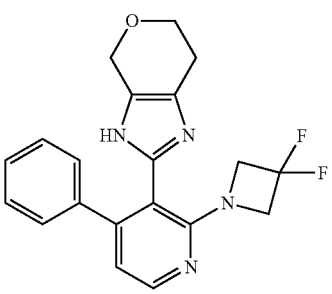 [SMILES: FC1(F)CN(c2nccc(-c3ccccc3)c2-c2nc3c([nH]2)COCC3)C1]

Step 1. Preparation of 2-(3,3-difluoroazetidin-1-yl)-4-phenylnicotinaldehyde

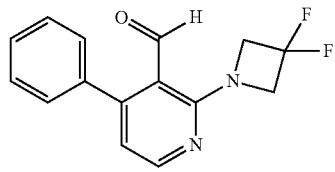 [SMILES: O=Cc1c(-c2ccccc2)ccnc1N1CC(F)(F)C1]

To a solution of 2-fluoro-4-phenylnicotinaldehyde (0.50 g, 2.5 mmol) and 3,3-difluoroazetidine hydrochloride (0.64 g, 5.0 mmol) in anhydrous dimethylsulfoxide (6.2 mL) was added potassium carbonate (1.4 g, 9.9 mmol) and the reaction mixture was heated at 130° C. for 3 h. After cooling to ambient temperature, the reaction mixture was diluted with ethyl acetate (100 mL) and washed with water (100 mL) and brine (120 mL). The organic phase was dried over anhydrous sodium sulfate, filtered, and the filtrate concentrated in vacuo. The residue was purified by column chromatography, eluting with a gradient of 5 to 70% of ethyl acetate in heptane, to provide the title compound as a colorless solid (0.53 g, 78% yield): MS (ES+) m/z 275.2 (M+1).

Step 2. Preparation of 2-(2-(3,3-difluoroazetidin-1-yl)-4-phenylpyridin-3-yl)-3,4,6,7-tetrahydropyrano[3,4-d]imidazole

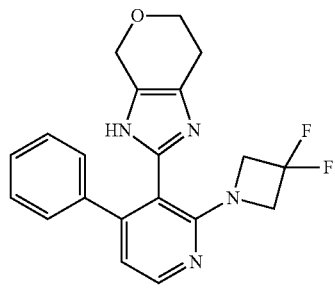 [SMILES: FC1(F)CN(c2nccc(-c3ccccc3)c2-c2nc3c([nH]2)COCC3)C1]

To a solution of 2-(3,3-difluoroazetidin-1-yl)-4-phenylnicotinaldehyde (0.20 g, 0.75 mmol) in N,N-dimethylformamide (6.0 mL) was added 3-bromooxan-4-one (0.20 g, 1.1 mmol), 28-30% ammonium hydroxide (0.31 mL, 7.8 mmol) and ammonium acetate (0.25 g, 3.3 mmol). The reaction mixture was stirred at ambient temperature for 30 minutes and stirred at 75° C. for another 20 h. After cooling to ambient temperature, the reaction mixture was diluted with ethyl acetate (20 mL) and washed with water (20 mL×3). The combined organic layers were washed with brine (40 mL), dried over anhydrous sodium sulfate, filtered and concentrated in vacuo. Purification by reverse phase preparative HPLC, using 10-50% acetonitrile in water containing 0.5% formic acid as eluent, afforded the title compound as a colorless solid (0.056 g, 20% yield): $^1$H-NMR (300 MHz; DMSO-$d_6$) δ 11.77 (m, 1H), 8.27 (d, J=5.2 Hz, 1H), 7.32-7.27 (m, 3H), 7.22-7.17 (m, 2H), 6.89 (d, J=5.2 Hz, 1H), 4.49 (m, 2H), 3.93 (t, J=12.7 Hz, 4H), 3.86-3.80 (m, 2H), 2.58-2.53 (m, 2H); MS (ESI+) m/z 369.2 (M+1).

Example 66

Synthesis of 2-(4-phenyl-2-(2-oxa-6-azaspiro[3.3]heptan-6-yl)pyridin-3-yl)-3,4,6,7-tetrahydropyrano[3,4-d]imidazole

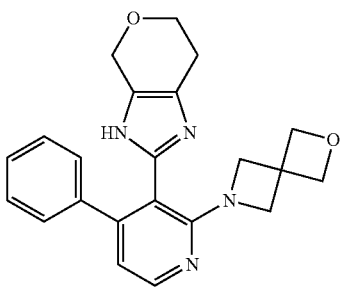 [SMILES: c1ccc(-c2ccnc(N3CC4(COC4)C3)c2-c2nc3c([nH]2)COCC3)cc1]

Step 1. Preparation of 4-phenyl-2-(2-oxa-6-azaspiro[3.3]heptan-6-yl)nicotinaldehyde

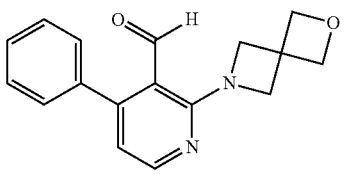 [SMILES: O=Cc1c(-c2ccccc2)ccnc1N1CC2(COC2)C1]

To a solution of 2-fluoro-4-phenylnicotinaldehyde (0.50 g, 2.5 mmol) and 2-oxa-6-azaspiro[3.3]heptane oxalic acid (0.94 g, 5.0 mmol) in anhydrous dimethylsulfoxide (6.2 mL) was added potassium carbonate (1.4 g, 9.9 mmol) and the reaction mixture was heated at 130° C. for 3 h. After cooling to ambient temperature, the reaction mixture was diluted with ethyl acetate (100 mL) and washed with water (100 mL) and brine (120 mL). The organic phase was dried over anhydrous sodium sulfate, filtered, and the filtrate concentrated in vacuo. The residue was purified by column chromatography, eluting with a gradient of 5 to 70% of ethyl acetate in heptane, to provide the title compound as a colorless solid (0.46 g, 65% yield): MS (ES+) m/z 281.2 (M+1).

Step 2. Preparation of 2-(4-phenyl-2-(2-oxa-6-azaspiro[3.3]heptan-6-yl)pyridin-3-yl)-3,4,6,7-tetrahydropyrano[3,4-d]imidazole

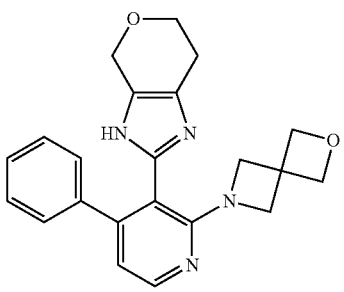 [SMILES: c1ccc(-c2ccnc(N3CC4(COC4)C3)c2-c2nc3c([nH]2)COCC3)cc1]

To a solution of 4-phenyl-2-(2-oxa-6-azaspiro[3.3]heptan-6-yl) nicotinaldehyde (0.20 g, 0.75 mmol) in N,N-dimethylformamide (6 mL) were added 3-bromooxan-4-one (0.20 g, 1.1 mmol), 28-30% ammonium hydroxide (0.31 mL, 7.8 mmol) and ammonium acetate (0.25 g, 3.3 mmol). The reaction mixture was stirred at ambient temperature for 30 minutes and stirred at 75° C. for another 20 h. After cooling to ambient temperature, the reaction mixture was diluted with ethyl acetate (20 mL), extracted with water (20 mL×3). The combined organic layers were washed with brine (40 mL), dried over anhydrous sodium sulfate, filtered and concentrated in vacuo. Purification by reverse phase preparative HPLC, using 10-50% acetonitrile in water containing 0.5% formic acid as eluent afforded the colorless compound (0.0030 g, 0.97% yield): $^1$H-NMR (500 MHz; DMSO-$d_6$) δ 8.29 (s, 1H), 8.18 (d, J=5.1 Hz, 1H), 7.28-7.26 (m, 3H), 7.16-7.14 (m, 2H), 6.71 (d, J=5.1 Hz, 1H), 4.60 (s, 4H), 4.49 (s, 2H), 3.85-3.83 (m, 2H), 3.72 (s, 4H), 2.58-2.56 (m, 2H); MS (ESI+) m/z 375.2 (M+1).

Example 67

Synthesis of 2-(2-cyclobutoxy-4-phenylpyridin-3-yl)-3,4,6,7-tetrahydropyrano[3,4-d]imidazole

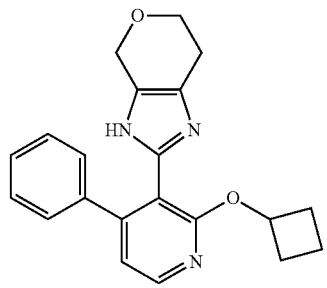 [SMILES: c1ccc(-c2ccnc(OC3CCC3)c2-c2nc3c([nH]2)COCC3)cc1]

Step 1. Preparation of (2-cyclobutoxy-4-phenylpyridin-3-yl)methanol

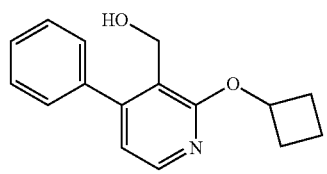 [SMILES: OCc1c(-c2ccccc2)ccnc1OC1CCC1]

To a solution of cyclobutanol (0.21 g, 2.9 mmol) in N,N-dimethylformamide (4 mL) under nitrogen at 0° C. was added sodium hydride (60%, 0.13 g, 2.7 mmol) in one portion. The reaction was stirred for 20 min and a solution of 2-fluoro-4-phenyl-pyridine-3-carbaldehyde (0.40 g, 2.0 mmol) in N,N-dimethylformamide (3 mL) was added dropwise at 0° C. The resulting mixture was stirred at ambient temperature for 12 h. The mixture was diluted with ether and washed with water and brine. The organic layer was dried over anhydrous sodium sulfate, filtered, and concentrated in vacuo. Purification by column chromatography, eluting with a gradient of 20-100% ethyl acetate, in heptane gave the title compound as an orange solid (0.50 g, 99% yield): MS (ESI+) m/z 256.0 (M+1).

Step 2. Preparation of 2-cyclobutoxy-4-phenylnicotinaldehyde

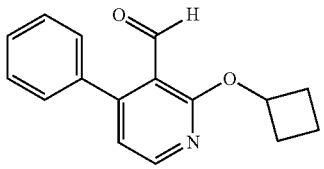 [SMILES: O=Cc1c(-c2ccccc2)ccnc1OC1CCC1]

To a stirred solution of (2-cyclobutoxy-4-phenylpyridin-3-yl)methanol (0.50 g, 1.95 mmol) in dichloromethane (16 mL) was added Dess-Martin periodinane (1.7 g, 3.9 mmol) in one portion. The reaction was stirred at ambient temperature for 3 h. Upon completion, the reaction was filtered and concentrated in vacuo. Purification by column chromatography, eluting with a gradient of 5-100% ethyl acetate in heptane, gave the title compound as a yellow solid (0.14 g, 28% yield): MS (ESI+) m/z 254.2 (M+1).

Step 3. Preparation of 2-(2-cyclobutoxy-4-phenylpyridin-3-yl)-3,4,6,7-tetrahydropyrano[3,4-d]imidazole

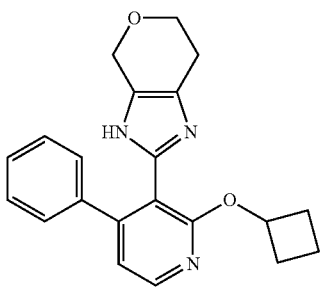 [SMILES: c1ccc(-c2ccnc(OC3CCC3)c2-c2nc3c([nH]2)COCC3)cc1]

To a solution of 2-cyclobutoxy-4-phenylnicotinaldehyde (0.13 g, 0.51 mmol) in N,N-dimethylformamide 1.1 mL) was added 3-bromooxan-4-one (0.14 g, 0.77 mmol), 28-30% ammonium hydroxide (0.28 mL, 7.1 mmol) and ammonium acetate (0.18 g, 2.31 mmol). The reaction mixture was stirred at ambient temperature for 90 minutes and stirred at 65° C. for another 12 h. After cooling to ambient temperature, the reaction mixture was diluted with ethyl acetate (20 mL) and extracted with water (20 mL×3). The combined organic layers were washed with brine (40 mL), dried over anhydrous sodium sulfate, filtered and concentrated in vacuo. Purification by reverse phase preparative HPLC, using acetonitrile in water containing 0.5% formic acid as eluent, afforded the title compound as a colorless solid (0.021 g, 12% yield): $^1$H-NMR (300 MHz; CDCl$_3$) δ 8.13 (d, J=5.2 Hz, 1H), 7.34-7.30 (m, 1H), 7.28-7.23 (m, 2H), 7.11-7.07 (m, 2H), 6.90 (d, J=5.2 Hz, 1H), 4.53 (s, 2H), 3.95 (t, J=5.5 Hz, 2H), 2.67-2.64 (m, 2H), 2.58-2.48 (m, 2H), 2.28-2.13 (m, 2H), 1.93-1.64 (m, 4H); MS (ESI+) m/z 348.2 (M+1).

Example 68

Synthesis of (S)-2-(2-(3-fluoropyrrolidin-1-yl)-4-phenylpyridin-3-yl)benzo[d]oxazole

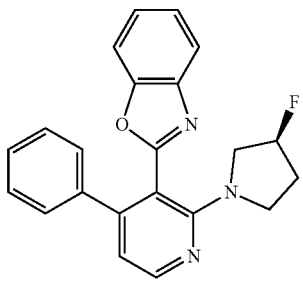 [SMILES: F[C@H]1CCN(c2nccc(-c3ccccc3)c2-c2nc3ccccc3o2)C1]

Step 1. Preparation of 3-bromo-2-fluoro-4-phenylpyridine

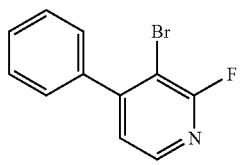 [SMILES: Fc1nccc(-c2ccccc2)c1Br]

To a solution of 3-bromo-2-fluoro-4-iodopyridine (0.900 g, 2.98 mmol), phenylboronic acid (0.364 g, 2.99 mmol) and potassium carbonate (0.824 g, 5.96 mmol) in 1,4-dioxane (10 mL) under a nitrogen atmosphere was added [1,1'-bis(diphenylphosphino)ferrocene]dichloropalladium(II) (0.219 g, 0.299 mmol) at 25° C. The mixture was stirred at 85° C. for 12 h. The mixture was cooled to 25° C. and concentrated under reduced pressure. The residue was purified by column chromatography on silica gel, eluting with a gradient of 5-10% of ethyl acetate in petroleum ether, to afford 3-bromo-2-fluoro-4-phenylpyridine as a colorless solid (0.720, 71% yield); $^1$H NMR (400 MHz, DMSO-d$_6$) δ 8.26 (dd, J=0.4, 4.8 Hz, 1H), 7.57-7.47 (m, 5H), 7.40 (dd, J=0.8, 4.8 Hz, 1H); MS (ES+) m/z 251.9, 253.9 (M+1).

Step 2. Preparation of (S)-3-bromo-2-(3-fluoropyrrolidin-1-yl)-4-phenylpyridine

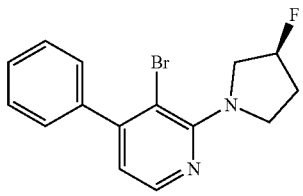 [SMILES: F[C@H]1CCN(c2nccc(-c3ccccc3)c2Br)C1]

To a mixture of (S)-3-fluoropyrrolidine (0.224 g, 1.79 mmol, hydrochloride) and potassium carbonate (0.657 mg, 4.76 mmol) in dimethylsulfoxide (5 mL) was added 3-bromo-2-fluoro-4-phenyl-pyridine (0.300 g, 1.19 mmol) at 25° C. The mixture was stirred at 110° C. for 2 h. After cooling to 25° C., the mixture was diluted with ethyl acetate (100 mL) and washed with water (6×50 mL). The organic layer was dried over sodium sulfate, filtered and concentrated under reduced pressure. The residue was purified by column chromatography on silica gel, eluting with a gradient of 0-5% ethyl acetate in petroleum ether, to afford the title compound as a colorless solid (0.270 g, 68% yield); MS (ES+) m/z 321.0, 323.0 (M+1).

Step 3. Preparation of (S)-2-(2-(3-fluoropyrrolidin-1-yl)-4-phenylpyridin-3-yl)benzo[d]oxazole

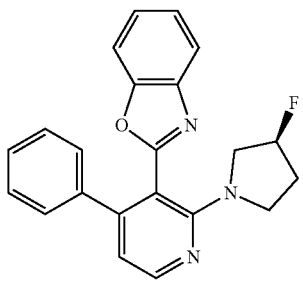 [SMILES: F[C@H]1CCN(c2nccc(-c3ccccc3)c2-c2nc3ccccc3o2)C1]

A mixture of (S)-3-bromo-2-(3-fluoropyrrolidin-1-yl)-4-phenylpyridine (0.320 g, 0.996 mmol), benzo[d]oxazole (0.474 g, 3.99 mmol), palladium(II) acetate (0.022 g, 0.099 mmol), cupric acetate (0.090 g, 0.498 mmol), triphenylphosphine (0.261 g, 0.996 mmol) and potassium carbonate (0.688 g, 4.98 mmol) in toluene (10 mL) was degassed and heated to 100° C. for 12 h under a nitrogen atmosphere. The mixture was cooled to 25° C. and concentrated under reduced pressure. The residue was purified by column chromatography on silica gel, eluting with a mixture of 7:3 petroleum ether and ethyl acetate, then preparative reversed phase chromatography, eluting with a gradient of 50-74% of acetonitrile in aqueous formic acid (0.225%), to afford the title compound as a colorless solid (0.0907 g, 25% yield, 99% purity): $^1$H NMR (400 MHz, DMSO-$d_6$) δ 8.37 (d, J=5.2 Hz, 1H), 7.78-7.69 (m, 1H), 7.67-7.58 (m, 1H), 7.43-7.31 (m, 2H), 7.22 (dd, J=1.6, 5.2 Hz, 3H), 7.16-7.06 (m, 2H), 6.78 (d, J=5.2 Hz, 1H), 5.40-5.09 (m, 1H), 3.42 (d, J=3.2 Hz, 1H), 3.33-3.28 (m, 1H), 3.24-3.12 (m, 2H), 2.10-1.85 (m, 2H); MS (ES+) m/z 360.2 (M+1).

Example 69

Synthesis of (S)-2-(3-fluoropyrrolidin-1-yl)-4-phenyl-3-(3-phenyl-1H-1,2,4-triazol-5-yl)pyridine

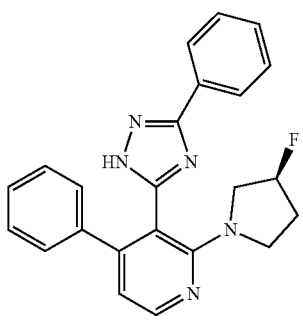 [SMILES: F[C@H]1CCN(c2nccc(-c3ccccc3)c2-c2nc(-c3ccccc3)n[nH]2)C1]

Step 1. Preparation of 3,5-dibromo-1-((2-(trimethylsilyl)ethoxy)methyl)-1H-1,2,4-triazole

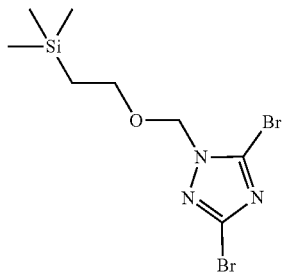

To a solution of triethylamine (1.34 g, 13.2 mmol) and 3,5-dibromo-1H-1,2,4-triazole (2.00 g, 8.82 mmol) in dichloromethane (40 mL) was added (2-(chloromethoxy)ethyl)trimethylsilane (1.54 g, 9.26 mmol) at 25° C. and the mixture was stirred at 25° C. for 12 h. The mixture was concentrated under reduced pressure. The residue was purified by flash silica gel chromatography, eluting with a gradient of 0-8% of ethyl acetate in petroleum ether to afford the title compound as a colorless oil (2.00 g, 64% yield): $^1$H NMR (400 MHz, CDCl$_3$) δ 5.46 (s, 2H), 3.73-3.64 (m, 2H), 1.00-0.87 (m, 2H), 0.01 (s, 9H).

Step 2. Preparation of 3-bromo-5-phenyl-1-((2-(trimethylsilyl)ethoxy)methyl)-1H-1,2,4-triazole and 5-bromo-3-phenyl-1-((2-(trimethylsilyl)-ethoxy)methyl)-1H-1,2,4-triazole

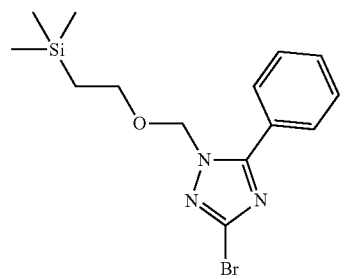

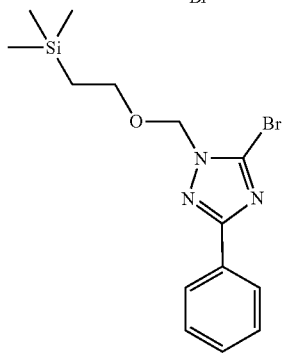

A mixture of phenylboronic acid (0.512 g, 4.20 mmol), 3,5-dibromo-1-((2-(trimethylsilyl)ethoxy)methyl)-1H-1,2,4-triazole (1.50 g, 4.20 mmol), [1,1'-bis(diphenylphosphino)ferrocene]dichloropalladium(II) (0.343 g, 0.420 mmol) and cesium carbonate (4.11 g, 12.6 mmol) in dioxane (20 mL) and water(4 mL) was stirred at 90° C. for 12 h under a nitrogen atmosphere. The reaction mixture was cooled to ambient temperature and concentrated under reduced pressure. The residue was purified by reversed-phase column chromatography, eluting with 0.1% aqueous formic acid, to afford a mixture of the title compounds as a black oil (0.800 g, crude): $^1$H NMR (400 MHz, CDCl$_3$) δ 8.14-7.87 (m, 2H), 7.61-7.38 (m, 3H), 5.69-5.41 (m, 2H), 4.01-3.63 (m, 2H), 1.02-0.98 (m, 2H), 0.03-0.01 (m, 9H).

Step 3. Preparation of 5-phenyl-1-((2-(trimethylsilyl)ethoxy)methyl)-3-(trimethylstannyl)-1H-1,2,4-triazole and 3-phenyl-1-((2-(trimethylsilyl)ethoxy)methyl)-5-(trimethylstannyl)-1H-1,2,4-triazole

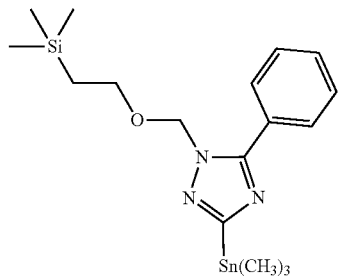

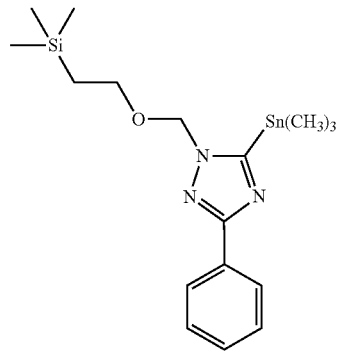

A mixture of 3-bromo-5-phenyl-1-((2-(trimethylsilyl)ethoxy)methyl)-1H-1,2,4-triazole;5-bromo-3-phenyl-1-((2-(trimethylsilyl)ethoxy)methyl)-1H-1,2,4-triazole (0.500 g, 0.705 mmol) and trimethyl(trimethylstannyl) stannane (2.10 g, 6.41 mmol), tetrakis(triphenylphosphine)palladium(0) (0.163 g, 0.141 mmol) in toluene (10 mL) was stirred at 110° C. for 12 h under a nitrogen atmosphere. The reaction mixture was cooled to ambient temperature. To the mixture was added saturated potassium fluoride (30 mL) and the mixture was stirred at 25° C. for 0.5 h. The mixture was extracted with ethyl acetate (3×30 mL). The combined organic layers were washed with brine (30 mL), dried over sodium sulfate, filtered and concentrated under reduced pressure. The residue was purified by reversed-phase column chromatography, eluting with 0.1% aqueous formic acid, to afford a mixture of the title compounds as a black oil (0.180 g, crude).

Step 4. Preparation of 2-fluoro-4-phenyl-3-(5-phenyl-1-((2-(trimethylsilyl)ethoxy)methyl)-1H-1,2,4-triazol-3-yl) pyridine and 2-fluoro-4-phenyl-3-(3-phenyl-1-((2-(trimethylsilyl)ethoxy)methyl)-1H-1,2,4-triazol-5-yl) pyridine

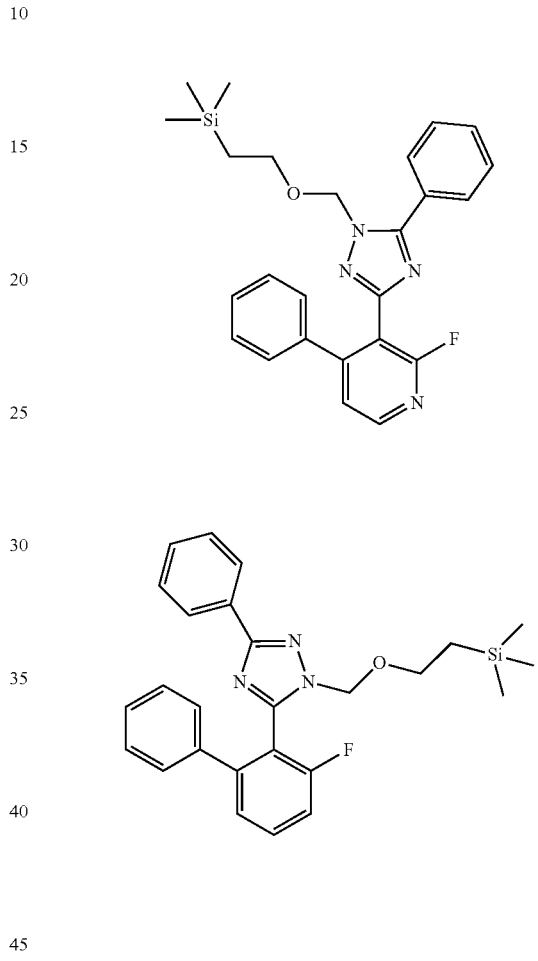

A mixture of 3-bromo-5-phenyl-1-((2-(trimethylsilyl)ethoxy)methyl)-1H-1,2,4-triazole; 5-bromo-3-phenyl-1-((2-(trimethylsilyl)ethoxy)methyl)-1H-1,2,4-triazole (0.500 g, 0.705 mmol) and trimethyl(trimethylstannyl)stannane (2.10 g, 6.41 mmol), tetrakis(triphenylphosphine)palladium(0) (0.163 g, 0.141 mmol) in toluene (10 mL) was stirred at 110° C. for 12 h under a nitrogen atmosphere. The reaction mixture was cooled to ambient temperature. To the mixture was added saturated potassium fluoride (30 mL) and the mixture was stirred at 25° C. for 0.5 h. The mixture was extracted with ethyl acetate (3×30 mL). The combined organic layers were washed with brine (30 mL), dried over sodium sulfate, filtered and concentrated under reduced pressure. The residue was purified by reversed-phase column chromatography, eluting with 0.1% aqueous formic acid, to afford the title compound as a black oil (0.180 g, crude): $^1$H NMR (400 MHz, CDCl$_3$) δ 8.33 (d, J=5.2 Hz, 1H), 7.88-7.79 (m, 2H), 7.55-7.41 (m, 4H), 7.35-7.30 (m, 5H), 5.50-5.42 (m, 2H), 3.69-3.58 (m, 2H), 0.97-0.86 (m, 2H), 0.02-0.06 (m, 9H).

Step 5. Preparation of (S)-2-(3-fluoropyrrolidin-1-yl)-4-phenyl-3-(5-phenyl-1-((2-(trimethylsilyl)ethoxy)methyl)-1H-1,2,4-triazol-3-yl)pyridine

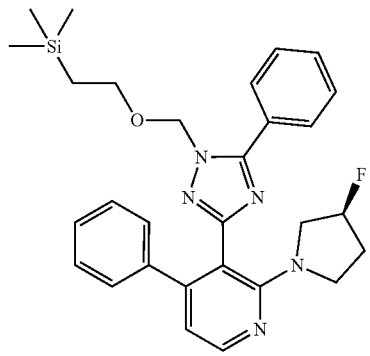 [SMILES: C[Si](C)(C)CCOCn1nc(-c2c(-c3ccccc3)ccnc2N2CC[C@H](F)C2)nc1-c1ccccc1]

A mixture of 5-phenyl-1-((2-(trimethylsilyl)ethoxy)methyl)-3-(trimethylstannyl)-1H-1,2,4-triazole; 3-phenyl-1-((2-(trimethylsilyl)ethoxy)methyl)-5-(trimethylstannyl)-1H-1,2,4-triazole (0.0700 g, 0.078 mmol), (S)-3-fluoropyrrolidine hydrochloride (0.0492 g, 0.391 mmol) and potassium carbonate (0.108 g, 0.783 mmol) in N,N-dimethylformamide (2 mL) was stirred at 90° C. for 12 h. The reaction mixture was cooled to ambient temperature. To the mixture was added water (10 mL) and then the mixture was extracted with ethyl acetate (3×20 m). The combined organic layers were washed with brine (3×10 mL), dried over sodium sulfate, filtered and concentrated under reduced pressure. The residue was purified by preparative reversed phase chromatography, eluting with a gradient of 48-87% of acetonitrile in aqueous formic acid (0.225%), to afford the title compound as a yellow solid (0.0300 g, 74% yield): $^1$H NMR (400 MHz, CDCl$_3$) δ 8.28 (d, J=5.2 Hz, 1H), 7.84 (dd, J=2.2, 7.4 Hz, 2H), 7.56-7.41 (m, 3H), 7.24-7.12 (m, 5H), 6.69 (d, J=5.2 Hz, 1H), 5.38 (s, 2H), 5.26-5.00 (m, 1H), 3.68-3.33 (m, 6H), 2.25-2.08 (m, 1H), 2.05-1.90 (m, 1H), 0.96-0.84 (m, 2H), 0.00 (s, 9H).

Step 6. Preparation of (S)-2-(3-fluoropyrrolidin-1-yl)-4-phenyl-3-(3-phenyl-1H-1,2,4-triazol-5-yl)pyridine

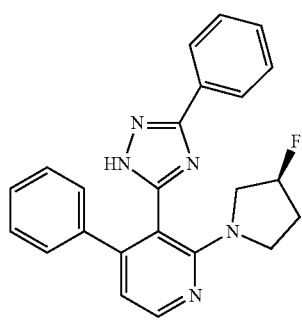 [SMILES: F[C@H]1CCN(c2nccc(-c3ccccc3)c2-c2nc(-c3ccccc3)n[nH]2)C1]

To a solution of (S)-2-(3-fluoropyrrolidin-1-yl)-4-phenyl-3-(5-phenyl-1-((2-(trimethylsilyl)ethoxy)methyl)-1H-1,2,4-triazol-3-yl)pyridine (0.0250 g, 0.0485 mmol) in methanol (0.5 mL) was added hydrogen chloride in methanol (4 M, 5 mL), and the mixture was shirred at 25° C. for 24 h. The reaction mixture was concentrated under reduced pressure. The residue was purified by preparative reversed phase HPLC eluting with a gradient of 22-42% of acetonitrile in aqueous hydrochloric acid (0.05%), to afford the title compound as an off-white solid (0.0120 g, 58% yield): $^1$H NMR (400 MHz, MeOD-d$_4$) δ 8.16 (d, J=6.6 Hz, 1H), 7.95-7.81 (m, 2H), 7.59-7.43 (m, 3H), 7.37-7.23 (m, 5H), 7.14 (d, J=6.6 Hz, 1H), 5.46-5.16 (m, 1H), 3.67-3.45 (m, 4H), 2.40-2.05 (m, 2H); MS (ES+) m/z 386.2 (M+1).

Example 70

Synthesis of (S)-2-(2-(3-fluoropyrrolidin-1-yl)-4-phenylpyridin-3-yl)imidazo[1,2-a]pyridine

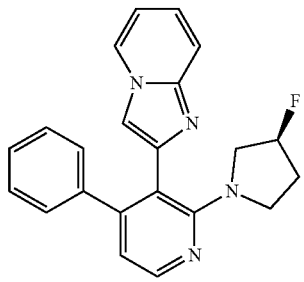 [SMILES: F[C@H]1CCN(c2nccc(-c3ccccc3)c2-c2cn3ccccc3n2)C1]

Step 1. Preparation of 2-(2-fluoro-4-phenylpyridin-3-yl)imidazo[1,2-a]pyridine

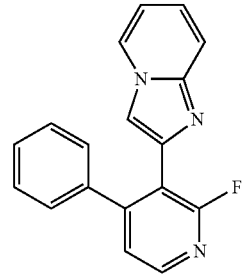 [SMILES: Fc1nccc(-c2ccccc2)c1-c1cn2ccccc2n1]

To a mixture of 2-bromoimidazo[1,2-a]pyridine (0.300 g, 1.52 mmol) and 1,1,1,2,2,2-hexamethyldistannane (2.00 g, 6.09 mmol) in toluene (5 mL) was added tetrakis(triphenylphosphine)palladium(0) (0.352 g, 0.305 mmol). The reaction mixture was stirred at 110° C. under a nitrogen atmosphere for 4 h. After the mixture was cooled to ambient temperature, 3-bromo-2-fluoro-4-phenylpyridine (0.422 g, 1.67 mmol) and tetrakis(triphenylphosphine)palladium(0) (0.352 g, 0.305 mmol) were added under a nitrogen atmosphere. The mixture was stirred at 110° C. for another 12 h. The reaction mixture was cooled to ambient temperature. To the mixture was added saturated aqueous potassium fluoride (20 mL) and the mixture was stirred at 25° C. for 0.5 h. The mixture was extracted with ethyl acetate (3×20 mL). The combined organic layers were washed with brine (20 mL), dried over sodium sulfate, filtered and concentrated under reduced pressure. The residue was purified by preparative reversed phase column chromatography, eluting with a gradient of 9-29% of acetonitrile in aqueous formic acid, to afford the title compound as a colorless solid (0.0170 g, 4% yield): ¹H NMR (400 MHz, DMSO-d₆) δ 8.47 (td, J=1.2, 6.8 Hz, 1H), 8.33 (d, J=5.2 Hz, 1H), 7.83 (s, 1H), 7.53-7.44 (m, 2H), 7.33-7.18 (m, 6H), 6.88 (dt, J=1.2, 6.8 Hz, 1H); MS (ES+) m/z 290.1 (M+1).

Step 2. Preparation of (S)-2-(2-(3-fluoropyrrolidin-1-yl)-4-phenylpyridin-3-yl)imidazo[1,2-a]pyridine

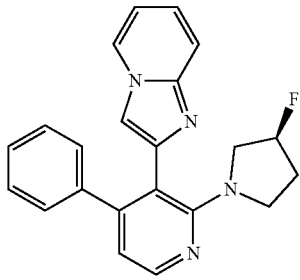 [SMILES: F[C@H]1CCN(c2nccc(-c3ccccc3)c2-c2cn3ccccc3n2)C1]

To a mixture of 2-(2-fluoro-4-phenylpyridin-3-yl)imidazo[1,2-a]pyridine (0.0170 g, 0.0588 mmol) and (S)-3-fluoropyrrolidine hydrochloride (0.0221 g, 0.176 mmol) in dimethylsulfoxide (1.5 mL) was added N,N-diisopropylethylamine (0.0379 g, 0.294 mmol). The mixture was stirred at 110° C. for 12 h. After being cooled to ambient temperature, the residue was poured into water (10 mL) and extracted with ethyl acetate (3×10 mL). The combined organic extracts were dried over anhydrous sodium sulfate, filtered and concentrated in vacuo. The residue was purified by preparative reversed phase HPLC, eluting with a gradient of 27-57% of acetonitrile in aqueous ammonium hydroxide (0.05%), to afford the title compound as a yellow solid (0.0124 g, 58% yield): ¹H NMR (400 MHz, CDCl₃) δ 8.16 (d, J=5.2 Hz, 1H), 7.85-7.80 (d, 1H), 7.49 (d, J=9.0 Hz, 1H), 7.08-6.98 (m, 7H), 6.64 (dt, J=1.2, 6.8 Hz, 1H), 6.59 (d, J=5.2 Hz, 1H), 4.99 (d, J=13.6 Hz, 1H), 3.42-3.22 (m, 4H), 2.07-1.98 (m, 1H), 1.92-1.75 (m, 1H): MS (ES+) m/z 359.0 (M+1).

Example 71

Synthesis of (S)-2-(2-(3-fluoropyrrolidin-1-yl)-4-phenylpyridin-3-yl)-[1,2,4]triazolo[1,5-a]pyridine

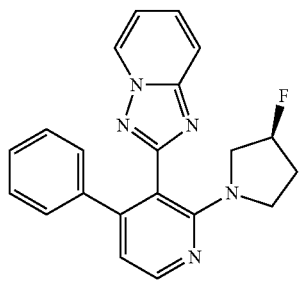 [SMILES: F[C@H]1CCN(c2nccc(-c3ccccc3)c2-c2nc3ccccn3n2)C1]

Step 1. Preparation of 2-(2-fluoro-4-phenylpyridin-3-yl)-[1,2,4] triazolo[1,5-a]pyridine

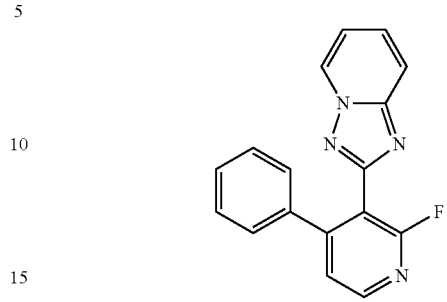

Following the procedure as described for Example 50, step 1, replacing—bromoimidazo[1,2-a]pyridine with 2-bromo-[1,2,4]triazolo[1,5-a]pyridine, the title compound was obtained as a brown solid (0.0100 g, 2% yield): ¹H NMR (400 MHz, CDCl₃) δ 8.64-8.36 (m, 3H), 7.82-7.68 (m, 2H), 7.62-7.51 (m, 2H), 7.41-7.34 (m, 2H), 7.07 (d, J=6.0 Hz, 2H); MS (ES+) m/z 291.0 (M+1).

Step 2. Preparation of (S)-2-(2-(3-fluoropyrrolidin-1-yl)-4-phenylpyridin-3-yl)-[1,2,4]triazolo[1,5-a] pyridine

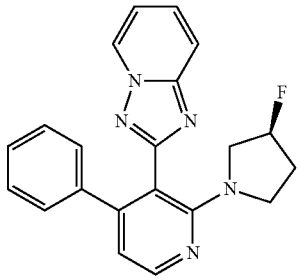 [SMILES: F[C@H]1CCN(c2nccc(-c3ccccc3)c2-c2nc3ccccn3n2)C1]

To a mixture of 2-(2-fluoro-4-phenylpyridin-3-yl)-[1,2,4]triazolo[1,5-a]pyridine (0.0100 g, 0.0344 mmol) and (S)-3-fluoropyrrolidine hydrochloride (0.00368 g, 0.0414 mmol) in dimethylsulfoxide (1 mL) was added N,N-diisopropylethylamine (0.0133 g, 0.103 mmol). The mixture was stirred at 110° C. for 12 h. After being cooled to ambient temperature, the residue was poured into water (20 mL) and extracted with ethyl acetate (3×15 mL). The combined organic extracts were dried over anhydrous sodium sulfate, filtered and concentrated in vacuo. The residue was purified by preparative reversed phase HPLC, eluting with a gradient of 8-39% of acetonitrile in aqueous formic acid (0.225%) to afford the title compound as a colorless solid (0.00600 g, 48% yield): ¹H NMR (400 MHz, CDCl₃) δ 8.47 (d, J=6.8 Hz, 1H), 8.32 (d, J=5.2 Hz, 1H), 7.67 (d, J=9.0 Hz, 1H), 7.50 (t, J=7.8 Hz, 1H), 7.14 (s, 5H), 7.00 (t, J=6.8 Hz, 1H), 6.72 (d, J=5.2 Hz, 1H), 5.09 (d, J=53.6 Hz, 1H), 3.53-3.29 (m, 4H), 2.18-2.04 (m, 1H), 1.99-1.84 (m, 1H); MS (ES+) m/z 360.1 (M+1).

Example 72

Synthesis of 2-[2-(3,3-difluoropyrrolidin-1-yl)-4-(2-fluorophenyl)-3-pyridyl]-1,4,6,7-tetrahydropyrano[3,4-d]imidazole

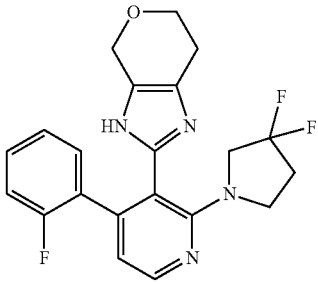 [SMILES: Fc1ccccc1-c1ccnc(N2CCC(F)(F)C2)c1-c1nc2c([nH]1)COCC2]

Step 1. Preparation of 2-[2-(3,3-difluoropyrrolidin-1-yl)-4-iodo-3-pyridyl]-1,4,6,7-tetrahydropyrano[3,4d]imidazole

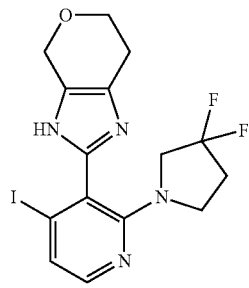 [SMILES: FC1(F)CCN(c2nccc(I)c2-c2nc3c([nH]2)COCC3)C1]

To a solution of 2-(3,3-difluoropyrrolidin-1-yl)-4-iodopyridine-3-carbaldehyde (0.300 g, 0.887 mmol), 3-bromotetrahydropyran-4-one (0.159 mg, 0.887 mmol) and ammonia (2 M in methanol, 0.44 mL, 0.869 mmol) was added ammonium acetate (103 mg, 1.33 mmol), and the mixture was stirred at 40° C. for 4 h. To the mixture was added 3-bromotetrahydropyran-4-one (0.159 g, 0.887 mmol), ammonium acetate (0.068 g, 0.887 mmol) and ammonia (2 M in methanol, 0.44 mL, 0.869 mmol), and the mixture was stirred at 40° C. for 18 h. To the mixture was then added 3-bromotetrahydropyran-4-one (0.079 g, 0.441 mmol). The mixture was stirred at 70° C. for 24 h. After cooling to ambient temperature, the mixture was diluted with saturated aqueous sodium bicarbonate (30 mL). The aqueous phase was extracted with ethyl acetate (3×30 mL). The combined organic phases were washed with brine (60 mL), dried over anhydrous sodium sulfate, filtered and concentrated in vacuo. Purification of the residue by column chromatography, eluting with a gradient of 0-60% of ethyl acetate in hexanes, afforded the title compound as a solid (0.075 g, 19% yield): $^1$H NMR (400 MHz; DMSO-$d_6$) δ 12.05 (broad singlet, 1H), 7.83 (d, J=5.2 Hz, 1H), 7.29 (d, J=5.2 Hz, 1H), 4.67-4.63 (m, 1H), 4.54 (s, 1H), 4.00 (t, J=5.8 Hz, 1H), 3.89 (t, J=5.5 Hz, 2H), 3.22 (t, J=6.9 Hz, 2H), 2.92 (t, J=5.8 Hz, 1H), 2.74-2.57 (m, 2H), 2.40-2.28 (m, 2H); MS (ES+) m/z 433.3 (M+1).

Step 2. Preparation of 2-[2-(3,3-difluoropyrrolidin-1-yl)-4-(2-fluorophenyl)-3-pyridyl]-1,4,6,7-tetrahydropyrano[3,4-d]imidazole

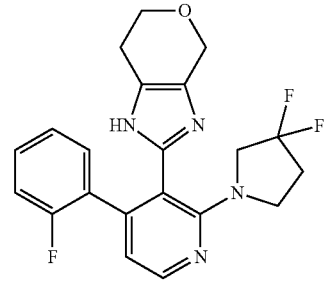 [SMILES: Fc1ccccc1-c1ccnc(N2CCC(F)(F)C2)c1-c1nc2c([nH]1)CCOC2]

To a solution of 2-[2-(3,3-difluoropyrrolidin-1-yl)-4-iodo-3-pyridyl]-1,4,6,7-tetrahydropyrano[3,4-d]imidazole (0.0500 g, 0.110 mmol), (2-fluorophenyl)boronic acid (0.0320 g, 0.217 mmol), and potassium carbonate (0.0380 g, 0.275 mmol) in 1,4-dioxane (1.30 mL) and water (0.420 mL) was added [1,1'-bis(diphenylphosphino)ferrocene]dichloropalladium(II) complex with dichloromethane (0.0270 g, 0.0331 mmol) at 22° C. The mixture was stirred at 100° C. for 4.5 h. After cooling to ambient temperature, the mixture was diluted with ethyl acetate (10 mL). The mixture was filtered through diatomaceous earth (i.e. Celite®) washing with ethyl acetate (30 mL), and concentrated in vacuo. Purification of the residue by column chromatography, eluting with a gradient of 0-10% of methanol in dichloromethane, followed by preparative reverse phase HPLC eluting with a gradient of 29-39% acetonitrile in water containing 10 mM of ammonium formate, and reversed phase chromatography, eluting with a gradient of 5-100% acetonitrile in water containing 10 mM of ammonium bicarbonate, afforded the title compound as a solid (0.00700 g, 16% yield): $^1$H NMR (400 MHz; DMSO-$d_6$) δ 11.74 (s, 0.7H), 11.62 (s, 0.3H), 8.19 (d, J=5.0 Hz, 1H), 7.29-7.21 (m, 1H), 7.15-7.06 (m, 1H), 7.05-6.93 (m, 2H), 6.69 (dd, J=5.0, 1.3 Hz, 1H), 4.39-4.32 (m, 2H), 3.73-3.69 (m, 2H), 3.3-3.19 (m, 5H), 2.40-2.24 (m, 3H); MS (ES+) m/z 401.3 (M+1).

Example 73

Synthesis of 2-[4-(2,5-difluorophenyl)-2-(3,3-difluoropyrrolidin-1-yl)-3-pyridyl]-1,4,6,7-tetrahydropyrano[3,4-d]imidazole

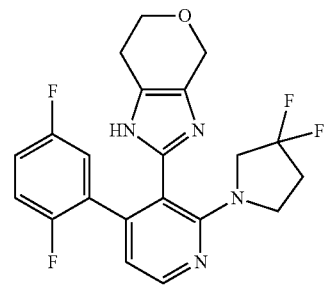 [SMILES: Fc1ccc(F)c(-c2ccnc(N3CCC(F)(F)C3)c2-c2nc3c([nH]2)CCOC3)c1]

To a solution of 2-[2-(3,3-difluoropyrrolidin-1-yl)-4-iodo-3-pyridyl]-1,4,6,7-tetrahydropyrano[3,4-d]imidazole (0.0500 g, 0.110 mmol), (2,5-difluorophenyl)boronic acid (0.0370 mg, 0.223 mmol), and potassium carbonate (0.0380 g, 0.275 mmol) in 1,4-dioxane (1.50 mL) and water (0.500 mL) was added [1,1'-bis(diphenylphosphino)ferrocene]dichloropalladium(II) complex with dichloromethane (0.0270 mg, 0.0331 mmol), and the mixture was stirred at 100° C. for 4.5 h. After cooling to ambient temperature, the mixture was diluted with ethyl acetate (10 mL). The mixture was filtered through diatomaceous earth (i.e. Celite®) washing with ethyl acetate (20 mL) and concentrated in vacuo. Purification of the residue by column chromatography, eluting with a gradient of 0-10% of methanol in dichloromethane, followed by preparative reverse phase HPLC eluting with a gradient of 32-42% acetonitrile in water containing 10 mM of ammonium formate, afforded the title compound as a colorless solid (0.0100 g, 21% yield): $^1$H NMR (400 MHz, DMSO-$d_6$) δ 11.86 (s, 0.7H), 11.73 (s, 0.3H), 8.27 (d, J=5.0 Hz, 1H), 7.30-7.07 (m, 2H), 6.89-6.80 (m, 1H), 6.77 (dd, J=5.0, 1.3 Hz, 1H), 4.47 (s, 0.6H), 4.39 (s, 1.2H), 3.77 (t, J=5.6 Hz, 2H), 3.37 (t, J=13.6 Hz, 2H), 3.28 (t, J=7.3 Hz, 2H), 2.55-2.44 (m, 2H), 2.43-2.26 (m, 2H); MS (ES+) m/z 419.3 (M+1).

Example 74

Synthesis of 2-[2-(3,3-difluoropyrrolidin-1-yl)-4-(1H-indazol-5-yl)-3-pyridyl]-1,4,6,7-tetrahydropyrano[3,4-d]imidazole

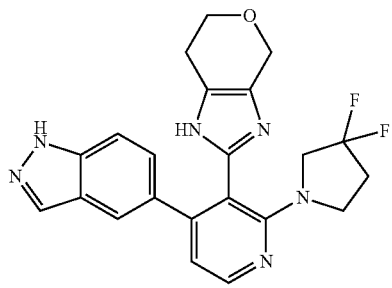 [SMILES: FC1(F)CCN(c2nccc(-c3ccc4[nH]ncc4c3)c2-c2nc3c([nH]2)CCOC3)C1]

To a solution of 2-[2-(3,3-difluoropyrrolidin-1-yl)-4-iodo-3-pyridyl]-1,4,6,7-tetrahydropyrano[3,4-d]imidazole (0.0500 g, 0.110 mmol), 1H-indazol-5-ylboronic acid (0.038 g, 0.223 mmol), and potassium carbonate (0.0380 g, 0.275 mmol) in 1,4-dioxane (1.500 mL) and water (0.500 mL) was added [1,1'-bis(diphenylphosphino)ferrocene]dichloropalladium(II) complex with dichloromethane (0.0270 mg, 0.0331 mmol), and the mixture was stirred at 100° C. for 4.5 h. After cooling to ambient temperature, the mixture was diluted with ethyl acetate (10 mL). The mixture was filtered through diatomaceous earth (i.e. Celite®) washing with ethyl acetate (30 mL) and concentrated in vacuo. Purification of the residue by column chromatography, eluting with a gradient of 0-10% of methanol in dichloromethane, followed by preparative reversed phase HPLC, eluting with a gradient of 21-31% acetonitrile in water containing 10 mM of ammonium formate, afforded the title compound as a solid (0.0120 g, 26% yield): $^1$H NMR (400 MHz; DMSO-$d_6$) δ 13.02 (s, 0.7H), 11.66 (s, 0.3H), 8.36 (s, 1H), 8.19 (d, J=5.1 Hz, 1H), 7.99 (s, 1H), 7.59-7.46 (m, 1H), 7.32 (d, J=8.7 Hz, 1H), 7.02 (dd, J=8.7, 1.6 Hz, 1H), 6.77 (d, J=5.1 Hz, 1H), 4.39 (s, 2H), 3.71 (s, 2H), 3.33-3.23 (m, 4H), 2.49-2.38 (m, 2H), 2.37-2.15 (m, 2H); MS (ES+) m/z 423.3 (M+1).

Example 75

Synthesis of 2-[2-(3,3-difluoropyrrolidin-1-yl)-4-(3-fluorophenyl)-3-pyridyl]-1,4,6,7-tetrahydropyrano[3,4-d]imidazole

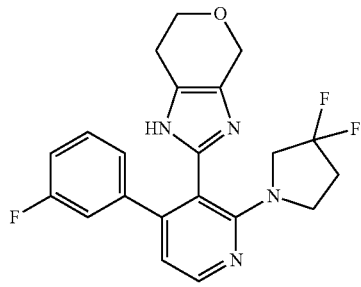 [SMILES: Fc1cccc(-c2ccnc(N3CCC(F)(F)C3)c2-c2nc3c([nH]2)CCOC3)c1]

To a solution of 2-[2-(3,3-difluoropyrrolidin-1-yl)-4-iodo-3-pyridyl]-1,4,6,7-tetrahydropyrano[3,4-d]imidazole (0.0500 g, 0.110 mmol), (3-fluorophenyl)boronic acid (0.0320 g, 0.217 mmol), and potassium carbonate (0.0380 g, 0.275 mmol) in 1,4-dioxane (1.50 mL) and water (0.500 mL) was added [1,1'-bis(diphenylphosphino)ferrocene]dichloropalladium(II) complex with dichloromethane (0.0270 mg, 0.0331 mmol), and the mixture was stirred at 100° C. for 1 h. After cooling to ambient temperature, the mixture was diluted with ethyl acetate (10 mL). The mixture was filtered through diatomaceous earth (i.e. Celite®) washing with ethyl acetate (30 mL) and methanol (20 mL), and concentrated in vacuo. Purification of the residue by column chromatography, eluting with a gradient of 0-10% of methanol in dichloromethane, followed by preparative reversed phase HPLC, eluting with a gradient of 38-48% acetonitrile in water containing 10 mM of ammonium carbonate, afforded the title compound as a solid (0.0130 g, 30% yield): $^1$H NMR (400 MHz; DMSO-$d_6$) δ 11.74 (s, 0.7H), 11.61 (s, 0.3H), 8.22 (d, J=5.1 Hz, 1H), 7.26 (dd, J=14.2, 8.0 Hz, 1H), 7.06 (dd, J=9.0, 6.5 Hz, 1H), 6.98-6.80 (m, 2H), 6.74 (d, J=5.1 Hz, 1H), 4.41 (s, 2H), 3.83-3.68 (m, 2H), 3.35-3.22 (m, 4H), 2.47 (d, J=8.3 Hz, 2H), 2.39-2.21 (m, 2H); MS (ES+) m/z 401.3 (M+1).

Example 76

Synthesis of 2-[2-(3,3-difluoropyrrolidin-1-yl)-4-(2-pyridyl)-3-pyridyl]-1,4,6,7-tetrahydropyrano[3,4-d]imidazole

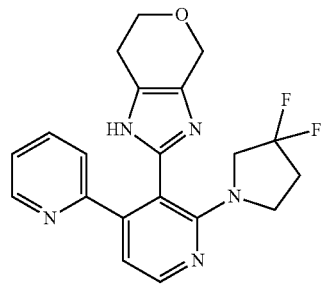 [SMILES: FC1(F)CCN(c2nccc(-c3ccccn3)c2-c2nc3c([nH]2)CCOC3)C1]

To a solution of 2-[2-(3,3-difluoropyrrolidin-1-yl)-4-iodo-3-pyridyl]-1,4,6,7-tetrahydropyrano[3,4-d]imidazole (0.150 g, 0.330 mmol), 2-(1,1,1-tributylstannyl)pyridine (0.150 mL, 0.396 mmol), and 2-dicyclohexylphosphino-2',4',6'-triisopropylbiphenyl (0.0860 g, 0.198 mmol) in 1,4-dioxane (3.40 mL) was added palladium acetate (0.0220 mg, 0.00980 mmol), and the mixture was stirred at 100° C. for 18 h. After cooling to ambient temperature, the mixture was diluted with ethyl acetate (10 mL). The mixture was filtered through diatomaceous earth (i.e. Celite®) washing with ethyl acetate (20 mL), and concentrated in vacuo. Purification of the residue by column chromatography, eluting with a gradient of 0-10% of methanol in dichloromethane, followed by preparative reversed phase HPLC, eluting with a gradient of 13-22% acetonitrile in water containing 10 mM of ammonium formate, and by reversed phase chromatography, eluting with a gradient of 5 to 100% acetonitrile in water containing 10 mM of ammonium carbonate, afforded the title compound as a solid (0.00300 g, 2% yield): $^1$H NMR (400 MHz; DMSO-d$_6$) δ 11.83 (s, 0.7H), 11.71 (s, 0.3H), 8.53 (d, J=4.1 Hz, 1H), 8.25 (d, J=5.1 Hz, 1H), 7.57 (td, J=7.6, 1.7 Hz, 1H), 7.34-7.12 (m, 1H), 6.93 (d, J=5.0 Hz, 1H), 6.89-6.85 (m, 1H), 4.55-4.30 (m, 2H), 3.86-3.66 (m, 2H), 3.36-3.23 (m, 4H), 2.50 (t, J=5.3 Hz, 2H), 2.37-2.21 (m, 2H); MS (ES+) m/z 384.2 (M+1).

Example 77

Synthesis of 2-[4-(2,3-difluorophenyl)-2-(3,3-difluoropyrrolidin-1-yl)-3-pyridyl]-1,4,6,7-tetrahydropyrano[3,4-d]imidazole

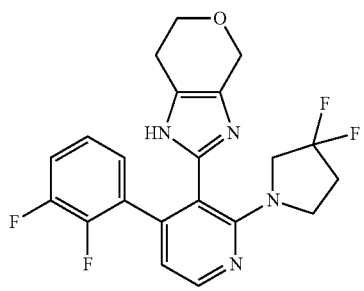 [SMILES: Fc1cccc(-c2ccnc(N3CCC(F)(F)C3)c2-c2nc3c([nH]2)CCOC3)c1F]

To a solution of 2-[2-(3,3-difluoropyrrolidin-1-yl)-4-iodo-3-pyridyl]-1,4,6,7-tetrahydropyrano[3,4-d]imidazole (0.05000 g, 0.110 mmol), (2,3-difluorophenyl)boronic acid (0.0370 g, 0.223 mmol), and potassium carbonate (0.0380 g, 0.275 mmol) in 1,4-dioxane (1.20 mL) and water (0.400 mL) was added [1,1'-bis(diphenylphosphino)ferrocene]dichloropalladium(II) complex with dichloromethane (0.0270 mg, 0.0331 mmol), and the mixture was stirred at 70° C. for 50 minutes. After cooling to ambient temperature, the mixture was diluted with ethyl acetate (10 mL). The mixture was filtered through diatomaceous earth (i.e. Celite®) washing with ethyl acetate (30 mL) and methanol (20 mL), and concentrated in vacuo. Purification of the residue by column chromatography, eluting with a gradient of 0-10% of methanol in dichloromethane, followed by preparative reverse phase HPLC, eluting with a gradient of 35-45% acetonitrile in water containing 10 mM of ammonium formate, afforded the title compound as a solid (0.015 g, 33% yield): $^1$H NMR (400 MHz; DMSO-d$_6$) δ 11.79 (s, 0.7H), 11.66 (s, 0.3H), 8.23 (d, J=5.0 Hz, 1H), 7.31-7.25 (d, 1H), 7.04-6.99 (m, 1H), 6.76-6.73 (m, 2H), 4.47-4.28 (m, 2H), 3.76-3.67 (m, 2H), 3.38-3.27 (m, 2H), 3.25-3.20 (m, 2H), 2.53-2.38 (m, 2H), 2.38-2.23 (m, 2H); MS (ES+) m/z 419.2 (M+1).

Example 78

Synthesis of 2-[2-(3,3-difluoropyrrolidin-1-yl)-4-(2-fluorophenyl)-3-pyridyl]-1H-imidazo[4,5-c]pyridine

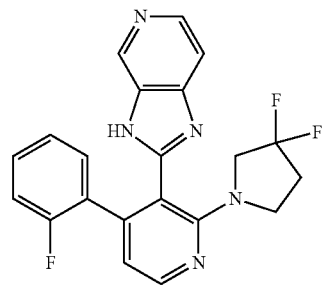 [SMILES: Fc1ccccc1-c1ccnc(N2CCC(F)(F)C2)c1-c1nc2ccncc2[nH]1]

Step 1. Preparation of 2-[[2-[2-(3,3-difluoropyrrolidin-1-yl)-4-(2-fluorophenyl)-3-pyridyl]imidazo[4,5-c]pyridin-1-yl]methoxy]ethyl-trimethyl-silane

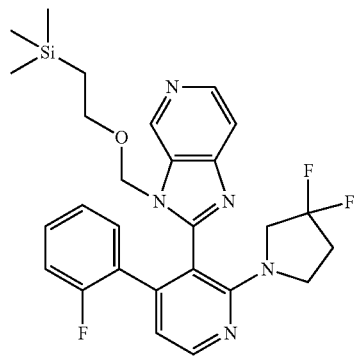 [SMILES: C[Si](C)(C)CCOCn1c(-c2c(-c3ccccc3F)ccnc2N2CCC(F)(F)C2)nc2ccncc21]

To a solution of 2-[[6-chloro-2-[2-(3,3-difluoropyrrolidin-1-yl)-4-(2-fluorophenyl)-3-pyridyl]imidazo[4,5-c]pyridin-3-yl]methoxy]ethyl-trimethyl-silane (0.150 g, 0.254 mmol) and palladium (10% on carbon matrix, 0.271 g, 0.254 mmol) in methanol (5.00 mL) was added ammonium formate (0.642 g, 10.2 mmol), and the mixture was stirred at 80° C. for 24 h. After cooling to ambient temperature, the mixture was diluted with saturated aqueous sodium bicarbonate solution (40 mL). The aqueous phase was extracted with ethyl acetate (3×40 mL), and the organic phase was washed with brine (40 mL), dried over anhydrous sodium sulfate, and filtered. Concentration in vacuo afforded the title compound as a brown solid (0.121 g, 86% yield): $^1$H NMR (400 MHz; CDCl$_3$) δ 9.04 (d, J=0.9 Hz, 1H), 8.43 (d, J=5.6 Hz, 1H), 8.39 (d, J=5.0 Hz, 1H), 7.31 (dd, J=5.6, 0.9 Hz, 1H), 7.18-7.12 (m, 1H), 7.04 (td, J=7.7, 1.8 Hz, 1H), 6.97-6.92 (m, 1H), 6.88-6.84 (m, 1H), 6.82 (dd, J=5.0, 1.3 Hz, 1H), 5.12 (d, J=10.3 Hz, 1H), 4.99 (d, J=10.3 Hz, 1H), 3.55-3.34 (m, 6H), 2.28-2.16 (m, 2H), 0.85 (dd, J=17.9, 9.4 Hz, 2H), −0.05 (s, 9H); MS (ES+) m/z 525.8 (M).

Step 2. Preparation of 2-[2-(3,3-difluoropyrrolidin-1-yl)-4-(2-fluorophenyl)-3-pyridyl]-1H-imidazo[4,5-c]pyridine

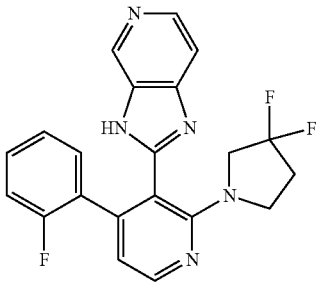 [SMILES: Fc1ccccc1-c1ccnc(N2CCC(F)(F)C2)c1-c1nc2ccncc2[nH]1]

To a solution of 2-[[2-[2-(3,3-difluoropyrrolidin-1-yl)-4-(2-fluorophenyl)-3-pyridyl]imidazo[4,5-c]pyridin-3-yl]methoxy]ethyl-trimethyl-silane (0.120 g, 0.217 mmol) in dichloromethane (2.0 mL) was added trifluoroacetic acid (2.00 mL, 26.9 mmol), and the mixture was stirred at 22° C. for 20 h. The mixture was diluted with saturated aqueous sodium bicarbonate solution (40 mL). The aqueous phase was extracted with ethyl acetate (3×40 mL), and the organic phase was washed with brine (40 mL), dried over anhydrous sodium sulfate, filtered and concentrated in vacuo. Purification of the residue by column chromatography, eluting with a gradient of 0-15% of methanol in dichloromethane, followed by preparative reversed phase HPLC, eluting with a gradient of 30-40% acetonitrile in water containing 10 mM of ammonium bicarbonate, afforded the title compound as a colorless solid (0.0590 g, 65% yield): $^1$H NMR (400 MHz; DMSO-$d_6$) δ 12.97 (s, 1H), 8.81 (s, 1H), 8.37 (d, J=5.0 Hz, 1H), 8.23 (d, J=5.5 Hz, 1H), 7.44 (s, 1H), 7.22 (dddd, J=8.3, 7.2, 5.4, 1.9 Hz, 1H), 7.08 (ddd, J=11.8, 6.4, 2.2 Hz, 1H), 7.03 (dt, J=7.6, 3.8 Hz, 1H), 6.95 (td, J=7.5, 1.1 Hz, 1H), 6.84 (dd, J=5.0, 0.9 Hz, 1H), 3.43 (t, J=13.2 Hz, 2H), 3.18 (t, J=7.3 Hz, 2H), 2.37-2.23 (m, 2H); MS (ES+) m/z 396.2 (M+1).

Example 79

Synthesis of 2-[2-(3,3-difluoropyrrolidin-1-yl)-4-(2-fluorophenyl)-3-pyridyl]-6-methyl-3H-imidazo[4,5-c]pyridine

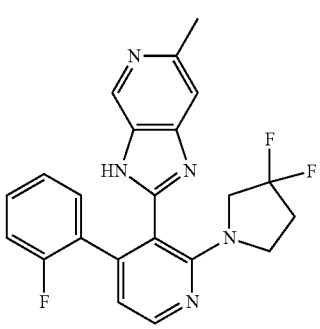 [SMILES: Cc1cc2nc(-c3c(-c4ccccc4F)ccnc3N3CCC(F)(F)C3)[nH]c2cn1]

Step 1. 2-[[2-[2-(3,3-difluoropyrrolidin-1-yl)-4-(2-fluorophenyl)-3-pyridyl]-6-methyl-imidazo[4,5-c]pyridin-3-yl]methoxy]ethyl-trimethyl-silane

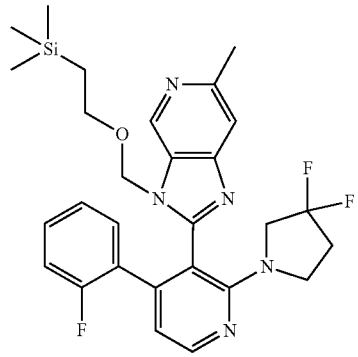 [SMILES: Cc1cc2nc(-c3c(-c4ccccc4F)ccnc3N3CCC(F)(F)C3)n(COCC[Si](C)(C)C)c2cn1]

To a solution of 2-[[6-chloro-2-[2-(3,3-difluoropyrrolidin-1-yl)-4-(2-fluorophenyl)-3-pyridyl]imidazo[4,5-c]pyridin-3-yl]methoxy]ethyl-trimethyl-silane (0.200 g, 0.304 mmol), methylboronic acid (0.0545 g, 0.911 mmol), and potassium carbonate (0.105 g, 0.759 mmol) in 1,4-dioxane (3.06 mL) and water (0.611 mL) was added [1,1'-bis(diphenylphosphino)ferrocene]dichloropalladium(II) complex with dichloromethane (0.0744 g, 0.0911 mmol), and the mixture was stirred at 100° C. for 20 h. After cooling to ambient temperature, the mixture was diluted with ethyl acetate (10 mL). The mixture was filtered through a bed of diatomaceous earth (i.e. Celite®). The solid was washed with ethyl acetate (50 mL), and the filtrate was concentrated in vacuo. Purification of the residue by column chromatography, eluting with a gradient of 0-100% of ethyl acetate in hexanes, afforded the title compound as a black solid (0.00680 g, 37% yield): $^1$H NMR (400 MHz; CDCl$_3$) δ 8.91 (d, J=1.0 Hz, 1H), 8.38 (d, J=5.0 Hz, 1H), 7.19-7.13 (m, 1H), 7.13-7.12 (m, 1H), 7.05 (td, J=7.7, 1.8 Hz, 1H), 6.98-6.92 (m, 1H), 6.87 (td, J=7.5, 1.1 Hz, 1H), 6.81-6.80 (m, 1H), 5.07 (d, J=10.3 Hz, 1H), 4.95 (d, J=10.3 Hz, 1H), 3.56-3.40 (m, 6H), 2.65 (s, 2H), 2.29-2.14 (m, 2H), 0.87-0.80 (m, 2H), −0.05 (s, 9H); MS (ES+) m/z 541.3 (M+1).

Step 2. Preparation of 2-[2-(3,3-difluoropyrrolidin-1-yl)-4-(2-fluorophenyl)-3-pyridyl]-6-methyl-3H-imidazo[4,5-c]pyridine

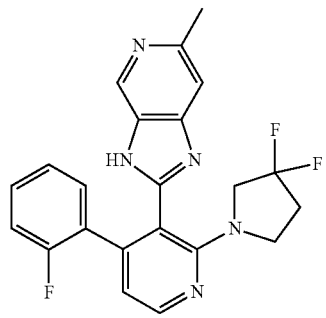 [SMILES: Cc1cc2nc(-c3c(-c4ccccc4F)ccnc3N3CCC(F)(F)C3)[nH]c2cn1]

To a solution of 2-[[2-[2-(3,3-difluoropyrrolidin-1-yl)-4-(2-fluorophenyl)-3-pyridyl]-6-methyl-imidazo[4,5-c]pyridin-3-yl]methoxy]ethyl-trimethyl-silane (0.0630 g, 0.111 mmol) in dichloromethane (1.00 mL) was added trifluoroacetic acid (1.00 mL, 13.5 mmol), and the mixture was stirred at 22° C. for 20 h. The mixture was diluted with saturated aqueous sodium bicarbonate solution (40 mL). The aqueous phase was extracted with ethyl acetate (3×40 mL), and the organic phase was washed with brine (40 mL), dried over anhydrous sodium sulfate, filtered and concentrated in vacuo. Purification of the residue by column chromatography, eluting with a gradient of 0-15% of methanol in dichloromethane, followed by preparative reversed phase HPLC, eluting with a gradient of 33-43% acetonitrile in water containing 10 mM of ammonium bicarbonate, afforded the title compound as a colorless solid (0.0210 g, 45% yield): $^1$H NMR (400 MHz; DMSO-$d_6$) δ 12.79 (s, 1H), 8.68 (s, 1H), 8.36 (d, J=5.0 Hz, 1H), 7.22 (dddd, J=8.3, 7.2, 5.3, 1.9 Hz, 2H), 7.12-7.06 (m, 1H), 7.03 (td, J=7.6, 1.8 Hz, 1H), 6.95 (td, J=7.5, 1.0 Hz, 1H), 6.83 (dd, J=5.0, 0.9 Hz, 1H), 3.43 (t, J=13.3 Hz, 2H), 3.19 (t, J=7.3 Hz, 2H), 2.49 (s, 3H), 2.30 (tt, J=14.7, 7.5 Hz, 2H); MS (ES+) m/z 410.2 (M+1).

Example 80

Synthesis of 5-[2-(3,3-difluoropyrrolidin-1-yl)-4-(2-fluorophenyl)-3-pyridyl]-2-methyl-4H-imidazo[4,5-c]pyrazole

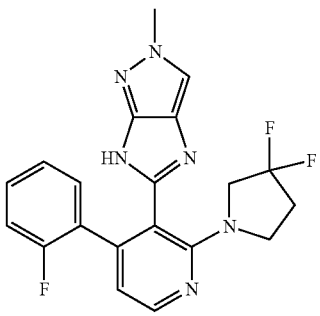 [SMILES: Cn1cc2nc(-c3c(-c4ccccc4F)ccnc3N3CCC(F)(F)C3)[nH]c2n1]

Step 1. Preparation of 2-(3,3-difluoropyrrolidin-1-yl)-4-(2-fluorophenyl)pyridine-3-carbaldehyde

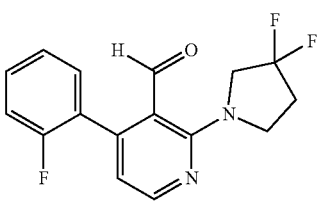 [SMILES: O=Cc1c(-c2ccccc2F)ccnc1N1CCC(F)(F)C1]

To a solution of 2-(3,3-difluoropyrrolidin-1-yl)-4-iodopyridine-3-carbaldehyde (1.58 g, 4.44 mmol), (2-fluorophenyl)boronic acid (1.27 g, 8.88 mmol), and potassium carbonate (1.53 g, 11.1 mmol) in degassed 1,4-dioxane (40.0 mL) and water (8.00 mL) was added [1,1'-bis(diphenylphosphino)ferrocene]dichloropalladium(II), complex with dichloromethane (1.09 g, 1.33 mmol), and the mixture was stirred at 95° C. for 1 h. After cooling to ambient temperature, the mixture was concentrated in vacuo. The residue was diluted with saturated aqueous sodium bicarbonate solution (200 mL), and the aqueous phase was extracted with ethyl acetate (3×200 mL). The organic phase was washed with brine (200 mL), dried over anhydrous sodium sulfate, filtered and concentrated in vacuo. Purification of the residue by column chromatography, eluting with a gradient of 0-100% of ethyl acetate in hexanes, afforded the title compound as a brown solid (1.31 g, 96% yield): $^1$H NMR (400 MHz; CDCl$_3$) δ 9.82 (d, J=2.4 Hz, 1H), 8.37 (d, J=4.7 Hz, 1H), 7.46 (dddd, J=8.3, 7.2, 5.2, 1.9 Hz, 1H), 7.36 (td, J=7.4, 1.8 Hz, 1H), 7.27 (td, J=7.5, 1.1 Hz, 1H), 7.18 (ddd, J=9.5, 8.3, 1.0 Hz, 1H), 6.70 (d, J=4.8 Hz, 1H), 3.95-3.53 (m, 4H), 2.53-2.39 (m, 2H); MS (ES+) m/z 307.2 (M+1).

Step 2. Preparation of 5-[2-(3,3-difluoropyrrolidin-1-yl)-4-(2-fluorophenyl)-3-pyridyl]-2-methyl-4H-imidazo[4,5-c]pyrazole

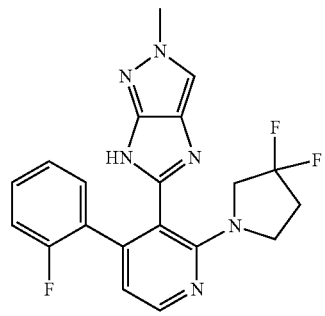 [SMILES: Cn1cc2nc(-c3c(-c4ccccc4F)ccnc3N3CCC(F)(F)C3)[nH]c2n1]

To a solution of 2-(3,3-difluoropyrrolidin-1-yl)-4-iodopyridine-3-carbaldehyde (0.250 g, 0.735 mmol) and 1-methylpyrazole-3,4-diamine dihydrochloride (0.272 mg, 1.47 mmol) in ethanol (7.50 mL) was added iron(Ill)chloride (0.0953 mg, 0.588 mmol), and the mixture was stirred at 22° C. for 30 minutes. The mixture was diluted with saturated aqueous sodium bicarbonate solution (70 mL). The aqueous phase was extracted with ethyl acetate (3×70 mL), and the organic phase was washed brine (70 mL), dried over anhydrous sodium sulfate, filtered and concentrated in vacuo. The residue was diluted with dichloromethane (7.50 mL). To the mixture was added N-iodosuccinimide (0.182 g, 0.808 mmol), and the mixture was stirred at 22° C. for 1 h. The mixture was diluted with saturated aqueous sodium bicarbonate solution (70 mL). The aqueous phase was extracted with dichloromethane (3×80 mL), and the organic phase was dried over anhydrous sodium sulfate, filtered, and concentrated in vacuo. Purification of the residue by column chromatography, eluting with a gradient of 0-15% of methanol in dichloromethane, followed by preparative reverse phase chromatography, eluting with a gradient of 32-42% of acetonitrile in water containing 10 mM of ammonium formate, and by reversed phase chromatography, eluting with a gradient of 5-100% of acetonitrile in water containing 10 mM of ammonium bicarbonate, afforded the title compound as a yellow solid (0.0230 g, 7%): $^1$H NMR (400 MHz; DMSO-$d_6$) δ 11.92 (s, 0.3H), 11.68 (s, 0.7H), 8.31 (d, J=5.0 Hz, 0.7H), 8.30 (d, J=5.0 Hz, 0.3H), 7.61 (s, 0.3H), 7.48 (s, 0.7H), 7.25 (dd, J=13.6, 5.6 Hz, 1H), 7.15-7.04 (m, 2H), 6.99 (t, J=7.4 Hz, 1H), 6.77 (d, J=5.0 Hz, 1H), 3.88 (s, 2H), 3.86 (s, 1H), 3.44 (t, J=13.4 Hz, 2H), 3.34-3.27 (m, 2H), 2.39-2.25 (m, 2H); MS (ES+) m/z 399.2 (M+1).

Biological Example 1

As disclosed above, typical assays for testing compounds of the disclosure are known, for example as disclosed in Crestey, F. et al., *ACS Chem Neurosci* (2015), Vol. 6, pp. 1302-1308, AA43279 (Frederiksen, K. et al., *Eur J Neurosci* (2017), Vol. 46, pp. 1887-1896) and Lu AE98134 (von Schoubyea, N. L. et al., *Neurosci Lett* (2018), Vol. 662, pp. 29-35) which employs the use of automated planar patch clamp techniques to study the effects of the chemical agent on the gating of sodium channels. The sodium channel isoforms of interest are stably expressed in Human Embryonic Kidney Cells and the currents that flow through those channels in response to a depolarizing voltage clamp step from −120 mV to 0 mV are measured in the presence of increasing concentrations of the chemical agents. The area under the sodium current trace which correlates to the magnitude of sodium flux through the cell membrane is used to quantify the effects on gating of the channels. Other parameters that are measured in the assay include the peak current, time constant of open state inactivation and the voltage dependence of steady state inactivation properties. The concentration responses are used to determine potency of each chemical agents effects on modulating the sodium channel isoform gating.

Each of the aforementioned references are hereby incorporated by reference in their entirety.

TABLE 2

Biological activity of representative compounds of formula (I)

| Example No. | $EC_{50}$ | Empirical $E_{max}$ |
|---|---|---|
| 1 | ++++ | ++++ |
| 2 | +++ | ++++ |
| 3 | +++ | ++++ |
| 4 | + | +++ |
| 5 | +++ | + |
| 6 | +++ | ++ |
| 7 | +++ | ++ |
| 8 | ++ | +++ |
| 9 | + | ++ |
| 10 | ++ | ++ |
| 11 | +++ | ++++ |
| 12 | ++ | ++ |
| 13 | + | + |
| 14 | +++ | ++ |
| 15 | ++ | ++++ |
| 16 | +++ | +++ |
| 17 | +++ | ++++ |
| 18 | +++ | ++++ |
| 19 | ++ | ++ |
| 20 | ++ | ++ |
| 21 | − | − |
| 22 | − | − |
| 23 | +++ | ++ |
| 24 | +++ | + |
| 25 | +++ | + |
| 26 | +++ | + |
| 27 | +++ | ++ |
| 28 | ++ | ++ |
| 29 | ++++ | ++ |
| 30 | +++ | + |
| 31 | +++ | +++ |
| 32 | ++++ | + |
| 33 | ++ | ++ |
| 34 | +++ | +++ |
| 35 | + | + |
| 36 | ++ | + |
| 37 | ++ | ++ |
| 38 | + | + |
| 39 | ++ | ++ |
| 40 | +++ | +++ |
| 41 | + | + |
| 42 | ++++ | ++ |
| 43 | ++++ | +++ |
| 44 | +++ | +++ |
| 45 | ++++ | +++ |
| 46 | +++ | +++ |
| 47 | +++ | +++ |
| 48 | +++ | +++ |
| 49 | ++ | ++ |
| 50 | ++ | ++ |
| 51 | ++++ | + |
| 52 | ++++ | +++ |
| 53 | +++ | ++ |
| 54 | +++ | +++ |
| 55 | ++++ | +++ |
| 56 | +++ | ++++ |
| 57 | ++++ | ++++ |
| 58 | +++ | ++ |
| 59 | ++++ | ++ |
| 60 | ++++ | ++ |
| 61 | +++ | ++ |
| 62 | +++ | + |
| 63 | +++ | ++ |
| 64 | ++ | + |
| 65 | + | ++ |
| 66 | +++ | +++ |
| 67 | + | + |
| 68 | + | + |
| 69 | +++ | ++ |
| 70 | − | − |
| 71 | − | − |
| 72 | ++++ | ++++ |
| 73 | ++++ | +++ |
| 74 | +++ | ++++ |
| 75 | ++++ | ++++ |
| 76 | ++ | +++ |
| 77 | ++++ | ++++ |
| 78 | ++++ | ++++ |
| 79 | ++++ | ++++ |
| 80 | +++ | +++ |

For $EC_{50}$ values:
++++ indicates a value less than 1 μM
+++ indicates a value from 1 up to 10 μM
++ indicates a value from 10 up to 50 μM
+ indicates a value of 50 μM or more For Empirical $E_{max}$ values:
++++ indicates a value greater than 7.5
+++ indicates a value from 5.0 up to 7.5 μM
++ indicates a value from 2.0 up to 5.0 μM
+ indicates a value less than 2.0 μM All of the U.S. patents, U.S. patent application publications, U.S. patent applications, foreign patents, foreign patent applications and non-patent publications referred to in this specification are incorporated herein by reference in their entireties.

Although the foregoing disclosure has been described in some detail to facilitate understanding, it will be apparent that certain changes and modifications may be practiced within the scope of the appended claims. Accordingly, the described embodiments are to be considered as illustrative and not restrictive, and the disclosure is not to be limited to the details given herein, but may be modified within the scope and equivalents of the appended claims.

What is claimed is:
1. A compound of formula (I):

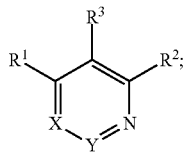

or a stereoisomer, enantiomer, tautomer, or mixture thereof, or a pharmaceutically acceptable salt or solvate of said compound, stereoisomer, enantiomer, tautomer, or mixture thereof;
wherein:
X is =C(R$^9$)— or =N—;
Y is =C(R$^9$)— or —N=; provided that X is not =N— when Y is —N= and Y is not —N= when X is =N—;
R$^1$ is selected from:

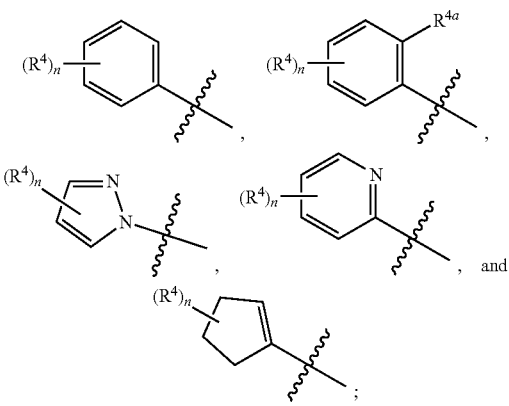

wherein:
each n is independently 1, 2 or 3;
each R$^4$ is independently hydrogen, halo, alkyl, haloalkyl, or —R$^{10}$—OR$^{11}$;
or two adjacent R$^4$'s, together with the carbons to which they are attached, form an optionally substituted N-heteroaryl; and
R$^{4a}$ is hydrogen;
R$^2$ is selected from —R$^{10}$—OR$^{11}$, —R$^{10}$—N(R$^{11}$)$_2$,

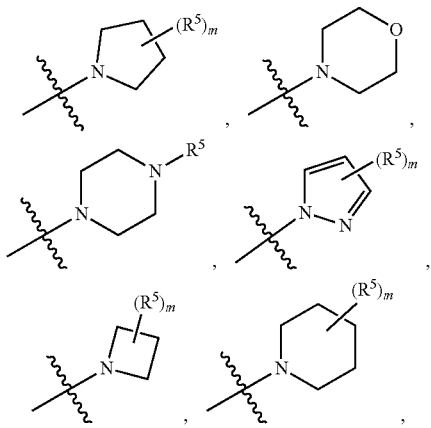

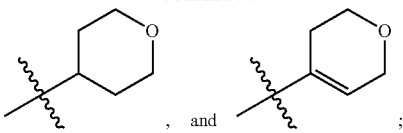

each m is independently 1 or 2;
each R$^5$ is independently hydrogen, halo, alkyl, haloalkyl or —R$^{10}$—CN;
or two R$^5$'s, together with the carbon to which they are both attached, form an optionally substituted O-heterocyclyl or an optionally substituted cycloalkyl;
R$^3$ is selected from:

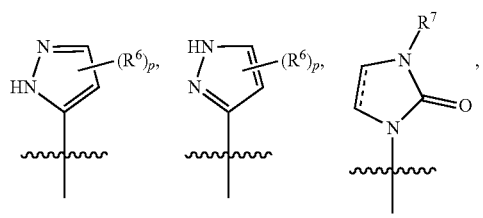

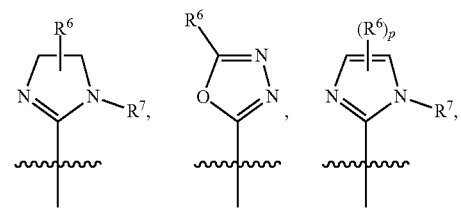

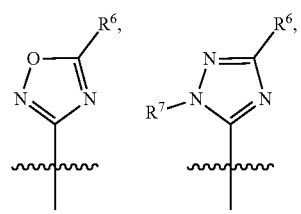

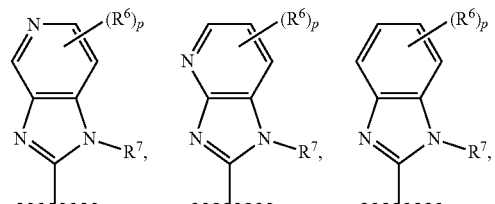

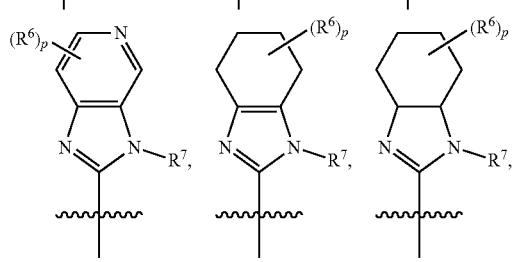

185

-continued

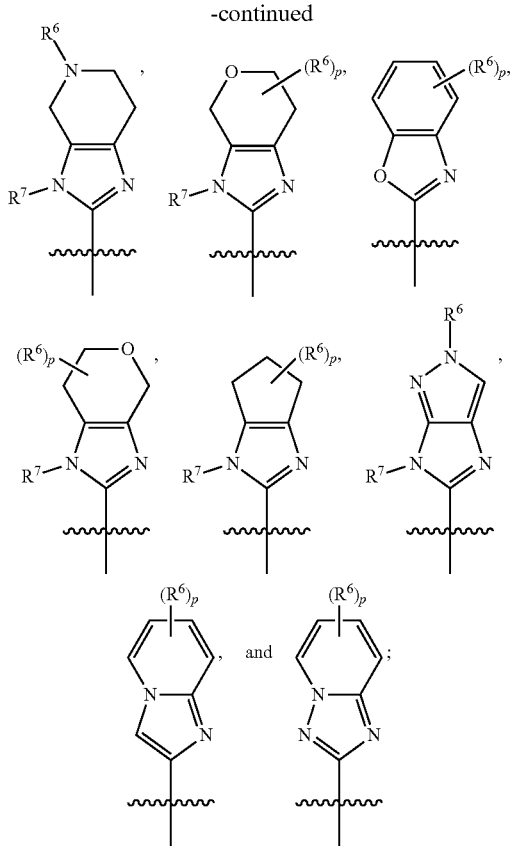

---- is a double or single bond;
each p is independently 1, 2, 3, or 4;
each R⁶ is independently hydrogen, halo, alkyl, haloalkyl, optionally substituted aryl, optionally substituted aralkyl, —R¹⁰—OR¹¹, —R¹⁰—C(O)OR¹², —R¹⁰—C(O)R¹², —R¹⁰—N(R¹¹)₂, an optionally substituted O-heterocyclyl or

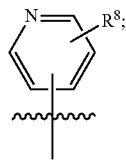

or two R⁶'s, together with the carbon to which they are both attached, form an optionally substituted cycloalkyl;
each R⁷ is independently hydrogen, alkyl, —R¹⁰—C(O)OR¹² or

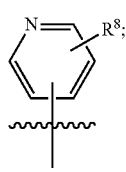

or the nitrogen to which R⁷ is attached together with the carbon to which R⁴ᵃ is attached form a bond; and

186 wherein when R³ is

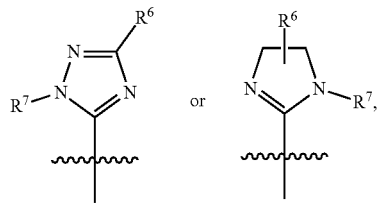

then at least one of R⁶ and R⁷ is not hydrogen;
each R⁸ is independently hydrogen, alkyl or halo;
each R⁹ is independently hydrogen or alkyl;
each R¹⁰ is independently a direct bond or an optionally substituted alkylene chain;
each R¹¹ is independently hydrogen, alkyl, haloalkyl, optionally substituted cycloakyl or optionally substituted cycloalkylalkyl; and
each R¹² is hydrogen, alkyl or optionally substituted aralkyl.

2. The compound of claim 1 wherein:
X is =C(R⁹)—;
Y is =C(R⁹)—;
R¹ is selected from:

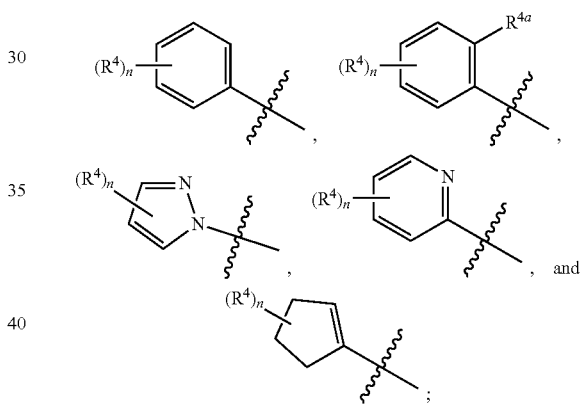

wherein:
each n is independently 1, 2 or 3;
each R⁴ is independently hydrogen, halo, alkyl, haloalkyl, or —R¹⁰—OR¹¹;
or two adjacent R⁴'s, together with the carbons to which they are attached, form an optionally substituted N-heteroaryl; and
R⁴ᵃ is hydrogen;
R² is selected from —R¹⁰—OR¹¹, —R¹⁰—N(R¹¹)₂,

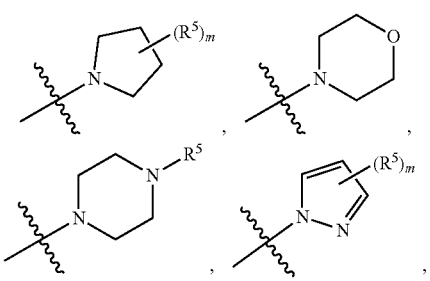

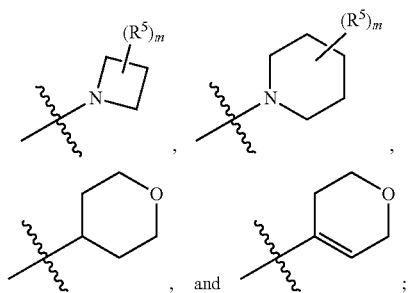

each m is independently 1 or 2;

each $R^5$ is independently hydrogen, halo, alkyl, haloalkyl or —$R^{10}$—CN;

or two $R^5$'s, together with the carbon to which they are both attached, form an optionally substituted O-heterocyclyl or $R^3$ is selected from:

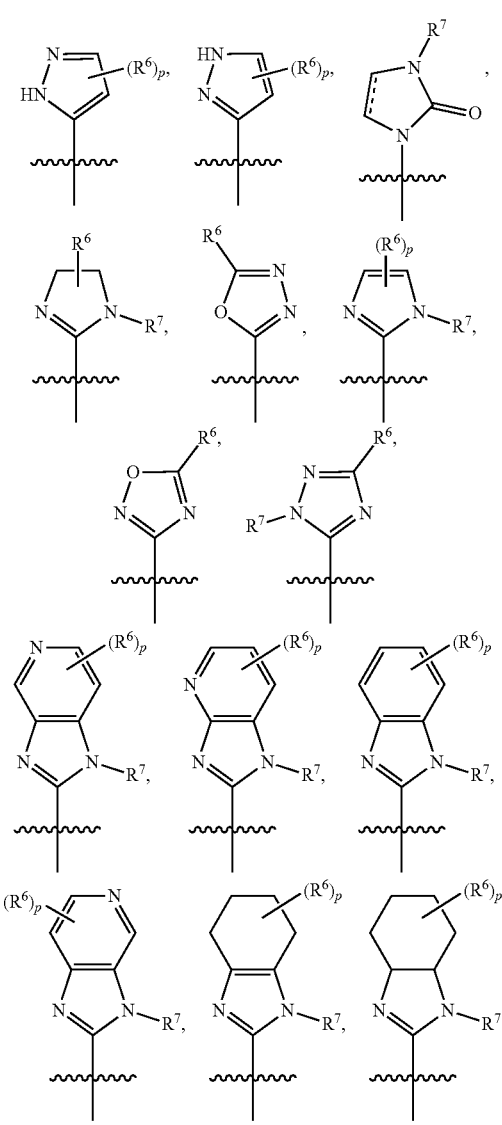

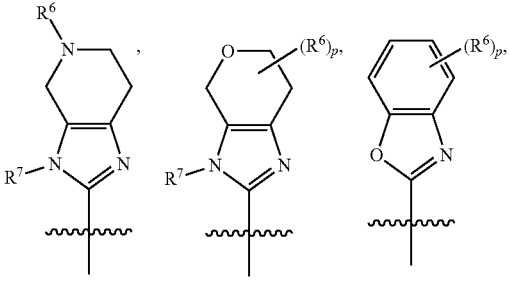

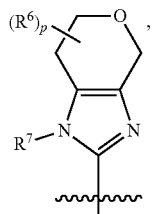

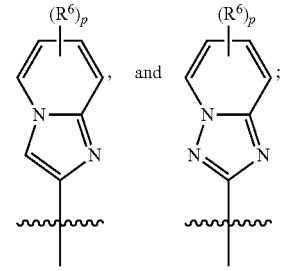

wherein:

=== is a double or single bond;

each p is independently 1, 2, 3, or 4;

each $R^6$ is independently hydrogen, halo, alkyl, haloalkyl, optionally substituted aryl, optionally substituted aralkyl, —$R^{10}$—$OR^{11}$, —$R^{10}$—$C(O)OR^{12}$, —$R^{10}$—$C(O)R^{12}$, —$R^{10}$—$N(R^{11})_2$, an optionally substituted O-heterocyclyl or

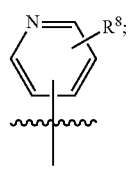

or two $R^6$'s, together with the carbon to which they are both attached, form an optionally substituted cycloalkyl;

each $R^7$ is independently hydrogen, alkyl, —$R^{10}$—C(O)$OR^{12}$ or

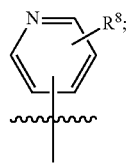

or the nitrogen to which $R^7$ is attached together with the carbon to which $R^{4a}$ is attached form a bond; and each R⁸ is independently hydrogen, alkyl or halo, each R⁹ is independently hydrogen or alkyl;

each R¹⁰ is independently a direct bond or an optionally substituted alkylene chain;

each R¹¹ is independently hydrogen, alkyl, haloalkyl, optionally substituted cycloakyl or optionally substituted cycloalkylalkyl; and each R¹² is hydrogen, alkyl or optionally substituted aralkyl;

or a stereoisomer, enantiomer, tautomer, or mixture thereof, or a pharmaceutically acceptable salt or solvate of said compound, stereoisomer, enantiomer, tautomer, or mixture thereof.

3. The compound of claim 2 wherein:

X is =C(R⁹)—;

Y is =C(R⁹)—;

R¹ is

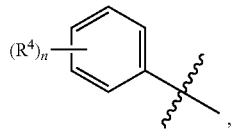

, wherein:

n is 1, 2 or 3; and each R⁴ is independently hydrogen, halo, alkyl, haloalkyl, or —R¹⁰—OR¹¹;

or two adjacent R⁴'s, together with the carbons to which they are attached, form an optionally substituted N-heteroaryl;

R² is selected from —R¹⁰—OR¹¹, —R¹⁰—N(R¹¹)₂,

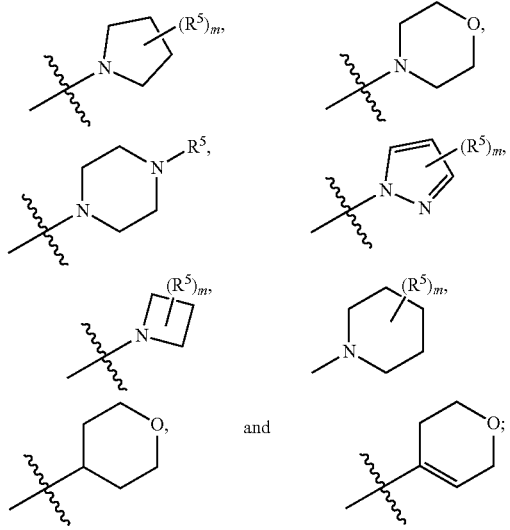

each m is independently 1 or 2;

each R⁵ is independently hydrogen, halo, alkyl, haloalkyl or —R¹⁰—CN;

or two R⁵'s, together with the carbon to which they are both attached, form an optionally substituted O-heterocyclyl or R³ is selected from:

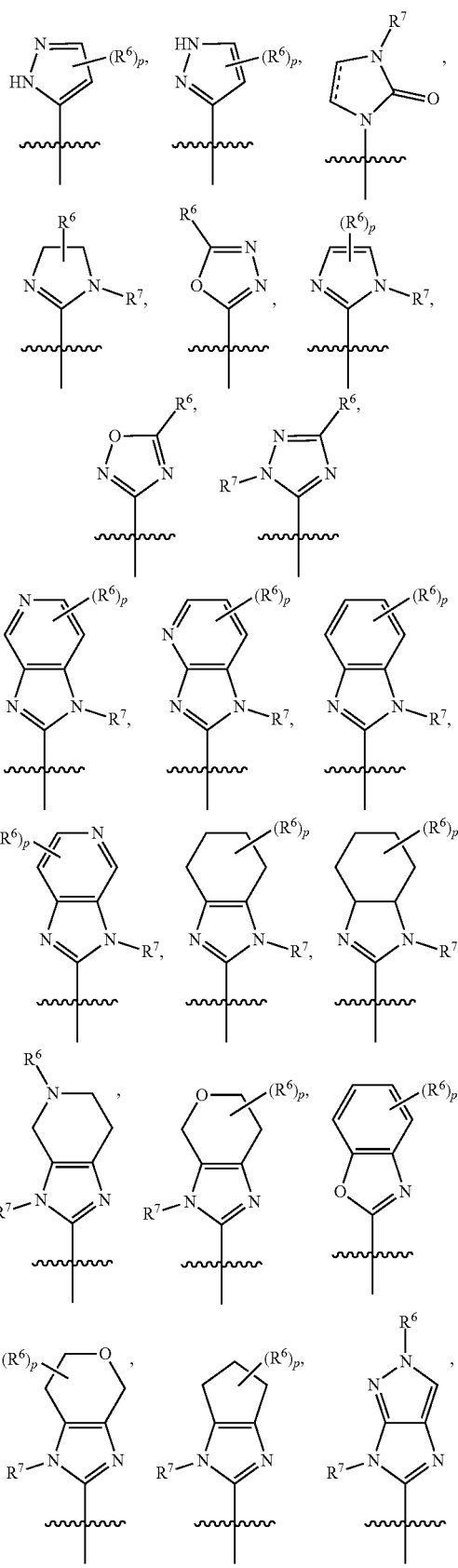

-continued

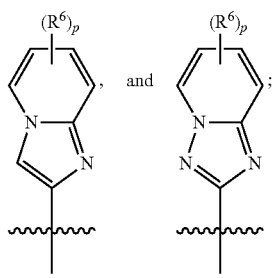

wherein:

---- is a double or single bond;

each p is independently 1, 2, 3, or 4;

each $R^6$ is independently hydrogen, halo, alkyl, haloalkyl, optionally substituted aryl, optionally substituted aralkyl, —$R^{10}$—$OR^{11}$, —$R^{10}$—C(O)$OR^{12}$, —$R^{10}$—C(O)$R^{12}$, —$R^{10}$—N($R^{11}$)$_2$, an optionally substituted O-heterocyclyl or

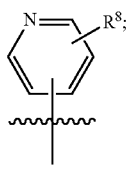

or two $R^6$'s, together with the carbon to which they are both attached, form an optionally substituted cycloalkyl;

each $R^7$ is independently hydrogen, alkyl, —$R^{10}$—C(O)$OR^{12}$ or

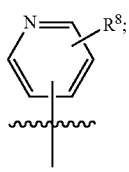

and each $R^8$ is independently hydrogen, alkyl or halo, each $R^9$ is independently hydrogen or alkyl;

each $R^{10}$ is independently a direct bond or an optionally substituted alkylene chain;

each $R^{11}$ is independently hydrogen, alkyl, haloalkyl, optionally substituted cycloakyl or optionally substituted cycloalkylalkyl; and each $R^{12}$ is hydrogen, alkyl or optionally substituted aralkyl;

or a stereoisomer, enantiomer, tautomer, or mixture thereof, or a pharmaceutically acceptable salt or solvate of said compound, stereoisomer, enantiomer, tautomer, or mixture thereof.

4. A compound of formula (I):

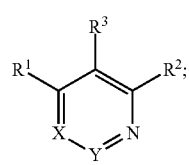

or a stereoisomer, enantiomer, tautomer, or mixture thereof, or a pharmaceutically acceptable salt or solvate of said compound, stereoisomer, enantiomer, tautomer, or mixture thereof;

wherein:

X is =C($R^9$)—;

Y is =C($R^9$)—;

$R^1$ is

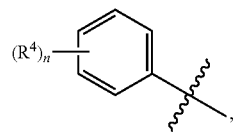

wherein:

n is 1, 2 or 3; and each $R^4$ is independently hydrogen, halo, alkyl, haloalkyl, or —$R^{10}$—$OR^{11}$;

or two adjacent $R^4$'s, together with the carbons to which they are attached, form an optionally substituted N-heteroaryl;

$R^2$ is

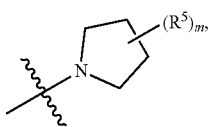

wherein:

m is 1 or 2;

each $R^5$ is independently hydrogen, halo, alkyl, haloalkyl or —$R^{10}$—CN;

or two $R^5$'s, together with the carbon to which they are both attached, form an optionally substituted O-heterocyclyl or;

$R^3$ is selected from:

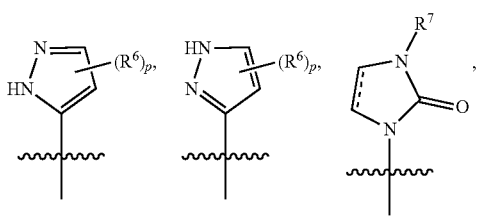

-continued

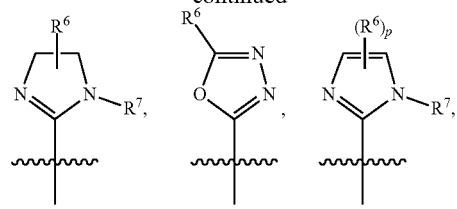

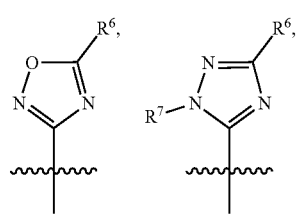

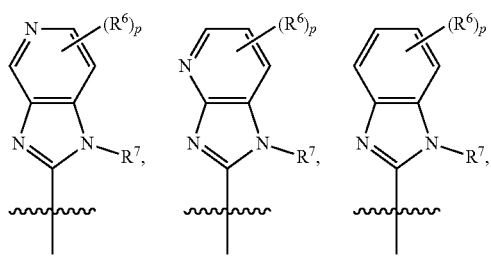

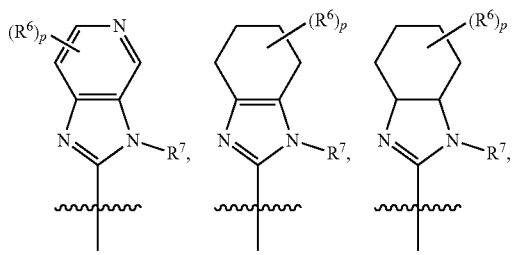

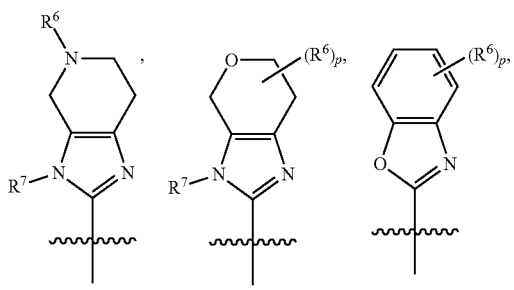

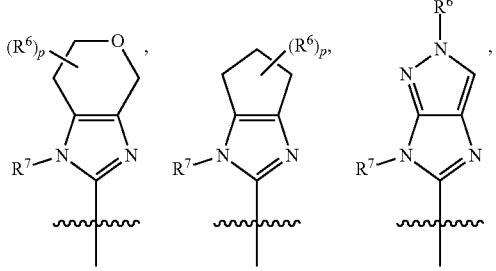

-continued

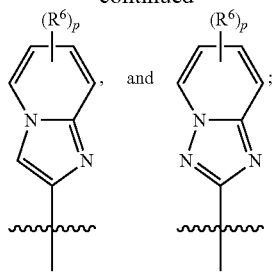

wherein:

=== is a double or single bond;

each p is independently 1, 2, 3, or 4;

each $R^6$ is independently hydrogen, halo, alkyl, haloalkyl, optionally substituted aryl, optionally substituted aralkyl, —$R^{10}$—$OR^{11}$, —$R^{10}$—C(O)$OR^{12}$, —$R^{10}$—C(O)$R^{12}$, —$R^{10}$—N($R^{11}$)$_2$, an optionally substituted O-heterocyclyl or

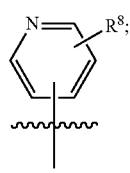

or two $R^6$'s, together with the carbon to which they are both attached, form an optionally substituted cycloalkyl;

each $R^7$ is independently hydrogen, alkyl, —$R^{10}$—C(O)$OR^{12}$ or

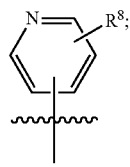

and each $R^8$ is independently hydrogen, alkyl or halo, each $R^9$ is independently hydrogen or alkyl;

each $R^{10}$ is independently a direct bond or an optionally substituted alkylene chain;

each $R^{11}$ is independently hydrogen, alkyl, haloalkyl, optionally substituted cycloakyl or optionally substituted cycloalkylalkyl; and each $R^{12}$ is hydrogen, alkyl or optionally substituted aralkyl.

5. The compound of claim 4 wherein:

X is =C($R^9$)—;

Y is =C($R^9$)—;

$R^1$ is

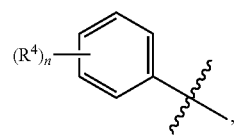

wherein:
n is 1, 2 or 3; and
each $R^4$ is independently hydrogen, halo, alkyl, haloalkyl, or —$R^{10}$—$OR^{11}$;
$R^2$ is

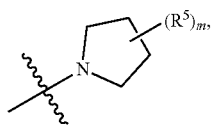

wherein:
m is 1 or 2;
each $R^5$ is independently hydrogen, halo, alkyl, haloalkyl or —$R^{10}$—CN;
$R^3$ is selected from:

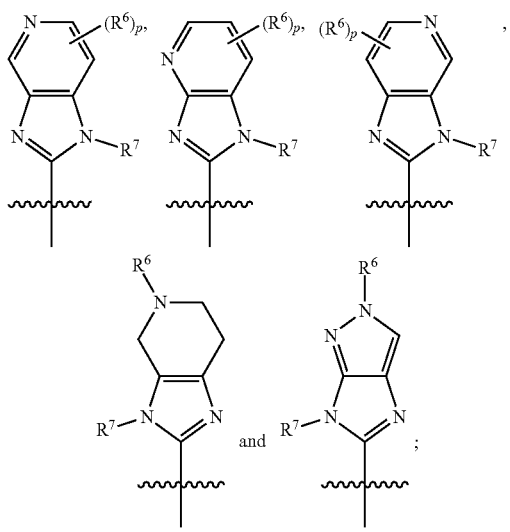

wherein:
each p is independently 1, 2, 3, or 4;
each $R^6$ is independently hydrogen, halo, alkyl, haloalkyl, optionally substituted aryl, optionally substituted aralkyl, —$R^{10}$—$OR^{11}$, —$R^{10}$—C(O)$OR^{12}$, —$R^{10}$—C(O)$R^{12}$, —$R^{10}$—N($R^{11}$)$_2$, or an optionally substituted O-heterocyclyl;
or two $R^6$'s, together with the carbon to which they are both attached, form an optionally substituted cycloalkyl; and
each $R^7$ is independently hydrogen, alkyl, or —$R^{10}$—C(O)$OR^{12}$;
each $R^9$ is independently hydrogen or alkyl;
each $R^{10}$ is independently a direct bond or an optionally substituted alkylene chain;
each $R^{11}$ is independently hydrogen, alkyl, haloalkyl, optionally substituted cycloakyl or optionally substituted cycloalkylalkyl; and
each $R^{12}$ is hydrogen, alkyl or optionally substituted aralkyl;
or a stereoisomer, enantiomer, tautomer, or mixture thereof, or a pharmaceutically acceptable salt or solvate of said compound, stereoisomer, enantiomer, tautomer, or mixture thereof.

6. The compound of claim 1 selected from:
(S)-6-chloro-2-(4-(2,5-difluorophenyl)-2-(3-fluoropyrrolidin-1-yl)pyridin-3-yl)-3H-imidazo[4,5-c]pyridine;
2-(4-(2-fluorophenyl)-2-(pyrrolidin-1-yl)pyridin-3-yl)-3H-imidazo[4,5-b]pyridine;
2-(4-(2-fluorophenyl)-2-(pyrrolidin-1-yl)pyridin-3-yl)-3H-imidazo[4,5-c]pyridine formic acid salt;
tert-butyl (S)-2-(2-(3-fluoropyrrolidin-1-yl)-4-phenylpyridin-3-yl)-3,4,6,7-tetrahydro-5H-imidazo[4,5-c]pyridine-5-carboxylate;
(S)-2-(2-(3-fluoropyrrolidin-1-yl)-4-phenylpyridin-3-yl)-4,5,6,7-tetrahydro-3H-imidazo[4,5-c]pyridine;
(S)-2-(2-(3-fluoropyrrolidin-1-yl)-4-phenylpyridin-3-yl)-5-methyl-4,5,6,7-tetrahydro-3H-imidazo[4,5-c]pyridine;
(S)-1-(2-(2-(3-fluoropyrrolidin-1-yl)-4-phenylpyridin-3-yl)-3,4,6,7-tetrahydro-5H-imidazo[4,5-c]pyridin-5-yl)ethan-1-one;
(S)-2-(2-(3-fluoropyrrolidin-1-yl)-4-phenylpyridin-3-yl)-5-isopropyl-4,5,6,7-tetrahydro-3H-imidazo[4,5-c]pyridine;
(S)-2-(2-(3-fluoropyrrolidin-1-yl)-4-phenylpyridin-3-yl)-5-(oxetan-3-yl)-4,5,6,7-tetrahydro-3/I-imidazo[4,5-c]pyridine;
diethyl (S)-2-(2-(3-fluoropyrrolidin-1-yl)-4-phenylpyridin-3-yl)-6,7-dihydro-3H-imidazo[4,5-c]pyridine-3,5(4H)-dicarboxylate;
(S)-1-(2-(2-(3-fluoropyrrolidin-1-yl)-4-phenylpyridin-3-yl)-3,4,6,7-tetrahydro-5H-imidazo[4,5-c]pyridin-5-yl)-2-methylpropan-1-one;
(S)-5-benzyl-2-(2-(3-fluoropyrrolidin-1-yl)-4-phenylpyridin-3-yl)-4,5,6,7-tetrahydro-3H-imidazo[4,5-c]pyridine;
tert-butyl 2-(2-(3,3-difluoropyrrolidin-1-yl)-4-phenylpyridin-3-yl)-3,4,6,7-tetrahydro-5/I-imidazo[4,5-c]pyridine-5-carboxylate;
2-(2-(3,3-difluoropyrrolidin-1-yl)-4-(2-fluorophenyl)pyridin-3-yl)-3H-imidazo[4,5-c]pyridine;
2-(2-(3,3-difluoropyrrolidin-1-yl)-4-(2-fluorophenyl)pyridin-3-yl)-6-methyl-3H-imidazo[4,5-c]pyridine; and
5-(2-(3,3-difluoropyrrolidin-1-yl)-4-(2-fluorophenyl)pyridin-3-yl)-2-methyl-2,4-dihydroimidazo[4,5-c]pyrazole;
or a stereoisomer, enantiomer, tautomer, or mixture thereof, or a pharmaceutically acceptable salt or solvate of said compound, stereoisomer, enantiomer, tautomer, or mixture thereof.

7. The compound of claim 4 wherein:
X is =C($R^9$)—;
Y is =C($R^9$)—;
$R^1$ is

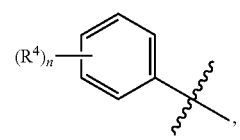

wherein:
n is 1, 2 or 3; and
each $R^4$ is independently hydrogen, halo, alkyl, haloalkyl, or —$R^{10}$—$OR^{11}$;

R² is

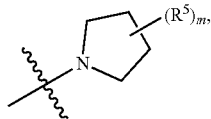

wherein:
m is 1 or 2;
each R⁵ is independently hydrogen, halo, alkyl, haloalkyl or —R¹⁰—CN;
R³ is selected from:

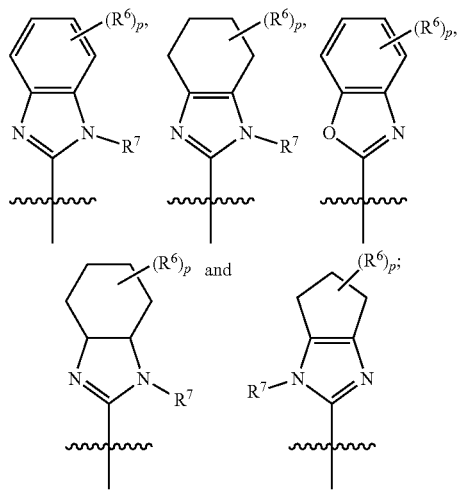

wherein:
each p is independently 1, 2, 3, or 4;
each R⁶ is independently hydrogen, halo, alkyl, haloalkyl, optionally substituted aryl, optionally substituted aralkyl, —R¹⁰—OR¹¹, —R¹⁰—C(O)OR¹², —R¹⁰—C(O)R¹², —R¹⁰—N(R¹¹)₂, or an optionally substituted O-heterocyclyl; and
each R⁷ is independently hydrogen, alkyl or —R¹⁰—C(O)OR¹²;
each R⁹ is independently hydrogen or alkyl;
each R¹⁰ is independently a direct bond or an optionally substituted alkylene chain;
each R¹¹ is independently hydrogen, alkyl, haloalkyl, optionally substituted cycloakyl or optionally substituted cycloalkylalkyl; and
each R¹² is hydrogen, alkyl or optionally substituted aralkyl;
or a stereoisomer, enantiomer, tautomer, or mixture thereof, or a pharmaceutically acceptable salt or solvate of said compound, stereoisomer, enantiomer, tautomer, or mixture thereof.

8. The compound of claim 1 selected from:
2-(4-(2-fluorophenyl)-2-(pyrrolidin-1-yl)pyridin-3-yl)-1H-benzo[d]imidazole;
2-(4-(2-chlorophenyl)-2-(pyrrolidin-1-yl)pyridin-3-yl)-1H-benzo[d]imidazole;
2-(2-(pyrrolidin-1-yl)-4-(o-tolyl)pyridin-3-yl)-1H-benzo[d]imidazole;
2-(2-(pyrrolidin-1-yl)-4-(4-(trifluoromethyl)phenyl)pyridin-3-yl)-1H-benzo[d]imidazole;
2-(4-phenyl-2-(pyrrolidin-1-yl)pyridin-3-yl)-1H-benzo[d]imidazole;
(S)-2-(2-(3-fluoropyrrolidin-1-yl)-4-phenylpyridin-3-yl)-1H-benzo[d]imidazole;
(S)-2-(4-(2-fluorophenyl)-2-(3-fluoropyrrolidin-1-yl)pyridin-3-yl)-1H-benzo[d]imidazole;
2-(4-(3,5-difluorophenyl)-2-(pyrrolidin-1-yl)pyridin-3-yl)-1H-benzo[d]imidazole;
(3aR,7aR)-2-(2-((S)-3-fluoropyrrolidin-1-yl)-4-phenylpyridin-3-yl)-3a,4,5,6,7,7a-hexahydro-1H-benzo[d]imidazole;
(S)-2-(2-(3-fluoropyrrolidin-1-yl)-4-phenylpyridin-3-yl)-4,5,6,7-tetrahydro-1H-benzo[d]imidazole;
6-(tert-butyl)-2-(4-phenyl-6-(pyrrolidin-1-yl)pyrimidin-5-yl)-1H-benzo[d]imidazole;
2-(2-(3,3-difluoropyrrolidin-1-yl)-4-phenylpyridin-3-yl)-1,4,5,6-tetrahydrocyclopenta[d]imidazol-5-ol;
2-(2-(3,3-difluoropyrrolidin-1-yl)-4-phenylpyridin-3-yl)-6-methoxy-4,5,6,7-tetrahydro-1H-benzo[d]imidazole;
(S)-2-(2-((S)-3-fluoropyrrolidin-1-yl)-4-phenylpyridin-3-yl)-6-methoxy-4,5,6,7-tetrahydro-1H-benzo[d]imidazole;
(R)-2-(2-((S)-3-fluoropyrrolidin-1-yl)-4-phenylpyridin-3-yl)-6-methoxy-4,5,6,7-tetrahydro-1H-benzo[d]imidazole;
2-(2-((S)-3-fluoropyrrolidin-1-yl)-4-phenylpyridin-3-yl)-6-methoxy-4,5,6,7-tetrahydro-1H-benzo[d]imidazole;
(S)-2-(2-(3-fluoropyrrolidin-1-yl)-4-phenylpyridin-3-yl)benzo[d]oxazole; and
2-(2-(3,3-difluoropyrrolidin-1-yl)-4-phenylpyridin-3-yl)-4,5,6,7-tetrahydro-1H-benzo[d]imidazole;
or a stereoisomer, enantiomer, tautomer, or mixture thereof, or a pharmaceutically acceptable salt or solvate of said compound, stereoisomer, enantiomer, tautomer, or mixture thereof.

9. The compound of claim 4 wherein:
X is =C(R⁹)—;
Y is =C(R⁹)—;
R¹ is

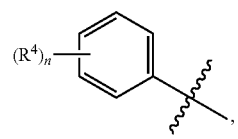

wherein:
n is 1, 2 or 3; and
each R⁴ is independently hydrogen, halo, alkyl, haloalkyl, or —R¹⁰—OR¹¹;
or two adjacent R⁴'s, together with the carbons to which they are attached, form an optionally substituted N-heteroaryl;
R² is

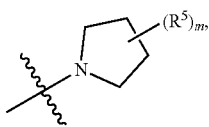

wherein:
m is 1 or 2;
each R⁵ is independently hydrogen, halo, alkyl, haloalkyl or —R¹⁰—CN;

or two adjacent R⁵'s, together with the carbons to which they are attached, form an optionally substituted cycloalkyl;

R³ is selected from:

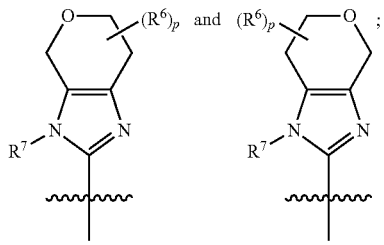

wherein:
each p is independently 1, 2, 3, or 4;
each R⁶ is independently hydrogen, halo, alkyl, haloalkyl, optionally substituted aryl, optionally substituted aralkyl, —R¹⁰—OR¹¹, —R¹⁰—C(O)OR¹², —R¹⁰—C(O)R¹², —R¹⁰—N(R¹¹)₂, or an optionally substituted O-heterocyclyl;
or two R⁶'s, together with the carbon to which they are both attached, form an optionally substituted cycloalkyl; and
each R⁷ is independently hydrogen, alkyl or —R¹⁰—C(O)OR¹²;
each R⁹ is independently hydrogen or alkyl;
each R¹⁰ is independently a direct bond or an optionally substituted alkylene chain;
each R¹¹ is independently hydrogen, alkyl, haloalkyl, optionally substituted cycloakyl or optionally substituted cycloalkylalkyl; and
each R¹² is hydrogen, alkyl or optionally substituted aralkyl; or a stereoisomer, enantiomer, tautomer, or mixture thereof, or a pharmaceutically acceptable salt or solvate of said compound, stereoisomer, enantiomer, tautomer, or mixture thereof.

10. The compound of claim 1 selected from:
2-(2-(3,3-difluoropyrrolidin-1-yl)-4-phenylpyridin-3-yl)-3,4,6,7-tetrahydropyrano[3,4-d]imidazole;
2-(2-(3,3-difluoropyrrolidin-1-yl)-4-phenylpyridin-3-yl)-6,6-dimethyl-3,4,6,7-tetrahydropyrano[3,4-d]imidazole;
(S)-2-(4-(2,5-difluorophenyl)-2-(3-fluoropyrrolidin-1-yl)pyridin-3-yl)-3,4,6,7-tetrahydropyrano[3,4-d]imidazole;
2-(2-(3,3-difluoropyrrolidin-1-yl)-4-(2-fluorophenyl)pyridin-3-yl)-1,4,6,7-tetrahydropyrano[3,4-d]imidazole;
2-(4-(2,5-difluorophenyl)-2-(3,3-difluoropyrrolidin-1-yl)pyridin-3-yl)-1,4,6,7-tetrahydropyrano[3,4-d]imidazole;
2-(2-(3,3-difluoropyrrolidin-1-yl)-4-(1H-indazol-5-yl)pyridin-3-yl)-1,4,6,7-tetrahydropyrano[3,4-d]imidazole;
2-(2-(3,3-difluoropyrrolidin-1-yl)-4-(3-fluorophenyl)pyridin-3-yl)-1,4,6,7-tetrahydropyrano[3,4-d]imidazole;
2-(4-phenyl-2-(pyrrolidin-1-yl)pyridin-3-yl)-3,4,6,7-tetrahydropyrano[3,4-d]imidazole;
2-(2-(6,6-difluoro-3-azabicyclo[3.1.0]hexan-3-yl)-4-phenylpyridin-3-yl)-3,4,6,7-tetrahydropyrano[3,4-d]imidazole;
2-(4-(2,5-difluorophenyl)-2-(3,3-difluoropyrrolidin-1-yl)pyridin-3-yl)-6,6-dimethyl-3,4,6,7-tetrahydropyrano[3,4-d]imidazole;
2-(2-((3S,4R)-3,4-difluoropyrrolidin-1-yl)-4-phenylpyridin-3-yl)-3,4,6,7-tetrahydropyrano[3,4-d]imidazole;
2-(4-(2,3-difluorophenyl)-2-(3,3-difluoropyrrolidin-1-yl)pyridin-3-yl)-3,4,6,7-tetrahydropyrano[3,4-d]imidazole;
1-(4-phenyl-3-(3,4,6,7-tetrahydropyrano[3,4-d]imidazol-2-yl)pyridin-2-yl)pyrrolidine-3-carbonitrile;
2'-(2-(3,3-difluoropyrrolidin-1-yl)-4-phenylpyridin-3-yl)-4',7'-dihydro-3'H-spiro[cyclobutane-1,6'-pyrano[3,4-d]imidazole];
2-(4-phenyl-2-(3-(trifluoromethyl)pyrrolidin-1-yl)pyridin-3-yl)-3,4,6,7-tetrahydropyrano[3,4-d]imidazole; and
2-(2-(3,3-difluoropyrrolidin-1-yl)-4-phenylpyridin-3-yl)-4,4-dimethyl-3,4,6,7-tetrahydropyrano[3,4-d]imidazole;
or a stereoisomer, enantiomer, tautomer, or mixture thereof, or a pharmaceutically acceptable salt or solvate of said compound, stereoisomer, enantiomer, tautomer, or mixture thereof.

11. The compound of claim 4 wherein:
X is =C(R⁹)—;
Y is =C(R⁹)—;
R¹ is

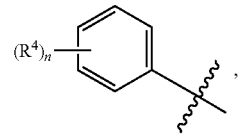

wherein:
n is 1, 2 or 3; and
each R⁴ is independently hydrogen, halo, alkyl, haloalkyl, or —R¹⁰—OR¹¹;
R² is

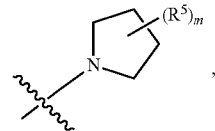

wherein;
m is 1 or 2;
each R⁵ is independently hydrogen, halo, alkyl, haloalkyl or —R¹⁰—CN;
R³ is selected from:

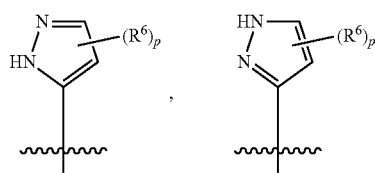

-continued

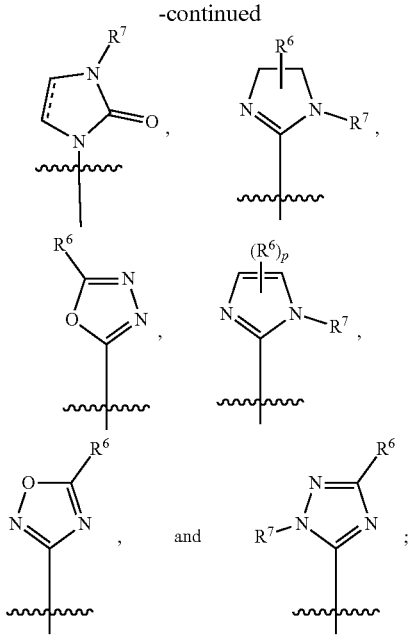

wherein:
each p is independently 1, 2, 3, or 4;
each $R^6$ is independently hydrogen, halo, alkyl, haloalkyl, optionally substituted aryl, optionally substituted aralkyl, —$R^{10}$—$OR^{11}$, —$R^{10}$—$C(O)OR^{12}$, —$R^{10}$—$C(O)R^{12}$, —$R^{10}$—$N(R^{11})_2$, an optionally substituted O-heterocyclyl or

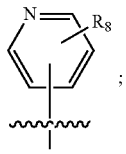

each $R^7$ is independently hydrogen, alkyl, —$R^{10}$—$C(O)OR^{12}$ or

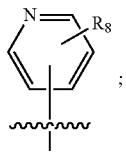

and
each $R^8$ is independently hydrogen, alkyl or halo,
each $R^9$ is independently hydrogen or alkyl;
each $R^{10}$ is independently a direct bond or an optionally substituted alkylene chain;
each $R^{11}$ is independently hydrogen, alkyl, haloalkyl, optionally substituted cycloakyl or optionally substituted cycloalkylalkyl; and
each $R^{12}$ is hydrogen, alkyl or optionally substituted aralkyl;
or a stereoisomer, enantiomer, tautomer, or mixture thereof, or a pharmaceutically acceptable salt or solvate of said compound, stereoisomer, enantiomer, tautomer, or mixture thereof.

12. The compound of claim 1 selected from:
5-(4-(2-fluorophenyl)-2-(pyrrolidin-1-yl)pyridin-3-yl)-1,3,4-oxadiazol-2-amine;
4-(2-fluorophenyl)-3-(5-isobutyl-4,5-dihydro-1H-imidazol-2-yl)-2-(pyrrolidin-1-yl)pyridine;
(S)-2-(4-(2-fluorophenyl)-2-(3-fluoropyrrolidin-1-yl)pyridin-3-yl)-1,3,4-oxadiazole;
(S)-N-butyl-5-(4-(2-fluorophenyl)-2-(3-fluoropyrrolidin-1-yl)pyridin-3-yl)-1,3,4-oxadiazol-2-amine;
(S)-2-(2-(3-fluoropyrrolidin-1-yl)-3-(5-isopentyl-1,3,4-oxadiazol-2-yl)pyridin-4-yl)phenol;
(S)-2-(4-(2-fluorophenyl)-2-(3-fluoropyrrolidin-1-yl)pyridin-3-yl)-5-isopentyl-1,3,4-oxadiazole;
(S)-2-(3-fluoropyrrolidin-1-yl)-4-phenyl-3-(3-(pyridin-3-yl)-1H-pyrazol-5-yl)pyridine;
(S)-2-(3-fluoropyrrolidin-1-yl)-3-(3-(4-isopropylphenyl)-1H-pyrazol-5-yl)-4-phenylpyridine;
(S)-1-(6-chloropyridin-3-yl)-3-(4-(2-fluorophenyl)-2-(3-fluoropyrrolidin-1-yl)pyridin-3-yl)imidazolidin-2-one;
(S)-1-(6-chloropyridin-3-yl)-3-(4-(2-fluorophenyl)-2-(3-fluoropyrrolidin-1-yl)pyridin-3-yl)-1,3-dihydro-2H-imidazol-2-one;
2-((S)-3-fluoropyrrolidin-1-yl)-3-(5-methyl-4,5-dihydro-1H-imidazol-2-yl)-4-phenylpyridine;
(S)-3-(4-bromo-5-methyl-1H-imidazol-2-yl)-2-(3-fluoropyrrolidin-1-yl)-4-phenylpyridine;
(S)-2-(2-(3-fluoropyrrolidin-1-yl)-4-phenylpyridin-3-yl)-5-(4-isopropylphenyl)-1,3,4-oxadiazole;
tert-butyl (S)-2-(2-(3-fluoropyrrolidin-1-yl)-4-phenylpyridin-3-yl)-3,4,6,7-tetrahydro-5H-imidazo[4,5-c]pyridine-5-carboxylate;
(S)-2-(3-fluoropyrrolidin-1-yl)-3-(4-methyl-5-(trifluoromethyl)-1H-imidazol-2-yl)-4-phenylpyridine;
2-(3,3-difluoropyrrolidin-1-yl)-3-(5-methyl-4-phenyl-1H-imidazol-2-yl)-4-phenylpyridine;
5-(tert-butyl)-3-(2-(3,3-difluoropyrrolidin-1-yl)-4-phenylpyridin-3-yl)-1,2,4-oxadiazole; and
(S)-2-(3-fluoropyrrolidin-1-yl)-4-phenyl-3-(3-phenyl-1H-1,2,4-triazol-5-yl)pyridine;
or a stereoisomer, enantiomer, tautomer, or mixture thereof, or a pharmaceutically acceptable salt or solvate of said compound, stereoisomer, enantiomer, tautomer, or mixture thereof.

13. The compound of claim 3 wherein:
X is =C($R^9$)—;
Y is =C($R^9$)—;
$R^1$ is

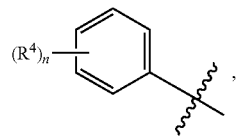

wherein:
n is 1, 2 or 3; and
each $R^4$ is independently hydrogen, halo, alkyl, haloalkyl, or —$R^{10}$—$OR^{11}$;
$R^2$ is selected from —$R^{10}$—$OR^{11}$, —$R^{10}$—$N(R^{11})_2$,

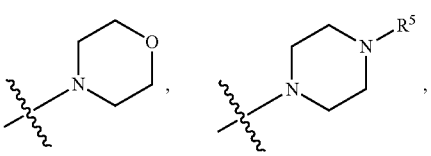

-continued

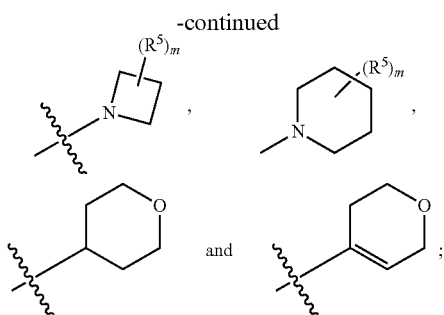

each m is independently 1 or 2;
each $R^5$ is independently hydrogen, halo, alkyl, haloalkyl or —$R^{10}$—CN;
or two $R^5$'s, together with the carbon to which they are both attached, form an optionally substituted O-heterocyclyl or
an optionally substituted cycloalkyl;
$R^3$ is selected from:

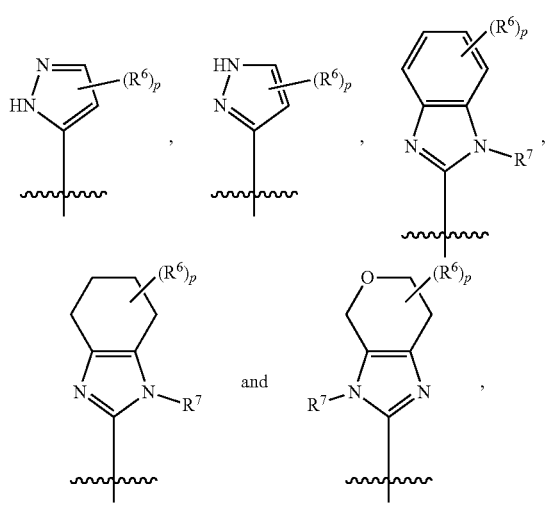

wherein:
each p is independently 1, 2, 3, or 4;
each $R^6$ is independently hydrogen, halo, alkyl, haloalkyl, optionally substituted aryl, optionally substituted aralkyl, —$R^{10}$—$OR^{11}$, —$R^{10}$—C(O)$OR^{12}$, o-$R^{10}$—C(O)$R^{12}$, —$R^{10}$—N($R^{11}$)$_2$, or an optionally substituted O-heterocyclyl;
or two $R^6$'s, together with the carbon to which they are both attached, form an optionally substituted cycloalkyl; and
each $R^7$ is independently hydrogen, alkyl, or —$R^{10}$—C(O)$OR^{12}$;
each $R^9$ is independently hydrogen or alkyl;
each $R^{10}$ is independently a direct bond or an optionally substituted alkylene chain;
each $R^{11}$ is independently hydrogen, alkyl, haloalkyl, optionally substituted cycloakyl or optionally substituted cycloalkylalkyl; and
each $R^{12}$ is hydrogen, alkyl or optionally substituted aralkyl;
or a stereoisomer, enantiomer, tautomer, or mixture thereof,
or a pharmaceutically acceptable salt or solvate of said compound, stereoisomer, enantiomer, tautomer, or mixture thereof.

14. The compound of claim 1 selected from:
4-(3-(1H-benzo[d]imidazol-2-yl)-4-(o-tolyl)pyridin-2-yl)morpholine;
2-(2-(4-methylpiperazin-1-yl)-4-(o-tolyl)pyridin-3-yl)-1H-benzo[d]imidazole;
4-(3-(3-(4-isopropylphenyl)-1H-pyrazol-5-yl)-4-phenylpyridin-2-yl)morpholine;
4-(3-((3aR,7aR)-3a,4,5,6,7,7a-hexahydro-1H-benzo[d]imidazol-2-yl)-4-phenylpyridin-2-yl)morpholine-;
4-(4-phenyl-3-(4,5,6,7-tetrahydro-1H-benzo[d]imidazol-2-yl)pyridin-2-yl)morpholine;
2-(2-morpholino-4-phenylpyridin-3-yl)-3,4,6,7-tetrahydropyrano[3,4-d]imidazole;
2-(2-(3,3-difluoroazetidin-1-yl)-4-phenylpyridin-3-yl)-3,4,6,7-tetrahydropyrano[3,4-d]imidazole;
2-(4-phenyl-2-(2-oxa-6-azaspiro[3.3]heptan-6-yl)pyridin-3-yl)-3,4,6,7-tetrahydropyrano[3,4-d]imidazole;
2-(2-cyclobutoxy-4-phenylpyridin-3-yl)-3,4,6,7-tetrahydropyrano[3,4-d]imidazole;
2-(2-(3,3-difluoropiperidin-1-yl)-4-phenylpyridin-3-yl)-3,4,6,7-tetrahydropyrano[3,4-d]imidazole;
2-(2-(6,6-difluoro-2-azaspiro[3.3]heptan-2-yl)-4-phenylpyridin-3-yl)-3,4,6,7-tetrahydropyrano[3,4-d]imidazole;
4-phenyl-3-(3,4,6,7-tetrahydropyrano[3,4-d]imidazol-2-yl)-N-((1-(trifluoromethyl)cyclobutyl)methyl)pyridin-2-amine;
2-(4-phenyl-2-(tetrahydro-2H-pyran-4-yl)pyridin-3-yl)-3,4,6,7-tetrahydropyrano[3,4-d]imidazole; and
2-(2-(3,6-dihydro-2H-pyran-4-yl)-4-phenylpyridin-3-yl)-3,4,6,7-tetrahydropyrano[3,4-d]imidazole;
or a stereoisomer, enantiomer, tautomer, or mixture thereof, or a pharmaceutically acceptable salt or solvate of said compound, stereoisomer, enantiomer, tautomer, or mixture thereof.

15. The compound of claim 2 wherein:
X is =C($R^9$)—;
Y is =C($R^9$)—;
$R^1$ is

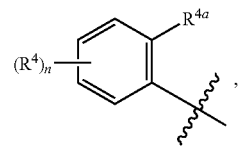

wherein:
n is 1, 2 or 3;
each $R^4$ is independently hydrogen, halo, alkyl, haloalkyl, or —$R^{10}$—$OR^{11}$; and
$R^{4a}$ is hydrogen;
$R^2$ is selected from:

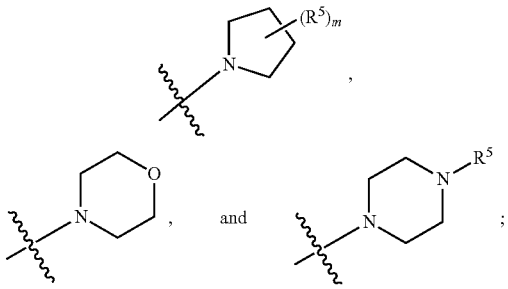

wherein:
m is 1 or 2;
each $R^5$ is independently hydrogen, halo, alkyl, haloalkyl or —$R^{10}$—CN;
$R^3$ is

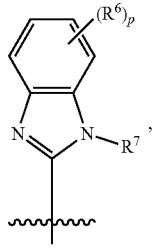

wherein:
p is 1, 2, 3, or 4;
each $R^6$ is independently hydrogen, halo, alkyl, haloalkyl, optionally substituted aryl, optionally substituted aralkyl, —$R^{10}$—$OR^{11}$, —$R^{10}$—$C(O)OR^{12}$, —$R^{10}$—$C(O)R^{12}$ or —$R^{10}$—$N(R^{11})_2$; and
$R^7$ together with $R^{4a}$ form a bond;
each $R^9$ is independently hydrogen or alkyl;
each $R^{10}$ is independently a direct bond or an optionally substituted alkylene chain;
each $R^{11}$ is independently hydrogen, alkyl, haloalkyl, optionally substituted cycloakyl or optionally substituted cycloalkylalkyl; and
each $R^{12}$ is hydrogen, alkyl or optionally substituted aralkyl;
or a stereoisomer, enantiomer, tautomer, or mixture thereof, or a pharmaceutically acceptable salt or solvate of said compound, stereoisomer, enantiomer, tautomer, or mixture thereof.

16. The compound of claim 1 selected from:
4-(benzo[c]benzo[4,5]imidazo[2,1-a][2,7]naphthyridin-1-yl)morpholine;
1-(4-methylpiperazin-1-yl)benzo[c]benzo[4,5]imidazo[2,1-α][2,7]naphthyridine; and
1-(pyrrolidin-1-yl)benzo[c]benzo[4,5]imidazo[2,1-α][2,7]naphthyridine;
or a stereoisomer, enantiomer, tautomer, or mixture thereof, or a pharmaceutically acceptable salt or solvate of said compound, stereoisomer, enantiomer, tautomer, or mixture thereof.

17. The compound of claim 2 wherein:
X is =C($R^9$)—;
Y is =C($R^9$)—;
$R^1$ is selected from:

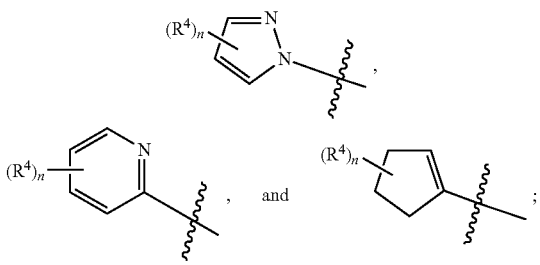

wherein:
each n is independently 1, 2 or 3; and each $R^4$ is independently hydrogen, halo, alkyl, haloalkyl, or —$R^{10}$—$OR^{11}$;
$R^2$ is selected from:

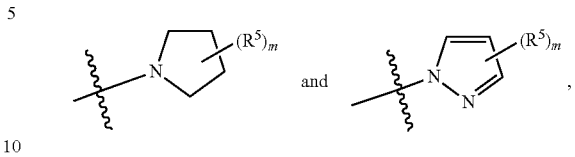

wherein:
each m is independently 1 or 2; and
each $R^5$ is independently hydrogen, halo, alkyl or haloalkyl;
$R^3$ is selected from:

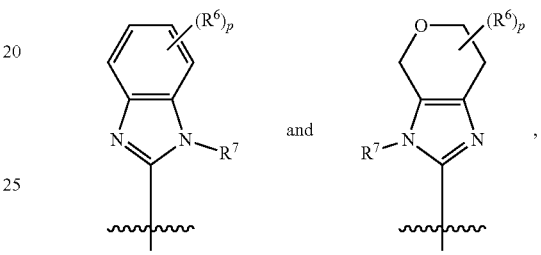

wherein:
each p is independently 1, 2, 3, or 4;
each $R^6$ is independently hydrogen, halo, alkyl, haloalkyl, optionally substituted aryl, optionally substituted aralkyl, —$R^{10}$—$OR^{11}$, —$R^{10}$—$C(O)OR^{12}$, or —$R^{10}$—$C(O)R^{12}$, —$R^{10}$—$N(R^{11})_2$; and
each $R^7$ is independently hydrogen, alkyl or —$R^{10}$—$C(O)OR^{12}$;
each $R^9$ is independently hydrogen or alkyl;
each $R^{10}$ is independently a direct bond or an optionally substituted alkylene chain;
each $R^{11}$ is independently hydrogen, alkyl, haloalkyl, optionally substituted cycloakyl or optionally substituted cycloalkylalkyl; and
each $R^{12}$ is hydrogen, alkyl or optionally substituted aralkyl;
or a stereoisomer, enantiomer, tautomer, or mixture thereof, or a pharmaceutically acceptable salt or solvate of said compound, stereoisomer, enantiomer, tautomer, or mixture thereof.

18. The compound of claim 1 selected from:
2-(2,4-di(1H-pyrazol-1-yl)pyridin-3-yl)-1H-benzo[d]imidazole;
2-(2'-(pyrrolidin-1-yl)-[2,4'-bipyridin]-3'-yl)-1H-benzo[d]imidazole;
2-(4-(1H-pyrazol-1-yl)-2-(pyrrolidin-1-yl)pyridin-3-yl)-1H-benzo[d]imidazole;
(S)-2-(4-(cyclopent-1-en-1-yl)-2-(3-fluoropyrrolidin-1-yl)pyridin-3-yl)-1H-benzo[d]imidazole; and
2-(2'-(3,3-difluoropyrrolidin-1-yl)-[2,4'-bipyridin]-3'-yl)-3,4,6,7-tetrahydropyrano[3,4-d]imidazole;
or a stereoisomer, enantiomer, tautomer, or mixture thereof, or a pharmaceutically acceptable salt or solvate of said compound, stereoisomer, enantiomer, tautomer, or mixture thereof.

19. The compound of claim 1 wherein:
X is =N— and Y is =C($R^9$) or
X is =C($R^9$) and Y is =N—;

$R^1$ is

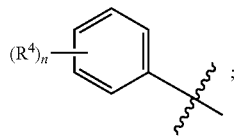

wherein:
n is 1, 2 or 3;
each $R^4$ is independently hydrogen, halo, alkyl, haloalkyl, or —$R^{10}$—$OR^{11}$;
$R^2$ is selected from:

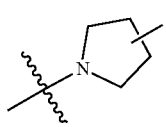 and 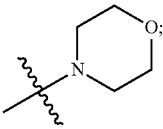

wherein:
m is 1 or 2;
$R^5$ is hydrogen, halo, alkyl, haloalkyl or —$R^{10}$—CN;
$R^3$ is selected from:

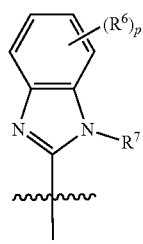 and 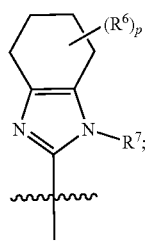;

wherein:
each p is independently 1, 2, 3, or 4;
each $R^6$ is independently hydrogen, halo, alkyl, haloalkyl, optionally substituted aryl, optionally substituted aralkyl, —$R^{10}$—$OR^{11}$, —$R^{10}$—$C(O)OR^{12}$, —$R^{10}$—$C(O)R^{12}$, —$R^{10}$—$N(R^{11})_2$, or an optionally substituted O-heterocyclyl; and
each $R^7$ is independently hydrogen, alkyl or —$R^{10}$—C(O)$OR^{12}$;
each $R^9$ is independently hydrogen or alkyl;
each $R^{10}$ is independently a direct bond or an optionally substituted alkylene chain;
each $R^{11}$ is independently hydrogen, alkyl, haloalkyl, optionally substituted cycloakyl or optionally substituted cycloalkylalkyl; and
each $R^{12}$ is hydrogen, alkyl or optionally substituted aralkyl;
or a stereoisomer, enantiomer, tautomer, or mixture thereof, or a pharmaceutically acceptable salt or solvate of said compound, stereoisomer, enantiomer, tautomer, or mixture thereof.

20. The compound of claim 1 selected from:
2-(5-phenyl-3-(pyrrolidin-1-yl)pyridazin-4-yl)-1H-benzo[d]imidazole; and
4-(5-phenyl-4-(4,5,6,7-tetrahydro-1H-benzo[d]imidazol-2-yl)pyridazin-3-yl)morpholine;
or a stereoisomer, enantiomer, tautomer, or mixture thereof, or a pharmaceutically acceptable salt or solvate of said compound, stereoisomer, enantiomer, tautomer, or mixture thereof.

21. The compound of claim 1 wherein:
X is =C($R^9$) and Y is =C($R^9$);
$R^1$ is

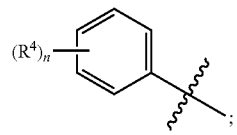

wherein:
n is 1, 2 or 3;
each $R^4$ is independently hydrogen, halo, alkyl, haloalkyl, or —$R^{10}$—$OR^{11}$;
$R^2$ is

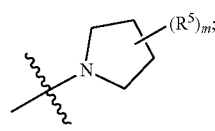

wherein:
m is 1 or 2;
$R^5$ is hydrogen, halo, alkyl, haloalkyl or —$R^{10}$—CN;
$R^3$ is selected from:

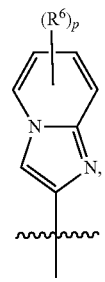 and 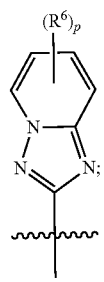

wherein:
each p is independently 1, 2, 3, or 4; and
each $R^6$ is independently hydrogen, halo, alkyl, haloalkyl, optionally substituted aryl, optionally substituted aralkyl, —$R^{10}$—$OR^{11}$, —$R^{10}$—$C(O)OR^{12}$, —$R^{10}$—$C(O)R^{12}$, —$R^{10}$—$N(R^{11})_2$, or an optionally substituted O-heterocyclyl;
each $R^9$ is independently hydrogen or alkyl;
each $R^{10}$ is independently a direct bond or an optionally substituted alkylene chain;
each $R^{11}$ is independently hydrogen, alkyl, haloalkyl, optionally substituted cycloakyl or optionally substituted cycloalkylalkyl; and
each $R^{12}$ is hydrogen, alkyl or optionally substituted aralkyl;
or a stereoisomer, enantiomer, tautomer, or mixture thereof, or a pharmaceutically acceptable salt or solvate of said compound, stereoisomer, enantiomer, tautomer, or mixture thereof.

22. The compound of claim 1 selected from:
(S)-2-(2-(3-fluoropyrrolidin-1-yl)-4-phenylpyridin-3-yl)imidazo[1,2-a]pyridine; and
(S)-2-(2-(3-fluoropyrrolidin-1-yl)-4-phenylpyridin-3-yl)-[1,2,4]triazolo[1,5-a]pyridine;

or a stereoisomer, enantiomer, tautomer, or mixture thereof, or a pharmaceutically acceptable salt or solvate of said compound, stereoisomer, enantiomer, tautomer, or mixture thereof.

23. A pharmaceutical composition comprising a pharmaceutically acceptable excipient and a compound of formula (I):

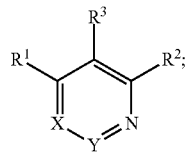
(I)

or a stereoisomer, enantiomer, tautomer, or mixture thereof, or a pharmaceutically acceptable salt or solvate of said compound, stereoisomer, enantiomer, tautomer, or mixture thereof;

wherein:
X is =C($R^9$)— or =N—;
Y is =C($R^9$)— or —N=; provided that X is not =N— when Y is —N= and Y is not —N= when X is =N—;
$R^1$ is selected from:

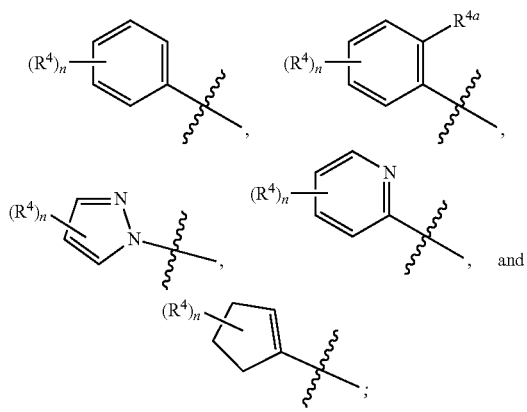

wherein:
each n is independently 1, 2 or 3;
each $R^4$ is independently hydrogen, halo, alkyl, haloalkyl, or —$R^{10}$—$OR^{11}$;
or two adjacent $R^4$'s, together with the carbons to which they are attached, form an optionally substituted N-heteroaryl; and
$R^{4a}$ is hydrogen;
$R^2$ is selected from —$R^{10}$-$OR^{11}$, —$R^{10}$—N($R^{11}$)$_2$,

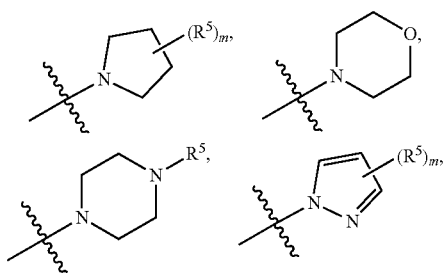

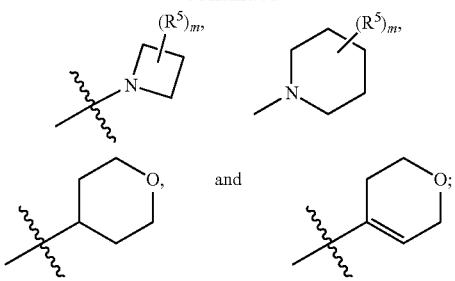

each m is independently 1 or 2;
each $R^5$ is independently hydrogen, halo, alkyl, haloalkyl or —$R^{10}$—CN;
or two $R^5$'s, together with the carbon to which they are both attached, form an optionally substituted O-heterocyclyl or
an optionally substituted cycloalkyl;
$R^3$ is selected from:

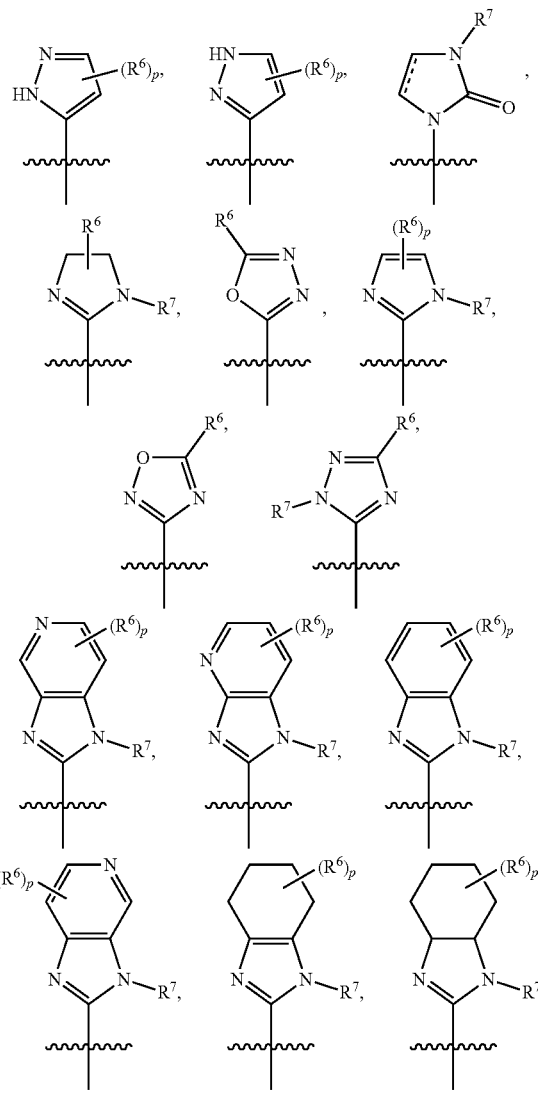

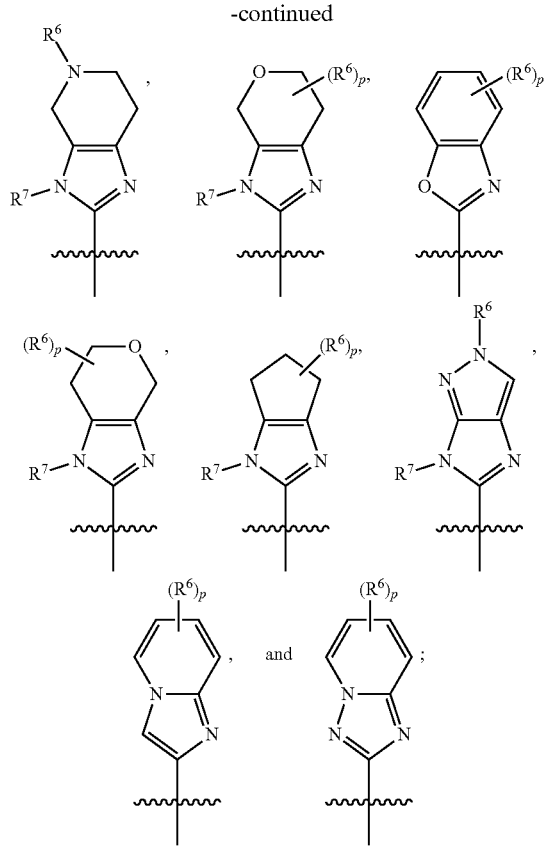

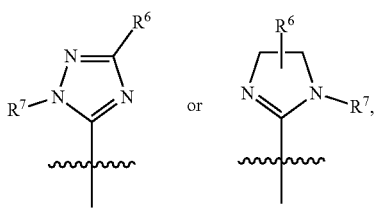

wherein when R³ is then at least one of R⁶ and R⁷ is not hydrogen;
each R⁸ is independently hydrogen, alkyl or halo,
each R⁹ is independently hydrogen or alkyl;
each R¹⁰ is independently a direct bond or an optionally substituted alkylene chain;
each R¹¹ is independently hydrogen, alkyl, haloalkyl, optionally substituted cycloakyl or optionally substituted cycloalkylalkyl; and
each R¹² is hydrogen, alkyl or optionally substituted aralkyl.

24. A method of treating a disease or condition in a mammal modulated by a voltage-gated sodium channel, wherein the method comprises administering to a mammal in need thereof a therapeutically effective amount of a compound of claim 1.

25. The method of claim 24, wherein the compound of formula (I) is selected from:
(S)-6-chloro-2-(4-(2,5-difluorophenyl)-2-(3-fluoropyrrolidin-1-yl)pyridin-3-yl)-3H-imidazo[4,5-c]pyridine;
2-(4-(2-fluorophenyl)-2-(pyrrolidin-1-yl)pyridin-3-yl)-3H-imidazo[4,5-b]pyridine;
2-(4-(2-fluorophenyl)-2-(pyrrolidin-1-yl)pyridin-3-yl)-3H-imidazo[4,5-c]pyridine formic acid salt;
tert-butyl (S)-2-(2-(3-fluoropyrrolidin-1-yl)-4-phenylpyridin-3-yl)-3,4,6,7-tetrahydro-5H-imidazo[4,5-c]pyridine-5-carboxylate;
(S)-2-(2-(3-fluoropyrrolidin-1-yl)-4-phenylpyridin-3-yl)-4,5,6,7-tetrahydro-3H-imidazo[4,5-c]pyridine;
(S)-2-(2-(3-fluoropyrrolidin-1-yl)-4-phenylpyridin-3-yl)-5-methyl-4,5,6,7-tetrahydro-3H-imidazo[4,5-c]pyridine;
(S)-1-(2-(2-(3-fluoropyrrolidin-1-yl)-4-phenylpyridin-3-yl)-3,4,6,7-tetrahydro-5H-imidazo[4,5-c]pyridin-5-yl)ethan-1-one;
(S)-2-(2-(3-fluoropyrrolidin-1-yl)-4-phenylpyridin-3-yl)-5-isopropyl-4,5,6,7-tetrahydro-3H-imidazo[4,5-c]pyridine;
(S)-2-(2-(3-fluoropyrrolidin-1-yl)-4-phenylpyridin-3-yl)-5-(oxetan-3-yl)-4,5,6,7-tetrahydro-3H-imidazo[4,5-c]pyridine;
diethyl (S)-2-(2-(3-fluoropyrrolidin-1-yl)-4-phenylpyridin-3-yl)-6,7-dihydro-3H-imidazo[4,5-c]pyridine-3,5(4H)-dicarboxylate;
(S)-1-(2-(2-(3-fluoropyrrolidin-1-yl)-4-phenylpyridin-3-yl)-3,4,6,7-tetrahydro-5H-imidazo[4,5-c]pyridin-5-yl)-2-methylpropan-1-one;
(S)-5-benzyl-2-(2-(3-fluoropyrrolidin-1-yl)-4-phenylpyridin-3-yl)-4,5,6,7-tetrahydro-3H-imidazo[4,5-c]pyridine;
tert-butyl 2-(2-(3,3-difluoropyrrolidin-1-yl)-4-phenylpyridin-3-yl)-3,4,6,7-tetrahydro-5H-imidazo[4,5-c]pyridine-5-carboxylate;
2-(2-(3,3-difluoropyrrolidin-1-yl)-4-(2-fluorophenyl)pyridin-3-yl)-3H-imidazo[4,5-c]pyridine;
2-(2-(3,3-difluoropyrrolidin-1-yl)-4-(2-fluorophenyl)pyridin-3-yl)-6-methyl-3H-imidazo[4,5-c]pyridine;

wherein:
---- is a double or single bond;
each p is independently 1, 2, 3, or 4;
each R⁶ is independently hydrogen, halo, alkyl, haloalkyl, optionally substituted aryl, optionally substituted aralkyl, —R¹⁰—OR¹¹, —R¹⁰—C(O)OR¹², —R¹⁰—C(O)R¹², —R¹⁰—N(R¹¹)₂, an optionally substituted O-heterocyclyl or

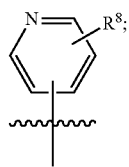

or two R⁶'s, together with the carbon to which they are both attached, form an optionally substituted cycloalkyl;
each R⁷ is independently hydrogen, alkyl, —R¹⁰—C(O)OR¹² or

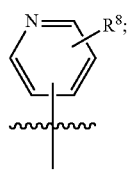

or the nitrogen to which R⁷ is attached together with the carbon to which R⁴ᵃ is attached form a bond; and 5-(2-(3,3-difluoropyrrolidin-1-yl)-4-(2-fluorophenyl) pyridin-3-yl)-2-methyl-2,4-dihydroimidazo[4,5-c] pyrazole;
2-(4-(2-fluorophenyl)-2-(pyrrolidin-1-yl)pyridin-3-yl)-1H-benzo[d]imidazole;
2-(4-(2-chlorophenyl)-2-(pyrrolidin-1-yl)pyridin-3-yl)-1H-benzo[d]imidazole;
2-(2-(pyrrolidin-1-yl)-4-(o-tolyl)pyridin-3-yl)-1H-benzo[d]imidazole;
2-(2-(pyrrolidin-1-yl)-4-(4-(trifluoromethyl)phenyl)pyridin-3-yl)-1H-benzo[d]imidazole;
2-(4-phenyl-2-(pyrrolidin-1-yl)pyridin-3-yl)-1H-benzo[d]imidazole;
(S)-2-(2-(3-fluoropyrrolidin-1-yl)-4-phenylpyridin-3-yl)-1H-benzo[d]imidazole;
(S)-2-(4-(2-fluorophenyl)-2-(3-fluoropyrrolidin-1-yl) pyridin-3-yl)-1H-benzo[d]imidazole;
2-(4-(3,5-difluorophenyl)-2-(pyrrolidin-1-yl)pyridin-3-yl)-1H-benzo[d]imidazole;
(3aR,7aR)-2-(2-((S)-3-fluoropyrrolidin-1-yl)-4-phenylpyridin-3-yl)-3a,4,5,6,7,7a-hexahydro-1H-benzo[d]imidazole;
(S)-2-(2-(3-fluoropyrrolidin-1-yl)-4-phenylpyridin-3-yl)-4,5,6,7-tetrahydro-1H-benzo[d]imidazole;
6-(tert-butyl)-2-(4-phenyl-6-(pyrrolidin-1-yl)pyrimidin-5-yl)-1H-benzo[d]imidazole;
2-(2-(3,3-difluoropyrrolidin-1-yl)-4-phenylpyridin-3-yl)-1,4,5,6-tetrahydrocyclopenta[d]imidazol-5-ol;
2-(2-(3,3-difluoropyrrolidin-1-yl)-4-phenylpyridin-3-yl)-6-methoxy-4,5,6,7-tetrahydro-1H-benzo[d]imidazole;
(S)-2-(2-((S)-3-fluoropyrrolidin-1-yl)-4-phenylpyridin-3-yl)-6-methoxy-4,5,6,7-tetrahydro-1H-benzo[d]imidazole;
(R)-2-(2-((S)-3-fluoropyrrolidin-1-yl)-4-phenylpyridin-3-yl)-6-methoxy-4,5,6,7-tetrahydro-1H-benzo[d]imidazole;
2-(2-((S)-3-fluoropyrrolidin-1-yl)-4-phenylpyridin-3-yl)-6-methoxy-4,5,6,7-tetrahydro-1H-benzo[d]imidazole;
(S)-2-(2-(3-fluoropyrrolidin-1-yl)-4-phenylpyridin-3-yl) benzo[d]oxazole;
2-(2-(3,3-difluoropyrrolidin-1-yl)-4-phenylpyridin-3-yl)-4,5,6,7-tetrahydro-1H-benzo[d]imidazole;
2-(2-(3,3-difluoropyrrolidin-1-yl)-4-phenylpyridin-3-yl)-3,4,6,7-tetrahydropyrano[3,4-d]imidazole;
2-(2-(3,3-difluoropyrrolidin-1-yl)-4-phenylpyridin-3-yl)-6,6-dimethyl-3,4,6,7-tetrahydropyrano[3,4-d]imidazole;
(S)-2-(4-(2,5-difluorophenyl)-2-(3-fluoropyrrolidin-1-yl) pyridin-3-yl)-3,4,6,7-tetrahydropyrano[3,4-d]imidazole;
2-(2-(3,3-difluoropyrrolidin-1-yl)-4-(2-fluorophenyl) pyridin-3-yl)-1,4,6,7-tetrahydropyrano[3,4-d]imidazole;
2-(4-(2,5-difluorophenyl)-2-(3,3-difluoropyrrolidin-1-yl) pyridin-3-yl)-1,4,6,7-tetrahydropyrano[3,4-d]imidazole;
2-(2-(3,3-difluoropyrrolidin-1-yl)-4-(1H-indazol-5-yl) pyridin-3-yl)-1,4,6,7-tetrahydropyrano[3,4-d]imidazole;
2-(2-(3,3-difluoropyrrolidin-1-yl)-4-(3-fluorophenyl) pyridin-3-yl)-1,4,6,7-tetrahydropyrano[3,4-d]imidazole;
2-(4-phenyl-2-(pyrrolidin-1-yl)pyridin-3-yl)-3,4,6,7-tetrahydropyrano[3,4-d]imidazole;
2-(2-(6,6-difluoro-3-azabicyclo[3.1.0]hexan-3-yl)-4-phenylpyridin-3-yl)-3,4,6,7-tetrahydropyrano[3,4-d]imidazole;
2-(4-(2,5-difluorophenyl)-2-(3,3-difluoropyrrolidin-1-yl) pyridin-3-yl)-6,6-dimethyl-3,4,6,7-tetrahydropyrano[3,4-d]imidazole;
2-(2-((3S,4R)-3,4-difluoropyrrolidin-1-yl)-4-phenylpyridin-3-yl)-3,4,6,7-tetrahydropyrano[3,4-d]imidazole;
2-(4-(2,3-difluorophenyl)-2-(3,3-difluoropyrrolidin-1-yl) pyridin-3-yl)-3,4,6,7-tetrahydropyrano[3,4-d]imidazole;
1-(4-phenyl-3-(3,4,6,7-tetrahydropyrano[3,4-d]imidazol-2-yl)pyridin-2-yl)pyrrolidine-3-carbonitrile;
2'-(2-(3,3-difluoropyrrolidin-1-yl)-4-phenylpyridin-3-yl)-4',7'-dihydro-3'H-spiro[cyclobutane-1,6'-pyrano[3,4-d]imidazole];
2-(4-phenyl-2-(3-(trifluoromethyl)pyrrolidin-1-yl)pyridin-3-yl)-3,4,6,7-tetrahydropyrano[3,4-d]imidazole;
2-(2-(3,3-difluoropyrrolidin-1-yl)-4-phenylpyridin-3-yl)-4,4-dimethyl-3,4,6,7-tetrahydropyrano[3,4-d]imidazole;
5-(4-(2-fluorophenyl)-2-(pyrrolidin-1-yl)pyridin-3-yl)-1,3,4-oxadiazol-2-amine;
4-(2-fluorophenyl)-3-(5-isobutyl-4,5-dihydro-1H-imidazol-2-yl)-2-(pyrrolidin-1-yl)pyridine;
(S)-2-(4-(2-fluorophenyl)-2-(3-fluoropyrrolidin-1-yl) pyridin-3-yl)-1,3,4-oxadiazole;
(S)-N-butyl-5-(4-(2-fluorophenyl)-2-(3-fluoropyrrolidin-1-yl)pyridin-3-yl)-1,3,4-oxadiazol-2-amine;
(S)-2-(2-(3-fluoropyrrolidin-1-yl)-3-(5-isopentyl-1,3,4-oxadiazol-2-yl)pyridin-4-yl)phenol;
(S)-2-(4-(2-fluorophenyl)-2-(3-fluoropyrrolidin-1-yl) pyridin-3-yl)-5-isopentyl-1,3,4-oxadiazole;
(S)-2-(3-fluoropyrrolidin-1-yl)-4-phenyl-3-(3-(pyridin-3-yl)-1H-pyrazol-5-yl)pyridine;
(S)-2-(3-fluoropyrrolidin-1-yl)-3-(3-(4-isopropylphenyl)-1H-pyrazol-5-yl)-4-phenylpyridine;
(S)-1-(6-chloropyridin-3-yl)-3-(4-(2-fluorophenyl)-2-(3-fluoropyrrolidin-1-yl)pyridin-3-yl)imidazolidin-2-one;
(S)-1-(6-chloropyridin-3-yl)-3-(4-(2-fluorophenyl)-2-(3-fluoropyrrolidin-1-yl)pyridin-3-yl)-1,3-dihydro-2H-imidazol-2-one;
2-((S)-3-fluoropyrrolidin-1-yl)-3-(5-methyl-4,5-dihydro-1H-imidazol-2-yl)-4-phenylpyridine;
(S)-3-(4-bromo-5-methyl-1H-imidazol-2-yl)-2-(3-fluoropyrrolidin-1-yl)-4-phenylpyridine;
(S)-2-(2-(3-fluoropyrrolidin-1-yl)-4-phenylpyridin-3-yl)-5-(4-isopropylphenyl)-1,3,4-oxadiazole;
tert-butyl (S)-2-(2-(3-fluoropyrrolidin-1-yl)-4-phenylpyridin-3-yl)-3,4,6,7-tetrahydro-5H-imidazo[4,5-c] pyridine-5-carboxylate;
(S)-2-(3-fluoropyrrolidin-1-yl)-3-(4-methyl-5-(trifluoromethyl)-1H-imidazol-2-yl)-4-phenylpyridine;
2-(3,3-difluoropyrrolidin-1-yl)-3-(5-methyl-4-phenyl-1H-imidazol-2-yl)-4-phenylpyridine;
5-(tert-butyl)-3-(2-(3,3-difluoropyrrolidin-1-yl)-4-phenylpyridin-3-yl)-1,2,4-oxadiazole;
(S)-2-(3-fluoropyrrolidin-1-yl)-4-phenyl-3-(3-phenyl-1H-1,2,4-triazol-5-yl)pyridine;
4-(3-(1H-benzo[d]imidazol-2-yl)-4-(o-tolyl)pyridin-2-yl) morpholine;
2-(2-(4-methylpiperazin-1-yl)-4-(o-tolyl)pyridin-3-yl)-1H-benzo[d]imidazole;
4-(3-(3-(4-isopropylphenyl)-1H-pyrazol-5-yl)-4-phenylpyridin-2-yl)morpholine;
4-(3-((3aR,7aR)-3a,4,5,6,7,7a-hexahydro-1H-benzo[d] imidazol-2-yl)-4-phenylpyridin-2-yl)morpholine-;
4-(4-phenyl-3-(4,5,6,7-tetrahydro-1H-benzo[d]imidazol-2-yl)pyridin-2-yl)morpholine;

2-(2-morpholino-4-phenylpyridin-3-yl)-3,4,6,7-tetrahydropyrano[3,4-d]imidazole;
2-(2-(3,3-difluoroazetidin-1-yl)-4-phenylpyridin-3-yl)-3,4,6,7-tetrahydropyrano[3,4-d]imidazole;
2-(4-phenyl-2-(2-oxa-6-azaspiro[3.3]heptan-6-yl)pyridin-3-yl)-3,4,6,7-tetrahydropyrano[3,4-d]imidazole;
2-(2-cyclobutoxy-4-phenylpyridin-3-yl)-3,4,6,7-tetrahydropyrano[3,4-d]imidazole;
2-(2-(3,3-difluoropiperidin-1-yl)-4-phenylpyridin-3-yl)-3,4,6,7-tetrahydropyrano[3,4-d]imidazole;
2-(2-(6,6-difluoro-2-azaspiro[3.3]heptan-2-yl)-4-phenylpyridin-3-yl)-3,4,6,7-tetrahydropyrano[3,4-d]imidazole;
4-phenyl-3-(3,4,6,7-tetrahydropyrano[3,4-d]imidazol-2-yl)-N-((1-(trifluoromethyl)cyclobutyl)methyl)pyridin-2-amine;
2-(4-phenyl-2-(tetrahydro-2H-pyran-4-yl)pyridin-3-yl)-3,4,6,7-tetrahydropyrano[3,4-d]imidazole;
2-(2-(3,6-dihydro-2H-pyran-4-yl)-4-phenylpyridin-3-yl)-3,4,6,7-tetrahydropyrano[3,4-d]imidazole;
4-(benzo[c]benzo[4,5]imidazo[2,1-a][2,7]naphthyridin-1-yl)morpholine;
1-(4-methylpiperazin-1-yl)benzo[c]benzo[4,5]imidazo[2,1-a][2,7]naphthyridine;
1-(pyrrolidin-1-yl)benzo[c]benzo[4,5]imidazo[2,1-a][2,7]naphthyridine;
2-(2,4-di(1H-pyrazol-1-yl)pyridin-3-yl)-1H-benzo[d]imidazole;
2-(2'-(pyrrolidin-1-yl)-[2,4'-bipyridin]-3'-yl)-1H-benzo[d]imidazole;
2-(4-(1H-pyrazol-1-yl)-2-(pyrrolidin-1-yl)pyridin-3-yl)-1H-benzo[d]imidazole;
(S)-2-(4-(cyclopent-1-en-1-yl)-2-(3-fluoropyrrolidin-1-yl)pyridin-3-yl)-1H-benzo[d]imidazole;
2-(2'-(3,3-difluoropyrrolidin-1-yl)-[2,4'-bipyridin]-3'-yl)-3,4,6,7-tetrahydropyrano[3,4-d]imidazole;
2-(5-phenyl-3-(pyrrolidin-1-yl)pyridazin-4-yl)-1H-benzo[d]imidazole;
4-(5-phenyl-4-(4,5,6,7-tetrahydro-1H-benzo[d]imidazol-2-yl)pyridazin-3-yl)morpholine;
(S)-2-(2-(3-fluoropyrrolidin-1-yl)-4-phenylpyridin-3-yl)imidazo[1,2-a]pyridine; and
(S)-2-(2-(3-fluoropyrrolidin-1-yl)-4-phenylpyridin-3-yl)-[1,2,4]triazolo[1,5-a]pyridine;
or a stereoisomer, enantiomer, tautomer, or mixture thereof, or a pharmaceutically acceptable salt or solvate of said compound, stereoisomer, enantiomer, tautomer, or mixture thereof.

26. The method of claim 24, wherein the disease or condition is selected from epilepsy, seizure disorders, partial seizures, generalized seizures, photosensitive epilepsy, self-induced syncope, intractable epilepsy, Angelman syndrome, benign rolandic epilepsy, CDKL5 disorder, childhood and juvenile absence epilepsy, Dravet syndrome, frontal lobe epilepsy, Glut1 deficiency syndrome, hypothalamic hamartoma, infantile spasms/West's syndrome, juvenile myoclonic epilepsy, Landau-Kleffner syndrome, Lennox-Gastaut syndrome (LGS), epilepsy with myoclonic-absences, Ohtahara syndrome, Panayiotopoulos syndrome, PCDH19 epilepsy, progressive myoclonic epilepsies, Rasmussen's syndrome, ring chromosome 20 syndrome, reflex epilepsies, temporal lobe epilepsy, Lafora progressive myoclonus epilepsy, neurocutaneous syndromes, tuberous sclerosis complex, early infantile epileptic encephalopathy, early onset epileptic encephalopathy, generalized epilepsy with febrile seizures plus (GEFS+), Rett syndrome, multiple sclerosis, Schizophrenia, autism, ataxia, hypotonia and paroxysmal dyskinesia, Alzheimer's disease, Tauopathies, Pick's disease, progressive supranuclear palsy, corticobasal syndrome, frontotemporal dementias, Argyrophilic grain disease, frontotemporal lobar degeneration, globular glial tauopathies, MAPT mutation, primary age-related tauopathy, neurofibrillary tangle dementia, chronic traumatic encephalopathy (CTE), aging-related tau astrogliopathy, Richardson syndrome, Down Syndrome, parkinsonism, pure akinesia with gait freezing, motor neuron symptoms or cerebellar ataxia, posttraumatic stress disorders (PTSD), and any combination thereof.

27. The method of claim 24, wherein the disease or condition is selected from epilepsy and a seizure disorder.

28. The method of claim 24, wherein the disease or condition is selected from epilepsy and Dravet syndrome.

29. A method of treating a disease or condition in a mammal, wherein the method comprises administering to a mammal in need thereof a therapeutically effective amount of a compound of claim 1, wherein the disease or condition is selected from epilepsy, seizure disorders, partial seizures, generalized seizures, photosensitive epilepsy, self-induced syncope, intractable epilepsy, Angelman syndrome, benign rolandic epilepsy, CDKL5 disorder, childhood and juvenile absence epilepsy, Dravet syndrome, frontal lobe epilepsy, Glut1 deficiency syndrome, hypothalamic hamartoma, infantile spasms/West's syndrome, juvenile myoclonic epilepsy, Landau-Kleffner syndrome, Lennox-Gastaut syndrome (LGS), epilepsy with myoclonic-absences, Ohtahara syndrome, Panayiotopoulos syndrome, PCDH19 epilepsy, progressive myoclonic epilepsies, Rasmussen's syndrome, ring chromosome 20 syndrome, reflex epilepsies, temporal lobe epilepsy, Lafora progressive myoclonus epilepsy, neurocutaneous syndromes, tuberous sclerosis complex, early infantile epileptic encephalopathy, early onset epileptic encephalopathy, generalized epilepsy with febrile seizures plus (GEFS+), Rett syndrome, multiple sclerosis, Schizophrenia, autism, ataxia, hypotonia and paroxysmal dyskinesia, Alzheimer's disease, Tauopathies, Pick's disease, progressive supranuclear palsy, corticobasal syndrome, frontotemporal dementias, Argyrophilic grain disease, frontotemporal lobar degeneration, globular glial tauopathies, MAPT mutation, primary age-related tauopathy, neurofibrillary tangle dementia, chronic traumatic encephalopathy (CTE), aging-related tau astrogliopathy, Richardson syndrome, Down Syndrome, parkinsonism, pure akinesia with gait freezing, motor neuron symptoms or cerebellar ataxia, posttraumatic stress disorders (PTSD), and any combination thereof.

30. The method of claim 29, wherein the compound of formula (I) is selected from:
(S)-6-chloro-2-(4-(2,5-difluorophenyl)-2-(3-fluoropyrrolidin-1-yl)pyridin-3-yl)-3H-imidazo[4,5-c]pyridine;
2-(4-(2-fluorophenyl)-2-(pyrrolidin-1-yl)pyridin-3-yl)-3H-imidazo[4,5-b]pyridine;
2-(4-(2-fluorophenyl)-2-(pyrrolidin-1-yl)pyridin-3-yl)-3H-imidazo[4,5-c]pyridine formic acid salt;
tert-butyl (S)-2-(2-(3-fluoropyrrolidin-1-yl)-4-phenylpyridin-3-yl)-3,4,6,7-tetrahydro-5H-imidazo[4,5-c]pyridine-5-carboxylate;
(S)-2-(2-(3-fluoropyrrolidin-1-yl)-4-phenylpyridin-3-yl)-4,5,6,7-tetrahydro-3H-imidazo[4,5-c]pyridine;
(S)-2-(2-(3-fluoropyrrolidin-1-yl)-4-phenylpyridin-3-yl)-5-methyl-4,5,6,7-tetrahydro-3H-imidazo[4,5-c]pyridine;
(S)-1-(2-(2-(3-fluoropyrrolidin-1-yl)-4-phenylpyridin-3-yl)-3,4,6,7-tetrahydro-5H-imidazo[4,5-c]pyridin-5-yl)ethan-1-one;

(S)-2-(2-(3-fluoropyrrolidin-1-yl)-4-phenylpyridin-3-yl)-5-isopropyl-4,5,6,7-tetrahydro-3H-imidazo[4,5-c]pyridine;

(S)-2-(2-(3-fluoropyrrolidin-1-yl)-4-phenylpyridin-3-yl)-5-(oxetan-3-yl)-4,5,6,7-tetrahydro-3/I-imidazo[4,5-c]pyridine;

diethyl (S)-2-(2-(3-fluoropyrrolidin-1-yl)-4-phenylpyridin-3-yl)-6,7-dihydro-3H-imidazo[4,5-c]pyridine-3,5(4H)-dicarboxylate;

(S)-1-(2-(2-(3-fluoropyrrolidin-1-yl)-4-phenylpyridin-3-yl)-3,4,6,7-tetrahydro-5H-imidazo[4,5-c]pyridin-5-yl)-2-methylpropan-1-one;

(S)-5-benzyl-2-(2-(3-fluoropyrrolidin-1-yl)-4-phenylpyridin-3-yl)-4,5,6,7-tetrahydro-3H-imidazo[4,5-c]pyridine;

tert-butyl 2-(2-(3,3-difluoropyrrolidin-1-yl)-4-phenylpyridin-3-yl)-3,4,6,7-tetrahydro-5H-imidazo[4,5-c]pyridine-5-carboxylate;

2-(2-(3,3-difluoropyrrolidin-1-yl)-4-(2-fluorophenyl)pyridin-3-yl)-3H-imidazo[4,5-c]pyridine;

2-(2-(3,3-difluoropyrrolidin-1-yl)-4-(2-fluorophenyl)pyridin-3-yl)-6-methyl-3H-imidazo[4,5-c]pyridine;

5-(2-(3,3-difluoropyrrolidin-1-yl)-4-(2-fluorophenyl)pyridin-3-yl)-2-methyl-2,4-dihydroimidazo[4,5-c]pyrazole;

2-(4-(2-fluorophenyl)-2-(pyrrolidin-1-yl)pyridin-3-yl)-1H-benzo[d]imidazole;

2-(4-(2-chlorophenyl)-2-(pyrrolidin-1-yl)pyridin-3-yl)-1H-benzo[d]imidazole;

2-(2-(pyrrolidin-1-yl)-4-(o-tolyl)pyridin-3-yl)-1H-benzo[d]imidazole;

2-(2-(pyrrolidin-1-yl)-4-(4-(trifluoromethyl)phenyl)pyridin-3-yl)-1H-benzo[d]imidazole;

2-(4-phenyl-2-(pyrrolidin-1-yl)pyridin-3-yl)-1H-benzo[d]imidazole;

(S)-2-(2-(3-fluoropyrrolidin-1-yl)-4-phenylpyridin-3-yl)-1H-benzo[d]imidazole;

(S)-2-(4-(2-fluorophenyl)-2-(3-fluoropyrrolidin-1-yl)pyridin-3-yl)-1H-benzo[d]imidazole;

2-(4-(3,5-difluorophenyl)-2-(pyrrolidin-1-yl)pyridin-3-yl)-1H-benzo[d]imidazole;

(3aR,7aR)-2-(2-((S)-3-fluoropyrrolidin-1-yl)-4-phenylpyridin-3-yl)-3a,4,5,6,7,7a-hexahydro-1H-benzo[d]imidazole;

(S)-2-(2-(3-fluoropyrrolidin-1-yl)-4-phenylpyridin-3-yl)-4,5,6,7-tetrahydro-1H-benzo[d]imidazole;

6-(tert-butyl)-2-(4-phenyl-6-(pyrrolidin-1-yl)pyrimidin-5-yl)-1H-benzo[d]imidazole;

2-(2-(3,3-difluoropyrrolidin-1-yl)-4-phenylpyridin-3-yl)-1,4,5,6-tetrahydrocyclopenta[d]imidazol-5-ol;

2-(2-(3,3-difluoropyrrolidin-1-yl)-4-phenylpyridin-3-yl)-6-methoxy-4,5,6,7-tetrahydro-1H-benzo[d]imidazole;

(S)-2-(2-((S)-3-fluoropyrrolidin-1-yl)-4-phenylpyridin-3-yl)-6-methoxy-4,5,6,7-tetrahydro-1H-benzo[d]imidazole;

(R)-2-(2-((S)-3-fluoropyrrolidin-1-yl)-4-phenylpyridin-3-yl)-6-methoxy-4,5,6,7-tetrahydro-1H-benzo[d]imidazole;

2-(2-((S)-3-fluoropyrrolidin-1-yl)-4-phenylpyridin-3-yl)-6-methoxy-4,5,6,7-tetrahydro-1H-benzo[d]imidazole;

(S)-2-(2-(3-fluoropyrrolidin-1-yl)-4-phenylpyridin-3-yl)benzo[d]oxazole;

2-(2-(3,3-difluoropyrrolidin-1-yl)-4-phenylpyridin-3-yl)-4,5,6,7-tetrahydro-1H-benzo[d]imidazole;

2-(2-(3,3-difluoropyrrolidin-1-yl)-4-phenylpyridin-3-yl)-3,4,6,7-tetrahydropyrano[3,4-d]imidazole;

2-(2-(3,3-difluoropyrrolidin-1-yl)-4-phenylpyridin-3-yl)-6,6-dimethyl-3,4,6,7-tetrahydropyrano[3,4-d]imidazole;

(S)-2-(4-(2,5-difluorophenyl)-2-(3-fluoropyrrolidin-1-yl)pyridin-3-yl)-3,4,6,7-tetrahydropyrano[3,4-d]imidazole;

2-(2-(3,3-difluoropyrrolidin-1-yl)-4-(2-fluorophenyl)pyridin-3-yl)-1,4,6,7-tetrahydropyrano[3,4-d]imidazole;

2-(4-(2,5-difluorophenyl)-2-(3,3-difluoropyrrolidin-1-yl)pyridin-3-yl)-1,4,6,7-tetrahydropyrano[3,4-d]imidazole;

2-(2-(3,3-difluoropyrrolidin-1-yl)-4-(1H-indazol-5-yl)pyridin-3-yl)-1,4,6,7-tetrahydropyrano[3,4-d]imidazole;

2-(2-(3,3-difluoropyrrolidin-1-yl)-4-(3-fluorophenyl)pyridin-3-yl)-1,4,6,7-tetrahydropyrano[3,4-d]imidazole;

2-(4-phenyl-2-(pyrrolidin-1-yl)pyridin-3-yl)-3,4,6,7-tetrahydropyrano[3,4-d]imidazole;

2-(2-(6,6-difluoro-3-azabicyclo[3.1.0]hexan-3-yl)-4-phenylpyridin-3-yl)-3,4,6,7-tetrahydropyrano[3,4-d]imidazole;

2-(4-(2,5-difluorophenyl)-2-(3,3-difluoropyrrolidin-1-yl)pyridin-3-yl)-6,6-dimethyl-3,4,6,7-tetrahydropyrano[3,4-d]imidazole;

2-(2-((3S,4R)-3,4-difluoropyrrolidin-1-yl)-4-phenylpyridin-3-yl)-3,4,6,7-tetrahydropyrano[3,4-d]imidazole;

2-(4-(2,3-difluorophenyl)-2-(3,3-difluoropyrrolidin-1-yl)pyridin-3-yl)-3,4,6,7-tetrahydropyrano[3,4-d]imidazole;

1-(4-phenyl-3-(3,4,6,7-tetrahydropyrano[3,4-d]imidazol-2-yl)pyridin-2-yl)pyrrolidine-3-carbonitrile;

2'-(2-(3,3-difluoropyrrolidin-1-yl)-4-phenylpyridin-3-yl)-4',7'-dihydro-3'H-spiro[cyclobutane-1,6'-pyrano[3,4-d]imidazole];

2-(4-phenyl-2-(3-(trifluoromethyl)pyrrolidin-1-yl)pyridin-3-yl)-3,4,6,7-tetrahydropyrano[3,4-d]imidazole;

2-(2-(3,3-difluoropyrrolidin-1-yl)-4-phenylpyridin-3-yl)-4,4-dimethyl-3,4,6,7-tetrahydropyrano[3,4-d]imidazole;

5-(4-(2-fluorophenyl)-2-(pyrrolidin-1-yl)pyridin-3-yl)-1,3,4-oxadiazol-2-amine;

4-(2-fluorophenyl)-3-(5-isobutyl-4,5-dihydro-1H-imidazol-2-yl)-2-(pyrrolidin-1-yl)pyridine;

(S)-2-(4-(2-fluorophenyl)-2-(3-fluoropyrrolidin-1-yl)pyridin-3-yl)-1,3,4-oxadiazole;

(S)-N-butyl-5-(4-(2-fluorophenyl)-2-(3-fluoropyrrolidin-1-yl)pyridin-3-yl)-1,3,4-oxadiazol-2-amine;

(S)-2-(2-(3-fluoropyrrolidin-1-yl)-3-(5-isopentyl-1,3,4-oxadiazol-2-yl)pyridin-4-yl)phenol;

(S)-2-(4-(2-fluorophenyl)-2-(3-fluoropyrrolidin-1-yl)pyridin-3-yl)-5-isopentyl-1,3,4-oxadiazole;

(S)-2-(3-fluoropyrrolidin-1-yl)-4-phenyl-3-(3-(pyridin-3-yl)-1H-pyrazol-5-yl)pyridine;

(S)-2-(3-fluoropyrrolidin-1-yl)-3-(3-(4-isopropylphenyl)-1H-pyrazol-5-yl)-4-phenylpyridine;

(S)-1-(6-chloropyridin-3-yl)-3-(4-(2-fluorophenyl)-2-(3-fluoropyrrolidin-1-yl)pyridin-3-yl)imidazolidin-2-one;

(S)-1-(6-chloropyridin-3-yl)-3-(4-(2-fluorophenyl)-2-(3-fluoropyrrolidin-1-yl)pyridin-3-yl)-1,3-dihydro-2H-imidazol-2-one;

2-((S)-3-fluoropyrrolidin-1-yl)-3-(5-methyl-4,5-dihydro-1H-imidazol-2-yl)-4-phenylpyridine;

(S)-3-(4-bromo-5-methyl-1H-imidazol-2-yl)-2-(3-fluoropyrrolidin-1-yl)-4-phenylpyridine;

(S)-2-(2-(3-fluoropyrrolidin-1-yl)-4-phenylpyridin-3-yl)-5-(4-isopropylphenyl)-1,3,4-oxadiazole;

tert-butyl (S)-2-(2-(3-fluoropyrrolidin-1-yl)-4-phenylpyridin-3-yl)-3,4,6,7-tetrahydro-5H-imidazo[4,5-c]pyridine-5-carboxylate;

(S)-2-(3-fluoropyrrolidin-1-yl)-3-(4-methyl-5-(trifluoromethyl)-1H-imidazol-2-yl)-4-phenylpyridine;

2-(3,3-difluoropyrrolidin-1-yl)-3-(5-methyl-4-phenyl-1H-imidazol-2-yl)-4-phenylpyridine;

5-(tert-butyl)-3-(2-(3,3-difluoropyrrolidin-1-yl)-4-phenylpyridin-3-yl)-1,2,4-oxadiazole;

(S)-2-(3-fluoropyrrolidin-1-yl)-4-phenyl-3-(3-phenyl-1H-1,2,4-triazol-5-yl)pyridine;

4-(3-(1H-benzo[d]imidazol-2-yl)-4-(o-tolyl)pyridin-2-yl)morpholine;

2-(2-(4-methylpiperazin-1-yl)-4-(o-tolyl)pyridin-3-yl)-1H-benzo[d]imidazole;

4-(3-(3-(4-isopropylphenyl)-1H-pyrazol-5-yl)-4-phenylpyridin-2-yl)morpholine;

4-(3-((3aR,7aR)-3a,4,5,6,7,7a-hexahydro-1H-benzo[d]imidazol-2-yl)-4-phenylpyridin-2-yl)morpholine-;

4-(4-phenyl-3-(4,5,6,7-tetrahydro-1H-benzo[d]imidazol-2-yl)pyridin-2-yl)morpholine;

2-(2-morpholino-4-phenylpyridin-3-yl)-3,4,6,7-tetrahydropyrano[3,4-d]imidazole;

2-(2-(3,3-difluoroazetidin-1-yl)-4-phenylpyridin-3-yl)-3,4,6,7-tetrahydropyrano[3,4-d]imidazole;

2-(4-phenyl-2-(2-oxa-6-azaspiro[3.3]heptan-6-yl)pyridin-3-yl)-3,4,6,7-tetrahydropyrano[3,4-d]imidazole;

2-(2-cyclobutoxy-4-phenylpyridin-3-yl)-3,4,6,7-tetrahydropyrano[3,4-d]imidazole;

2-(2-(3,3-difluoropiperidin-1-yl)-4-phenylpyridin-3-yl)-3,4,6,7-tetrahydropyrano[3,4-d]imidazole;

2-(2-(6,6-difluoro-2-azaspiro[3.3]heptan-2-yl)-4-phenylpyridin-3-yl)-3,4,6,7-tetrahydropyrano[3,4-d]imidazole;

4-phenyl-3-(3,4,6,7-tetrahydropyrano[3,4-d]imidazol-2-yl)-N-((1-(trifluoromethyl)cyclobutyl)methyl)pyridin-2-amine;

2-(4-phenyl-2-(tetrahydro-2H-pyran-4-yl)pyridin-3-yl)-3,4,6,7-tetrahydropyrano[3,4-d]imidazole;

2-(2-(3,6-dihydro-2H-pyran-4-yl)-4-phenylpyridin-3-yl)-3,4,6,7-tetrahydropyrano[3,4-d]imidazole;

4-(benzo[c]benzo[4,5]imidazo[2,1-a][2,7]naphthyridin-1-yl)morpholine;

1-(4-methylpiperazin-1-yl)benzo[c]benzo[4,5]imidazo[2,1-a][2,7]naphthyridine;

1-(pyrrolidin-1-yl)benzo[c]benzo[4,5]imidazo[2,1-a][2,7]naphthyridine;

2-(2,4-di(1H-pyrazol-1-yl)pyridin-3-yl)-1H-benzo[d]imidazole;

2-(2'-(pyrrolidin-1-yl)-[2,4'-bipyridin]-3'-yl)-1H-benzo[d]imidazole;

2-(4-(1H-pyrazol-1-yl)-2-(pyrrolidin-1-yl)pyridin-3-yl)-1H-benzo[d]imidazole;

(S)-2-(4-(cyclopent-1-en-1-yl)-2-(3-fluoropyrrolidin-1-yl)pyridin-3-yl)-1H-benzo[d]imidazole;

2-(2'-(3,3-difluoropyrrolidin-1-yl)-[2,4'-bipyridin]-3'-yl)-3,4,6,7-tetrahydropyrano[3,4-d]imidazole;

2-(5-phenyl-3-(pyrrolidin-1-yl)pyridazin-4-yl)-1H-benzo[d]imidazole;

4-(5-phenyl-4-(4,5,6,7-tetrahydro-1H-benzo[d]imidazol-2-yl)pyridazin-3-yl)morpholine;

(S)-2-(2-(3-fluoropyrrolidin-1-yl)-4-phenylpyridin-3-yl)imidazo[1,2-a]pyridine; and (S)-2-(2-(3-fluoropyrrolidin-1-yl)-4-phenylpyridin-3-yl)-[1,2,4]triazolo[1,5-a]pyridine;

or a stereoisomer, enantiomer, tautomer, or mixture thereof, or a pharmaceutically acceptable salt or solvate of said compound, stereoisomer, enantiomer, tautomer, or mixture thereof.

31. The method of claim 29, wherein the disease or condition is epilepsy or a seizure disorder.

32. The method of claim 29, wherein the disease or condition is selected from epilepsy and Dravet syndrome.

33. A method of treating a disease or condition in a mammal, wherein the method comprises administering to a mammal in need thereof a therapeutically effective amount of a compound of claim 4, wherein the disease or condition is selected from epilepsy, seizure disorders, partial seizures, generalized seizures, photosensitive epilepsy, self-induced syncope, intractable epilepsy, Angelman syndrome, benign rolandic epilepsy, CDKL5 disorder, childhood and juvenile absence epilepsy, Dravet syndrome, frontal lobe epilepsy, Glut1 deficiency syndrome, hypothalamic hamartoma, infantile spasms/West's syndrome, juvenile myoclonic epilepsy, Landau-Kleffner syndrome, Lennox-Gastaut syndrome (LGS), epilepsy with myoclonic-absences, Ohtahara syndrome, Panayiotopoulos syndrome, PCDH19 epilepsy, progressive myoclonic epilepsies, Rasmussen's syndrome, ring chromosome 20 syndrome, reflex epilepsies, temporal lobe epilepsy, Lafora progressive myoclonus epilepsy, neurocutaneous syndromes, tuberous sclerosis complex, early infantile epileptic encephalopathy, early onset epileptic encephalopathy, generalized epilepsy with febrile seizures plus (GEFS+), Rett syndrome, multiple sclerosis, Schizophrenia, autism, ataxia, hypotonia and paroxysmal dyskinesia, Alzheimer's disease, Tauopathies, Pick's disease, progressive supranuclear palsy, corticobasal syndrome, frontotemporal dementias, Argyrophilic grain disease, frontotemporal lobar degeneration, globular glial tauopathies, MAPT mutation, primary age-related tauopathy, neurofibrillary tangle dementia, chronic traumatic encephalopathy (CTE), aging-related tau astrogliopathy, Richardson syndrome, Down Syndrome, parkinsonism, pure akinesia with gait freezing, motor neuron symptoms or cerebellar ataxia, posttraumatic stress disorders (PTSD), and any combination thereof.

34. The method of claim 33, wherein the disease or condition is epilepsy or a seizure disorder.

35. The method of claim 33, wherein the disease or condition is selected from epilepsy and Dravet syndrome.

* * * * *